US005622983A

United States Patent [19]
Horwell et al.

[11] Patent Number: 5,622,983
[45] Date of Patent: Apr. 22, 1997

[54] N-SUBSTITUTED CYCLOALKYL AND POLYCYCLOALKYL α-SUBSTITUTED TRP-PHE- AND PHENETHYLAMINE DERIVATIVES

[75] Inventors: David C. Horwell, Foxton; Martyn C. Pritchard, Swavesey; Edward Roberts, Wood Ditton; Reginald S. Richardson, Haverhill, all of England; Julian Aranda, Vorstetter, Germany

[73] Assignee: Warner-Lambert Company, Morris Plains, N.J.

[21] Appl. No.: 447,141

[22] Filed: May 22, 1995

Related U.S. Application Data

[60] Division of Ser. No. 235,814, Apr. 28, 1994, which is a continuation-in-part of Ser. No. 958,196, Oct. 7, 1992, abandoned, which is a division of Ser. No. 629,809, Dec. 19, 1990, Pat. No. 5,278,316, which is a continuation-in-part of Ser. No. 545,222, Jun. 28, 1990, abandoned, which is a continuation-in-part of Ser. No. 530,811, Jun. 5, 1990, abandoned, which is a continuation-in-part of Ser. No. 422,486, Oct. 16, 1989, abandoned, which is a continuation-in-part of Ser. No. 374,327, Jun. 29, 1989, abandoned.

[51] Int. Cl.$^6$ .................. A61K 31/405; A61K 31/41; C07D 403/12

[52] U.S. Cl. .................. 514/419; 514/359; 514/365; 514/378; 514/381; 514/383; 514/394; 514/397; 514/414; 514/415; 548/189; 548/248; 548/305.1; 548/312.1; 548/427; 548/455; 548/465; 548/469; 548/484; 548/494; 548/495; 548/496; 548/497; 548/361.1

[58] Field of Search .................. 548/189, 248, 548/336, 484, 455, 469, 465, 427, 305.1, 494, 312.1, 495, 497, 496; 514/359, 365, 378, 383, 381, 394, 397, 414, 415, 419

[56] References Cited

U.S. PATENT DOCUMENTS

| | | | |
|---|---|---|---|
| 3,775,466 | 11/1973 | Jager et al. | 560/158 |
| 3,839,396 | 10/1974 | Otsuka et al. | 558/270 |
| 4,757,151 | 7/1988 | Horwell | 548/469 |
| 5,218,123 | 6/1993 | Horwell | 546/273 |
| 5,244,915 | 9/1993 | Horwell | 514/419 |
| 5,264,419 | 11/1993 | Horwell | 514/18 |
| 5,340,825 | 8/1994 | Horwell | 514/339 |

FOREIGN PATENT DOCUMENTS

| | | |
|---|---|---|
| 0106281 | 10/1983 | European Pat. Off. . |
| 0230151 | 12/1986 | European Pat. Off. . |
| 0336356 | 10/1989 | European Pat. Off. . |

OTHER PUBLICATIONS

Bundgaard "Design of prodrugs" Elsevier, (1985) pp. 3, 346–353.
Notari et al "Biopharmaceutics and Pharmaco–kinetics" M. Decker Inc. (1975) pp. 216, 222.
Gould, et al., CA, 1979, 90:166522e/Tetrahedron Letters, 1978, 35, 3207–3210.
J. Hughes, et al., Proc Natl Acad Sci USA, 1990, 87, 6728–6732.
TiPS, 1990, 11, 271–273.
K.Q. Do, et al., CA, 1979, 91:57471n, 756.
W. Voelter & H. Kalbacher, CA, 1981, 94:140148v, 801.
G.W. Roberts, et al., Brain Research, 1983, 288, 199–211.
B.A. MacVicar, et al., Brain Research, 1987, 406, 130–135.
G.J. Dockray, British Med Bull, 1982, 38:3, 253–258.
P. Singh, et al., Cancer Research, 1986, 46, 1612–1616.
M.J. Sheehan, et al., CCK in the Nervous System, 1984, Ellis Horwood Ltd., Ch 7, 110–127.
J. Palmer Smith, et al., Gastroenterology, 1988, 95:6, 1541–1548.
V. Mutt, Gastrointestinal Hormones, 1980, Ch 7. 169–221.
L.R. Johnson, Ibid., Ch 22, 507–527. (1980).
S.J. Konturek, Ibid., Ch 23, 529–564. (1980).
F. Stadil, Ibid., Ch 30, 729–739. (1980).
K.Q. Do, et al., Helvetica Chimica Acta, 1979, 62:4, Nr 98.
J. E. Morley, Life Sciences, 1980, 27, 355–368.
J.F. Rehfeld & N.R. Goltermann, J of Neurochemistry, 32, 1339–1341. (1979).
R.G. Hill, et al., Neuropharmacology, 1987, 26:4, 289–300.
H. Demeulemeester, et al., J. of Neuroscience, 1988, 8:3, 988–1000.
S. Totterdell, et al., Neuroscience, 1986, 19:1, 181–192.
L.H. Schneider, et al., Peptides, 1983, 4, 749–753.
S.C. Harvey, Goodman & Gilman's Pharmacological Basis of Therapeutics,1985, 7th ed., Ch 17, 339–371.
F. Weiss, et al., Pharmacology Biochemistry & Behavior, 1988, 30, 309–317.
R.R. Schick, et al., Regulatory Peptides, 1986, 14, 277–291.
M.A. Della–Fera & C.A. Baile, Science, 1979, 206, 471–473.
Wall Street Journal, Sep. 29, 1989, B–3A, "Merck Advances . . .".
Int J Cancer, 57, 1994, 1–7.

Primary Examiner—Ceila Chang
Attorney, Agent, or Firm—Elizabeth M. Anderson

[57] ABSTRACT

Novel unnatural dipeptoids of α-substituted Trp-Phe derivatives useful as agents in the treatment of obesity, hypersecretion of gastric acid in the gut, gastrin-dependent tumors, colorectal tumors, or as antipsychotics are disclosed. Further the compounds are antianxiety agents, antiulcer agents, antidepressant agents, and are agents useful for preventing the withdrawal response produced by chronic treatment or use followed by chronic treatment followed by withdrawal from nicotine, diazepam, alcohol, cocaine, caffeine, or opiods. Also disclosed are pharmaceutical compositions and methods of treatment using the dipeptoids as well as processes for preparing them and novel intermediates useful in their preparation. An additional feature of the invention is the use of the subject compounds to prepare pharmaceutical and diagnostic compositions.

7 Claims, 26 Drawing Sheets

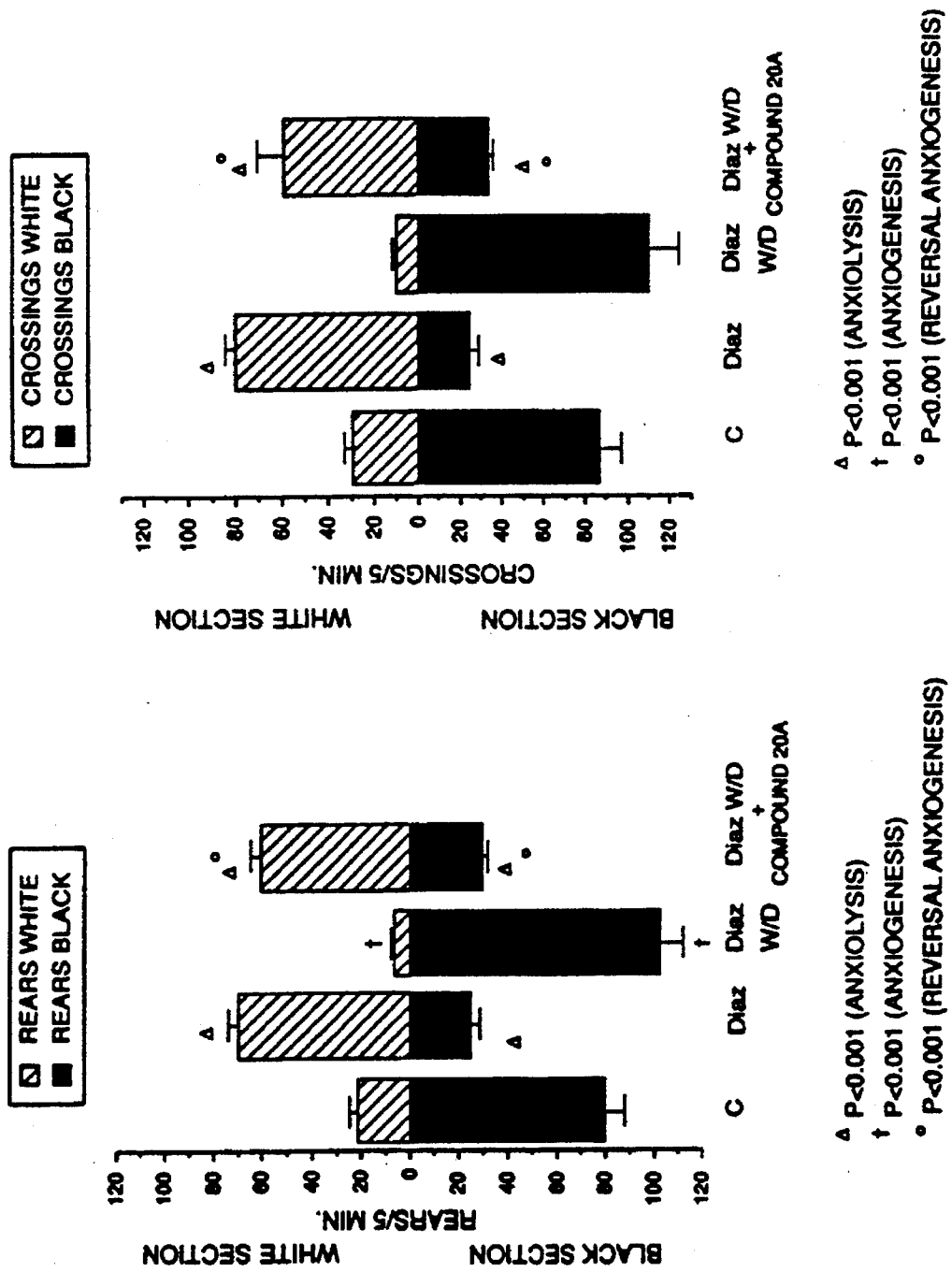

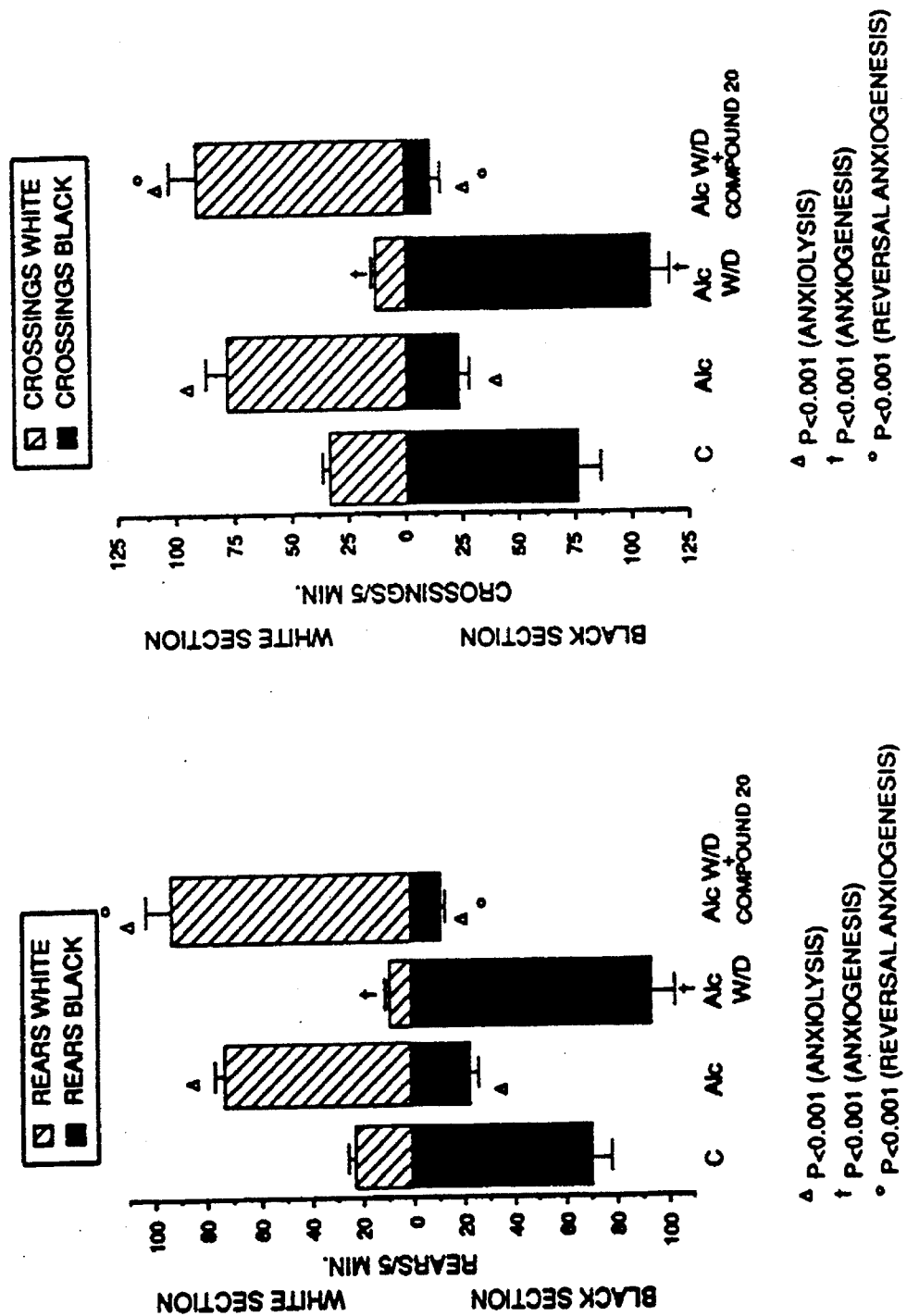

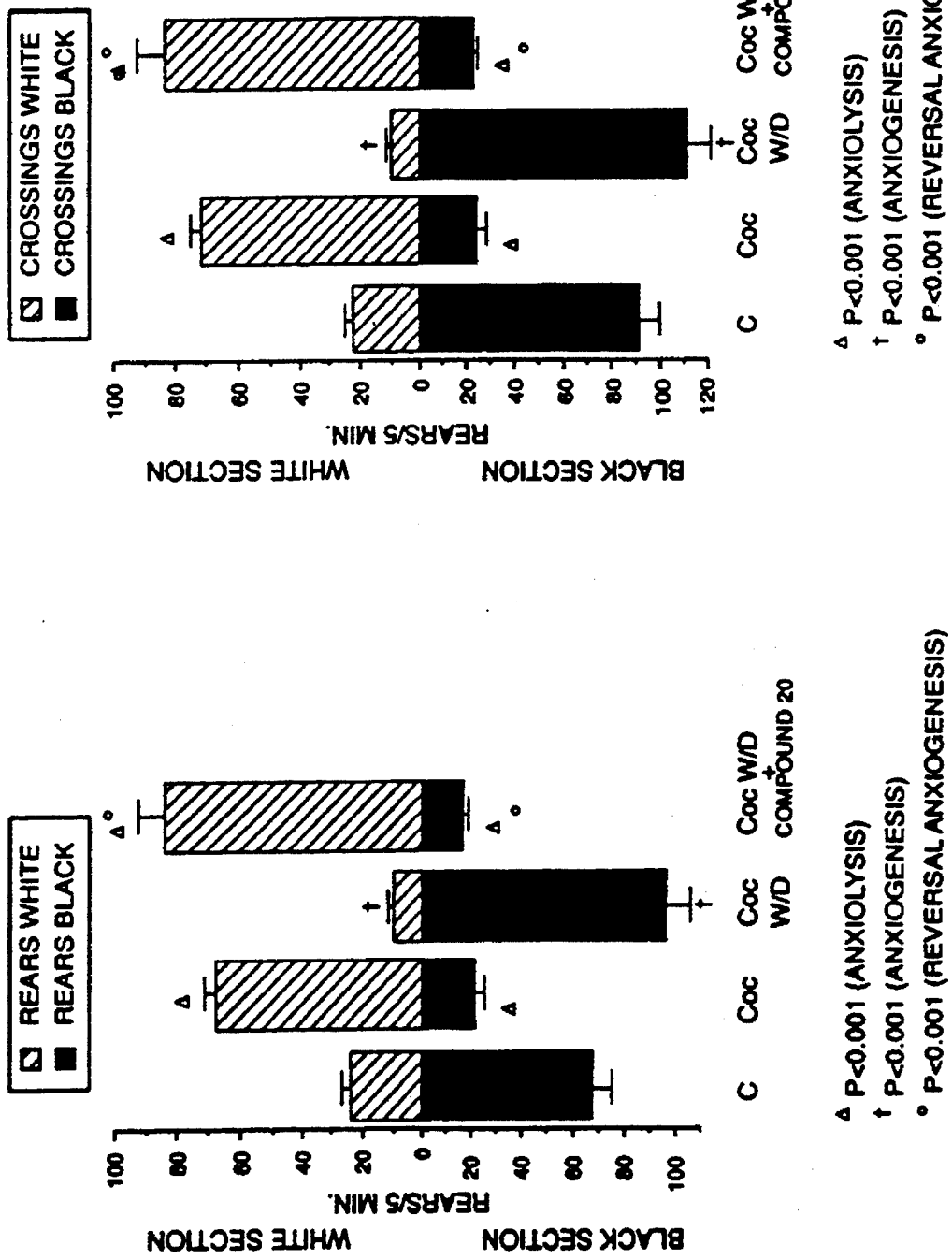

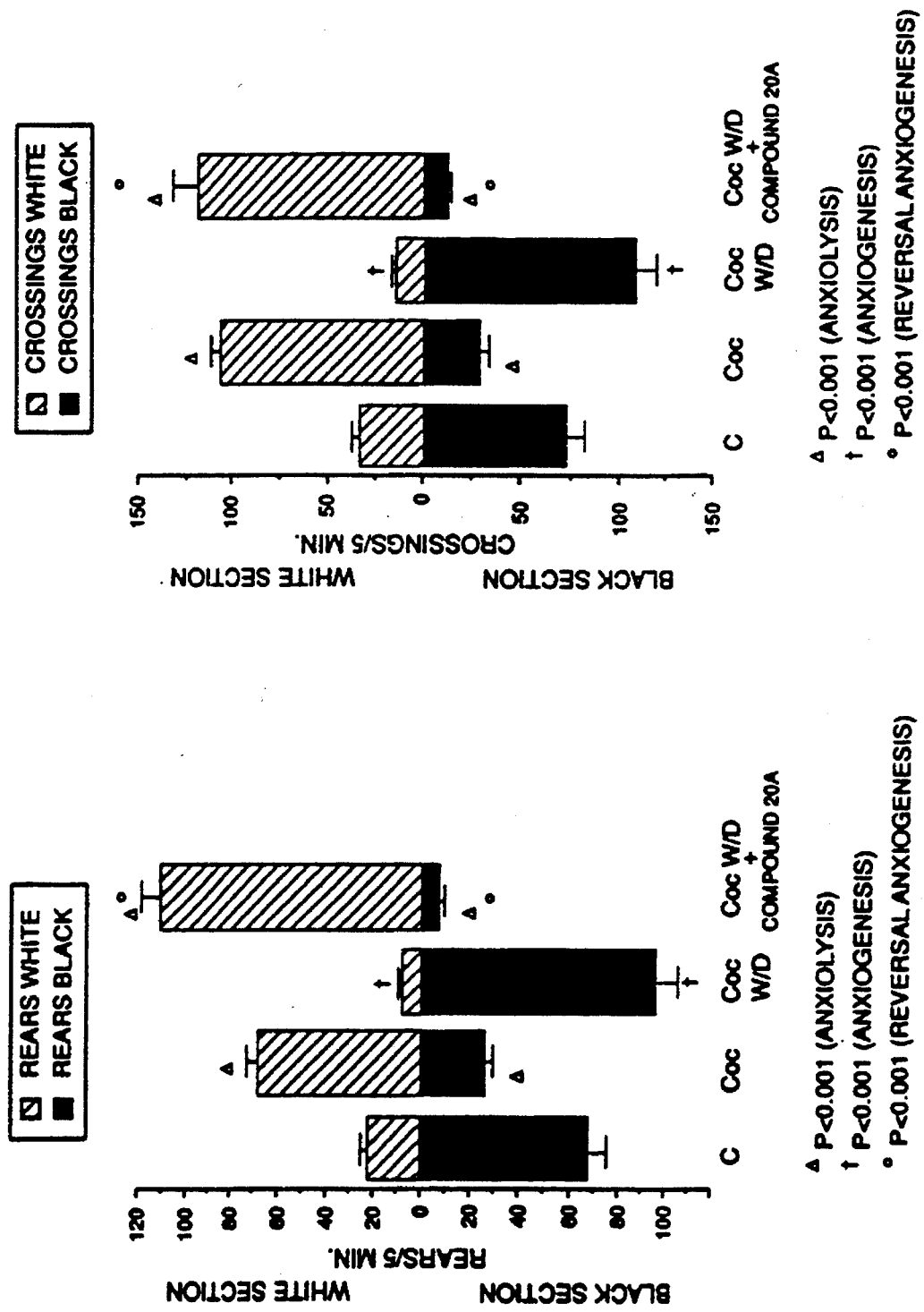

N-SUBSTITUTED CYCLOALKYL AND POLYCYCLOALKYL α-SUBSTITUTED TRP-PHE- AND PHENETHYLAMINE DERIVATIVES

CROSS-REFERENCE TO RELATED APPLICATIONS

This is a divisional application of U.S. patent application Ser. No. 08/235,814, filed Apr. 28, 1994 allowed; which is a continuation-in-part of Ser. No. 07/958,196, filed Oct. 7, 1992 abandoned; which is a division of Ser. No. 07/629,809, filed Dec. 19, 1990, now U.S. Pat. No. 5,278,316; which is a continuation-in-part of Ser. No. 07/545,222, filed Jun. 28, 1990, abandoned; which is a continuation-in-part of Ser. No. 07/530,811, filed Jun. 5, 1990, abandoned; which is a continuation-in-part of Ser. No. 07/422,486, filed Oct. 16, 1989, abandoned; which is a continuation-in-part of Ser. No. 07/374,327, filed Jun. 29, 1989, now abandoned.

BACKGROUND OF THE INVENTION

Agents acting at central cholecystokinin (CCK) receptors induce satiety (Schick, Yaksh and Go, *Regulatory Peptides* 14:277–291, 1986). They are also expected to act as analgesics (Hill, Hughes and Pittaway, *Neuropharmacology* 26:289–300, 1987), and as anticonvulsants (MacVicar, Kerrin and Davison, *Brain Research*, 406:130–135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak and Bloom. *Brain Research* 288, 199–211, 1983). It has been proposed that changes in the activity of CCK neurones projecting to the nucleus accumbens may play a role in schizophrenic processes by influencing dopaminergic function (Totterdell and Smith, *Neuroscience* 19, 181–192, 1986). This is consistent with numerous reports that CCK peptides modulate dopaminergic function in the basal ganglia and particularly the nucleus accumbens (Weiss, Tanzer, and Etteriberg, *Pharmcology, Biochemistry and Behaviour* 30, 309–317, 1988; Schneider, Allpert and Iversen, *Peptides* 4, 749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529–564, 1980, ed. G. B. J. Glass, Raven Press, N.Y.). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, *ibid.*, pp 507–527), actions which are associated with increased DNA and RNA synthesis. Moreover, gastrin secreting cells are associated with certain gastrointestinal tumors as in the Zollinger-Ellison syndrome (Stadil, ibid., pp 279–739), and some colorectal tumors may also be gastrin/CCK dependent (Singh, Walker, Townsend and Thompson, *Cancer Research*, 46, 1612 (1986), and Smith, J. P., *Gastroenterology*, 95 1541 (1988)). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26–33 and the tetrapeptide CCK30–33). (G. J. Dockray, *Br. Med. Bull.*, 38 (No. 3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169–221; J. E. Morley, *Life Sciences* 27:355–368, 1980; "Cholecystokinin in the Nervous System," J. de Belleroche and G. J. Dockray, Ed., Ellis Horwood, Chichester, England, 1984, pp 110–127.)

The high concentrations of CCK peptides in many brain areas also indicate major brain functions for these peptides (G. J. Dockray, *Br. Med. Bull,*, 38 (No. 3):253–258, 1982). The most abundant form of brain CCK found is CCK26–33, although small quantities of CCK30–33 exist (Rehfeld and Gotterman, *J. Neurochem.*, 32:1339–1341, 1979). The role of central nervous system CCK is not known with certainty, but it has been implicated in the control of feeding (Della-Fera and Baile, *Science* 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J Neuroscience* 8, 988–1000, 1988). Agents that modify GABA action may have utility as anxiolytic or hypnotic agents (S. C. Harvey, *The Pharmacological Basis of Therapeutics* (7th ed.) 1985, pp 339–371, MacMillan). Thus, agents which modify CCK action may have parallel arixiolytic or hypnotic activities.

The role of CCK in anxiety is disclosed in *TIPS* 11, 271–3 (1990).

SUMMARY OF THE INVENTION

The invention relates to novel compounds of the formula

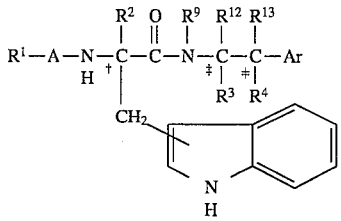

and the pharmaceutically acceptable salts thereof wherein $R^1$, $R^2$, $R^3$, $R^4$, $R^9$, $R^{12}$, $R^{13}$, A and Ar are as defined hereinbelow.

The invention also relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

The compounds of the instant invention are also useful as antidepressants. The invention further relates to a pharmaceutical composition for treating depression containing a therapeutically effective amount of a compound of formula I in combination with a pharmaceutically acceptable carrier in unit dosage form for treating depression.

The invention also relates to a method for treating and/or preventing depression in mammals which comprises administering an effective amount of the composition described above to a mammal in need of such treatment.

An additional use for compounds such as the iodinated compound of Example 26 is that the suitable radiolabelled iodine-127 isotope gives an agent suitable for treatment of gastrin dependent tumors such as those found in colonic cancers. I-125 radiolabelled compound of Example 26 can also be used as a diagnostic agent by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reducnion of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, nicotine, caffeine, and opioids. Withdrawal symptoms are treated by administration of an effective withdrawal treating amount of a compound of the instant invention; especially useful are compounds (20) and (20A).

The invention further relates to pharmaceutical compositions and to the use of the compounds of Formula I in the treatment of tumor growth, especially in colon cancer.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION

Figure 1B:
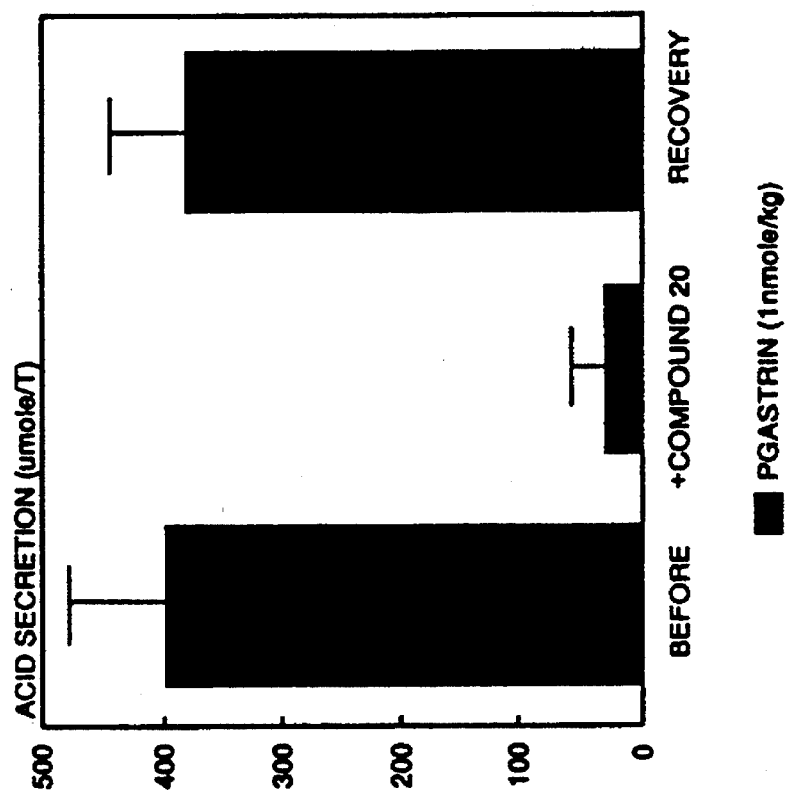
FIG. 1 shows inhibition of pentagastrin stimulated gastric acid secretion on the Ghosh and Schild by compound 20.

The compounds of the present invention are formed by the condensation of two modified amino acids and are therefore not peptides. Rather they are "dipeptoids", synthetic peptide-related compounds differing from natural dipeptides in that the substituent group $R^2$ is not hydrogen.

The compounds of the present invention are represented by the formula

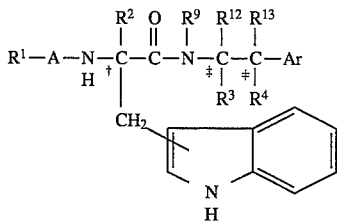

or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or —$(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is —$(CH_2)_nCO$—, —$SO_2$—, —SO—, —NHCO—,

—$(CH_2)_n$—OC—,

—SCO—, O—$(CH_2)_nCO$— or —HC=CHCO— wherein n is an integer from zero to six;

$R^2$ is a straight or branched alkyl of from one to six carbon atoms, —HC=$CH_2$, —C≡CH, —$CH_2$—CH=$CH_2$, —$CH_2$C≡CH, —$(CH_2)_nAr$, —$(CH_2)_nOR^*$, —$(CH_2)_nOAr$, —$(CH_2)_nCO_2R^*$, —$(CH_2)_nNR^5R^6$ wherein n, R, $R^5$ and $R^6$ are as defined above and Ar is as defined below;

$R^3$ and $R^4$ are each independently selected from hydrogen, $R^2$, and —$(CH_2)_{n'}$—B—D, wherein n' is an integer of from zero to three;

B is a bond

—OCO$(CH_2)_n$—

—O$(CH_2)_n$—

—$SO_2NH(CH_2)_n$—

—$NHSO_2(CH_2)_n$

—$NHCO(CH_2)_n$—

—$CONH(CH_2)_n$—

—NHCOCH=CH—

—$COO(CH_2)_n$—

—$CO(CH_2)_n$—

—S—$(CH_2)_n$—

—$SO(CH_2)_n$—

—$SO_2(CH_2)_n$—

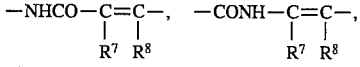

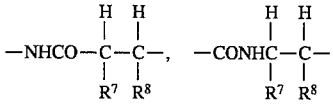

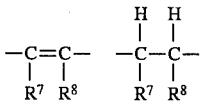

wherein $R^7$ and $R^8$ are independently selected from hydrogen and $R^2$ or together forIn a ring $(CH_2)_m$ wherein m is an integer of from 1 to 5 and n is as defined above;

D is

—COOR*,

—$CH_2OR^*$,

—$CHR^2OR^*$,

—$CH_2SR^*$,

—$CHR^2SR^*$,

—$CONR^5R^6$,

—CN,

—$NR^5R^6$,

—OH,

—H, and acid replacements such as tetrazole, and

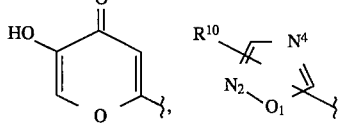

1, 2, 4 oxadiazole $R^{10}$ is OH, $NH_2$, $CH_3$, or Cl $HO_3S$—⟨

$H_2O_3P$—⟨

-continued

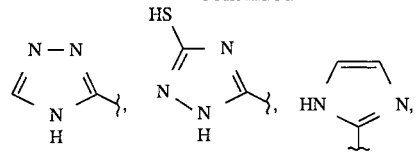

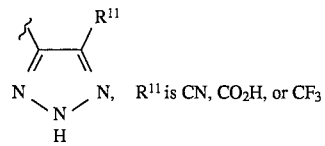 R¹¹ is CN, CO₂H, or CF₃

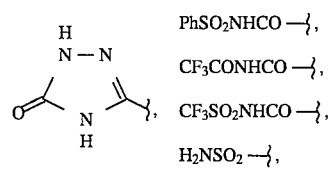 PhSO₂NHCO—⟩, CF₃CONHCO—⟩, CF₃SO₂NHCO—⟩, H₂NSO₂—⟩,

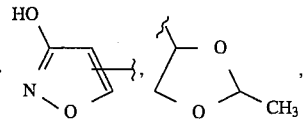

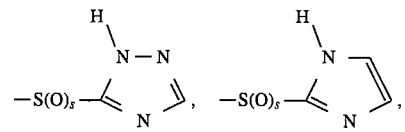

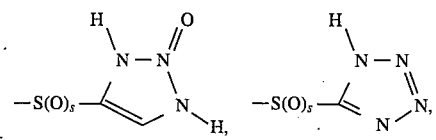

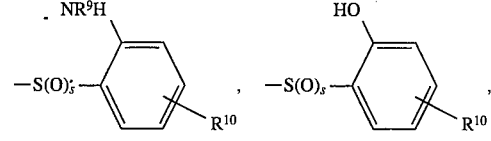

s is an integer of from 0 to 2, wherein R*, R², R⁵, and R⁶ are as defined above;

R⁹ is H, or a straight or branched alkyl of from one to six carbon atoms, —(CH₂)$_n$CO₂R*, (CH₂)$_n$OAr', (CH₂)$_n$Ar', (CH₂)$_n$NR⁵R⁶, wherein n, R*, R⁵, and R⁶ are as defined above or taken from R³ and Ar' is taken from Ar as defined below;

R¹² and R¹³ can each be independently hydrogen (in which case the carbon atom to which it is attached is a chiral center) or can each be taken with R³ and R⁴ respectively to form a moiety doubly bonded to the carbon atom (in which case the carbon atom is not chiral); and Ar is a mono- or polycyclic unsubstituted or substituted carbo- or heterocyclic aromatic or hydroaromatic moiety.

Preferred Ar is

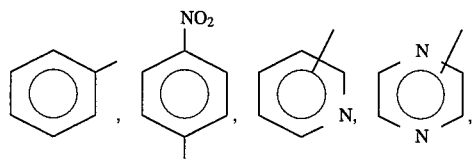

-continued

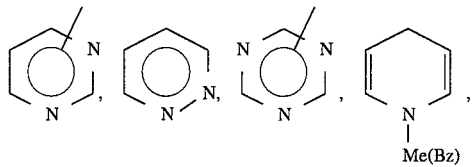

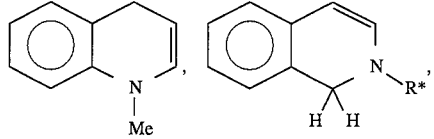

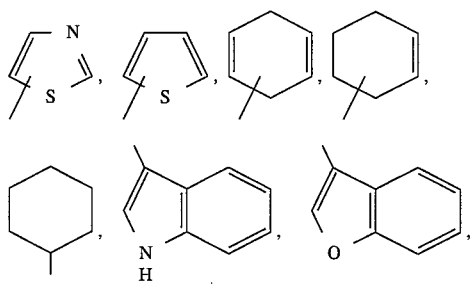

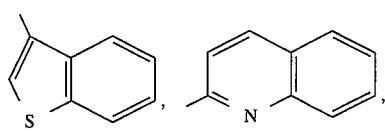

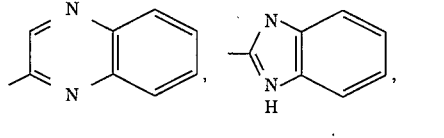

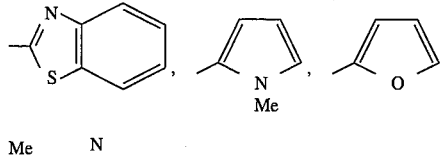

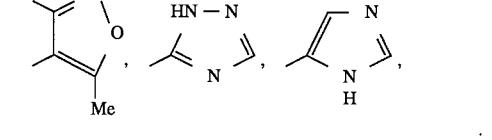

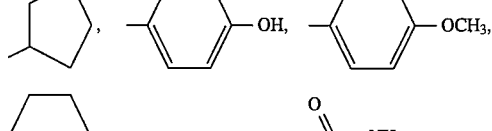

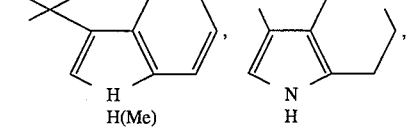

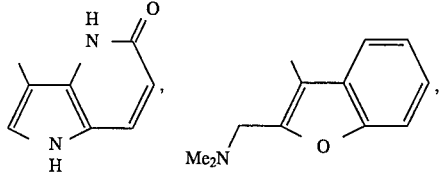

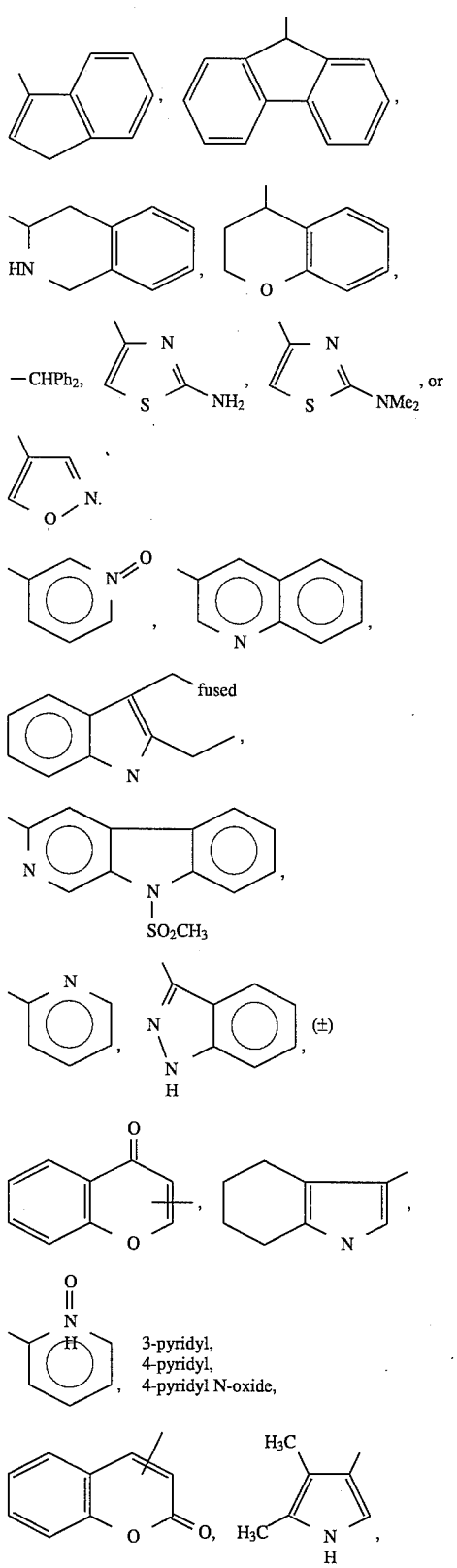
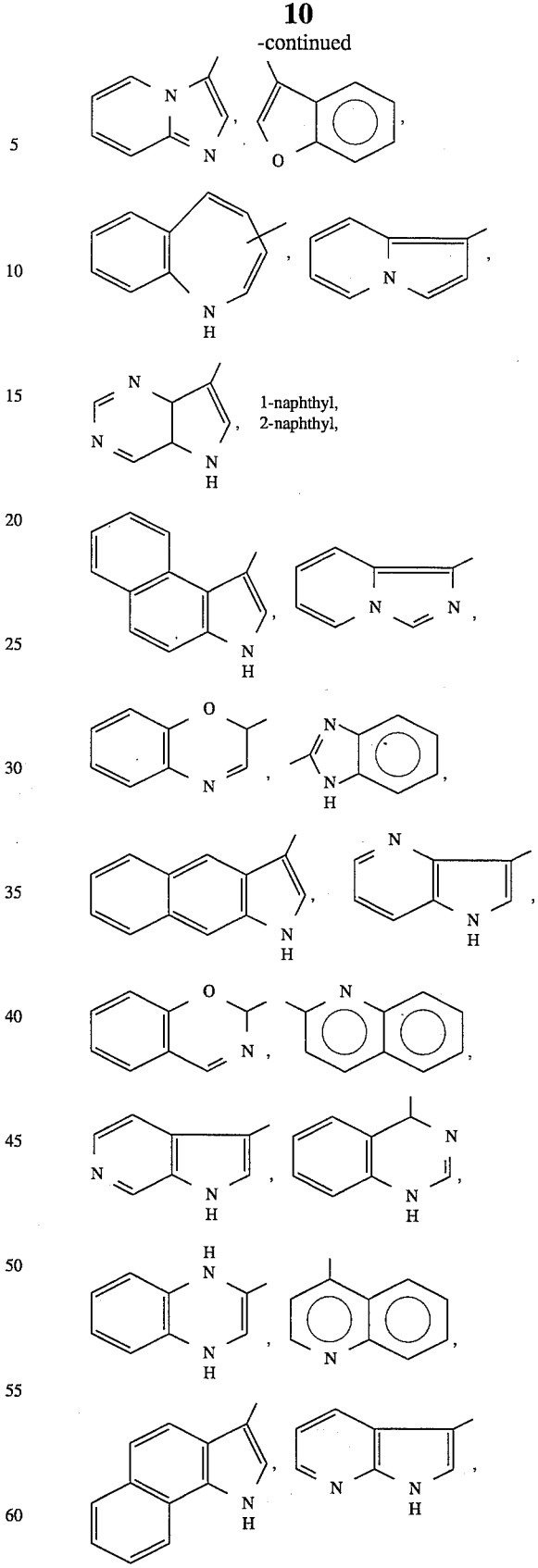

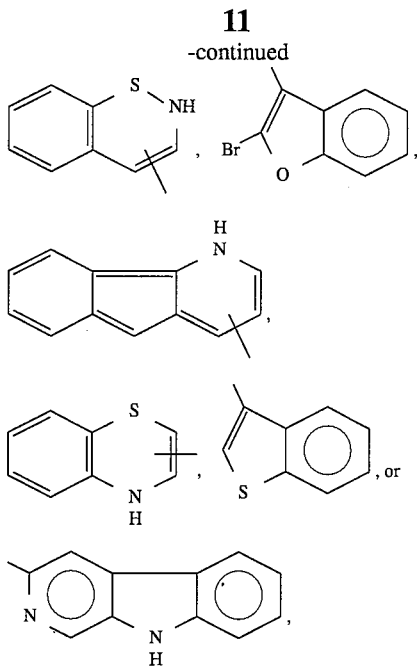

More preferred definitions of Ar are:

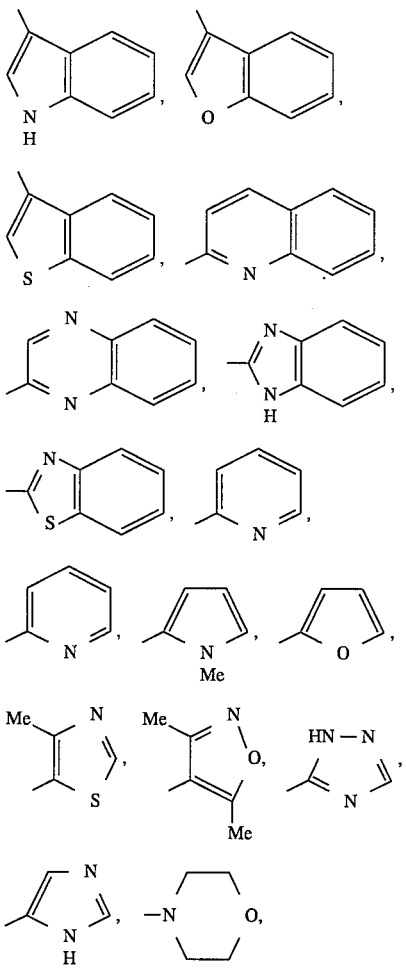

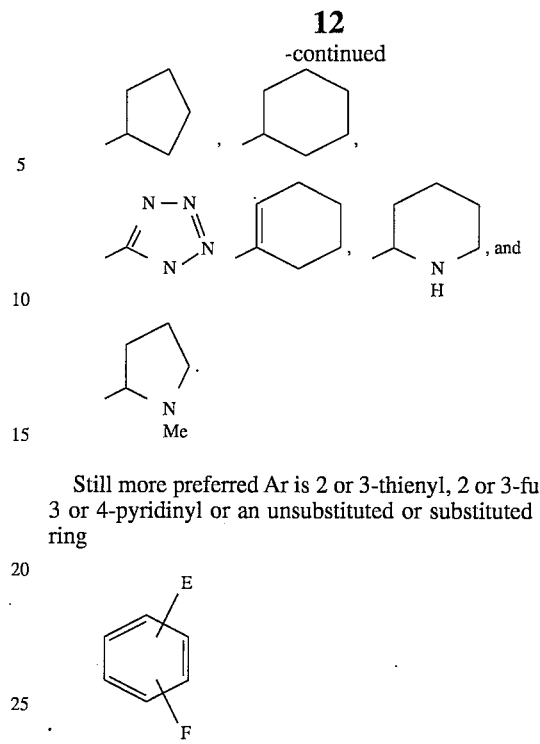

Still more preferred Ar is 2 or 3-thienyl, 2 or 3-furanyl, 2, 3 or 4-pyridinyl or an unsubstituted or substituted benzene ring

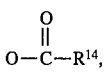

wherein E and F are each independently hydrogen, fluorine, chlorine, bromine, iodine, methyl, methoxy, trifluoromethyl, nitro, hydroxy, $NH_2$, $OCF_3$, and $R^3$ as defined above. Preferred definition for $R^3$ is $NHCOCH_2CH_2CO_2H$ or $CH_2CH_2CO_2H$.

The indole portion of formula I can be mono or disubstituted by halogen; lower alkyl; $CF_3$; lower alkoxy; benzyloxy; hydroxy;

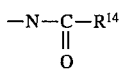

wherein $R^{14}$ is lower alkyl or phenyl; $-NO_2$; $NR_1^{15}R_2^{16}$ wherein $R_1^{15}$ and $R_2^{16}$ are each independently hydrogen or lower alkyl;

$$-N-C-R^{14}$$
$$\phantom{-N-}\|$$
$$\phantom{-N-C-}O$$

wherein $R^{14}$ is as defined above.

Preferred substituents are: 5-fluoro, 5-chloro; 5-hydroxy; 5-methyl; 5-methoxy; 5-benzyloxy; 5-$CF_3$, 5-$NO_2$; and 5-$NH_2$.

The indole is numbered

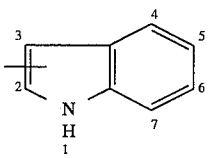

for purposes of the above substituents.

Further, the indole can be substituted on the nitrogen by —[(4-methylphenyl)sulfonyl] or by a methyl group.

Preferred cycloalkyl or polycycloalkyl substituents have from six to ten carbon atoms.

Preferred compounds of the instant invention are those wherein cycloalkyl is a substituted or unsubstituted

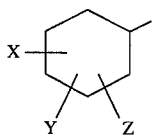

and wherein polycycloalkyl is selected from

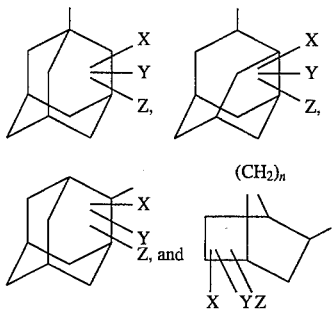

wherein W, X, Y, and Z are each independently hydrogen, a straight or branched alkyl of from one to six carbon atoms, $CF_3$, $NR^5R^6$, $(CH_2)_nCO_2R^*$, or CN, F, Cl, Br, $OR^*$, $SR^*$, wherein $R^*$ is hydrogen or a straight or branched alkyl of from one to six carbon atoms and $R^5$ and $R^6$ are as defined above and n is an integer of from 1 to 3.

Other preferred compounds of the instant invention are those wherein $R^1$ is 2- adamantyl or 1-(S)-2-endobornyl;

A is —NHCO—, —OCO—, —$SO_2$—, —S(=O)— or —$CH_2CO$—;

$R^2$ is —$CH_3$, —$CH_2CO_2CH_3$ or —$CH_2C\equiv CH$;

$R^3$ is —$(CH_2)_n$—B—D or H;

$R^4$ is —$(CH_2)_n$—B—D or H; and $R^9$ is hydrogen or methyl.

More preferred compounds of the instant invention are those wherein $R^1$ is 2-adamantyl, 1-(S)-2-endobornyl, or 2-methylcyclohexyl;

A is

$R^2$ is —$CH_3$;

$R^3$ is H; —$CH_2OH$, —$CH_2OCOCH_2CH_2CO_2H$, —$CH_2OCOCH=CHCO_2H$ or —$CH_2NHCOCH_2CH_2CO_2H$, —$CH_2NHCOCH=CHCO_2H$, and $R^4$ is H, —$CH_2SCH_2CO_2H$, —$CH_2SCH_2CH_2CO_2H$, —$NHCOCH=CHCO_2H$, —$NHCOCH_2CH_2CO_2H$ ([D] configuration or —$NHCOCH=CHCO_2H$ ([D] configuration).

The D and the L configurations are possible at the chiral centers and are included in the scope of the invention:

1. Preferred is when $R^2$ is —$CH_3$[D] configuration;

2. Preferred is when $R^3$ is —$CH_2OCOCH_2CH_2CO_2H$ or $CH_2CO_2H$ or —$CH_2NHCOCH_2CH_2CO_2H$ with the [D] configuration at the Trp α-carbon atom and the [L] configuration at the Phe-α-carbon atom; and 3. Preferred is when $R^4$ is —$NHCOCH_2CH_2CO_2H$[D] configuration or $NHCOCH=CHCO_2H$[D] configuration with the [D] configuration at the Trp α-carbon atom.

Most preferred compounds of the instant invention are:

1. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, 2. [1S-[1α,2β[S*(S*)],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]methylamino]-1-phenyl-ethyl]amino]-4-oxobutanoic acid, 3. [1S-[1α,2β[S*(S*)],4α]]-4-[[2-[[3-(1H-indol-3-yl)-2-methyl-1-oxo-2-[[[(1,7,7-trimethylbicyclo-[2.2.1]hept-2-yl)amino]carbonyl]amino]propyl]amino]-1-phenylethyl]amino]-4-oxobutanoic acid, 4. [R-(R*,R*)]-4-[[2-[[3-(1H-indol-3yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid, 5. [R-(R*,S*)]-4-[[2-[[3-(1H-indol-3-yl)-2-methyl-1-oxo-2-[(tricyclo[3.3.1.1$^{3,7}$]dec-2-ylsulfonyl)amino]-propyl]amino]-3-phenylpropyl]amino]-4-oxobutanoic acid, 6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid, 7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid, 8. [1R-[1α[R*(S*)],2β]] and [1S-[1α[S*(R*)],2β]-4-[[2-[[3-(1H-indol-3-yl)-2-methyl-1-oxo-2-[[[[2-(trifluoromethyl)cyclohexyl]oxy]carbonyl]amino]propyl]amino]-3-phenylpropyl]amino]-4-oxobutanoic acid, 9. [1R-[1α[R*(S*)],2β]] and [1S-[1α[S*(R*)],2β]]-4-[[2-[[3-(1H-indol-3-yl)-2-methyl-1-oxo-2-[[[[2-(trifluoromethyl)cyclohexyl]oxy ]carbonyl]amino]propyl]methylamino]-3- phenylpropyl]amino]-4-oxobutanoic acid, 10. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino] propyl]methylamino]-3-phenylpropyl]amino]-4-oxobutanoic acid, 11. [1S-[1α, 2β[S* (R*)], 4α]]-[1-(1H-indol-3-ylmethyl)-1-methyl-2-oxo-2-[[2-[[1-oxo-3-(1H-tetrazol-5-yl)propyl] amino]-1-(phenylmethyl) ethyl]amino]ethyl]carbamic acid, 1,7,7-trimethylbicyclo[2.2.1]hept -2-yl ester, 12. [1S-[1α,2β[S*(R*)],4α]]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamic acid, 1,7,7-trimethyl-bicyclo[2.2.1]hept-2-yl ester, 13. N-[2-methyl-N-[(tricyclo[3.3.1.1$^{3,7}$]dec-2-yloxy)carbonyl ]-D-tryptophyl]-L-phenylalanylglycine, 14. N-[2-methyl-N-[(tricyclo[3.3.1.1$^{3,7}$]dec-2-yloxy)carbonyl]-D-tryptophyl]-L-phenylalanyl-β- alanine and 15. (R)-tricyclo[3.3.1.1$^{3,7}$]dec-2-yl [1-(1H-indol-3-ylmethyl)-1-methyl-2-[methyl(2-phenylethyl)amino]-2-oxoethylcarbamate.

In addition most especially preferred compounds of the instant invention are:

16. (±)-Trans-2-chlorocyclohexyl [1-(1H-indol-3-ylmethyl)-1-methyl-2-oxo-2-[(2-phenylethyl)amino]ethyl] carbamate, 17. 2-chlorocyclohexyl [2-[[1-(hydroxymethyl)-2-phenylethyl]amino]-1-(1H-indol-3-ylmethyl)-1-methyl-2 -oxoethyl]carbamate, 18. 2-[[2-[[[(2-chlorocyclohexyl)oxy]carbonyl]amino]-3-(1H-indol-3-yl)-2-methyl-1-oxopropyl]amino]-3-phenylpropyl butanedioate, 19. 2-[[2-[[[(2-methylcyclohexyl)oxy]carbonyl]amino]-3-(1H-indol-3-yl)-2-methyl-1-oxopropyl]amino]-3-phenylpropyl butanedioate,
20. (±)-tricyclo[3.3.1.1$^{3,7}$]dec-2-yl [1-(1H-indol-3-ylmethyl)-1-methyl-2-oxo-2-[(2-phenylethyl)amino]ethyl]carbamate,
21. tricyclo[3.3.1.1$^{3,7}$]dec-2-yl [2-[[1-(hydroxymethyl)-2-phenylethyl]amino]-1-(1H-indol-3-ylmethyl)-1-methyl-2-oxoethyl]carbamate,
22. 2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl butanedioate,
23. 2-[[3-(1H-indol-3-yl)-2-methyl-1-oxo-2-[[(tricyclo[3.3.1.1$^{3,7}$]dec-2-yloxy)carbonyl]amino propyl]amino]-1-phenylethyl butanedioate,
24. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid,
25. [1S-[1α, 2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxobutanoic acid,
26. [R-[R*,S*-(E)]]-4-[[2-[[3-(1H-indol-3-yl)-2-methyl-1-oxo-2-[[(tricyclo[3,3.1.1$^{3,7}$]dec-2-yloxy)carbonyl]amino]propyl]amino]-3-phenylpropyl]amino]-4-oxo-2-butenoic acid,
27. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid,
28. (R)-tricyclo[3.3.1.1$^{3,7}$]dec-2-yl [1-(1H-indol-3-ylmethyl)-1-methyl-2-[methyl(2-phenylethyl)amino]-2-oxoethyl]carbamate,
29. [R-(R*,S*)]-[[2-[[3-(1H-indol-3-yl)-2-methyl-1-oxo-2-[[(tricyclo[3.31.1$^{3,7}$]dec-2-yloxy)carbonyl]amino]propyl]amino]-3-phenylpropyl]sulfinyl]acetic acid, ethyl ester,
30. [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfonyl]acetic acid, ethyl ester,
31. [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetic acid,
32. [R-[R*,R*-(E)]]-4-[[2-[[3-(1H-indol-3-yl)-2-methyl-1-oxo-2-[[(tricyclo[3.3.1.1$^{3,7}$]dec-2-yloxy)]carbonyl] amino]propyl]amino]-1-phenylethyl]amino]-4-oxo-2-butenoic acid,
33. [R-(R*,S*)]-[[2-[[2-[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]thio]acetic acid,
34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyi]amino]propyl]amino]-1-phenylethyl]amino]-4-oxo-2-butenoic acid, methyl ester, (Bicyclo system is 1S-endo),
35. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, (Bicyclo system is 1S-endo),
36. [R-(R*,R*)]-3-[[2-[[3-(1H-indol-3-yl)-2-methyl-1-oxo-2-[[(tricyclo[3.3.1.1$^{3,7}$]dec-2-yloxy)]carbonyl]amino propyl]amino]-1-phenylethyl]amino]-3-oxo-propanoic acid,
37. [R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1$^{3,7}$]dec-2-yl or ester,
38. [R-(R*,S*)]-β-[[3-(1H-indol-3-yl)-2-methyl-1-oxo-2-[[(tricyclo[3.3.1.1$^{3,7}$]dec-2-yloxy)]carbonyl]amino]propyl]amino]benzenebutanoic acid,
39. [R-(R*,S*)]-N-[3-[[3-(1H-indol-3-yl)-2-methyl-1-oxo-2-[[(tricyclo[3.3.1.1$^{3,7}$]dec-2-yloxy)]carbonyl]amino]propyl]amino]-4-phenylbutyl]glycine,
40. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]-amino]-3-phenylpropyl]amino]-4-oxo-2-butenoic acid,
41. mono [R-(R*,R*)]-2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioate,
42. 3-[[3-[[3-(1H-indol-3-yl)-2-methyl-1-oxo-2-[[(tricyclo[3.3.1.1$^{3,7}$]dec-2-yloxy)]carbonyl]amino]propyl]amino]-1-oxo-2-phenylpropyl]amino]propanoic acid (TRP is R, other center is RS),
43. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxo-2-butenoic acid, (−)-Isomer,
44. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxobutanoic acid, (−)-Isomer,
45. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-1-phenyl ethyl]amino]-4-oxo 2-butenoic acid, (−)-Isomer,
46. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxobutanoic acid, (−)-Isomer,
47. 2-methylcyclohexyl-[1R-[1α[R*(S*)]],2β]-[2-[[1-(hydroxymethyl)-2-phenylethyl]amino]-1-(1H-indol-3-ylmethyl)-1-methyl-2-oxoethyl]carbamate,
48. [R-[R*,S*-(E,E)]]-6-[[3-(1H-indol-3-yl)-2-methyl-1-oxo-2-[[(tricyclo-[3.3.1.1$^{3,7}$]dec-2-yloxy) carbonyl] amino]propyl]-amino]-7-phenyl-2,4-heptadienoic acid,
49. [R-(R*,R*)]-[2-[[2-[[1,4-dioxo-4-(1H-tetrazol-5-ylamino)-butyl]amino]-2-phenylethyl]amino]-1-(1H-indol-3-ylmethyl)-1-methyl-2-oxoethyl]carbamic acid,
50. tricyclo-[3.3.1.1$^{3,7}$]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate,
51. [R-(R*,S*)]-3-[[2-[[3-(1H-indol-3-yl)-2-methyl-1-oxo-2-[[(tricyclo-[3.3.1.1$^{3,7}$]dec-2-yloxy)carbonyl]amino]propyl]-amino]-3-phenylpropyl]amino]-3-oxopropanoic acid,
52. ethyl [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]-propyl]amino]-3-phenylpropyl]thio]acetate,
53. [R-(R*,S*)]-β-[[3-(1H-indol-3-yl)-2-methyl-1-oxo-2-[[tricyclo[3.3.1.1$^{3,7}$]dec-2-yloxy)carbonyl]amino]propyl]amino]-4-iodo-benzenebutanoic acid,
54. [R-(R*,R*)]-[2-[[3-(1H-indol-3-yl)-2-methyl-1-oxo-2-[[(1(tricyclo[[(3.3.1.1$^{3,7}$]dec-2-yloxy)carbonyl]amino]-propyl]amino]-1-phenylethoxy]acetic acid,
55. [[3-[[3-(1H-indol-3-yl)-2-methyl-1-oxo-2-[[tricyclo(3.3.1.1$^{3,7}$]dec-2-yloxy)carbonyl]amino]propyl]amino]-1-oxo-2-phenylpropyl]amino]acetic acid (TRP center is R, other center is RS),
56. (R)-[[[2-[[3-(1H-indol-3-yl)-1-oxo-2-methyl-2-[[(tricyclo[3.3.1.1$^{3,7}$]dec-2-yloxy)carbonyl]amino]propyl]amino]-1-phenylethylidene]amino]oxy]acetic acid,
57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]-amino]benzenebutanoic acid, 58. [R-(R*,S*)]-N-[3-[[3-(1H-indol-3-yl)-2-methyl-1-oxo-2-[[(tricyclo-[3.3.1.1³,⁷]dec-2-yloxy)carbonyl]propyl]amino]-4-phenylbutyl]glycine,
59. 2-[[[2-[[3-(1H-indol-3-yl)-2-methyl-1-oxo-2-[[(tricyclo-[3.3.1.1³,⁷]dec-2-yloxy)carbonyl]amino]propyl]amino]-1-phenylethyl]amino]carbonyl]cyclopropanecarboxylic acid (cyclopropane ring is trans-(±) other centers are R),
60. carbamic acid, [1-(1H-indol-3-ylmethyl)-1-methyl-2-oxo-2-[[2-[[1-oxo-3-(1H-tetrazol-5-yl)propyl]amino]-2-phenylethyl]-amino]ethyl]-, tricyclo[3.3.1.1³,⁷]dec-2-yl ester, [R, (R*, S*]-,
61. benzeneheptanoic acid, α-[[3-(1H-indol-3-yl)-2-methyl-1-oxo-2-[[(tricyclo[3.3.1.1³,⁷]dec-2-yloxy)carbonyl]amino]-propyl]amino]-, [R-(R*,S*)]-,
62. methyl-(±)-β-[[2-phenylethyl)amino]carbonyl]-1β-[[(tricyclo[3.3.1.1³,⁷]dec-2-yloxy)carbonyl]amino]-1H-indole-3-butanoate,
63. [R-(R*,S*)]-4-[[2-(1H-indol-3-yl)-2-methyl-1-oxo-2-[[tricyclo[3.3.1.1³,⁷]dec-2-yloxylcarbonyl]amino]propyl]-amino]-3-phenylpropyl]amino]-4-oxo-2-butenoic acid,
64. bicyclo[2.2.1]heptane-2-acetic acid, 3-[[[2-[[1-(hydroxymethyl)-2-phenyl ethyl]amino]-1-(1H-indol-3-ylmethyl)-1-methyl-2-oxoethyl]amino]carbonyl]oxy]-4,7,7-trimethyl-, [1R-[1α,2β,3α[R*(S*)],4α]]-,
65. butanoic acid, 4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxo[1R-[1α[R*(R*)]2β]]-((−)-isomer),
66. 2-butenoic acid, 4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxo[-1R-[1α[R*(R*)],2β]]-((−)-isomer),
67. butanoic acid, 4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxo-[-1R-[1α[R*(S*)],2β]]-((−)-isomer), and
68. 2-butenoic acid, 4-[[2-[[3-) 1H-indol-3-yl)-2-methyl-2-[[[(2-methyl-1-cyclohexyl)oxy]carbonyl]amino]-1-oxopropyl]-amino]-3-phenylpropyl]amino]-4-oxo-[IR[1α[R*(S*)], 2β]]-((−)-isomer).

Additionally preferred are the compounds:

69. [[3-[[3-(1H-indol-3-yl)-2-methyl-1-oxo-2[ [tricyclo[3.3.1.1³,⁷]dec-2-yloxy)carbonyl]amino]propyl ]amino]-1-oxo-2-phenylpropyl]amino]acetic acid (TRP center is R, other center is RS),
70. [R-(R*,R*)]-2-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]acetic acid,
71. [1R-[1α,2β[R*(R*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino] carbonyl]cyclopropane carboxylic acid,
72. [1S-[1α,2β[S*(S*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropane carboxylic acid,
73. [R-R*,R*)]-3-[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]propanoic acid,
74. [R-(R*,R*)]-mono 2-[[3-(1H-indol-3-yl)-2-methyl-2-oxo-2-[[(tricyclo[3.3.1.1³,⁷]dec-2-yloxy)carbonyl]amino]-1-phenylethyl butanedioic acid,
75. 3-[[3-[[3-(1H-indol-3-yl)-2-methyl-1-oxo-2-[[(tricyclo[3.3.1.1³,⁷]dec-2-yloxy)carbonyl]amino] propyl]amino]-1-oxo-2-phenylpropyl]amino]propanoic acid, (TRP is R, other center is RS),
76. [R-(R*,S*)]-β-[[3-(1H-indol-3-yl)-2-methyl-1-oxo-2-[[(tricyclo[3.3.1.1³,⁷]dec-2-yloxy)carbonyl]amino] propyl]amino]-4- iodobenzenebutanoic acid,
77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid, ((−)-isomer),
78. [1R-[1α[R*(S)], (S)*2β]]-4-[[2-[[3-(1H-indol-3-yl)-2-methyl-2-[[[(2-methyl-1- cyclohexyl)oxy]carbonyl]-amino]-1-oxopropyl]amino]-3-phenylpropyl]amino]-4-oxobutanoic acid, ((−)-isomer),
79. [1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethylamino]-4-oxo-2-butenoic acid, ((−)-isomer),
80. 1R-[1α[R*(R*)],2β]]-4-[[2-[[3-(1H-indol-3-yl)-2-methyl-2-[[[(2-methyl-1- cyclohexyl)oxy]carbonyl]amino]-1-oxopropyl]amino]-1-phenyl ethyl]amino]-4-oxobutanoic acid, ((−)-isomer),
81. [R-(R*,S*)]-1δ-[[3-(1H-indol-3-yl)-2-methyl-1-oxo-2-[[(tricyclo[3.3.1.1³,⁷]dec-2-yloxy)carbonyl]amino] propyl]amino]benzeneheptanoic acid,
82. 2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenyl ethyl]amino]carbonyl]cyclopropanecarboxylic acid (cyclopropyl ring is trans-(±), other centers are R),
83. 2-methylcyclohexyl [1R-[1α[R*(S*)]],2β]-2-[[1-(hydroxymethyl)-2-phenylethyl]amino]-1-(1H-indol-3-ylmethyl)-1-methyl-2-oxoethyl]carbamate, ((−)-isomer,
84. [R-[R*,S*-(E,E)]]-6-[[3-(1H-indol-3-yl)-2-methyl-1-oxo-2-[[(tricyclo[3.3.1.1³,⁷]dec-2-yloxy)carbonyl]amino] propyl]amino]-7-phenyl-2,4-heptadienoic acid,
85. tricyclo[3.3.1.1³,⁷]dec-2-yl [2-[[1-(hydroxymethyl)-2-hydroxy -2-phenyl ethyl]amino]-1-(1H-indol-3-ylmethyl)-1-methylethyl]carbamate,
86. tricyclo[3.3.1.1³,⁷]dec-2-yl [R-(R*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamate,
87. [R-(R*,S*)]-2-[[2-[[3-(1H-indol-3-yl)-2-methyl-1-oxo-2-[[(tricyclo[3.3.1.1³,⁷]dec-2-yloxy)carbonyl]amino] propyl]amino]-3-phenylpropyl]sulfinyl]acetic acid,
88. [R-(R*,S*)]-[[2-[[3-(1H-indol-3-yl)-2-methyl-1-oxo-2-[[(tricyclo[3.3.1.1³,⁷]dec-2-yloxy)]carbonyl]-amino]propyl]amino]-3-phenylpropyl]sulfonyl]acetic acid,
89. Ethyl [R-(R*,S*)]-[[2-[[3-(1H-indol-3-yl)-2-methyl-1-oxo-2-[[(tricyclo[3.3.1.1³,⁷]dec-2-yloxy)]carbonyl] amino]propyl]amino]-3-phenylpropyl]sulfonyl]acetate,
90. 2-chlorocyclohexyl [2-[[1-(hydroxymethyl)-2-phenylethyl] amino]-1-(1H-indol-3-ylmethyl)-1-methyl-2-oxoethyl]carbamate, Isomer II, ring centers are trans, trp center is D, other center is S) ((−) or (+) form),
91. [R-[R*,R*(E)]]-4-[[2-[[3-(1H-indol-3-yl)-2-methyl-1-oxo-2-[[(tricyclo[3.3.1.1³,⁷]dec-2-ylamino)carbonyl]amino]propyl]amino]-1-phenylethyl]amino]-4-oxo-2-butenoic acid,
92. [R-(R*,R*)]-4-[[2-[[3-(1H-indol-3-yl)-2-methyl-1-oxo-2-[[(tricyclo[3.3.1.1³,⁷]dec-2-yloxy)carbonyl]amino ]propyl]amino]-1-phenylethyl]amino]-4-oxobutanoic acid,
93. [R-(R*,S*)]-mono[2-[[3-(1H-indol-3-yl)-2-methyl-1-oxo-2-[[(tricyclo[3.3.1.1³,⁷]dec-2-yloxy)carbonyl]amino] propyl]amino]-3-phenylpropyl]butanedioate,
94. tricyclo[3.3.1.1³,⁷]dec-2-yl [R-(R*,S*)-2-[[1-(hydroxymethyl)-2-phenylethyl]amino]-1-(1H-indol-3-ylmethyl)-1-methyl-2-oxoethyl]- carbamate,
95. [1S-[1α,2β[S*[S*(E)]],4α]]-4-[[2-[[3-(1H-indol-3-yl-2-methyl-1-oxo-2-[[[(1,7,7-trimethylbicyclo[2.2.1]hept-2-yl)oxy]carbonyl]amino]-propyl]amino]-1-phenylethyl] amino]-4-oxo-2-butenoic acid (bicyclo system is 1S-endo), 96. [1S-[1α,2β[S*(S*)],4α]]-4-[[2-[[3-(1H-indol-3-yl-2-methyl-1-oxo-2-[[[(1,7,7-trimethylbicyclo[2.2.1]hept-2-yl)oxy]carbonyl]-amino]propyl]amino]-1-phenylethyl]amino]-4-oxo-2-butenoic acid (bicyclo system is 1S-endo), 97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid, 98. N-[2-methyl-N-[(tricyclo[3.3.1.1$^{3,7}$]dec-2-yloxy)carbonyl]-D-tryptophyl]-L-phenylalanylglycine, 99. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino] propyl]amino]-3-phenylpropyl]amino]-4 oxobutanoic acid, 100. [R-(R*,R*)]-[2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-3-oxopropanoic acid, 102. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino] propyl]amino]-3-phenylpropyl]amino]-3-oxopropanoic acid, 103. [R-[R*,S*[(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid, 104. [R-[R*,S*)]-5-[[2-[[3-(1H-indol-3-yl)-2-methyl-1-oxo-2-[[(tricyclo[3.3.1.1$^{3,7}$]dec-2-yloxy)carbonyl]amino] propyl]amino]-3-phenylpropyl]amino]-5-oxopentanoic acid, 105. ethyl [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetate, 106. [R-(R*,R*-(E)]]-4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]-amino]-4-oxo-2-butenoic acid, 107. [R-(R*,S*)]-N-[3-[[3-(1H-indol-3-yl)-2-methyl-1-oxo-2-[[(nricyclo[3.3.1.1$^{3,7}$]dec-2-yloxy)carbonyl]amino]propyl]amino]-1-oxo-4-phenylbutyl]-β-alanine, 108. N-[N-[α-methyl-N-[(tricyclo[3.3.1.1$^{3,7}$]dec-2-yloxy)carbonyl]-D-tryptophyl]-L-phenylalanyl]-L-alanine, 109. [R-R*,S*)]-3-[[2-[[3-(1H-indol-3-yl)-2-methyl-1-oxo-2-[[(tricyclo[3.3.1.1$^{3,7}$]dec-2-yloxy)carbonyl]amino] propyl]amino]-3-phenylpropyl]thio]propanoic acid, 110. [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino] propyl]amino]-3-phenylpropyl]thio]acetic acid, 111. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid, 112. tricyclo[3.3.1.1$^{3,7}$]dec-2-yl [R-(R*,S*)]-3-(1H-indol-3-ylmethyl)-3-methyl-4,10-dioxo-6-(phenylmethyl)-11-oxa-8-thia-2,5- diazatridecanoic acid, 113. Carbamic acid, [2-[[1-(hydroxymethyl)-2-phenylethyl]amino]-1-methyl-1-[(1-methyl-1H-indol-3-yl)methyl]-2-oxoethyl]-, tricyclo[3.3.1.1$^{3,7}$]dec-2-yl ester, [R-(R*,S*)]-, 114. Glycine, N-[3-(1H-indol-3-yl)-2-methyl-1-oxo-2-[[(tricyclo[3.3.1.1$^{3,7}$]dec -2-yloxy)carbonyl]amino]propyl]-N-(2-phenylethyl)-, (±)-, 115. Glycine, N-[3-(1H-indol-3-yl)-2-methyl-1-oxo-2-[[(tricyclo[3.3.1.1$^{3,7}$]dec -2-yloxy)carbonyl]amino]propyl]-N-(2-phenylethyl)-, methyl ester, (±)-, 116. Methyl (±)-7-[[3-(1H-indol-3-yl)-2-methyl-1-oxo-2-[[(tricyclo[3.3.1.1$^{3,7}$]dec-2-yloxy)carbonyl]amino]propyl](2-phenylethyl)amino]heptanoate, 117. (±)-7-[[3-(1H-indol-3-yl)-2-methyl-1-oxo-2-[[tricyclo[3.3.1.1$^{3,7}$]dec-2-yloxycarbonyl]amino]propyl](2-phenylethyl)amino]heptanoic acid, 118. Carbamic acid, [2-[[2-(1-cyclohexen-1-yl)ethyl]amino]-1-(1H-indol-3-ylmethyl)-1-methyl-2-oxoethyl]-, (R)-, 119. Carbamic acid, [1-(1H-indol-3-ylmethyl)-1-methyl-2-oxo-2-[[2-(2-pyridinyl) ethyl]amino]ethyl]-, tricyclo[3.3.1.1$^{3,7}$]dec-2-yl ester, (R)-, 120. Benzenebutanoic acid, 4-amino-β-[[3-(1H-indol-3-yl)-2-methyl-1-oxo-2-[[(tricyclo[3.3.1.1$^{3,7}$]dec-2-yloxy) carbonyl]amino]propyl]amino]-, [R-(R*, S* )]-, 121. Acetic acid, [[3-[[3-(1H-indol-3-yl)-2-methyl-1-oxo-2-[[(tricyclo[3.3.1.1$^{3,7}$]dec-2-yloxy)carbonyl]amino]propyl]amino]-2-phenylpropyl]thio]- (TRP center is R, other center is RS), 122. 12-oxa-9-thia-2,5-diazatetradecanoic acid, 3-(1H-indol-3-ylmethyl)-3-methyl-4,11-dioxo-7-phenyl-, tricyclo[3.3.1.1$^{3,7}$]dec-2-yl ester (TRP center is R, other center is RS), 123. Benzenebutanoic acid, γ-[[[3-(1H-indol-3-yl)-2-methyl-1-oxo-2-[[(tricyclo[3.3.1.1$^{3,7}$]dec-2yloxy) carbonyl]amino]propyl]amino]methyl]- (TRP center is R, other center is RS), 124. 2-pentenoic acid, 5-[[3-(1H-indol-3-yl)-2-methyl-1-oxo-2-[[(tricyclo[3.3.1.1$^{3,7}$]dec-2-yloxy]carbonyl]amino]propyl]amino]-4-phenyl-, methyl ester (TRP center is R, other center is RS, double bond is (E)), 125. Benzenebutanoic acid, γ-[[[3-(1H-indol-3-yl)-2-methyl-1-oxo-2-[[(tricyclo[3.3.1.1$^{3,7}$]dec-2-yloxy)carbonyl]amino]propyl]amino]methyl]-, methyl ester (TRP center is R, other center is RS), 126. Butanoic acid, 4-[[2-[2-[[3-(1H-indol-3-yl)-2-methyl-1-oxo-2-[[(tricyclo[3.3.1.1$^{3,7}$]dec-2-yloxy)carbonyl]amino]propyl]amino]ethyl]phenyl]amino]-4-oxo-, (R)-, 127. Carbamic acid, [1-(1H-indol-3-ylmethyl)-1-methyl-2-oxo-2-[[2-[[[(1H-1,2,4-triazol-5-ylthio)acetyl]amino]-2-phenylethyl]amino]ethyl]-, tricyclo[3.3.1.1$^{3,7}$]dec-2-yl ester, [R-(R*, R*)]-, 128. Carbamic acid, [2-[[2-[[(1H-imidazol-2-ylthio)acetyl]amino]-2-phenylethyl]amino]-1-(1H-indol-3-ylmethyl)-1-methyl-2-oxoethyl]-, tricyclo[3.3.1.1$^{3,7}$]dec-2-yl ester, [R-(R*,R*)]-, 129. Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-, (Phenyl center R, other center S or R) (Diastereomer II), 130. Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo- (Phenyl center R, other center R or S) (Diastereomer I), 131. 13-oxa-2,5,8-triazatetradecanoic acid, 3-(1H-indol-3-ylmethyl)-3-methyl-4,9,12-trioxo-7,14-diphenyl-, tricyclo[3.3.1.1$^{3,7}$]dec-2-yl ester (Phenyl center is R, other center is S or R) (Diastereomer 2), 132. 13-oxa-2,5,8-triazatetradecanoic acid, 3-(1H-indol-2-ylmethyl)-3-methyl-4,9,12-trioxo-7,14-diphenyl-, tricyclo[3.3.1.1$^{3,7}$]dec-2-yl ester (Phenyl center is R, other center is R or S) (Diastereomer 1), 133. Carbamic acid, [2-[[1-(hydroxymethyl)-2-phenylethyl]amino]-1-(1H-indol-2-ylmethyl)-1-methyl-2-oxoethyl]-, tricyclo[3.3.1.1$^{3,7}$]dec-2-yl ester (Hydroxymethyl center is S, other center is R or S) (Diastereomer 1 ), 134. Carbamic acid, [2-[[1-(hydroxymethyl)-2-phenylethyl]amino]-1(1H-indol-2-ylmethyl)-1-methyl-2-oxoethyl]-, tricyclo[3.3.1.1$^{3,7}$]dec-2-yl ester (Hydroxymethyl center is S, other center is S or R) (Diastereomer 2 ), and 135. Carbamic acid, [1-methyl-1-[[1-[(4-methylphenyl)sulfonyl]-1H-indol-2-yl]methyl]-2-oxo-2-[(2-phenylethyl)amino]ethyl], tricyclo[3.3.1.1³,⁷]dec-2-yl ester, (±)-.

Tables I and II below illustrate representative compounds of the invention. The numbers on the left hand column correspond to the compound numbers given above. Stereochemistry is not shown in the Table I.

In addition to the compounds of the above tables the compounds of the present invention include compounds of formula I wherein the indole moiety is a 2-indolyl.

The compounds include solvates and hydrates and pharmaceutically acceptable salts of the compounds of formula I.

Preferred pharmaceutically acceptable salts are benzathine, chloroprocaine, chol ine, diethanolamine, ethylenediamine, meglumine, procaine, aluminum, calcium, lithium, magnesium, potassium, sodium, zinc, diethylamine, and tromethane.

Especially preferred pharmaceutically acceptable salts are N-methylglucamine and sodium.

The compounds of the present invention can have multiple chiral centers including those designated in the above formula I by an †, ‡, ‡ depending on their structures. For example, when $R^3$ taken with $R^{12}$ and $R^4$ taken with $R^{13}$ form double bonds to these carbon atoms they are no longer chiral. In addition, centers of asymmetry may exist on substituents $R^1$, $R^9$, $R^3$, $R^4$ and/or Ar. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The preferred stereochemistry of the compounds of the invention is that exhibited by the compound of Example 20.

The compounds of the present invention can be formed by coupling individual substituted α-amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester—see Braña, M. F., et al, *J. Heterocyclic Chem.*, 1980, 17:829.)

A key intermediate in the preparation of compounds of formula I is a compound of formula

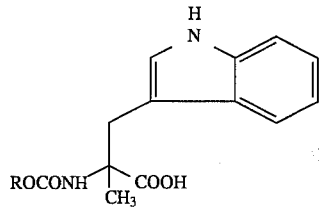

II wherein R is selected from $R^1$, 9-fluorenylmethyl, Bz and other suitable N-blocking groups. These are useful as intermediates in the preparation of compounds of formula I. The compounds wherein R is 1-adamantyl, 2-adamantyl, 4-protoadamantyl, exo-bornyl, endo-bornyl, exo-norbornyl, endo-norbornyl, 2-methylcyclohexyl, 2-chlorocyclohexyl, or camphoryl are novel and are preferred.

The disclosure of U.S. Pat. No. 4,757,151 is hereby incorporated by reference. It describes the 9-fluorenylmethyl blocking group.

Compounds of formula II are prepared by reacting

ROH    III wherein R is as defined above, with phosgene or a phosgene substitute to produce a corresponding compound of formula ROCOCl    IV and then reacting a compound of formula IV with α-methyltryptophan to produce the desired compound of formula II above.

Alternatively, a compound of formula IV can be reacted with an α-methyltryptophan methyl ester to produce

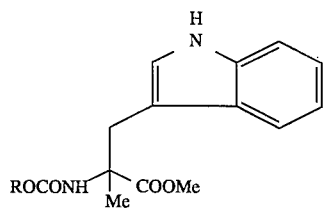

V which can be converted to a compound of formula II by known means such as hydrolysis with aqueous lithium hydroxide.

Scheme I below illustrates procedures for preparing intermediates useful in producing final products of formula I.

Key intermediate (2) is prepared from the alcohol form of a radical selected from 1-adamantyl, 2-adamantyl, 4-protoadamantyl, 9-fluorenylmethyl, exo-bornyl, endo-bornyl, exo-norbornyl, endo-norbornyl, 2-methylcyclohexyl, 2-chlorocyclohexyl, and camphoryl. The alcohol is dissolved in a solvent such as methylene chloride. It is then converted to the corresponding chloroformate by reaction with bis(trichloromethyl) carbonate in pyridine at about 0° C. The product is formed by condensation with an amine such as α-methyl-D-tryptophan methyl ester. The reaction is carried out in a solvent such as THF to produce, for example, N-[(2-adamantyloxy)carbonyl]-α-methyl-D-tryptophan methyl ester. This is then treated with lithium hydroxide and stirred at room temperature overnight to produce the corresponding carboxylic acid. This novel key intermediate (2) is useful in the production of compounds of formula I as described hereinafter in Schemes II and III.

Alternatively a chloroformate can be converted to (2) by reaction with an alkaline solution of α-methyl-DL-tryptophan.

In another process, (sequence 3,4,5,6,)tert-butyloxycarbonyl-L-phenylalaninol in pyridine is treated with p-toluene sulphonyl chloride to give the corresponding rosylate. The tosylate is treated with sodium azide in N,N-dimethylformamide to produce the corresponding azide. This is converted to the free aminoazide (6) by reaction with p-toluene sulphonic acid in dichloromethane solution at room temperature. This is then reacted with the desired compound of formula 2 to produce a compound of the instant invention as, for example in schemes I, II and II.

Similarly (sequence 7–12) tert-butyloxycarbonyl-D-2-phenyl glycinol can be converted to the corresponding amine-substituted azide (10) using the above procedure. A solution of benzyl hydrogen succinate is reacted with an equimolar mixture of N,N-dicyclohexyl-carbodiimide and 1-hydroxybenzotriazole. The reaction is carried out in ethyl acetate for about an hour. Subsequent addition of the free amine (10) to the reaction mixture yields an amide (11). The azide portion of (11) is hydrogenated over a Lindlar catalyst to form the amine (12).

A solution of 2-adamantyloxycarbonyl-α-methyl-D-tryptophan in ethyl acetate reacts with an equimolar solution of N,N-dicyclohexyl-carbodiimide and 1-hydroxybenzotriazole. The reaction mixture is left to stir at room temperature for about an hour. Subsequently the amine (12) in scheme I, in ethyl acetate is allowed to react for 18 hours at room temperature to form the dipeptoid benzyl ester (scheme II).

Finally, the benzyl ester is hydrogenolyzed for four hours using a palladium on carbon catalyst. After filtering and washing, the filtrate yields the desired product of formula I.

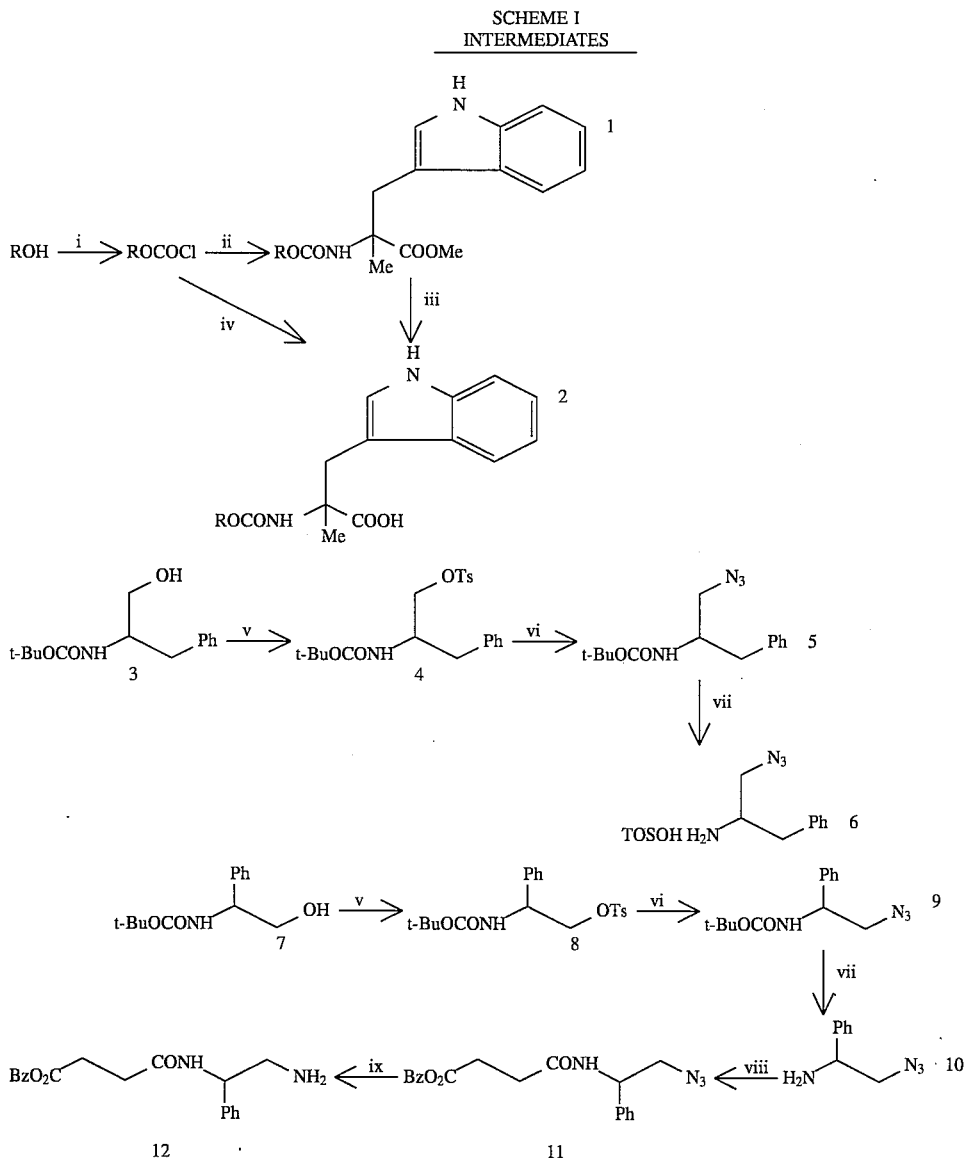

SCHEME I
INTERMEDIATES

KEY
(i) COCl$_2$, diphosgene or triphosgene, pyridine
(ii) α-methyl tyrptophan methylester
(iii) LiOH, aq. 1,4 dioxan
(iv) α-methyl tryptophan
(v) TsCl, pyridine or NEt$_3$
(vi) NaN$_3$, DMF
(vii) TSOH, CH$_2$Cl$_2$
(viii) Benzyl hydrogen succinate, DCCI, HOBT
(ix) Lindlar, EtOH Whenever R in intermediate of formula II is other than R$^1$, it may be removed at an appropriate point in the synthesis by methods known in the art for each respective group and the desired R$^1$ substituted therefore.

Scheme II below illustrates processes for the preparation of compounds of formula I using key intermediate, compound (2) from the Scheme I.

One process, as illustrated by sequence 2, 13, 14, involves reacting 2-adamantyloxycarbonyl-α-methyl-D-tryptophan with dicyclohexylcarbodiimide (DCCI) and 1-hydroxy-benzo-triazole (HOBT) in ethyl acetate solution.

Subsequent addition of 2-amino-1-phenyl ethanol produces an alcohol as in compound (13) of the scheme. This alcohol is then reacted with succinic anhydride to yield compound (14), a compound of the instant invention.

Another process of the invention is illustrated by sequence 2, 16, 15 of Scheme II. In this process intermediate (2) is reacted with DCCI and pentafluorophenol in ethyl acetate. After stirring for an hour at room temperature the mixture is reacted with L-phenylalaninol to yield a compound (16). This is then refluxed with succinic anhydride and DMAP for 24 hours. The reaction mixture is washed and the organic phase dried over MgSO$_4$. Evaporation of the solvent yields a compound as illustrated by (15).

In the sequence 2, 21, 22 intermediate (2) (R is 9-fluorenylmethyl) in solution with pentafluorophenol is treated with a solution of DCCI in ethyl acetate. This solution is stirred for one hour at 0° C. and then for four hours at room temperature. After filtering and washing the precipitated DCU, the combined filtrates react with 2-phenylethylamine to produce compound (21). This compound is converted to the free amine (22) by reaction with a 20% piperidine in DMF solution. This can be treated with a substituted chloroformate to produce the desired amide (21).

In another process, sequence 2, 16, 17, and then 18, or 19 or 20, compound (12) is converted to compound, (16) (R is 9-fluorenylmethyl) as discussed above. The amide (16) is converted to a free amine (17) by reaction with 20% pyridine in DMF.

A solution of the amine (17) is reacted with a substituted acetylchloride to form the corresponding substituted acylamide (18).

Alternatively, a solution of free amine (17) is reacted with a substituted sulphonylchloride to form the corresponding sulphonamide (19). The reaction takes place in THF and dimethylaminopyridine (DMAP) solution at room temperature for about four hours.

Additionally a solution of free amine (17) may be reacted with a substituted isocyanate to produce a desired compound (20). This may be converted, if desired, to a pharmaceutically acceptable salt.

SCHEME II

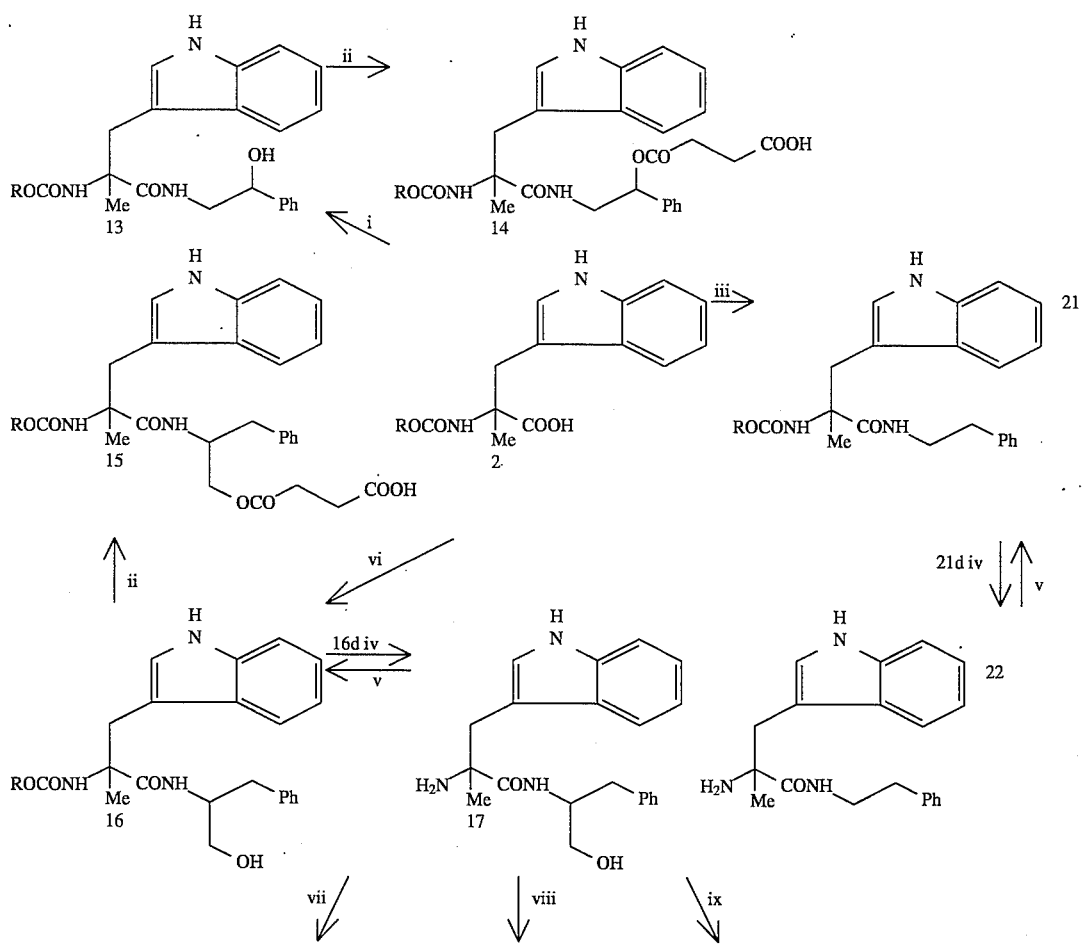

-continued
SCHEME II

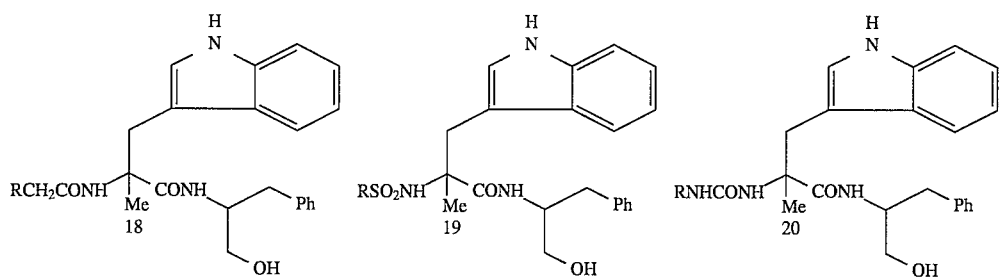

KEY
(i) DCCI, HOBT, (+) or (−) 2-amino-1-phenyl ethanol
(ii) Succinic anhydride, DMAP
(iii) DCCI, PFP, 2-phenethylamine
(iv) 20% piperidine in DMF
(v) ROCOCl
(vi) DCCI, PFP, L-phenylalaninol
(vii) R-acetylchloride
(viii) R-sulphonylchloride
(ix) R-isocyanate Scheme III below illustrates processes for preparing compounds of formula I.

One process is indicated by the sequence 2, 23, 24 of the scheme. The 2-adamantyloxycarbonyl-α-methyl-D-tryptophan intermediate in ethyl acetate is treated sequentially with DCCI and HOBT and later reacted with an amine (12 in Scheme I) to produce a desired benzyl ester (23). This is reduced to the free carboxylic acid (24) using hydrogen and a 10% palladium on carbon catalyst for about four hours. The reaction mixture is filtered, washed and concentrated in vacuo to yield (24).

Another process is illustrated by sequence 2, 25, 26 and 27 or 28. In this process compound (2) is reacted with DCCI and PFP in ethyl acetate. After stirring for an hour at room temperature the mixture is reacted with the amino-azide (6 in Scheme I) to yield a compound (25). This is then dissolved in five percent acetic acid; ninety-five percent ethanol and converted to a crude amine acetate (26) by hydrogenation in the presence of a catalyst such as ten percent palladium in carbon.

Compound (26) may then be reacted with succinic anhydride to form the free carboxylic acid (28).

Also compound (26) is reacted with fumaryl dichloride to produce compound (27).

Compound (27) or (28) may be converted, if desired, to a pharmaceutically acceptable salt thereof.

SCHEME III

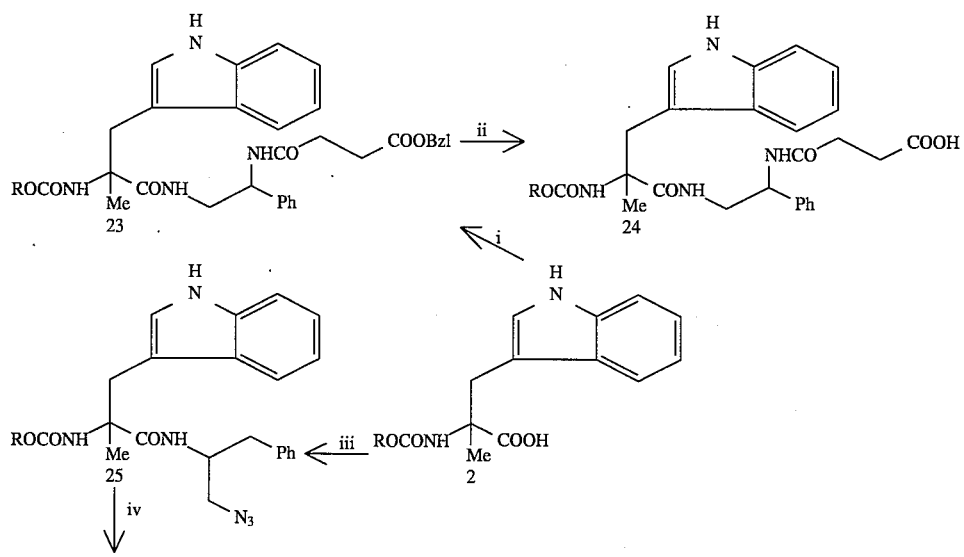

-continued
SCHEME III

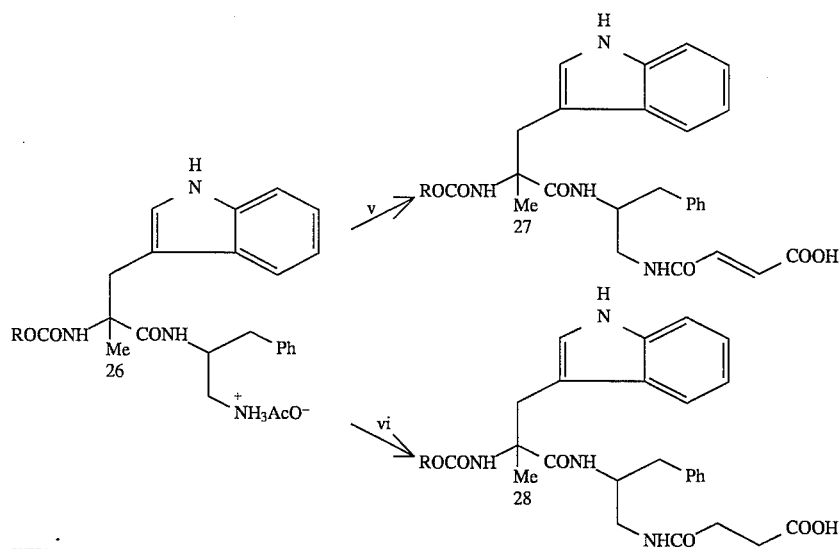

KEY
(i) 12, DCCI, HOBT
(ii) 10% Pd/C, EtOH
(iii) 6, DCCI, PFP
(iv) 10% Pd/C, 1% AcOH in EtOH
(v) i. Fumaryl dichloride; ii. OH⁻
(vi) Succinic anhydride, DMAP Scheme IV below describes the synthesis of the 2-substituted indole analogs of formula I.

The indole ethyl 2-carboxylate is protected on the indole nitrogen by tosylation to give (6) which is reduces by Red-Al to the corresponding 2-hydroxymethyl compound (7). The alcohol (7) is converted into the corresponding bromide (8) using bromine and triphenylphosphine. The bromide (8) is used to alkylate the anion of the Schiff's base (SA) derived from the methyl ester of alanine to give the Schiff's base (9) as a racemate. The hydrolysis of the Schiff's base gives the free amine (10) which is condensed with 2-adamantylchloroformate to give the methyl ester (11) which is hydrolyzed with potassium hydroxide in ethanol followed by further acidic work up to give the free carboxylic acid (12).

This acid, which is the 2-indole analog of the intermediate (2) is also condensed with amines such as previously illustrated in Schemes I and V to produce final products, for example, condensation of (12) with phenylethylamine gives compound (13a) and with (S)-(–)-2-amino-3-phenyl-1-propanol to give the (13b) as a mixture of diastereoisomers. These are separated by chromatography to give diastereoisomer 1 and diastereoisomer 2 foam with Rf 0.70 and 0.65 in MeOH/CH$_2$Cl$_2$ in ratio 1:9.

SCHEME IV

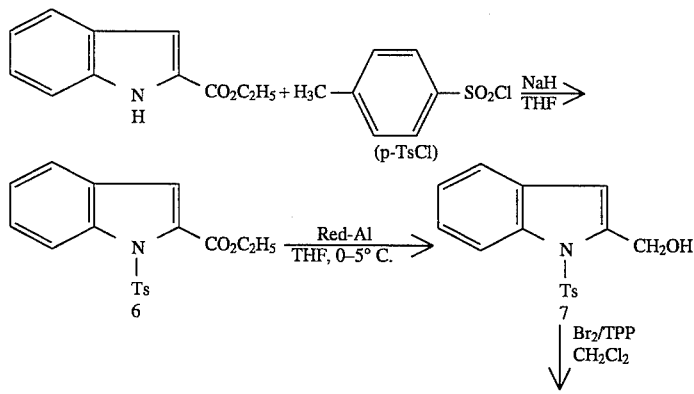

-continued
SCHEME IV

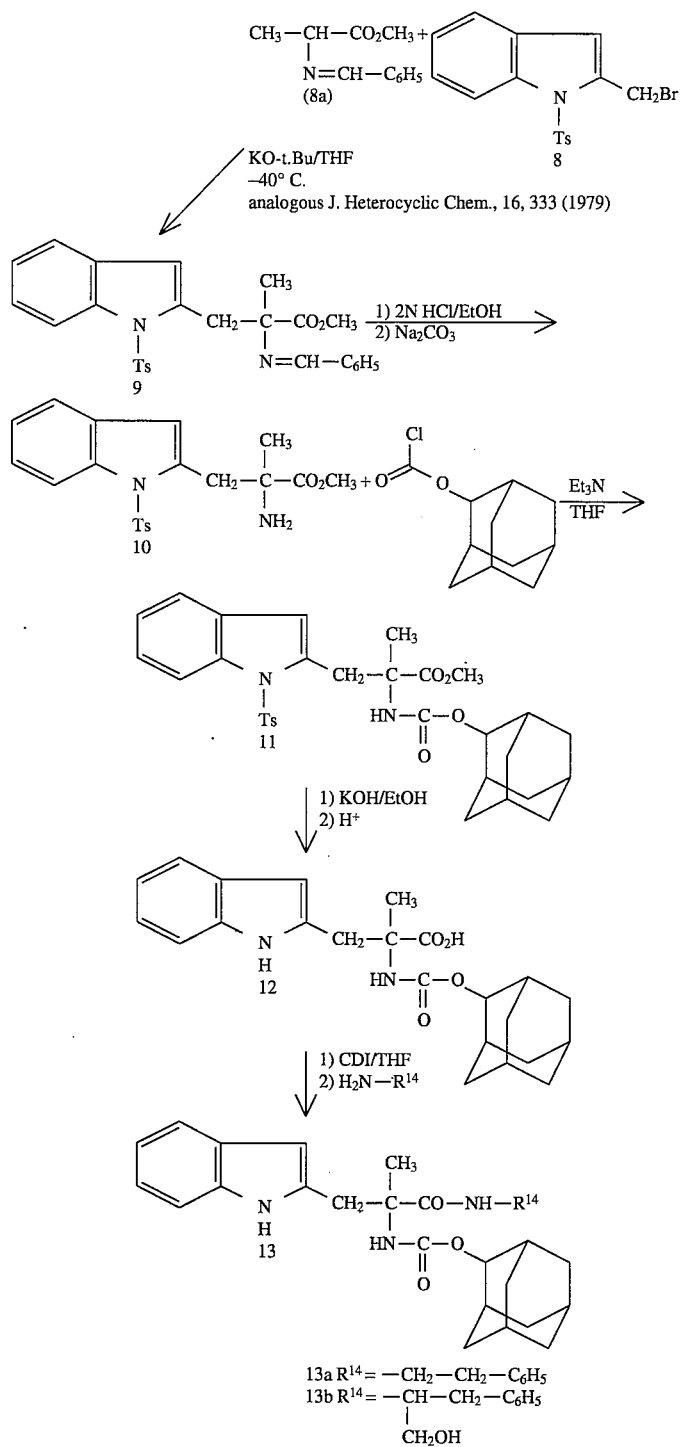

Scheme V below illustrates synthesis of preferred C-terminal side chains $R^3$ and $R^4$ used to prepare the final products illustrated in Scheme VI.

Thus the conversion of (35) to (37) is accomplished by condensing the isobutylformyl ester of (35) with 2-(trimethylsilyl)ethanol to give intermediate (36) followed by cleavage of the TMS group with TFA to give (37).

The oxime ester intermediate (40) is prepared by acylation of aminoacetophenone hydrochloric acid (38) with 2-(trimethylsilyl)ethylchloroformate in THF following by condensation with hydroxylamine hydrochloride and sodium acetate to give an oxime. Compound (39) was then prepared by adding methyl bromoacetate in the presence of 10% NaOH and TBAB in toluene. The trimethylsilylethyl group is then selectively removed with tetrabutylammonium fluoride.

Intermediate (42) is prepared from the alcohol (41) in the steps involving tosylation of the alcohol, displacement of the rosylate by sodium azide in DMF followed by catalytic reduction.

The tetrazole carboxylic acid intermediate (44) is prepared from the nitrile (43) in three steps by addition of azide to form a tetrazole which is protected by benzylation followed by hydrolysis of the methyl ester to the free carboxylic acid using an aqueous THF solution of lithium hydroxide.

The diene ester (47) is prepared from the BOCprotected phenylalanine (45) through aldehyde (46) using the Witrig reagent $Ph_3P=CHCH=CHCO_2CH_3$.

The intermediate ether (50) is prepared from the chlorohydroxy compound (48) involving displacement of the chloride with sodium azide followed by alkylation of the anion of the hydroxyl group with methyl iodoacetate to give the azido ether (49) which is then reduced under catalytic conditions.

The ethyl ester (52) is prepared by catalytic hydrogenation of nitrile (51).

In Scheme V below R is methyl when Ar is phenyl and R is 2-(trimethylsilyl)ethyl when Ar is p-iodophenyl.

SCHEME V

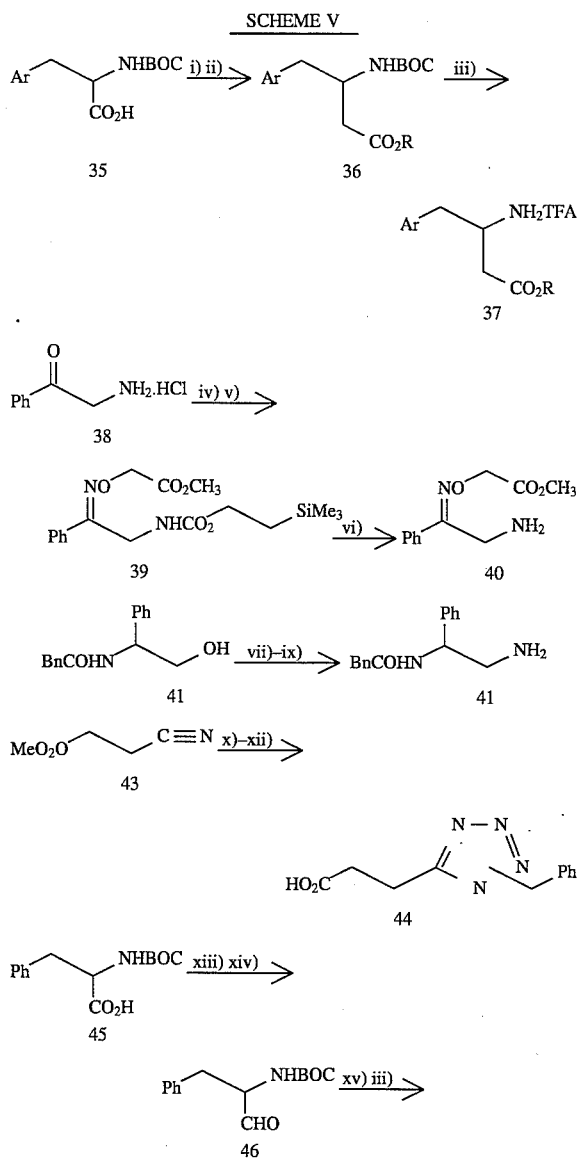

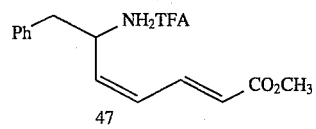

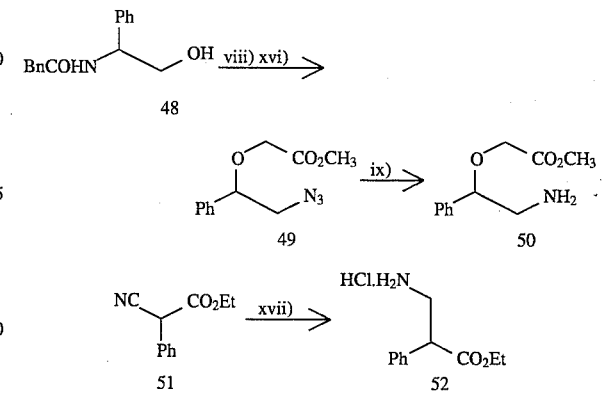

(i) N-methyl morpholine, isobutychloroformate, THF $CH_2NH_2$;
(ii) Silver benzoate, $Net_3$, MeOH or 2-(trimethylsilyl)ethanol;
(iii) TFA, $CH_2Cl_2$;
(iv) 2-(Trimethylsilyl)ethylchloroformate, $NEt_3$, THF;
(v) $NH_2OH.HCl$, $CH_3CO_2Na$, $EtOH/H_2O$; then $[CH_3(CH_2)_3]_4NBr$, $BRCH_2CO_2Me$, 10% NaOH, toluene;
(vi) TBAF; pTsCl, $NEt_3$, $CH_2Cl_2$;
(viii) $NaN_3$, DMF, $\Delta$;
(ix) $H_2$, Lindlar catalyst, EtOAc;
(x) $NaN_3$, $NH_4Cl$, DMF, $\Delta$;
(xi) BzBr, $Cs_2CO_3$, DMF;
(xii) LiOH, aq THF;
(xiii) $CH_3NHOCH_3.HCl$, isobutylchloroformate, N-methyl morpholine, THF;
(xiv) LAH, THF;
(xv) $Ph_3P=CH.CH=CHCO_2CH_3$, THF;
(xvi) NaH, $ICH_2CO_2CH_3$, TMEDA, THF;
(xvii) 10% Pd/C, $H_2$, HCl/EtOH.

Scheme VI below shows the synthesis of compounds further illustrating preferred examples of $R^3$ and $R^4$ of formula I.

Key intermediate (2) is converted into the O-ether-linked side chain carboxylic acid (54) by condensation with the amine (50 of Scheme V) as described above, with subsequent hydrolysis.

Compound (65) with an α-pentanoic acid side chain is prepared by hydrogenation followed by hydrolysis of the unsaturated ester (64) which is prepared by condensation of flexible acid (2) with amine (47 of Scheme V).

The glycyl derivative (56) is prepared by condensation of the benzyl ester of glycine with the acid (55) followed by catalytic hydrogenation to remove the benzyl group. The acid (55) in turn is prepared from the flexible acid (2) by condensation with the amine (52 of Scheme V).

The oxime ether carboxylic acid (57) is also prepared from the flexible acid intermediate (2) by condensation with intermediate (40) (Scheme V) followed by hydrolysis of the ethyl ester with aqueous lithium hydroxide in THF.

The tetrazole (62) is prepared by condensation of the amine (60) with the benzylated tetrazole carboxylic acid (44 of Scheme V) followed by removal of the benzyl group by catalytic hydrogenation.

The intermediate amine (60) is prepared from the flexible acid (2) by condensation of the amine (42) of Scheme V followed by removal of the benzyloxycarbonyl group by catalytic hydrogenation.

The α-glycinate derivative (59) is prepared by condensation of the α-acetic acid derivative (58) with ethylglycinate followed by hydrolysis of the ethyl ester with 1M NaOH in ethanol.

The acid (58) is prepared from the key intermediate (2) by condensation with (37) of Scheme V (wherein R is methyl and Ar is phenyl) followed by hydrolysis of the methyl ester with aqueous lithium hydroxide in THF.

The α-acetic acid (53) is prepared from the key acid (2) by condensation with (39) of Scheme V (wherein R is 2-(trimethylsilyl)ethyl and Ar is p-iodophenyl) followed by removal of the 2(trimethylsilyl)ethyl protecting group with tetrabutyl ammonium fluoride in THF.

SCHEME VI

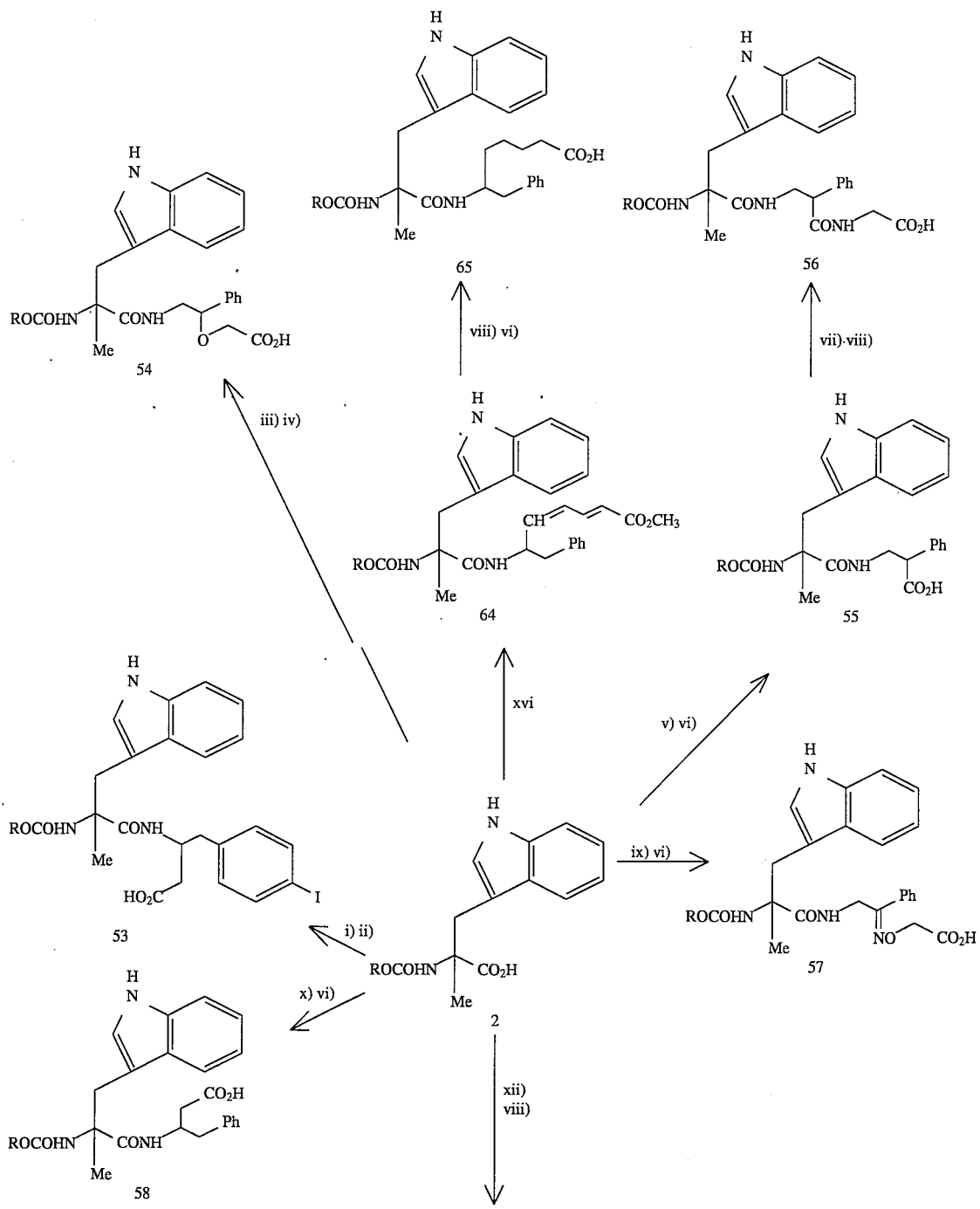

-continued
SCHEME VI

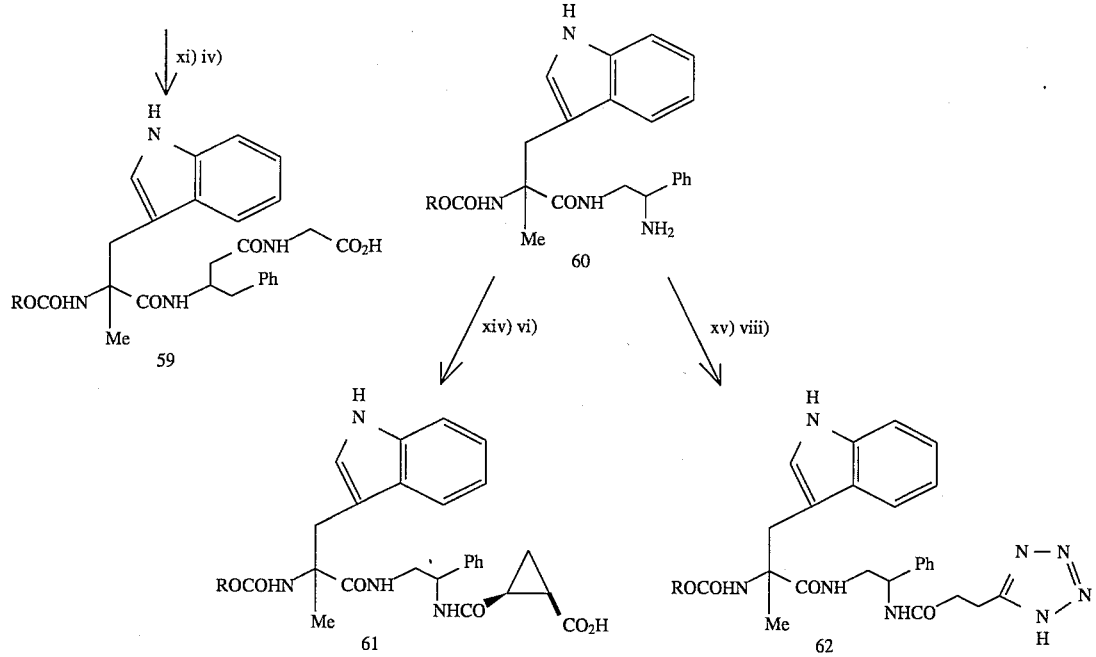

R = 2 Adamantyl
(i) DCC, HOBt, 37, EtOAc; (ii) TBAF, THF; (iii) DCC, HOBt, 50, NEt₃, EtOAc; (iv) 1M NaOH, EtOH;
(v) DCC, HOBt, 52, NEt₃, EtOAc; (vi) LiOH, aq THF; (vii) DCC, HOBt, HCl.NH₂CH₂CO₂Bn, NEt₃, EtOAc;
(viii) 20% Pd(OH)₂/C, H₂, EtOH; (ix) DCC, HOBt, 40, EtOAc; (x) DCC, HOBt, 37, NEt₃, EtOAc;
(xi) DCC, HOBt, HCl.H₂NCH₂CO₂Et, NEt₃, EtOAc; (xii) DCC, HOBt, 42, EtOAc;
(xiv) DCC, HOBt, mono methyl cyclopropanedicarboxylate, EtOAc; (xv) DCC, PFP, 44, EtOAc; (xvi) DCC, HOBt, 47, NEt₃, EtOAc.

Scheme VII below shows the synthesis of compound 71 which illustrates an example of formula I wherein $R^2$ is the functional group $CH_2CO_2Me$.

The starting formyl tryptophan (66) is protected on the indole nitrogen by BOC and protected on the carboxylic acid as benzyl ester (67). The N-formyl group is then dehydrated with triphosgene to form the corresponding isonitrile of which the anion of which is formed on treatment with LDA and then alkylated with methyl bromoacetate to give (68).

The isonitrile (68) is hydrolyzed using ethanolic HCl to the corresponding amine which is directly converted to (69) by acylation with 2-adamantylchloroformate. The benzyl ester group of (69) is then selectively removed by hydrogenation using 10% palladium on carbon and the resulting free carboxylic acid (70) is then condensed with phenylethylamine to generate the final product (71).

SCHEME VII

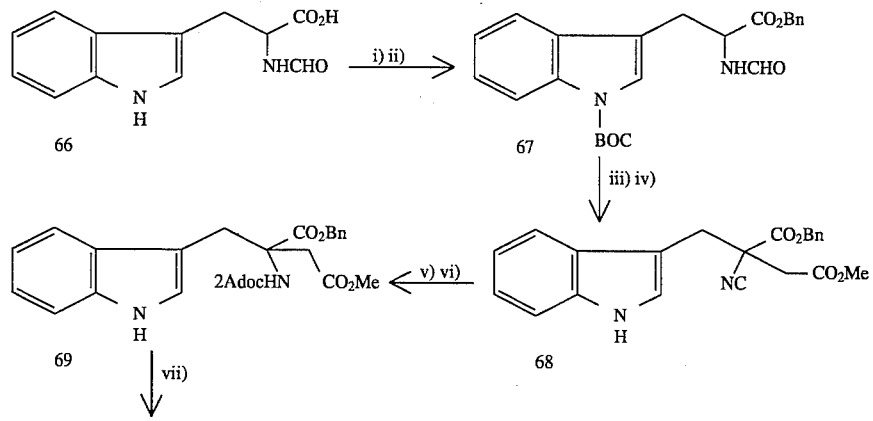

-continued
SCHEME VII

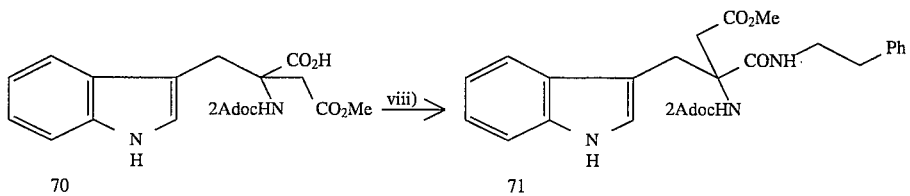

70 → 71

(i) Cs₂CO₃, BnBr, DMF; (ii) (Boc)₂O, DMAP, DMF; (iii) Triphosgene, NEt₃, CH₂Cl₂; (iv) BrCH₂CO₂CH₃, LDA, HMPA, THF; (v) Ethanolic HCl; (vi) 2-Adamantyl chloroformate, NEt₃, EtOAc; (vii) H₂, 10% Pd/C, ethanol; (viii) DCC, PFP, phenethylamine, EtOAc.

Scheme VIII below illustrates the synthesis of a difunctionalized derivative of formula I when $R^3$ is hydroxymethylene and $R^4$ is hydroxyl. Intermediate (2) is condensed with L-(+)-threo-2-amino-1-phenyl-1,3-propandiol using the PFP ester of (2).

SCHEME VIII

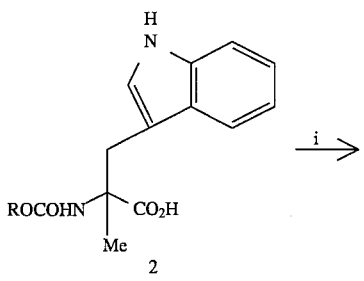

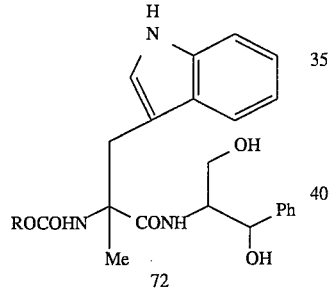

-continued
SCHEME VIII

Reagents:
(i) PFP, DCC, L-(+)threo-2-amino-1-phenyl-1,3-propanediol, EtOAc;

Scheme IX below illustrates a preferred mild procedure to prepare compound (82) when the TMS ester (81) is cleaved to the carboxylic acid (82) under mild conditions using tetrabutylammonium fluoride in THF. The scheme also illustrates the preparation of compound (80) by acetylation of amine (60K) with succinic anhydride in ethylacetate.

SCHEME IX

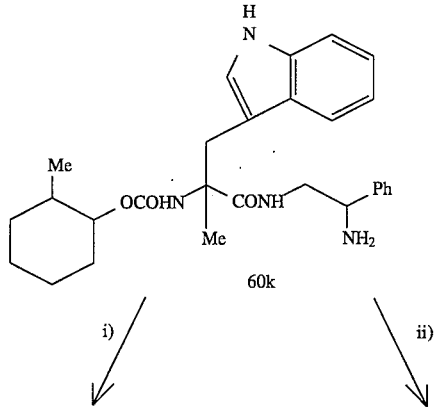

60k

-continued
SCHEME IX

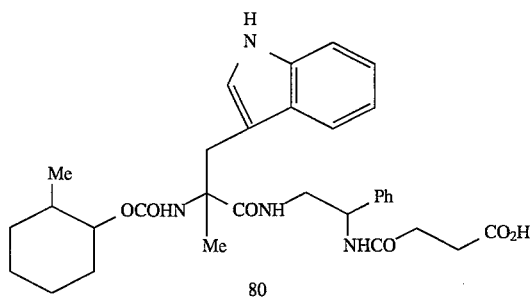

80

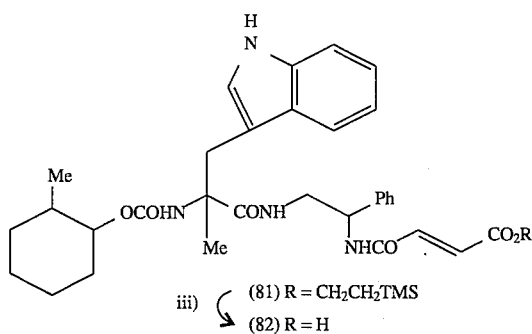

iii) ⎰ (81) R = CH$_2$CH$_2$TMS
   ⎱ (82) R = H

Reagents:
(i) Succinic anhydride, EtOAc; (ii) PFP, DCC, trans. Me$_3$SiCH$_2$CH$_2$OCOCH=CHCO$_2$H, EtOAc; (iii) (n-Bu)$_4$N$^+$F$^-$, THF.

Compounds of the formula

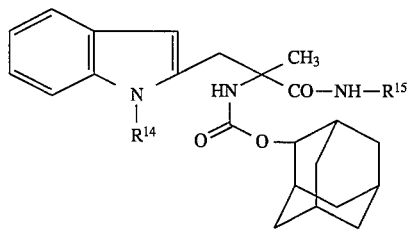
(I)

wherein R$^{14}$ is a hydrogen atom or a N-protecting group (Boc, Cbz, Ts; preferably Ts), and R$^{15}$ is

—CH$_2$—CH$_2$—C$_6$H$_5$,

—CH—CH$_2$—C$_6$H$_5$,
     |
     CH$_2$OH

—CH$_2$—CH—C$_6$H$_5$
        |
        NH—CO—CH$_2$CH$_2$—CO$_2$CH$_2$C$_6$H$_5$

—CH$_2$—CH—C$_6$H$_5$
        |
        NH—CO—CH$_2$CH$_2$—CO$_2$H are prepared using key intermediates of the present invention and are compounds of formula

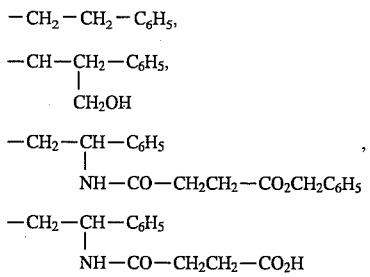
(II)

wherein R$^{14}$ is a hydrogen atom or a protecting group. These are useful as intermediates in the preparation of compounds of formula I.

Compounds of formula I can be synthesized as shown in Schemes X and Scheme XI below; Compound 12, a key intermediate, is part of the instant invention.

The indole ethyl 2-carboxylate is protected on the indole nitrogen by tosylation to give 1 which is reduced by Red-Al to the corresponding 2-hydroxymethyl compound 2. The alcohol 2 is converted into the corresponding bromide 3 using bromine and triphenylphosphine. The bromide 3 is used to alkylate the anion of the Schiff's base 3A derived from the methyl ester of alanine to give the Schiff's base 4 as a racemate. The hydrolysis of 4 gives the free amine 5 which is condensed with 2-adamantylchloroformate to give the methyl ester 6 which is hydrolyzed with potassium hydroxide in ethanol followed by further acidic work up to give the free carboxylic acid 9. The hydrolysis of 6 with LiOH/aq. dioxane gives the carboxylic acid 7. The acid 9 is condensed with amines to produce final products, for example, condensation of 9 with phenylethylamine gives compound 10 and with (S)-(−)-2-amino-3-phenyl-1-propanol to give 11 as a mixture of diastereoisomers which are separated by chromatography to give diastereoisomer 1 and diastereoisomer 2. The condensation of 9 with the amine 12 (Scheme XI) gives 13 as a mixture of diastereoisomers. These are separated by chromatography to give 13A and 13B. Finally, the benzyl ester in 13A and 13B is hydrogenolyzed to form the desired product 14 as separated diastereoisomers 14A and 14B.

SCHEME X

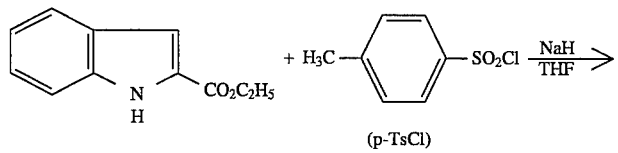
(p-TsCl)

-continued
SCHEME X
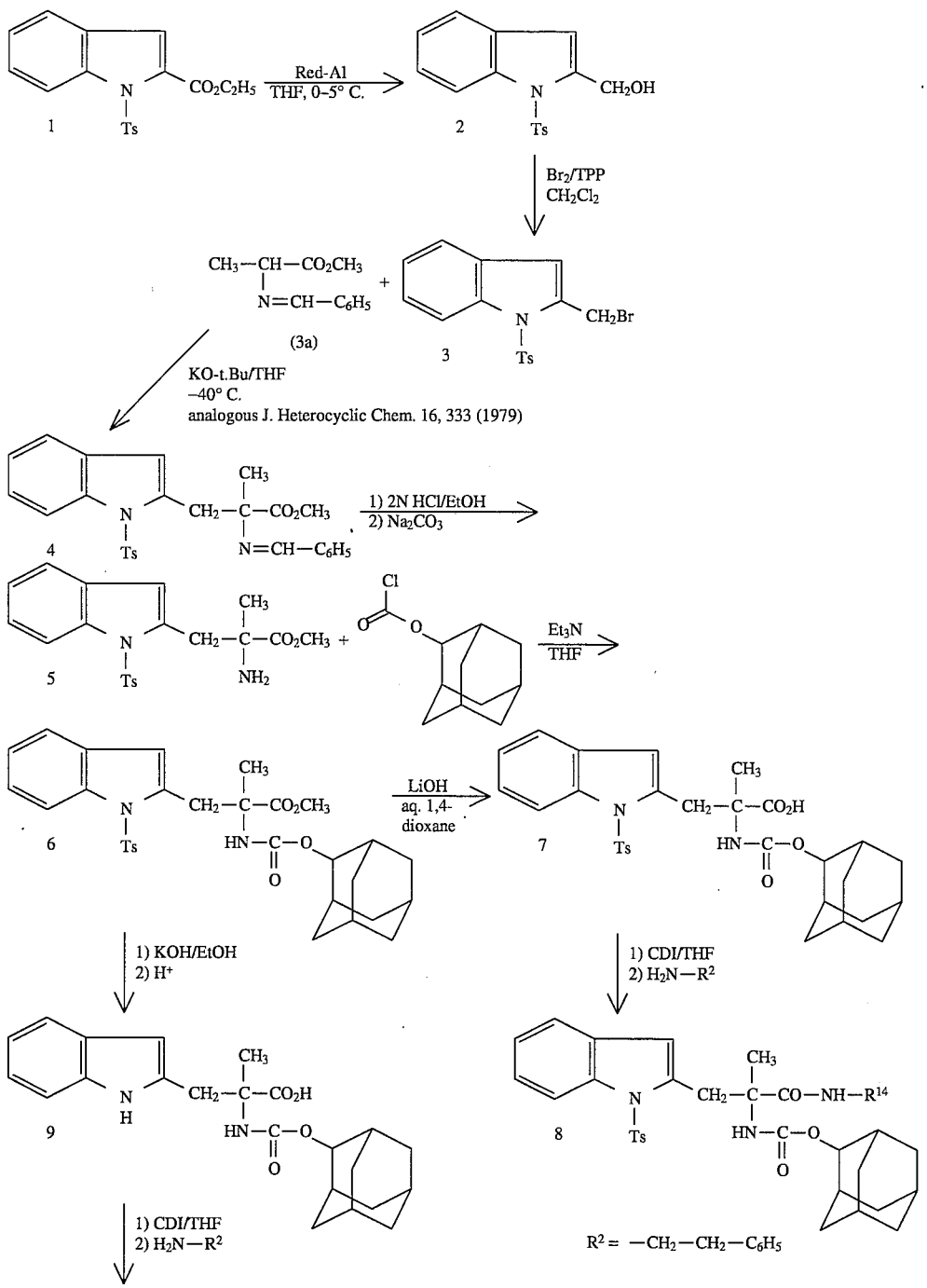

-continued
SCHEME X

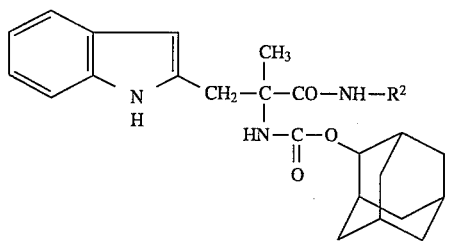

10 R² = —CH₂—CH₂—C₆H₅
11 R² = —CH—CH₂—C₆H₅
              |
              CH₂OH

Another process for the preparation of compounds 94a (13a) and 94b (13b) (see Scheme XI) is illustrated in Scheme XII below. In this process the intermediate 9 is condensed with the amine 15 (R configuration) to produce compound 16 as a mixture of diastereoisomers. These are converted to the free amine 17 by removal of the benzyloxycarbonyl group by catalytic hydrogenation. The pure amines (mixture of diastereoisomers) are treated with benzyl-hemisuccinate (18) and CDI in dry THF at room temperature to produce 93 as a mixture of diastereoisomers. These are separated by chromatography to give diastereoisomer 1 (93a) and diastereoisomer 2 (93b). The benzyl ester in 93a and 93b is hydrogenolyzed to form the desired product of formula 14 as separated diastereoisomers A and B as in Scheme XI.

SCHEME XI

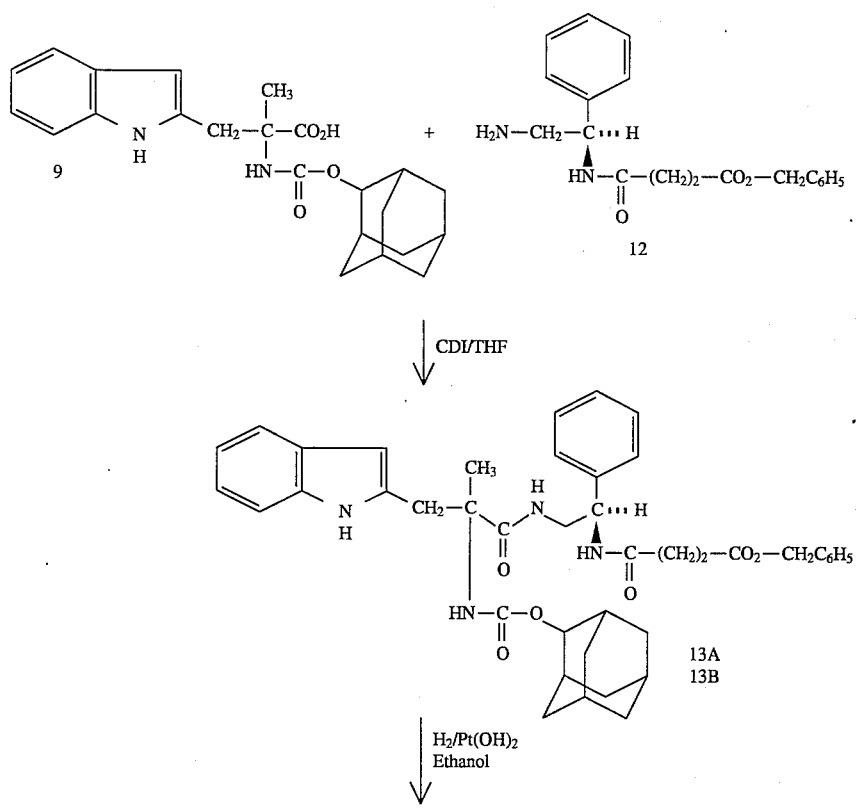

-continued
SCHEME XI
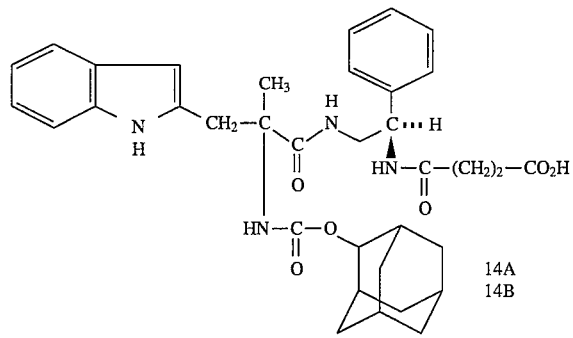
SCHEME XII
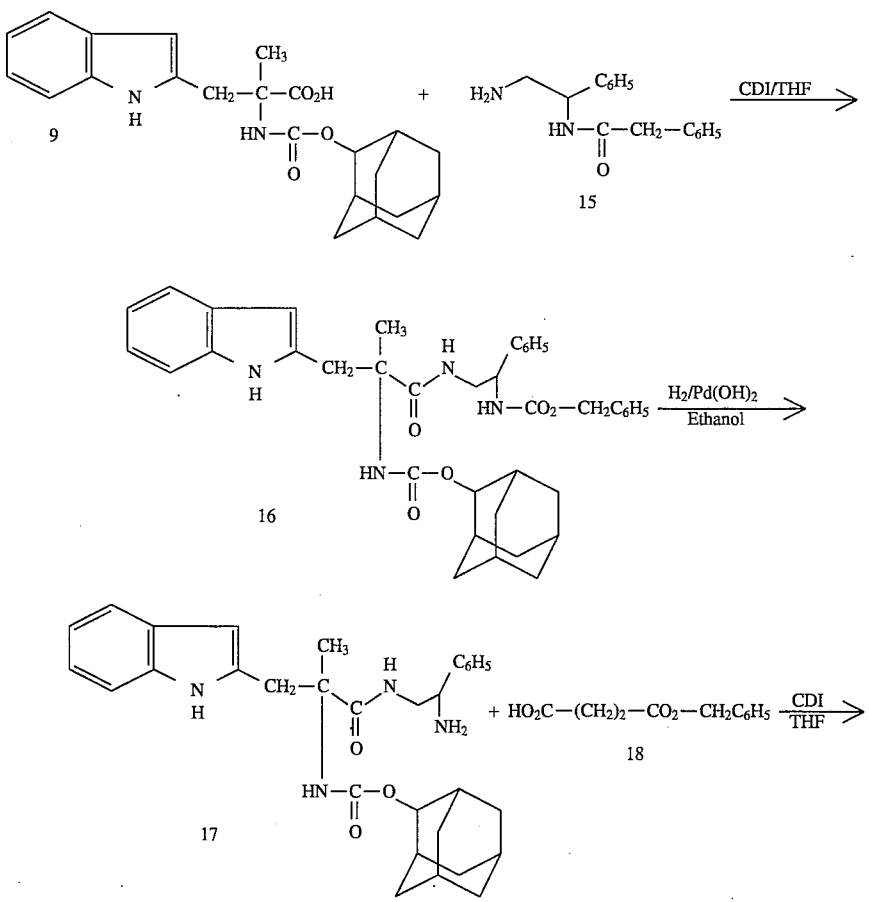

-continued
SCHEME XII

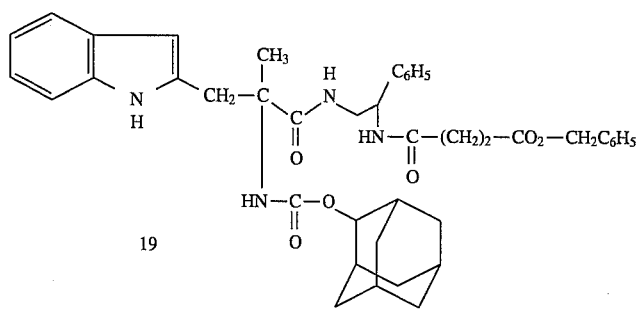

19

The biological activity of compounds of the present invention was evaluated employing an initial screening test which rapidly and accurately measured the binding of the tested compound to known CCK receptor sites. Specific CCK receptors have been shown to exist in the central nervous system. (See Hays et al, *Neuropeptides* 1:53–62, 1980; and Satuer et al, *Science*, 208:1155–1156, 1980.

In this screening test, the cerebral cortices taken from male CFLP mice weighing between 30–40 g were dissected on ice, weighed, and homogenized in 10 volumes of 50 mMTris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 µliter of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations ($10^{-11}$ to $10^{-14}$M) of competitive test compound. In each case, the nonspecific binding was defined as that persisting in the presence of the unlabeled octapeptide $CCK_{26-33}$ ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–VIII, 1910, to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient) values). ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1+[L]/K_a}$$

where [L] is the concentration of radiolabel and $K_a$ is the equilibrium dissociation constant.

The $K_i$/M values for several representative compounds of the present invention are present in Table III.

Compounds of the present invention are useful as appetite suppressants as based on the tests described hereinbelow.

In the Palatable Diet Feeding assay, adult male Hooded Lister rats weighing between 200–400 g were housed individually and trained to eat a palatable diet. This diet consisted of Nestles sweetened condensed milk, powdered rat food and rat water which when blended together set to a firm consistency. Each rat was presented with 20–30 g of the palatable diet for 30 minutes per day during the light phase of the light-dark cycle over a training period of five days. The intake of palatable diet was measured by weighing the food container before and after the 30-minute access period (limits of accuracy 0.1 g). Care was taken to collect and correct for any spillage of the diet. Rats had free access to pellet food and water except during the 30-minute test period.

After the training period, dose-response curves were constructed for CCK8 and several representative compounds of the present invention (n=8–10 rats per dose level). $MPE_{50}$ values (±95% confidence limits) were obtained for the anorectic effects of these compounds and are shown in Table III.

In therapeutic use as appetite suppression agents, the compounds of the instant invention are administered to the patient at dosage levels of from about 200 to about 2800 mg per day.

Table III below shows the binding and efficacy data.

TABLE III

Binding and Efficacy Data on Inhibition of Feeding in Rats

| Example No. | Binding to Central CCK Receptors | | Inhibition of Feeding on Rat Palatable Diet Assay |
| --- | --- | --- | --- |
| | $K_i$ (µM) | (n)[a] | I.P. $MPE_{50}$ (mg/kg) |
| 1 | 1.23 | (3) | NT |
| 2 | 3.15 | (3) | 9.6 |

TABLE III-continued

Binding and Efficacy Data on Inhibition of Feeding in Rats

| Example No. | Binding to Central CCK Receptors $K_i$ (μM) | (n)[a] | Inhibition of Feeding on Rat Palatable Diet Assay I.P. $MPE_{50}$ (mg/kg) |
|---|---|---|---|
| 3 | 0.26 | (3) | 30.7 |
| 4 | 0.17 | (3) | >20 |
| 5 | 2.23 | (3) | 33.6 |
| 6 | 0.44 | (3) | NT |
| 7 | 0.76 | (3) | NT |
| 8 | 0.84 | (3) | NT |
| 9 | 7.50 | (2) | NT |
| 10 | 8.80 | (2) | NT |
| 11 | 0.054 | (3) | NT |
| 12 | 0.085 | (3) | NT |
| 13 | 0.127 | (3) | NT |
| 14 | 10.5 | (1) | 19.5 |
| 15 | 0.026 | (3) | 15.7 |
| 16 | 0.03 | (2) | 10.5 |
| 17 | 0.063 | (2) | 13.1 |
| 18 | 21.02 | (1) | NT |
| 19 | 0.014 | (2) | NT |
| 19A | 0.00008 | (1) | NT |
| 20 | 0.0085 | (2) | 17.4 |
| 20A | 0.003 | (3) | NT |
| 33 | 0.006 | (1) | NT |
| 32 | 0.0051 | (1) | NT |
| 40 | 0.00390 | (1) | NT |
| 41 | 0.00029 | (1) | NT |
| 43 | 0.004 | (1) | NT |

NT = Not tested
*$MPE_{50}$ value = the dose of compound producing 50% of the maximum effect possible, which in these experiments would be zero food intake.
(n)[a] = Number of assays Male Hooded Lister rats (175–250 g) were housed individually and fasted overnight (free access to water). They were anesthetized with urethane (1.5 g/kg IP) and the trachea cannulated to aid spontaneous respiration. The stomach was perfused continuously using a modification of the original method of Ghosh & Schild in "Continuous recording of acid secretion in the rat", Br. J. Pharmac. 13:54–61, 1956 as described by Parsons in "Quantitative studies of drug-induced gastric acid secretion". (Ph.D. Thesis, University of London, 1969). The cavity of the stomach was perfused at a rate of 3 mL/min with 5.4% w/v glucose solution through both the esophageal and body cannula. The fluid was propelled by a roller pump (Gilson, Minipuls 2), through heating coils to bring its temperature to 37°±1° C. The perfusion fluid was collected by the fundic collecting funnel and passed to a pH electrode connected to a Jenway pH meter (PHM6). An output was taken from the pH meter to a Rikadenki chart recorder for the on-line recording of the pH of the gastric perfusate.

Pentagastrin was stored as a frozen aliquot and diluted to the required concentrations with sterile 0.9% w/v NaCl. Novel compounds were dissolved in sterile 0.9% w/v NaCl on the day of the experiment. Drugs were administered IV through a cannulated jugular vein as a bolus in a dose volume of 1 mL/kg washed in with 0.15 mL 0.9% w/v NaCl. Basal pH was allowed to stabilize before administration of compounds was begun. Typically 30 minutes elapsed between surgery and the first compound administration.

Figure 1A:
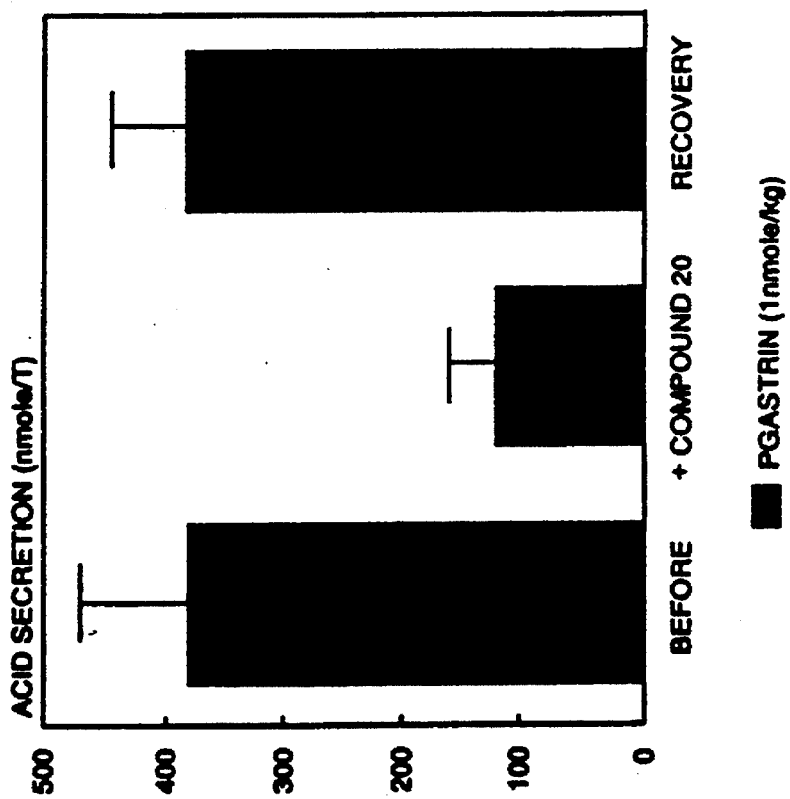
Figure 2B:
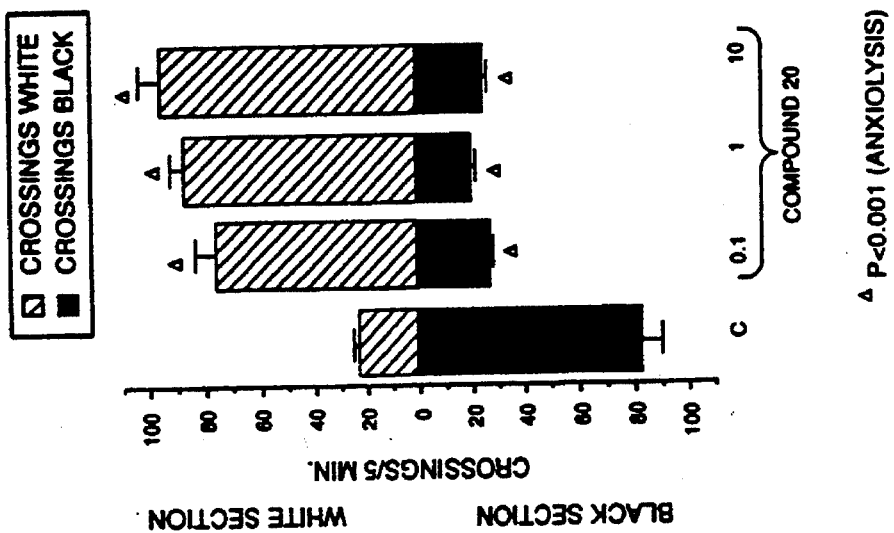
FIG. 2 shows anxiolytic activity of compound 20 dosed orally in the light/dark exploration test in the mouse.
Figure 2A:
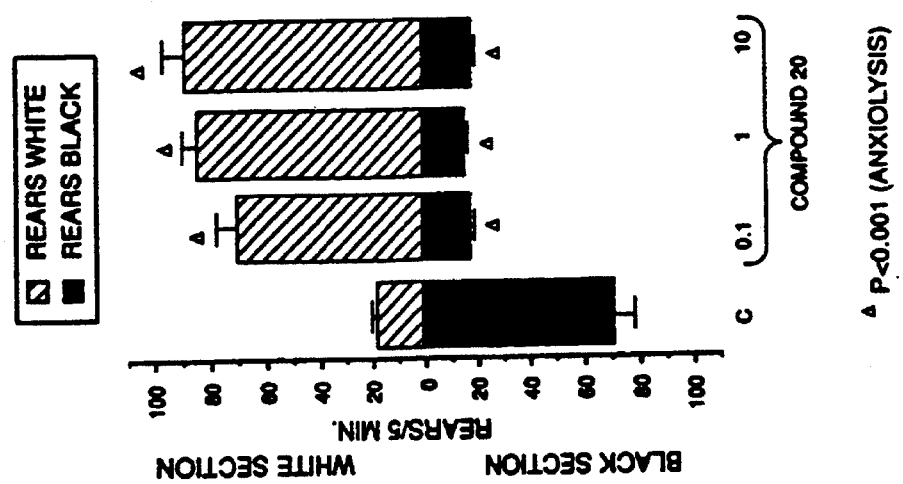
Figure 2D:
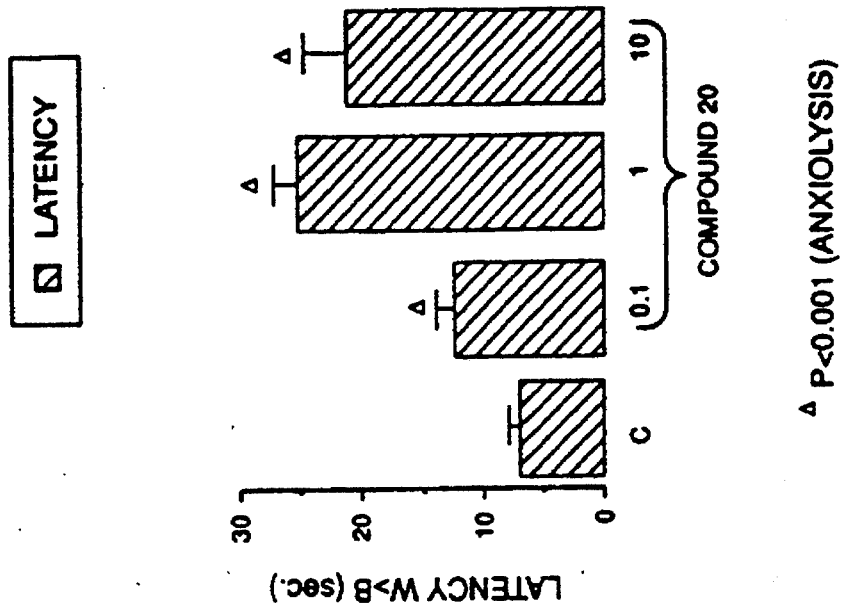
Figure 2C:
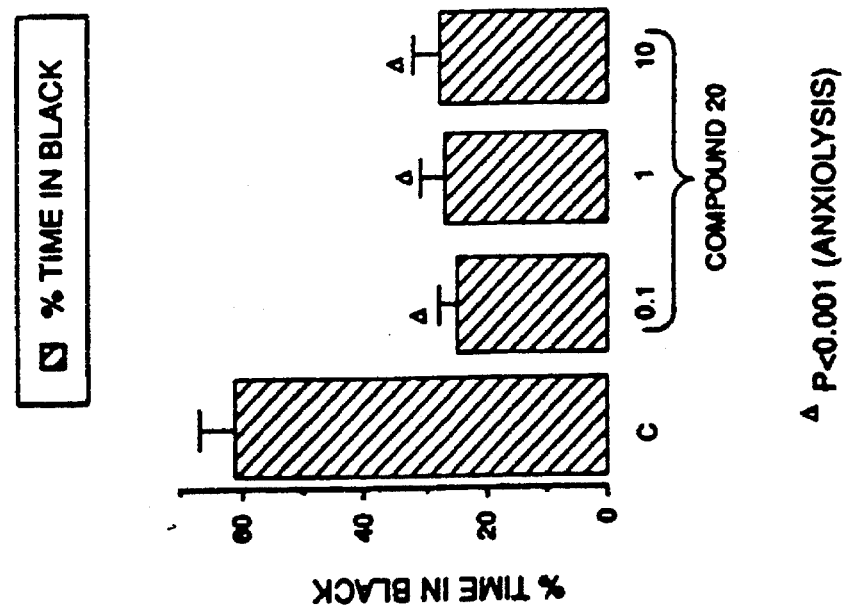

Compound (20) antagonized the stimulation of gastric acid secretion produced by a standard dose of 1 nmole/kg pentagastrin (FIG. 1). Compound (16) also attenuated the amount of gastric acid secreted in response to a 1 nmole/kg dose of pentagastrin (initial pentagastrin response 254 μmoles/1 $H^+$, after compound (16) (cumulative dose of 1.1 μmole/kg) 128 μmoles/1 $H^+$). With both compounds the antagonism was reversible with full recovery of the response to pentagastrin.

The compounds of the instant invention are also useful as antiulcer agents as discussed hereinbelow.

Aspirin-induced gastric damage was assessed in groups of 10 rats each.

All animals were fasted for 24 hours before and throughout the experiment. Drug or vehicle was given 10 minutes before an oral dose of 1 mL of a 45-mg/mL suspension of aspirin in 0.5% carboxymethylcellulose (CMC).

The animals were sacrificed five hours after aspirin administration and the stomachs removed and opened for examination.

Gastric damage was scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The mean ulcer score in the saline control group was 12.1±6.85 (±SD). Treatment with ranitidine (15 mg/kg PO) inhibited ulcer formation by 74% giving an ulcer score of 3.2±2.35 (p<0.001 compared with controls). Treatment with [R-(R*,R*)-4-[[2-[[3-(1H-indol-3-yl)-2-methyl-1-oxo-2-[[(tricyclo[3.3.1.1[3,7]]-dec-2-yloxy)carbonyl]amino]propyl]-amino]-1-phenylethyl]amino]-4-oxobutanoic acid (10 mg/kg PO) resulted in an ulcer score of 6.3±4.14 (p <0.05 compared with controls), a 48% reduction in ulcer formation.

The specific dosages employed, however, may be varied depending upon the patient, the severity of the condition being treated, and the activity of the compound employed. Determination of optimum dosages is within the skill of the art.

The compounds of the instant invention are also useful as anxiolytic agents as described and discussed below.

FIG. 2 illustrates the effectiveness of orally administered compound (20) as regards anxiolytic activity. Anxiolytic activity was assessed in the light/dark exploration test in the mouse (B. J. Jones, et al, Br. J. Pharmacol. 93:985–993, 1988).

In FIG. 2 the number of mice was 5 and the pretreatment time was 40 minutes. The compound was given p.o. in 0.1, 1, and 10 mg/kg doses.

The apparatus was an open-topped box, 45 cm long, 27 cm wide, and 27 cm high, divided into a small (⅖) area and a large (⅗) area by a partition that extended 20 cm above the walls. There was a 7.5×7.5 cm opening in the partition at floor level. The small compartment was painted black and the large compartment white. The floor of each compartment was marked into 9 cm squares. The white compartment was illuminated by a 100-watt tungsten bulb 17 cm above the box and the black compartment by a similarly placed 60-watt red bulb. The laboratory was illuminated with red light.

All tests were performed between 13 hundred hours, 0 minutes and 18 hundred hours, 0 minutes. Each mouse was tested by placing it in the center of the white area and allowing it to explore the novel environment for five minutes. Its behavior was recorded on videotape and the behavioral analysis was performed subsequently from the recording. Five parameters were measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs were dissolved in water or saline and administered either subcutaneously, intraperitoneally, or by mouth (PO) via a stomach needle.

Compound (20) and compound [R-(R*,R*)]-4-[[2-[[3-(1H-indol-3-yl)-2-methyl-1-oxo-2-[[(tricyclo[3.3.1$^{3,7}$]dec-2-yloxy)carbonyl]amino]propyl]amino]-1-phenylethyl]amino]-4-oxobutenoic acid were active by the subcutaneous route. Control animals showed 3% crossings into the dark area over five-minute measurement periods. Mice treated with 1 mg/kg (SC) of compound (20) showed 85 crossings into the light area and only 24 crossings into the dark area, a significant ($p < 0.01$) difference from the control anxious mice. Diazepam (0.25 mg/kg IP) had an effect identical to compound (20) in the same experiment. In additional experiments compound [R-(R*,R*)]-4-[[2-[[3-(1H-indol-3-yl)-2-methyl-1-oxo-2-[[(tricyclo[3.3.1$^{3,7}$]-dec-2-yloxy)carbonyl]amino]propyl]amino]-1-phenylethyl]amino]-4-oxobutenoic acid (a mg/kg SC) and compound (20) (1 mg/kg PO) significantly ($p < 0.01$) increased the time spent in the light area of the test box.

The compounds of the instant invention are useful as antipsychotic agents. Compound (20) (which is shown as compound (24) in Scheme III) and compound (20A) were tested for their ability to reduce the effects of intra-accumbens amphetamine in the rat as described hereinafter.

Male Sprague Dawley (CD) Bradford strain rats were used. The rats were housed in groups of five at a temperature of 21°±2° C. on a 12 hour light-dark cycle of lights-on between 07 hours 00 minutes and 20 hours 00 minutes. Rats were fed CRM diet (Labsure) and allowed water ad libitum.

Rats were anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) were implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides were kept patent during a 14-day recovery period using stainless steel stylers, 0.3 mm diameter, which extended 0.5 mm beyond the guide tips.

Rats were manually restrained and the stylers removed. Intracerebral injection cannulae, 0.3 mm diameter, were inserted and drugs delivered in a volume of 0.5 μl over 5 seconds (a further 55 seconds was allowed for deposition) from Hamilton syringes attached via polythene tubing to the injection units. Animals were used on a single occasion only.

Behavioral experiments were conducted between 07 hours 30 minutes and 21 hours 30 minutes in a quiet room maintained at 22°±2° C. Rats were taken from the holding room and allowed one hour to adapt to the new environment. Locomotor activity was assessed in individual screened Perspex cages (25×15×15 cm (high) (banked in groups of 30) each fitted with one photocell unit along the longer axis 3.5 cm from the side; this position has been found to minimize spurious activity counts due to, for example, preening and head movements when the animal is stationary. Interruptions of the light beam were recorded every 5 minutes. At this time animals were also observed for the presence of any nonspecific change in locomotor activity, e.g., sedation, prostration, stereotyped movements, that could interfere with the recording of locomotor activity.

The abilities of the compounds (20) and (20A) to inhibit the hyperactivity caused by the injection of amphetamine into the nucleus accumbens of the rat was measured.

An increase in locomotor activity followed the bilateral injection of amphetamine (20 μg) into the nucleus accumbens; peak hyperactivity (50 to 60 counts 5 minutes$^{-1}$) occurred 20 to 40 minutes after injection.

Figure 3:
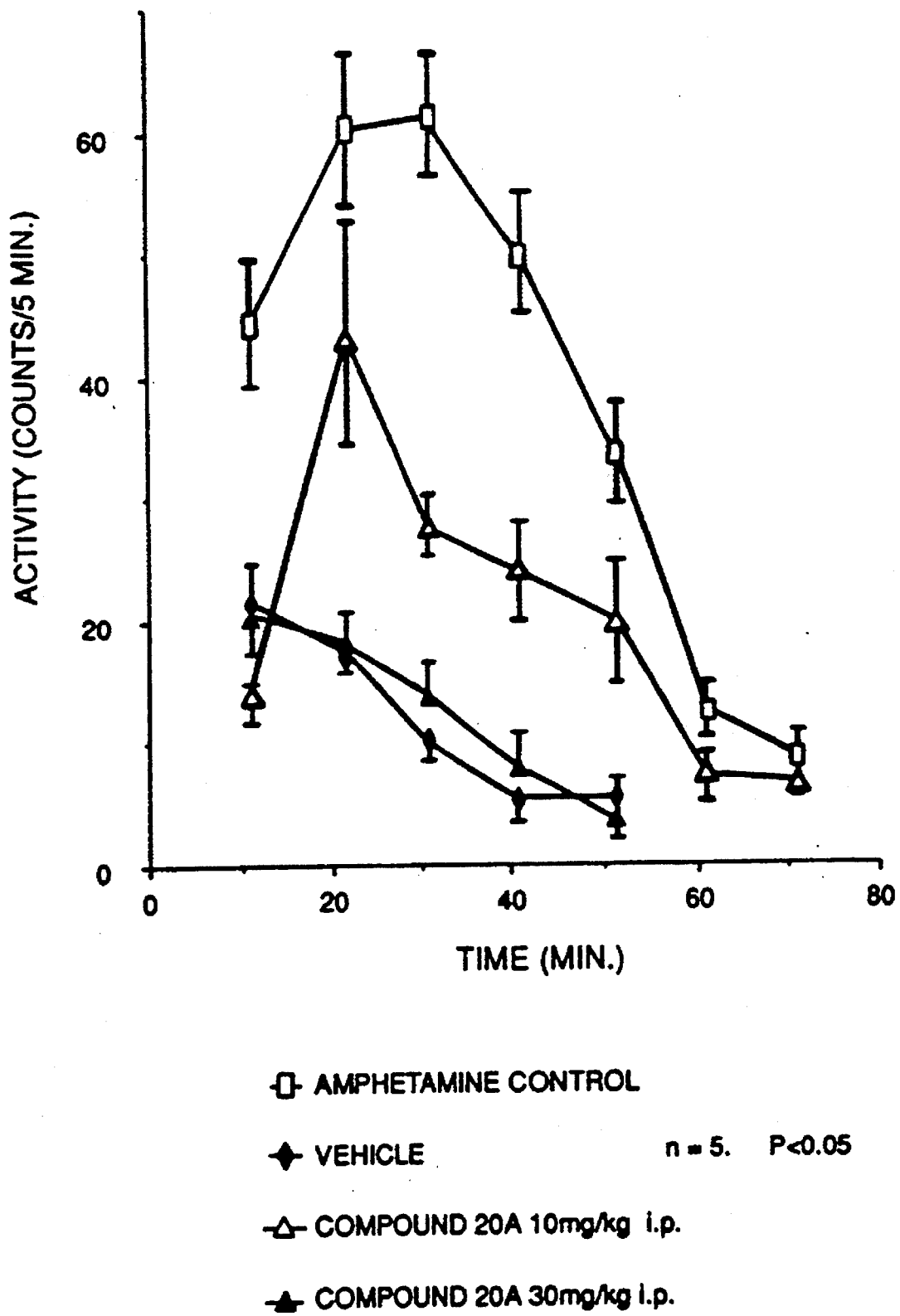
FIG. 3 shows antipsychotic activity of compound 20A by antagonism of intra-accumbens-dosed amphetamine.
Figure 4:
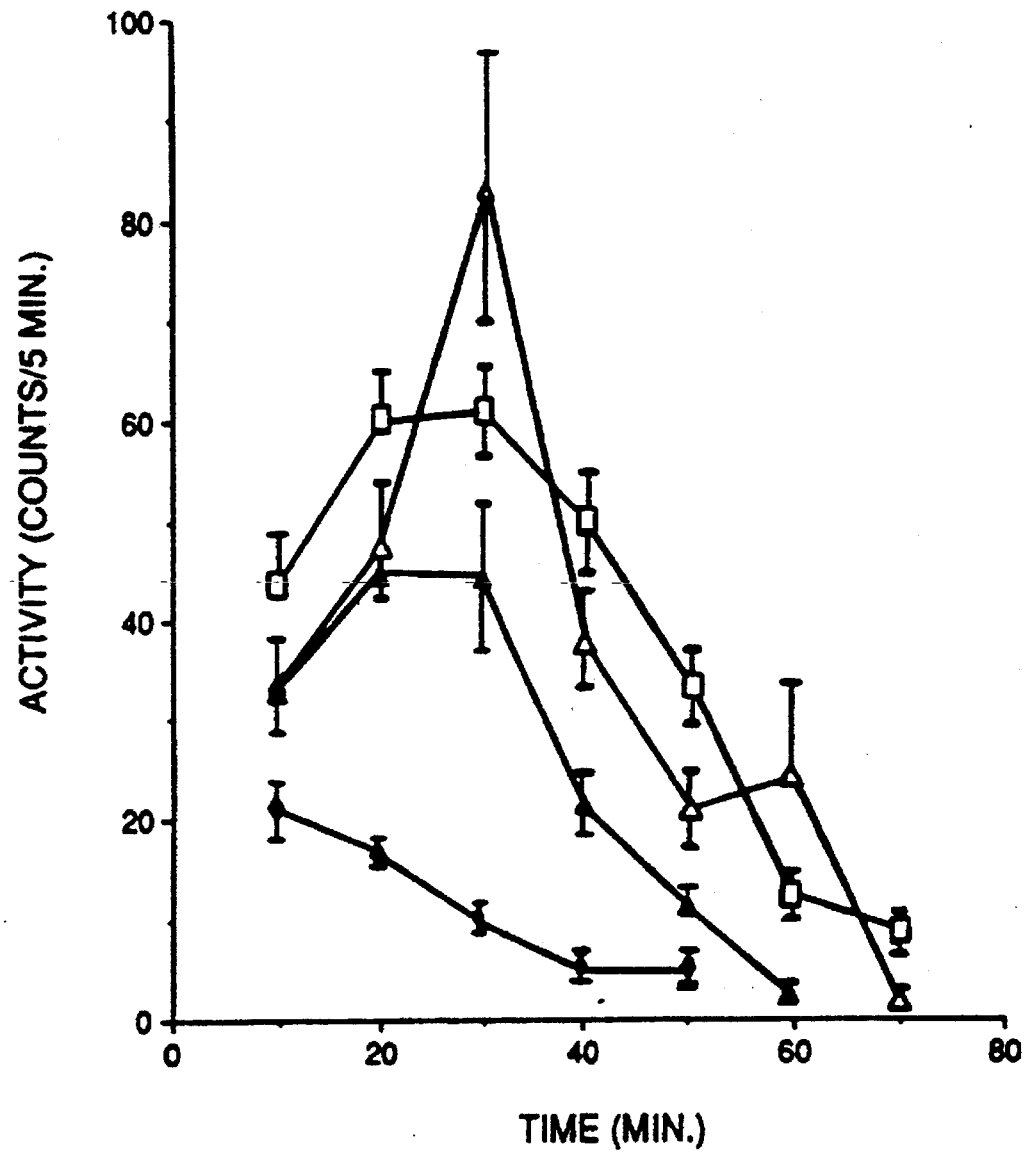
FIG. 4 shows antipsychotic activity of compound 20 by antagonism of intra-accumbens-dosed amphetamine.

Intraperitoneal injection of the rats with compound (20A) (20 mg/kg or 30 mg/kg) or compound (20) (10 mg/kg) reduced the hyperactivity caused by the intra-accumbens injection of amphetamine (FIGS. 3 and 4). This test is known to be predictive of antipsychotic activity (Costall, Domeney & Naylor & Tyers, *Brit J Pharmac* 92:881–894).

FIG. 3 shows the antagonism of intra-accumbens amphetamine (20 μg) by compound (20A). The amphetamine control is shown by -□-, the vehicle by -♦-, the -Δ- shows compound (20) at 1 mg/kg IP and -Δ- shows the compound at 10 mg/kg IP. The number tested was five. The *P is <0.05. The time in minutes is shown versus activity (counts/5 minutes).

FIG. 4 shows the antagonism of intra-accumbens amphetamine (20 μg) for compound (20). The figure is described as for FIG. 3 above.

The compounds of the instant invention prevent and treat the withdrawal response produced when chronic treatment by a drug is stopped or when alcohol abuse is stopped. These compounds are therefore useful as therapeutic agents in the treatment of chronic drug or alcohol abuse as discussed and described below.

The effect of the compounds of the instant invention is illustrated, for example, in the mouse "light/dark box" test in FIGS. 5–12.

Figures 5A, 5B:
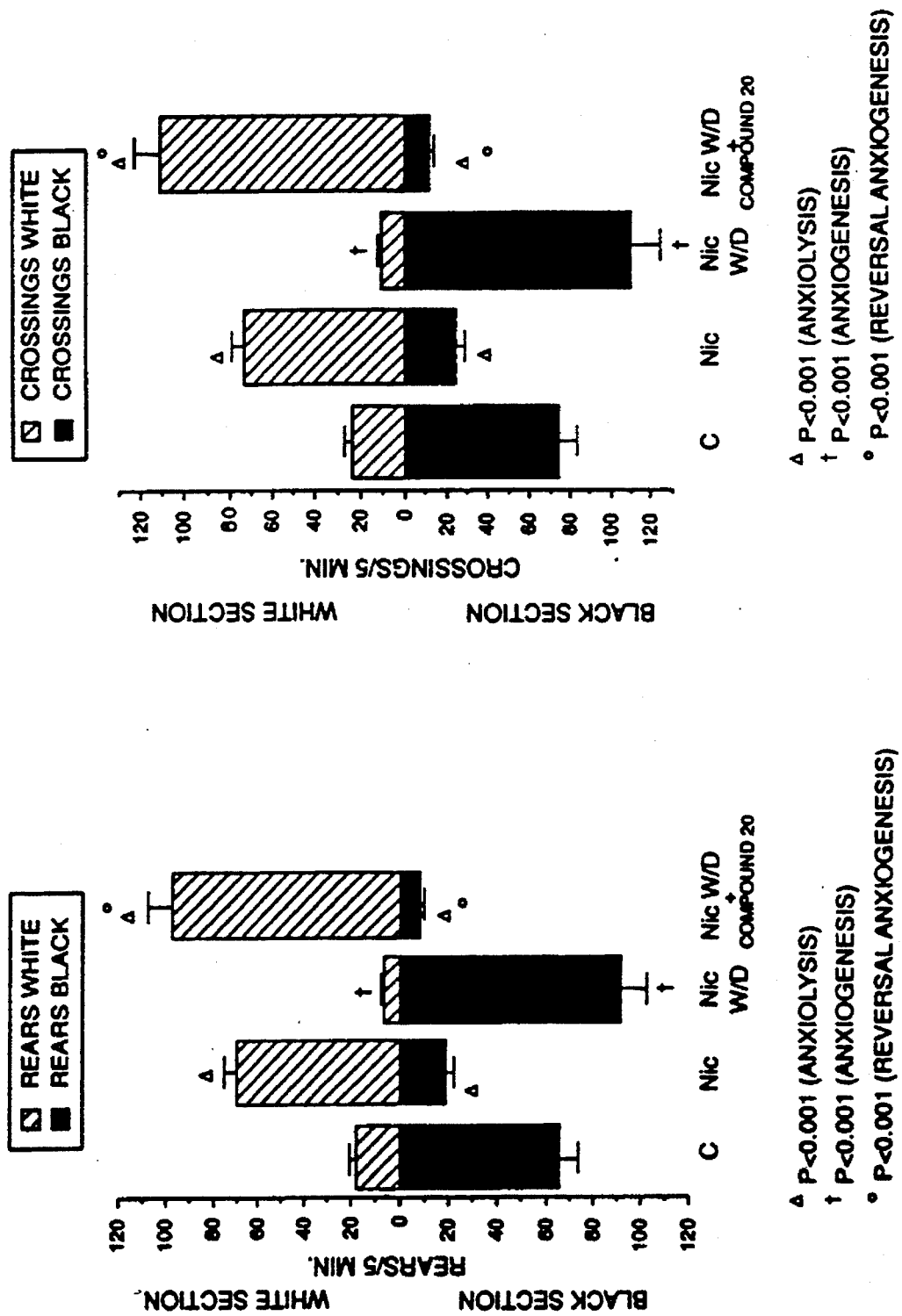
FIG. 5 shows the effect of long-term treatment and withdrawal from nicotine; intervention with compound 20.
Figure 5D:
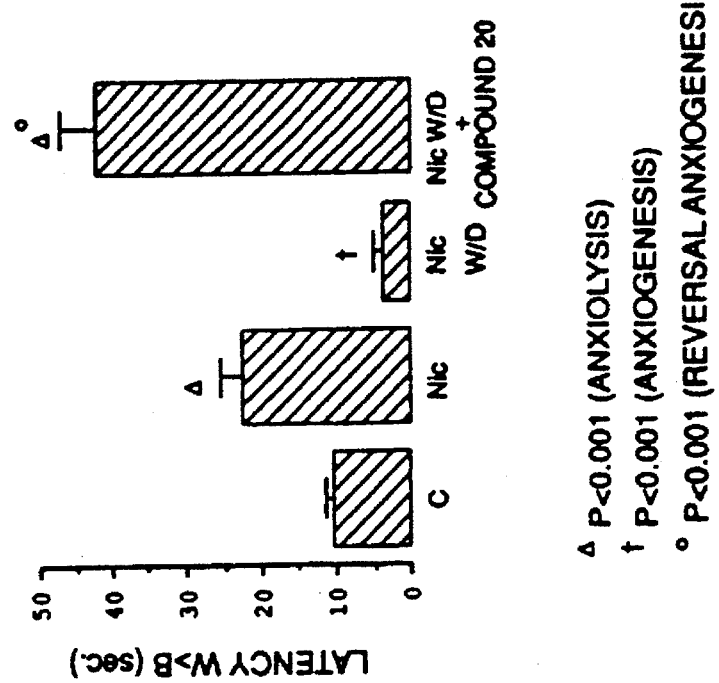
Figure 5C:
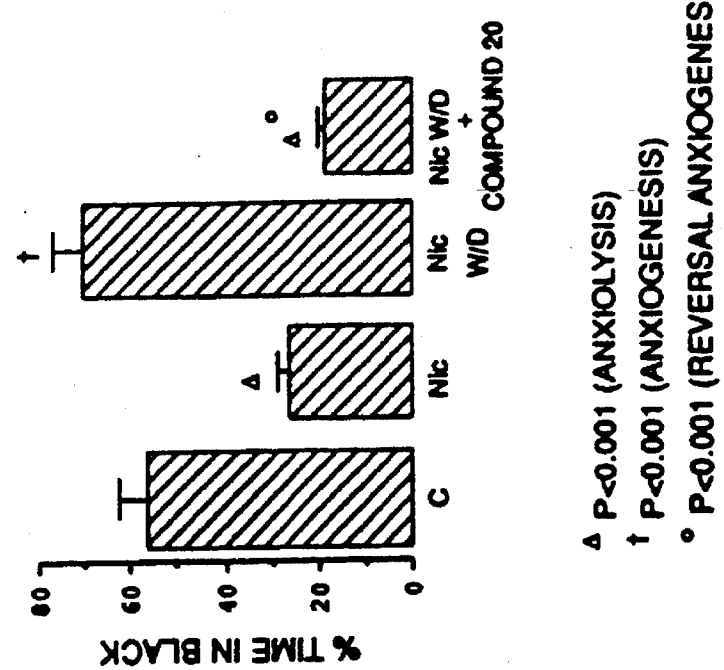
Figure 6B:
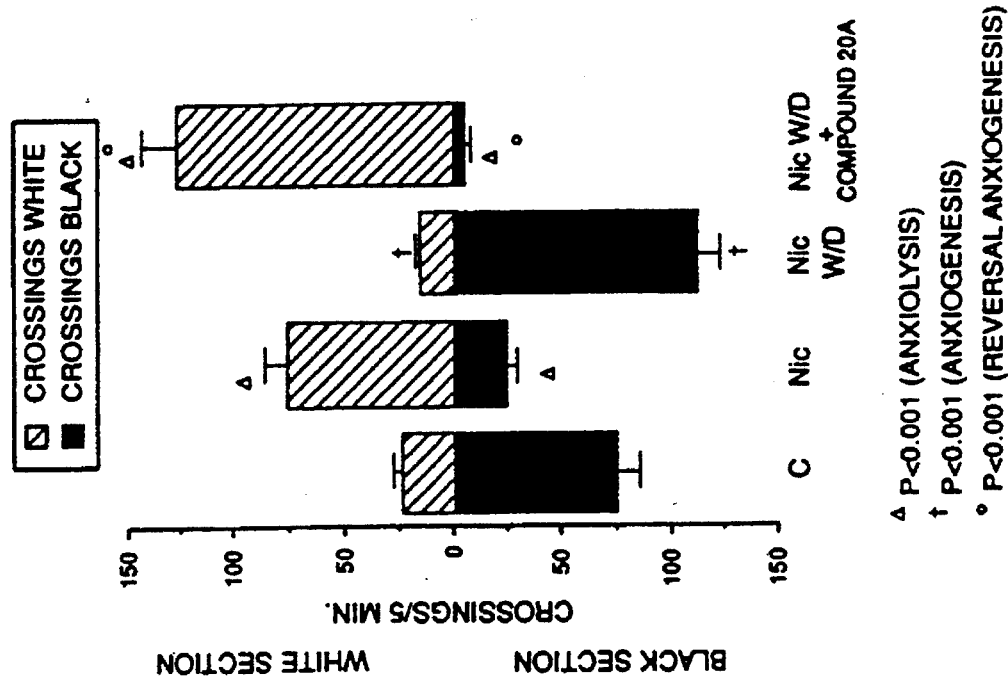
FIG. 6 shows the effect of long-term treatment and withdrawal from nicotine; intervention with compound 20A.
Figure 6A:
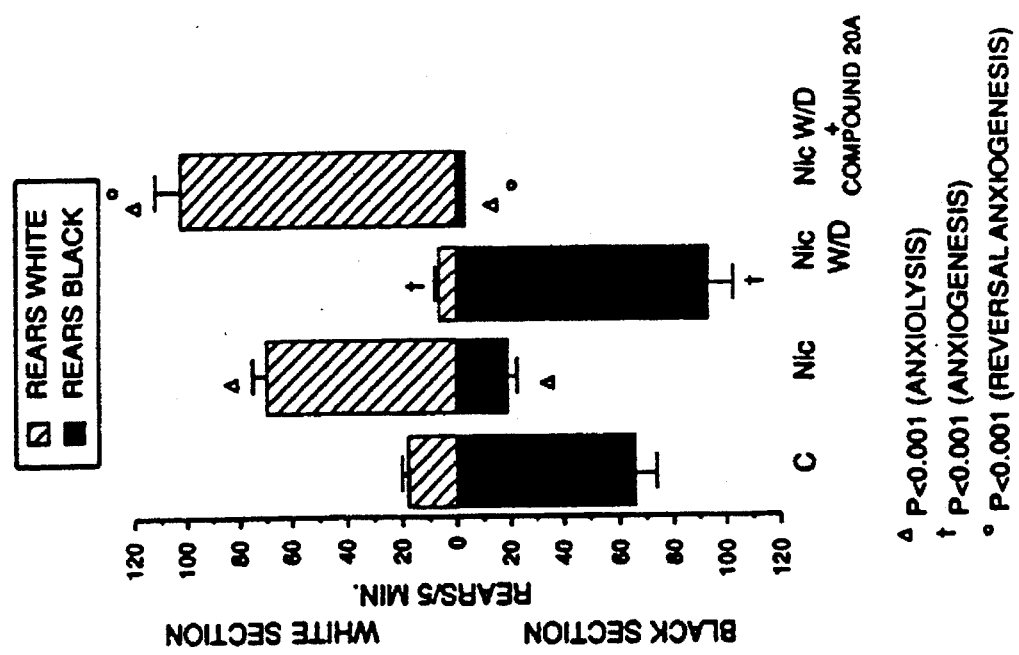
Figure 6D:
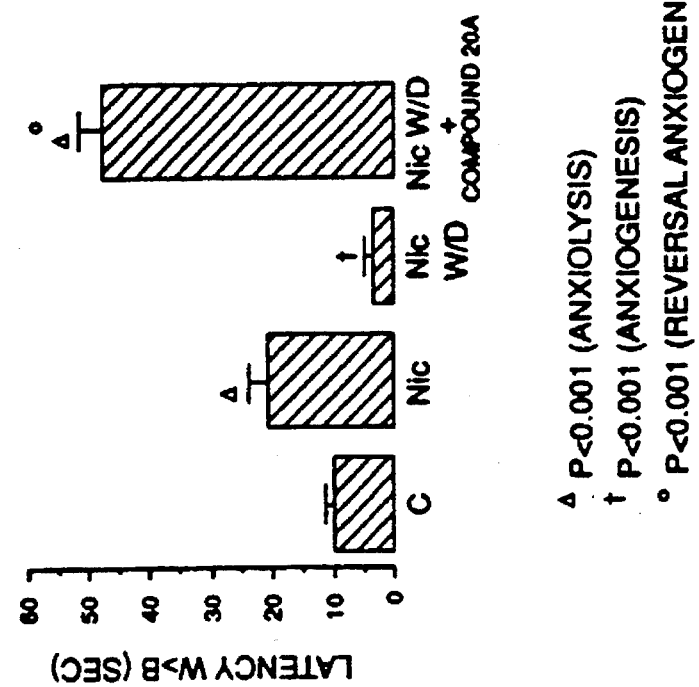
Figure 6C:
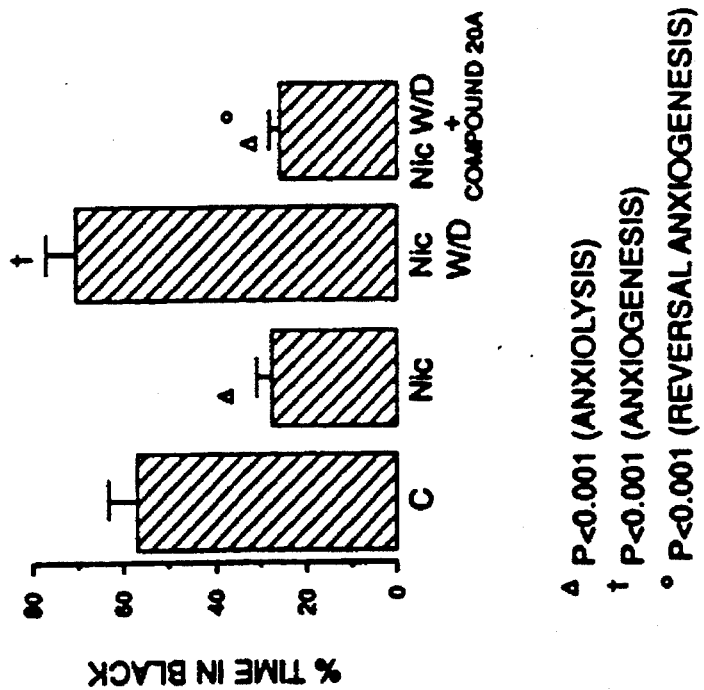

In FIG. 5, five animals were given nicotine, 0.1 mg/kg i.p.b.d. for 14 days. After a 24-hour withdrawal period, compound (20) was given at 1.0 mg/kg i.p.b.d. The increased time spent in the light area is a sensitive measure of the effect of compound (20) as an agent to treat withdrawal effects from nicotine.

FIG. 6 illustrates the effect of long-term treatment and withdrawal from nicotine using compound (20A). Five mice were given nicotine at 0.1 mg/kg i.p.b.d. for 14 days. After a withdrawal period of 24 hours, compound (20A) was given at 10 mg/kg i.p.b.d. The effect of compound (20A) can be seen in the increase of time spent in the light area.

Figures 7A, 7B:
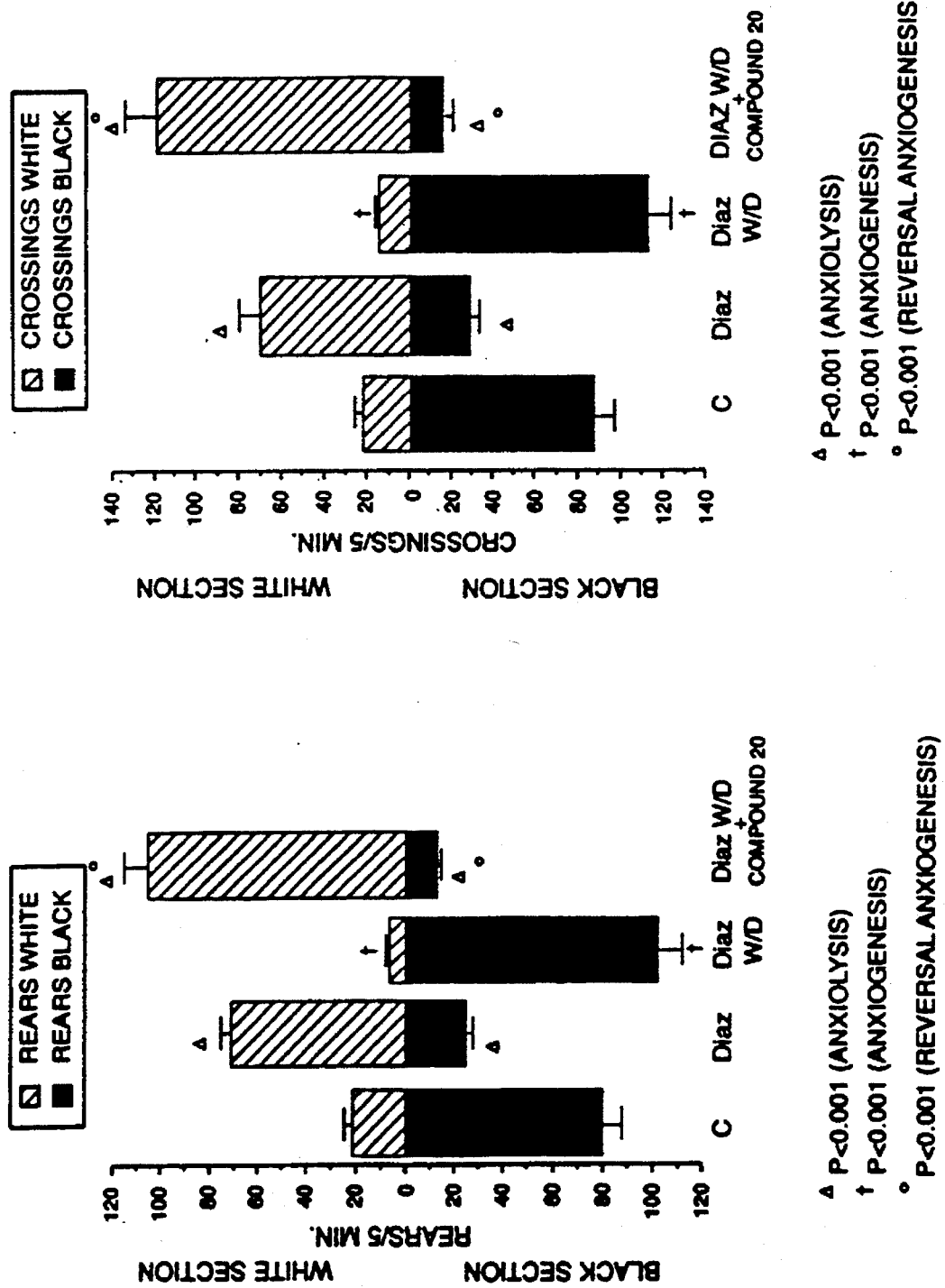
FIG. 7 shows the effect of long-term treatment and withdrawal from diazepam; intervention with compound 20.
Figure 7D:
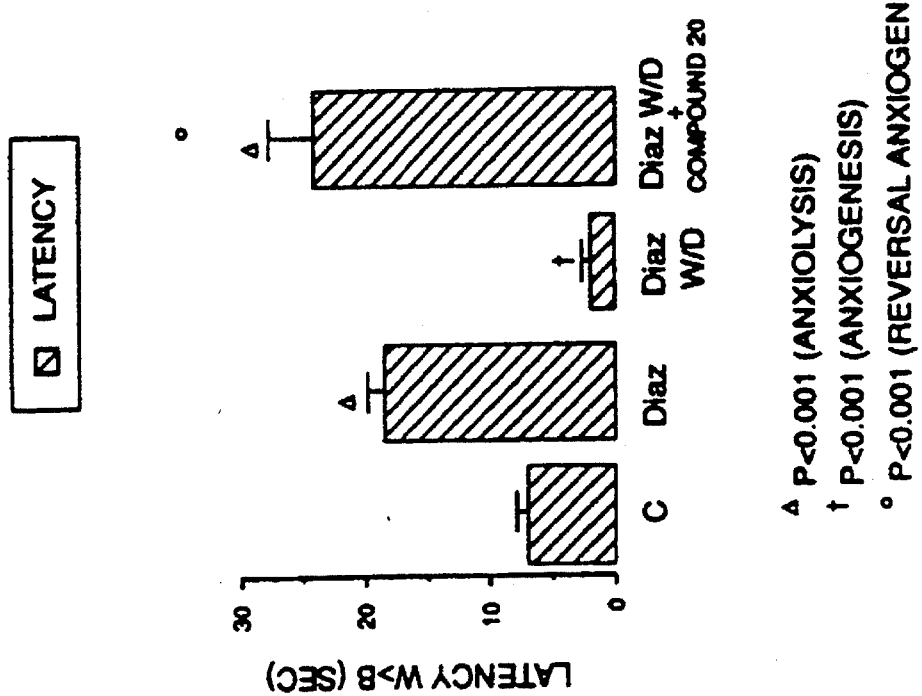
Figure 7C:
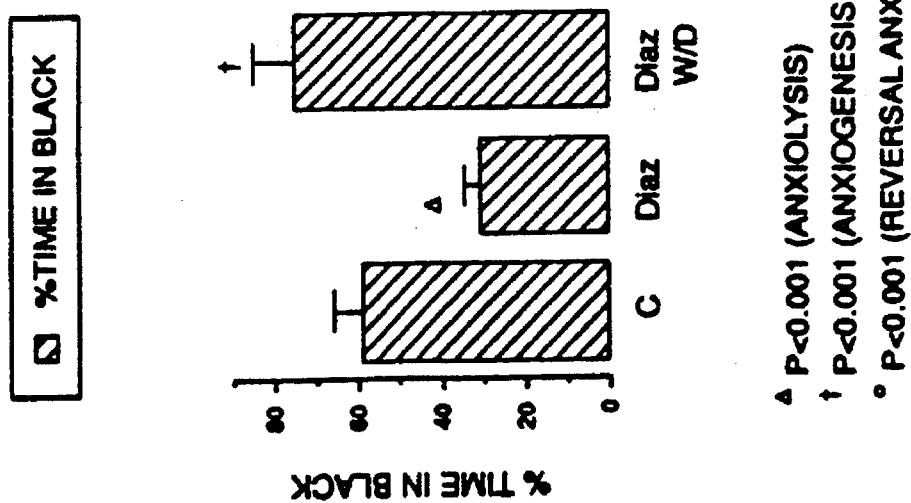

FIG. 7 illustrates the effect of long-term treatment and withdrawal from diazepam with intervention with compound (20). Five mice were given diazepam, at 10 mg/kg i.p.b.d. for seven days. Withdrawal was for a 24-hour period; compound 20 was given at 1.0 mg/kg i.p.b.d. The increased time spent in the light section shows the effect of compound (20).

Figures 8C, 8D:
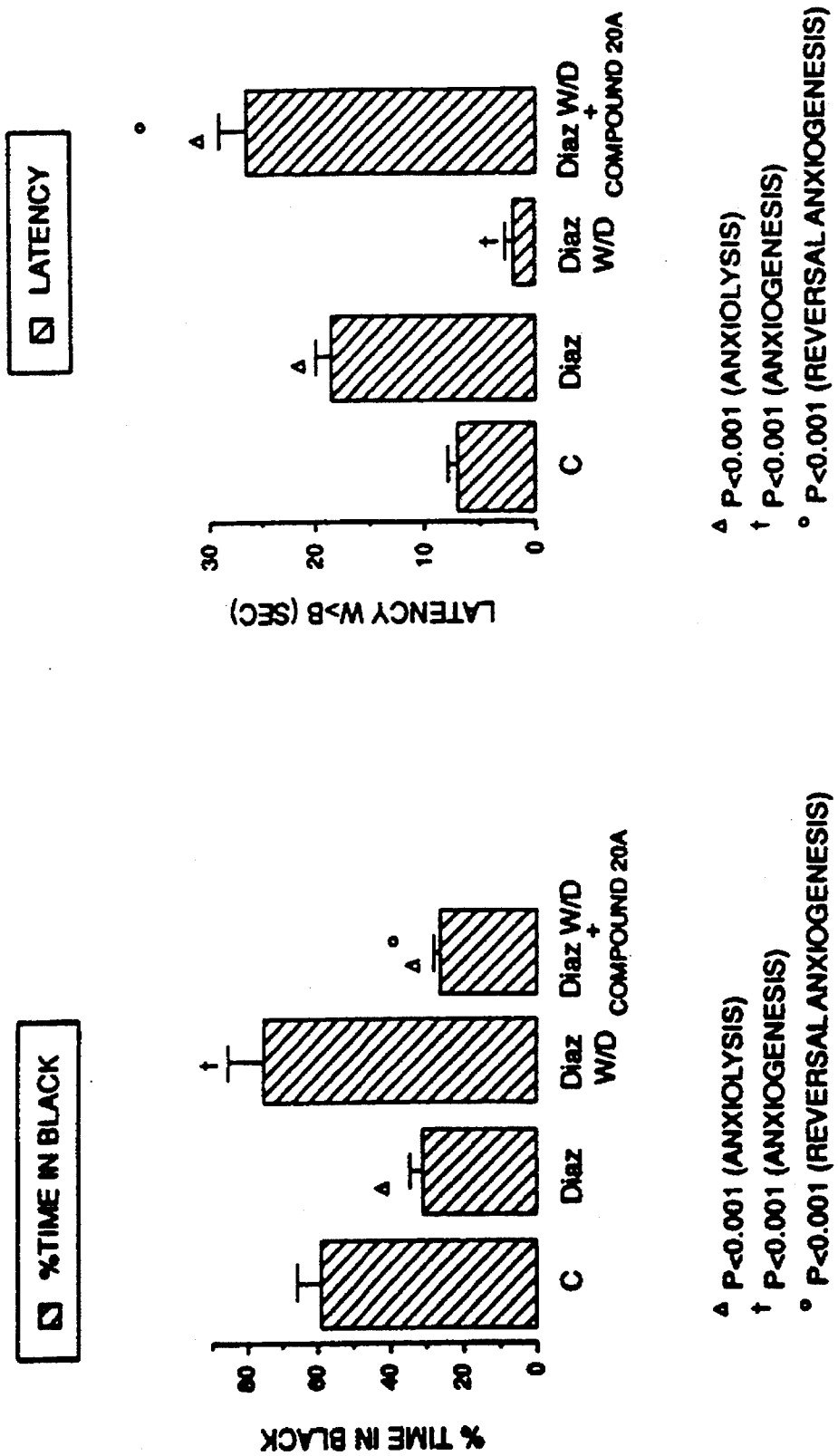
FIG. 8 shows the effect of long-term treatment and withdrawal from diazepam; intervention with compound 20A.

FIG. 8 illustrates the effect of compound (20A) on the long-term treatment and withdrawal from diazepam. Five mice were given diazepam at 10 mg/kg i.p.b.d. for seven days. After a withdrawal period of 24 hours, compound (20A) was given at 10 mg/kg i.p.b.d. The amount of time spent in the light section after compound (20A) is administered demonstrates the effectiveness of the compound.

Figure 9D:
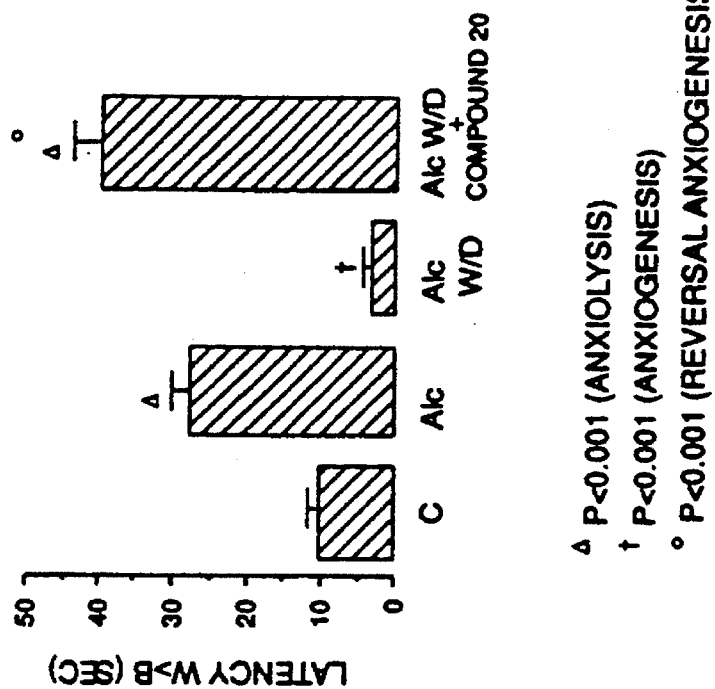
FIG. 9 shows the effect of long-term treatment and withdrawal from alcohol; intervention with compound 20.
Figure 9C:
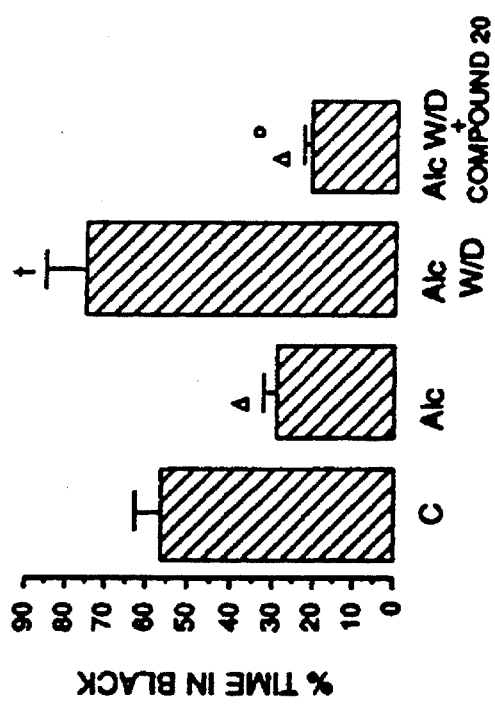

FIG. 9 illustrates the effect compound (20A) on the long-term treatment and withdrawal from alcohol. Five mice were given alcohol in drinking water 8% w/v for 14 days. After a withdrawal period of 24 hours, compound (20) was given at 1.0 mg/kg i.p.b.d. The amount of time spent in the light section after the compound was administered demonstrates the effectiveness of the compound.

Figures 10A, 10B:
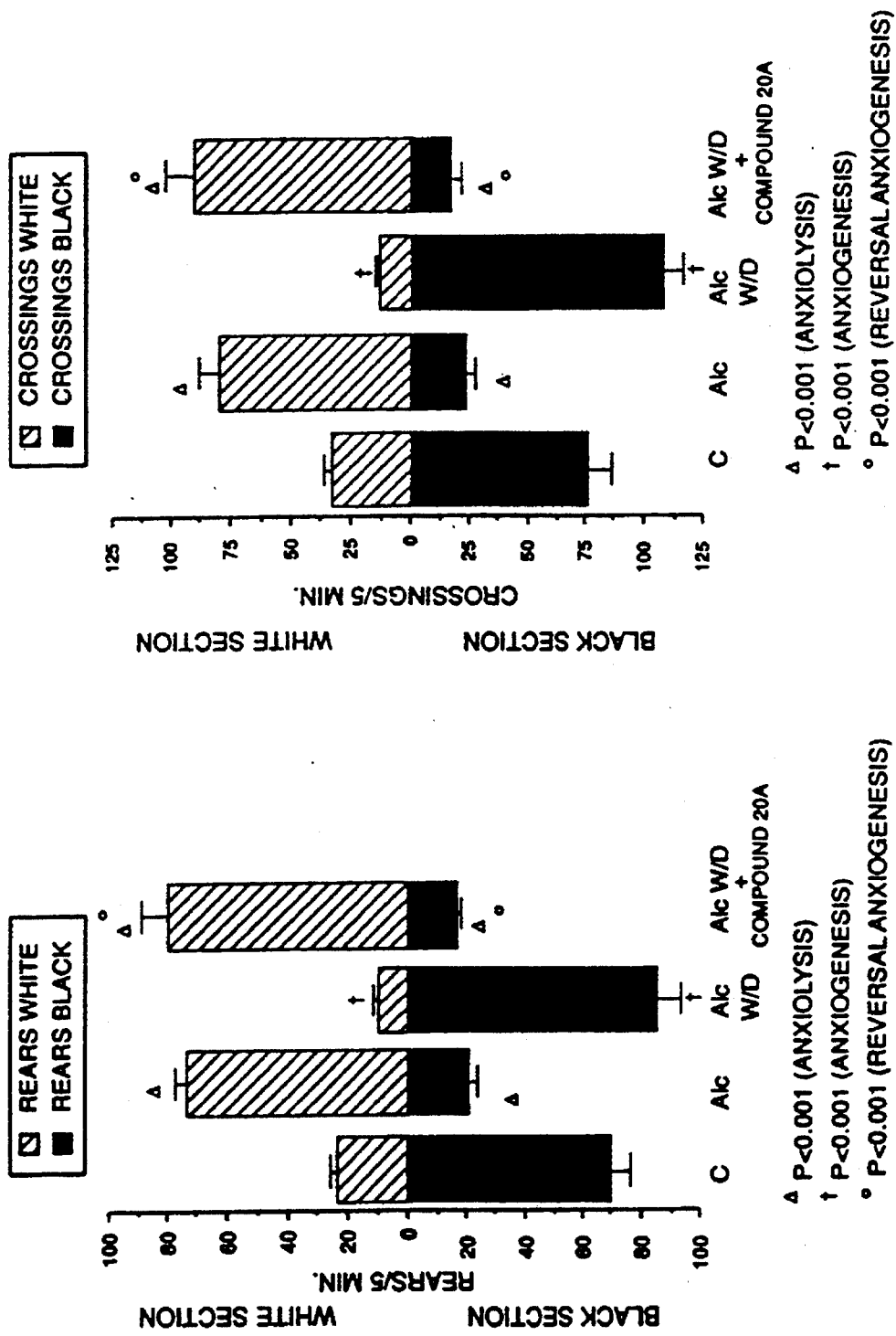
FIG. 10 shows the effect of long-term treatment and withdrawal from alcohol; intervention with compound 20A.
Figure 10D:
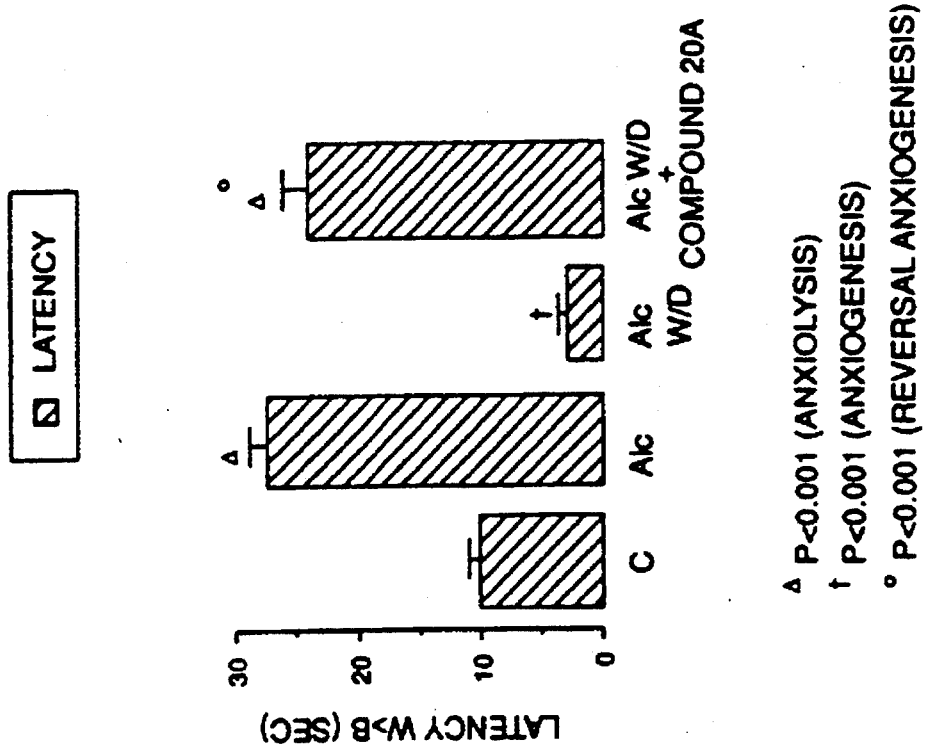
Figure 10C:
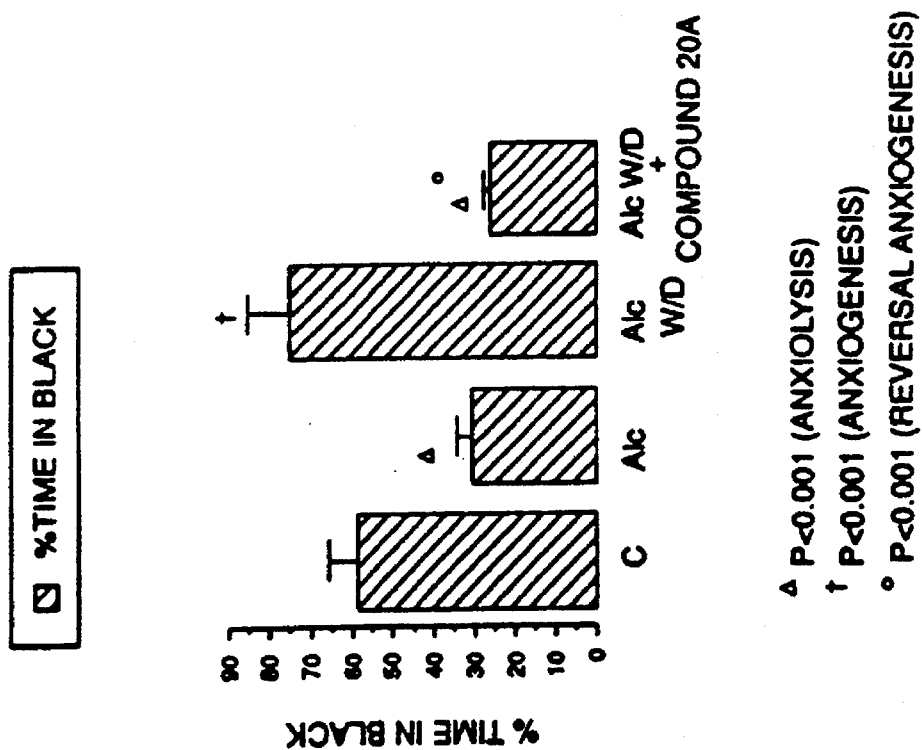

FIG. 10 shows the effect of compound (20A) on long-term treatment and withdrawal from alcohol. Five mice were given alcohol in drinking water, 8% w/v for 14 days. After a withdrawal period of 24 hours, compound (20A) was given at 10 mg/kg i.p.b.d. The increased time spent in the light section shows the effect of compound (20A) on the mice.

Figure 11D:
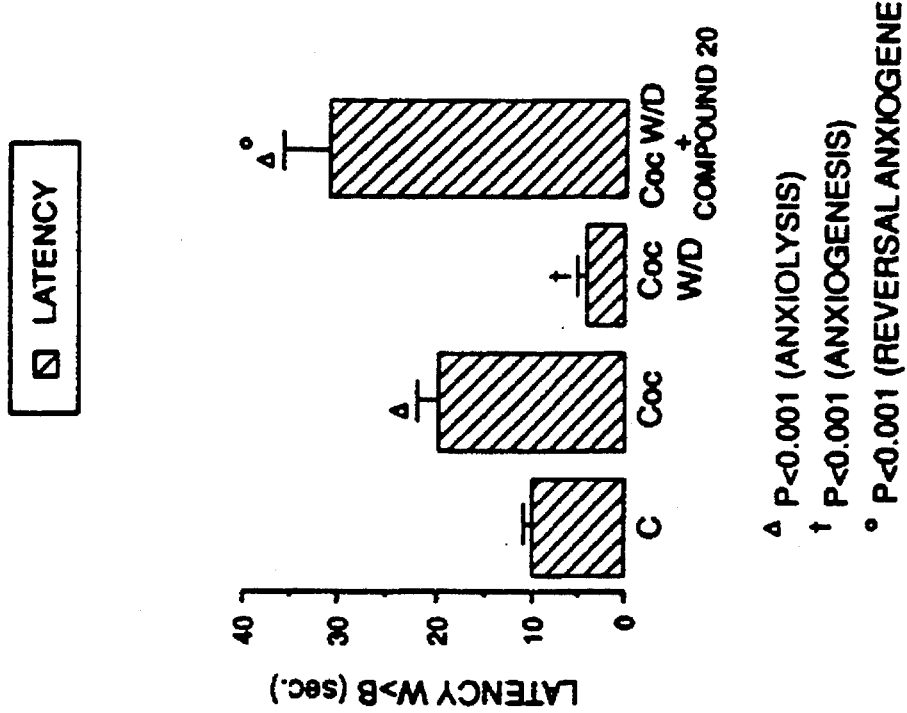
FIG. 11 shows the effect of long-term treatment and withdrawal from cocaine; intervention with compound 20.
Figure 11C:
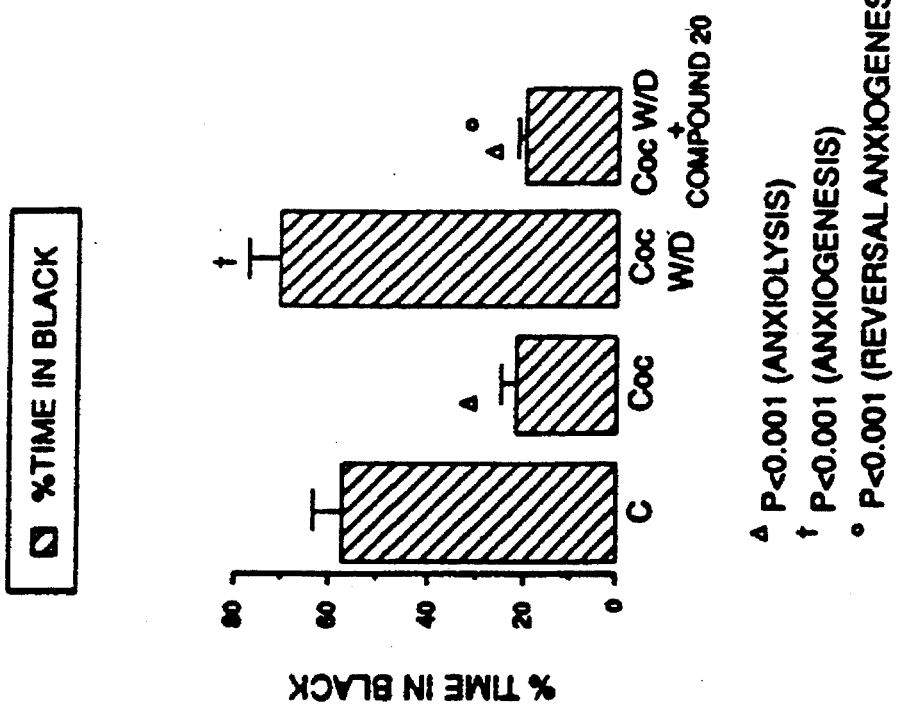

FIG. 11 illustrates the effectiveness in the long-term treatment and withdrawal from cocaine. Five mice were given cocaine as 1.0 mg/kg i.p.b.d. for 14 days. The increased time in the light section illustrates the effectiveness of compound (20) in the treatment.

Figure 12D:
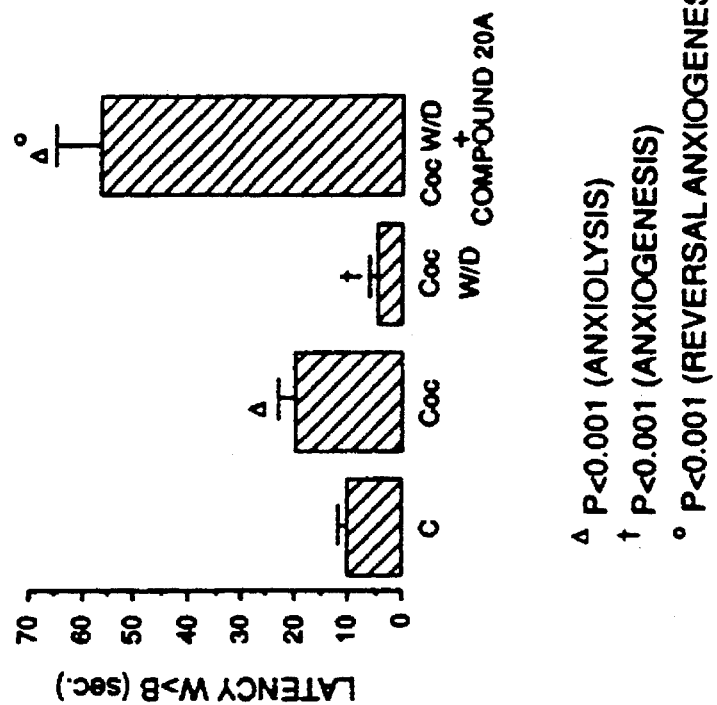
FIG. 12 shows the effect of long-term treatment and withdrawal from cocaine; intervention with compound 20A.
Figure 12C:
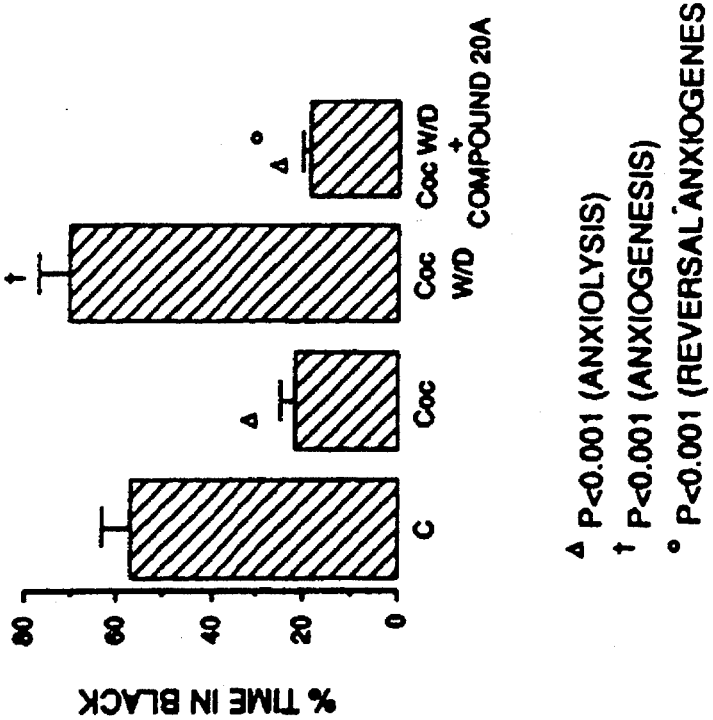

FIG. 12 shows the effect of long-term treatment and withdrawal from cocaine with the intervention of compound (20A). Five mice were given cocaine at 1.0 mg/kg i.p.b.d. for 14 days after a withdrawal period of 24 hours, compound (20a) was given at 1.0 mg/kg i.p.b.d. The effect of intervention with compound 20A is shown by the increase in time spent in the light section.

Figure 13:
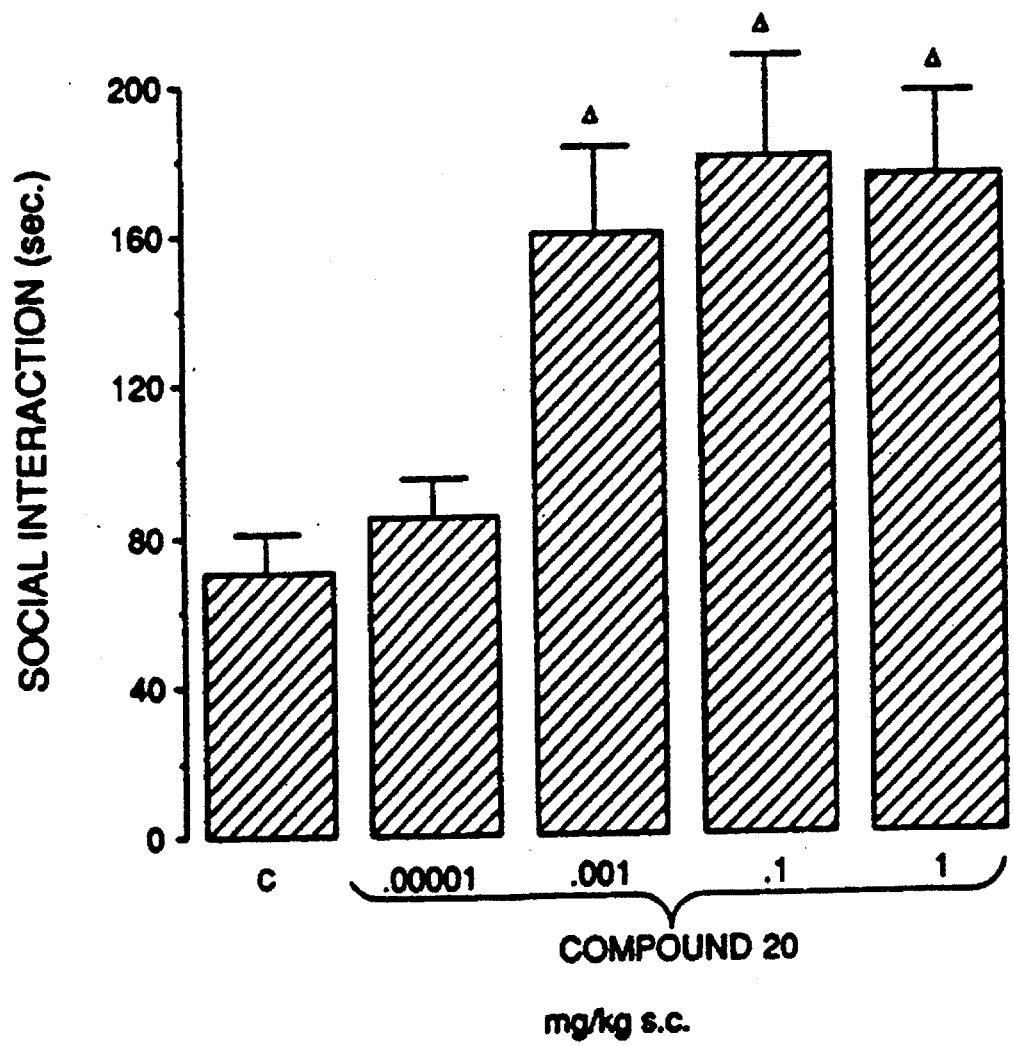
FIG. 13 shows the effect of compound 20 in the Rat Social Interaction Test for antianxiety agents.

FIG. 13 shows the anxiolytic effects of compound 20 in the Rat Social Interaction Test on a dose range of 0,001 to 1.0 mg/kg when paired rats are dosed s.c. The anxiolytic effect of compound 20 are indicated by the increase in time spent in social interaction compared with the control value C. (Costall, B., University of Bradford)

Figure 14:
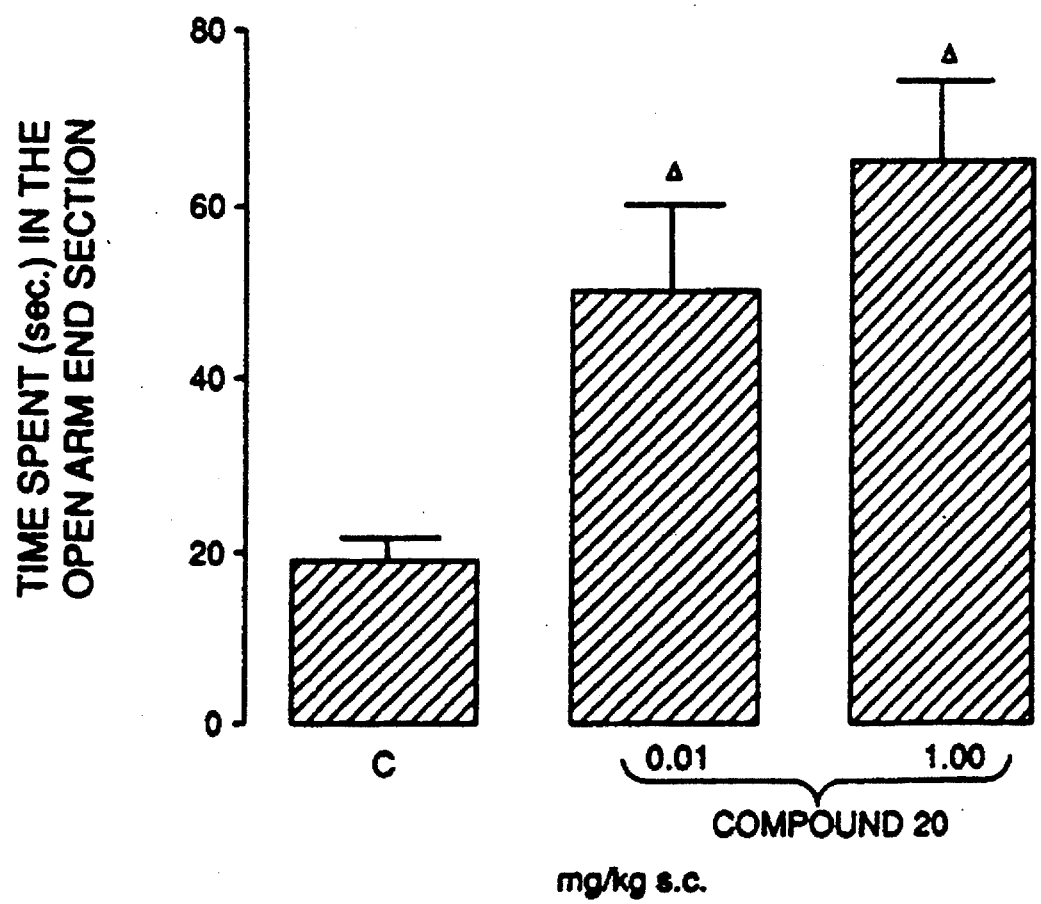
FIG. 14 shows the effect of compound 20 in the Rat Elevated X-Maze (+Maze) Test for antianxiety agents.

FIG. 14 shows the anxiolytic effects of compound 20 in the Rat Elevated X-Maze Test on a dose range of 0.01 to 1.0 mg/kg s.c. The anxiolytic effect is indicated by the time spent in the open arm end section compared with control C.

Figure 15:
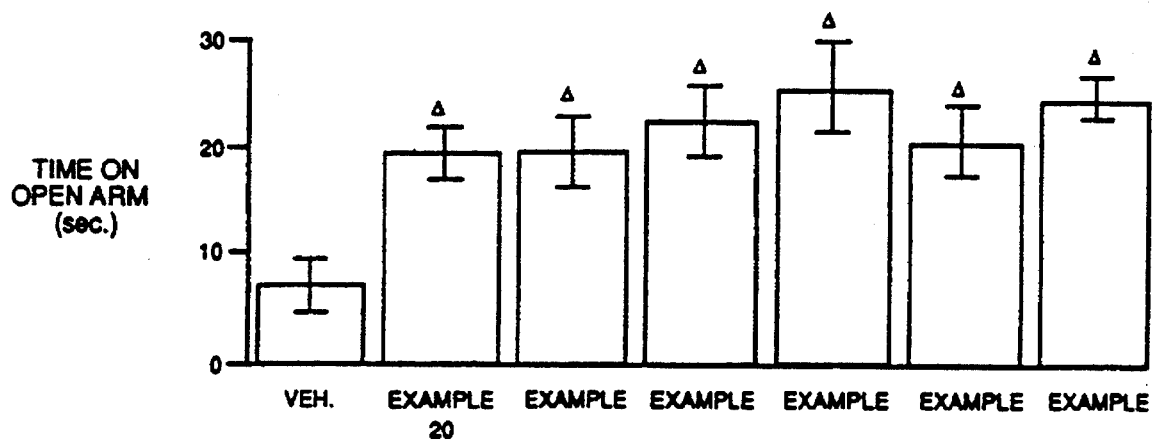
FIG. 15 shows the effects of five compounds of the instant invention as compared to the vehicle and to compound 20 in the Rat Elevated X-Maze Test for antianxiety agents.

FIG. 15 shows the anxiolytic effects of five compounds of the invention as compared to the vehicle alone and to compound 20 in the Rat Elevated X-Maze Test. The dose was equivalent to 0.1 mg/kg p.o. compound 20.

Figure 16A:
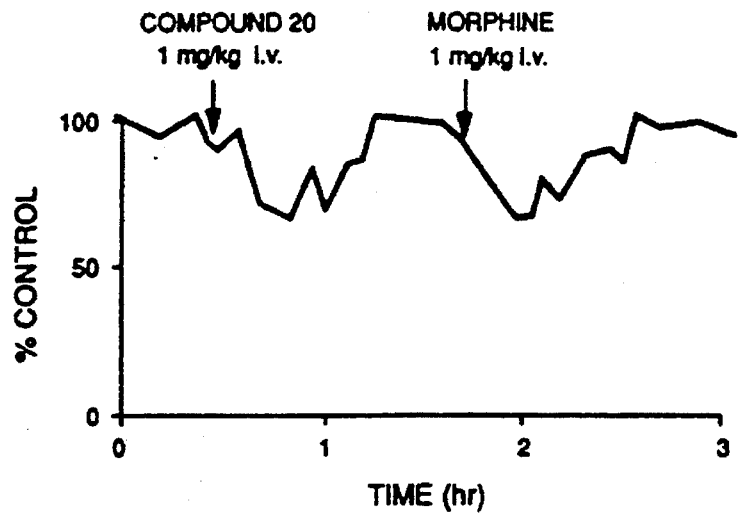
FIG. 16 shows that compound 20 depresses the flexor response in a stimulated spinalized decerebrated ran preparation similar to morphine. The effect (lower diagram) of giving compound 20 with morphine greatly potentiates the effect which lasts for 3 hours.
Figure 16B:
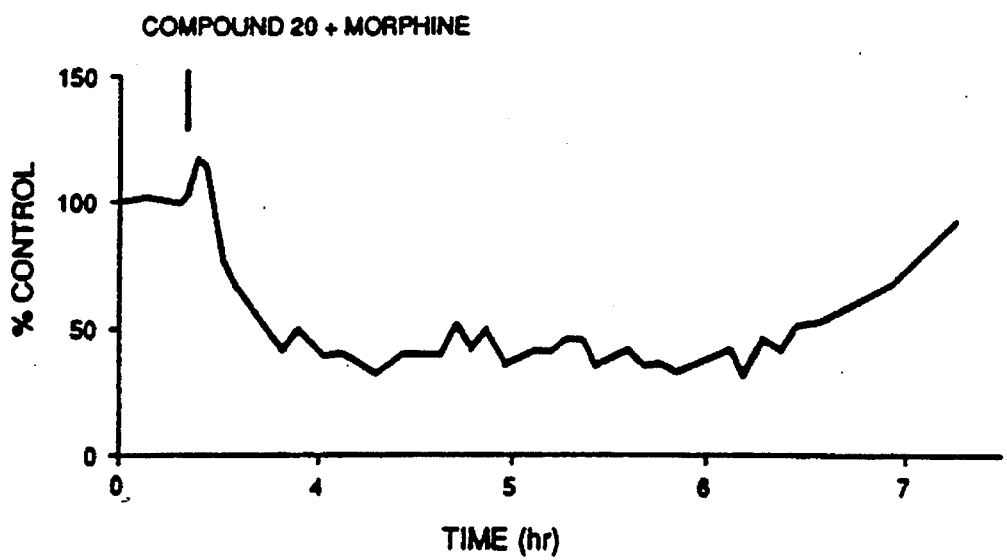

FIG. 16 shows that compound 20 depresses the flexor response in a stimulated spinalized decerebrated rat preparation similar to morphine. The effect (lower diagram) of giving compound 20 with morphine greatly potentiates the effect which lasts for 3 hours.

Figure 17:
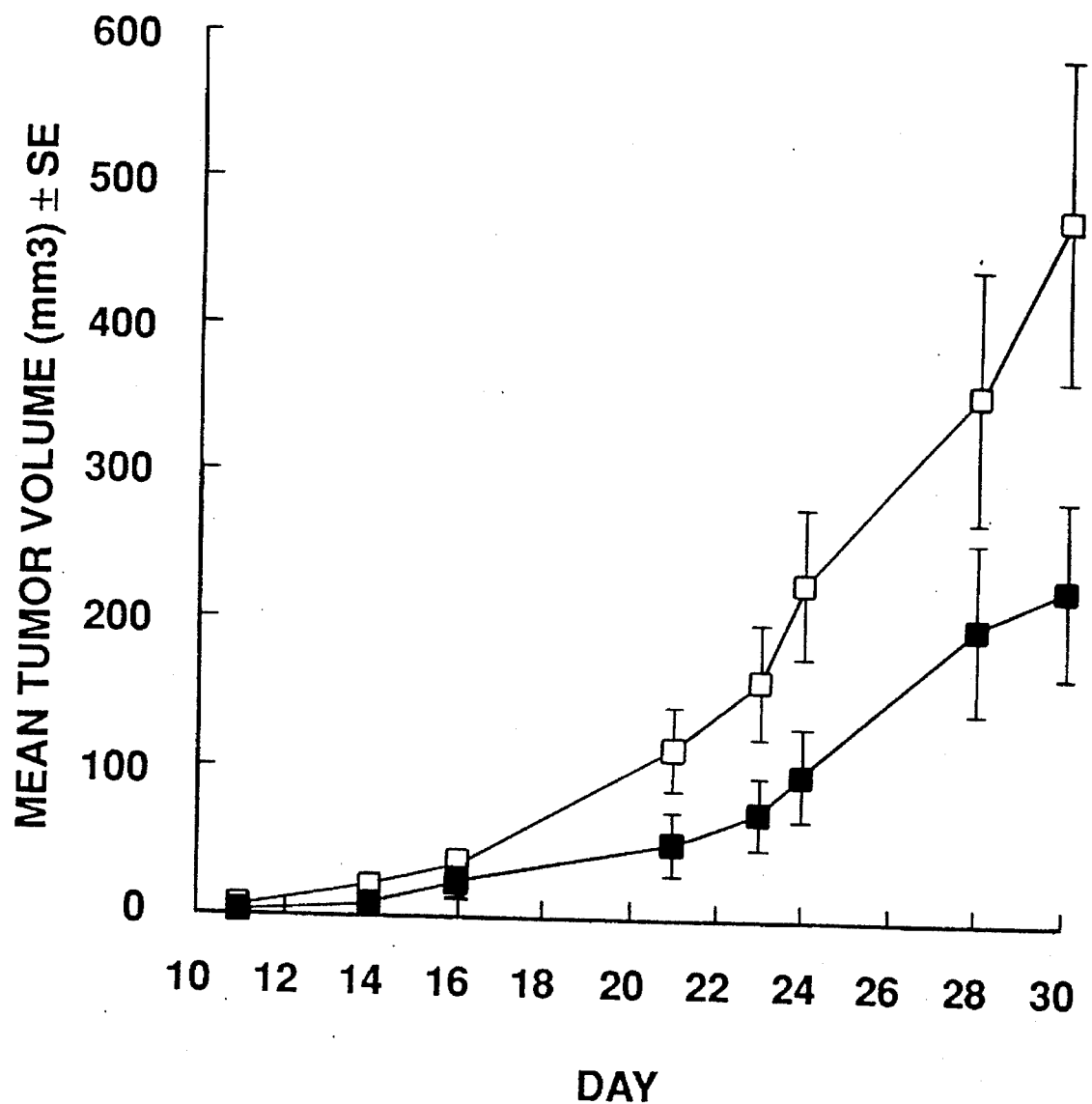
FIG. 17 shows that compound 20 significantly inhibited tumor growth overall.

FIG. 17 shows that compound 20 given (in saline) at 10 mg/kg/day effects the mean tumor volume as compared to the control □ (saline). The control number was 13 and the compound 14.

Mean tumor volume (mm$^3$) ±standard error (SE) of LoVo (xenograft) in vivo with 10 mg/kg/day compound 20 or saline administered orally. Compound 20 significantly inhibited tumor growth overall (p <0.05, ANOVA).

There is evidence that gastrin is capable of stimulating gastric and colorectal cancer cell growth (Morris DL, Watson SA, Durrant LG, Harrison JD. Hormonal control of gastric and colorectal cancer in man. *Gut*, 30:425–429 (1989)). Exogenous gastrin stimulates human colorectal cancer cell lines both in vitro and in vivo (Watson S, Durrant L, Elston P, Morris D. Inhibitory effects of the gastrin receptor antagonist (L-365,260) on gastrointestinal tumour cells. *Cancer*, 68:1255–1260 (1991) and Watson SA, Durrant LG, Chadderton R, Morris DL. The effect of a gastrin receptor antagonist on the growth of gastrin responsive primary human colorectal tumours. *Br. J. Surg*, 76:639 (1989)).

Compound 20 is a highly selective and a potent CCK B receptor antagonist in the central nervous system. FIG. 17 shows compound 20 capable of inhibiting the in vitro and in vivo proliferation of a human colorectal cell line, LoVo.

LoVo was obtained from the American Tissue Type Collection (ATCC CCL 229). Five×10$^3$ to 1×10$^4$ LoVo cells were cultured in 200 μL of serum containing RPMI in 96-well flat-bottomed titre plates for 24 hours. The media was removed and replaced with 250 μL of serum-free RPMI containing compound 20 ($1\times10^{-11}$ to $1\times10^{-7}$ M) and cultured for 24, 48, and 72 hours. Cell proliferation was measured indirectly using a tetrazolium salt colorimetric assay for cellular respiration (Merlin JL, Azzi S, Lignon D, Ramacci C, Zeghari N, Guillemin F. MTT assays allow quick and reliable measurement of the response of human tumor cell to photodynamic therapy. *Eur. J. Cancer*, 28(8/9):1452–1458 (1992)).

One×10$^6$ LoVo cells in 0.1 mL serum-free RPMI were injected subcutaneously into the backs of 27 male nude mice. Xenografts were grown for 10 days prior to treatment, then randomly allocated to receive twice daily gavage with either 0.1 mL saline alone or containing 10 mg/kg/day of compound 20 for 20 days. Bidirectional tumor diameter was measured using vernier calipers and converted to volumes [(½×length)+diameter$^2$]. The animals were sacrificed on Day 30. The protocol was approved by the UNSW Ethics committee.

Significant differences occurred at 24, 48, and 72 hours in vitro between untreated controls and compound 20-treated cells (15 wells per concentration) (p <0.001). At 24, 48, and 72 hours, respectively, the cellular proliferation expressed as a percentage of control in the presence of compound 20 was as follows: 66.47±6.72, 80.47±2.64, 78.87±3.25% (compound 20 $10^{-11}$ M) ; 58.93±7.30, 82.60±2.33, 80.53±3.06% (compound 20 $10^{-1}$ M) ; 62.47±7.20, 82.73±2.97, 79.07±3.18% (compound 20 $10^{-9}$ M); 70.13±7.15, 93.20±4.04, 85.93±4.19% (compound 20 $10^{-8}$ M); and 81.60±6.62, 95.33±2.50, 84.71±6.97% (compound 20 $10^{-7}$ M). Significant inhibition at individual concentrations occurred at $10^{-11}$ to $10^{-8}$ M after 24 and 72 hours and at $10^{-11}$ to $10^{-9}$ M at 48 hours (ANOVA). The maximum inhibition occurred at 24 hours, however, the in vitro cultures were not refed with compound 20.

In the in vivo study (FIG. 17) there was a significant divergence of tumor size between control and treated animals from Day 21 of treatment which was maintained over the 20-day experiment (p <0.05, ANOVA). The tumor volume at Day 30 was reduced by 53% by compound 20 compared to control. Unstimulated, in vitro growth of LoVo and the 53% inhibition of in vivo growth over 20 days is shown.

Therefore, compound 20 is capable of markedly inhibiting the basal growth of LoVo at concentrations which should be achieved in vivo by oral therapy and may be of use in the treatment of some human colorectal cancers.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

Examples A–I are illustrative of methods of preparing the precursors or intermediates of the final products which are illustrated in Examples 1–45 (corresponding to compounds 1–45 described in the figures and experimental) but not as numbers corresponding to the numbers given in the schemes.

Intermediate Example A

N-[(1-Adamantyloxy)carbonyl]-α-methyl-DL-tryptophan

To a solution of α-methyl-DL-tryptophan (2.18 g, 10 mmol) in 1M NaOH solution (10 mL) at 0° C. was added NaHCO$_3$ (0.92 g, 11 mmol) followed by a solution of 1-adamantylfluoroformate (2.18 g, 11 mmol) in 1,4 dioxan (10 mL). The mixture was stirred at 0° C. for one hour and then 24 hours at room temperature.

The dioxan was removed in vacuo and the aqueous phase extracted with three portions of ether (30 mL). The aqueous phase was cooled in ice and covered with ethyl acetate (30 mL) before acidifying to pH 2–3 with sodium hydrogen sulphate solution. Following a further two organic or ethyl acetate extractions, the organic layers were combined, washed with water (30 mL), and dried over MgSO$_4$. Ethyl acetate was removed in vacuo to give 1-adamantyloxycarbonyl-α-methyl-DL-tryptophan (1.154 g, 29%) as a white solid, recrystallized from ethyl acetate, mp 206°–218° C. (EtOAc); IR (film) 1681 cm$^{-1}$; NMR (CD$_3$OD) δ1.43 (3H, s), 1.68 (6H, br.s), 2.13 (9H, br.s), 3.35 (2H, ABq J 14Hz), 6.95–7.56 (5H, m).

Intermediate Example B

2-Adamantylchloroformate

To a stirred solution of 2-adamantanol (0.912 g, 6 mmol) in dry CH$_2$Cl$_2$ (15 mL) was added bis(trichloromethyl)carbonate (0.653 g), pyridine in dry CH$_2$Cl$_2$ (10 mL) at 0° C. The reaction mixture was warmed to room temperature and stirred for two hours. The solvent was removed in vacuo at 30° C., taken up in ethyl acetate (30 mL) and stirred for 10 minutes. The pyridinium hydrochloride precipitate was filtered off and the solvent removed in vacuo at 30° C., to give an oil which solidified upon standing (1.29 g, 100%). IR (film) 1778 cm$^{-1}$; NMR (CDCl$_3$) δ1.55–1.65 (2H, m), 1.70–1.80 (4H, m), 1.85–1.95 (4H, m), 2.00–2.10 (2H, m), 2.15–2.20 (2H, m), 5.02 (1H, 6, J 3.3 Hz CHOCOCl).

Intermediate Example C

N-[(2-Adamantyloxy)carbonyl]-α-methyl-D-tryptophan methyl ester

To a stirred solution of 2-adamantylchloroformate (0.965 g, 4.5 mmol) in dry THF (10 mL) was added a solution of α-methyl-D-tryptophan methyl ester (0.928 g, 4 mmol) in dry THF (20 mL) followed by a solution of triethylamine (0.808 g, 8 mmol) in dry THF (20 mL) dropwise. After 15 minutes, the reaction mixture was filtered, the solvent removed in vacuo and column chromatographed using 2% MeOH:98% CH$_2$Cl$_2$ as eluant to yield the title compound (1.42 g, 89%) as a syrup. IR (film) 1740–1695 b.r cm$^{-1}$; NMR (CDCl$_3$) δ1.50–1.60 (2H, m), 1.67 (3H, s), 1.70–2.10 (12H, m), 3.38 (1H, d, J=14.5Hz), 3.50–3.60 (1H, br.s), 3.68 (3H, s), 4.86 (1H, br.s), 5.28 (1H, br.s), 6.93 (1H, d, J 2.4Hz); 7.04–7.10 (2H, m), 7.33 (1H, d, J 8.2Hz) 7.54 (1H, d, J 7.8Hz), 8.18 (1H, br.s).

Intermediate Example D

N-[(2-Adamantyloxy)-carbonyl]-α-methyl-D-tryptophan

To a stirred solution of N-[(2-adamantyloxy)carbonyl]-α-methyl-D-tryptophan methyl ester (1.36 g, 3.3 mmol) in aqueous 1,4-dioxan (1:2) (20 mL) was added an excess of LiOH (0.210 g, 5 mmol) and stirred at room temperature overnight. After removing the solvent in vacuo the residue was chromatographed using 5% MeOH:95% CH$_2$Cl$_2$ then 10% MeOH:90% CH$_2$Cl$_2$ as eluants to yield the acid (0.953 mg, 90%) as a white solid, crystallized from n-hexane, mp 210°–215° C. (EtOAc/n-hexane); IR (film) 1689 cm$^{-1}$; NMR (CDCl$_3$-D$_2$O), δ1.3–2.2 (14H, m), 1.70 (3H, s), 3.26 (1H, d, J 13.5 Hz), 3.63 (1H, d, 13.5 Hz); 4.77 (1H, br.s), 6.85–7.60 (5H, m).

Intermediate Example E (±)-9H-Fluoren-9-ylmethyl [1-(1H-indol-3-ylmethyl)-1-methyl-2-oxo-2-[(2-phenylethyl)amino] ethyl]carbamate To a solution of N-[(9H-fluoren-9-ylmethyloxy)carbonyl]-α-methyl-DL-tryptophan (8.80 g, 20 mmol) in dry ethyl acetate (350 mL) was added pentafluorophenol (3.68 g, 20 mmol) and stirred for 10 minutes. The reaction mixture was cooled to 0° C. and a solution of dicyclohexylcarbodiimide (20 mmol) in ethyl acetate (25 mL) was added dropwise. This solution was stirred for one hour at 0° C. then at room temperature for four hours before leaving it at 4° C. overnight. The mixture was filtered and the precipitate washed with cold ethyl acetate (30 mL) and a solution of 2-phenethylamine (2.66 g, 22 mmol) in ethyl acetate (30 mL) was added dropwise to the combined filtrates. The mixture was left to stir for 48 hours at room temperature. The reaction mixture was filtered and the residue washed with cold ethyl acetate (2×30 mL) to give the title compound (3.73 g, 75%). The filtrates were combined and the solvent removed in vacuo and taken up again in ethyl acetate (5 mL) to give a second crop of 1.67 g (15%), a total of 90% yield as a white solid, mp 179°–181° C. (EtOAc); IR (film) 1708, 1652 $cm^{-1}$; NMR (DMSO $d_6$) $\delta 1.30$ (3H, s), 2.64 (2H, t, J 7.2Hz), 3.2–3.3 (4H, m), 4.19 (1H, t, J 6.7Hz), 4.25–4.40 (2H, m), 6.9–7.9 (20 H, m), 10.8 (1H, s).

Intermediate Example F (±)-α-amino-α-methyl-N-(2-phenylethyl)-1H-indole-3-propanamide (±)-9H-Fluoren-9-ylmethyl [1-(1H-indol-3-ylmethyl)-1-methyl-2-oxo-2-[(2-phenylethyl)amino]ethyl]carbamate (10 g, 18.4 mmol) was dissolved in a 20% piperidine in DMF solution (50 mL) and stirred for 12 hours at room temperature. The solvent was removed in vacuo and chromatographed over silica gel using $CH_2Cl_2$ then 5% MeOH:95% $CH_2Cl_2$ as eluants. The title compound was crystallized from ethyl acetate (4.73 g, 80%), mp 106°–110° C. (EtOAc); IR (film) 1646 $cm^{-1}$; NMR ($CDCl_3$) $\delta 1.39$ (3H, s), 2.56–2.74 (2H, m), 2.82 (1H, d, J 14Hz), 3.28–3.40 (1H, m), 3.48 (1H, d, J 14Hz), 3.44–3.53 (1H, m), 7.1–7.7 (11H, m), 8.3 (1H, s); Anal. ($C_{20}H_{23}N_3O$) C, H, N.

Intermediate Example G

9H-Fluoren-9-ylmethyl-[2-[[1-(hydroxymethyl)-2-phenyl]ethyl]amino]-1-(1H-indol-3-ylmethyl)-1-methyl-2-oxo-ethyl]carbamate, mixture of [S-(R*, R*)] and [R-(R*, S*)] isomers A solution of N-[(9H-fluoren-9-ylmethoxy)carbonyl]-α-methyl-DL-tryptophan (10 g, 22.7 mmol) and pentafluorophenol (4.18 g, 22.7 mmol) in dry ethyl acetate (200 mL) was treated dropwise at 0° C. with a solution of dicyclohexylcarbodiimide (4.9 g, 24 mmol) in ethyl acetate (20 mL). This was allowed to warm to room temperature and stirred for a further hour. This mixture was then treated with a solution of L-phenylalaninol (3.775 g, 25 mmol) in ethyl acetate (15 mL) dropwise and the resultant mixture left stirring for 15 hours. This mixture was filtered and the filtrate washed sequentially with 2M citric acid solution, 1M NaOH solution, saturated $NaHCO_3$ solution then water before being dried over $MgSO_4$ and concentrated to an oil in vacuo. This oil was subjected to silica gel chromatography using 4% MeOH:96% $CH_2Cl_2$ as eluant to give the title compound (11.7 g, 90%), as a white solid and a mixture of two diastereoisomers. These two diastereoisomeric forms were separated by further chromatographic purification using 1% i PrOH, 99% $CHCl_3$ as the eluant to give equal amounts of the pure diastereoisomers as white amorphous solids.

Isomer I

[R-(R*,S*)]-9H-Fluoren-9-ylmethyl [2-[[1-(hydroxymethyl)-2-phenylethyl]amino]-1-(1H-indol-3-ylmethyl)-1-methyl-2-oxoethyl]carbamate mp 89°–93° C. ($CHCl_3$); IR (KBr) 1696, 1651 $cm^{-1}$; NMR ($CDCl_3$) $\delta 1.35$ (3H, s) 2.74 (2H, m), 3.30 (2H, Abq, J, 14.5 Hz), 3.45 (1H, dd, J 11 and 6Hz), 3.70 (1H, m), 4.14 (2H, m), 4.46 (2H, dq, J 10.5 and 6Hz), 5.09 (1H, s), 6.10 (1H, d, J 8Hz), 6.65 (1H, d, J 2Hz), 7.07–7.80 (17H, m) 7.98 (1H, s); Anal. ($C_{36}H_{35}N_3O_4$), C, H, N.

Isomer II

[S-(R* ,R*)]-9H-Fluoren-9-ylmethyl [2-[[1-(hydroxymethyl)-2-phenylethyl]amino]-1-(1H-indol-3-ylmethyl)-1-methyl-2-oxoethyl]carbamate mp 89°–93° C. ($CHCl_3$); IR (KBr) 1703 and 1646 $cm^{-1}$; NMR ($CDCl_3$) $\delta 1.50$ (3H, s), 2.70 (2H, dq, J 14 and 8Hz), 3.20 (2H, Abq J 14.5Hz) 3.41 (1H, dd, J 11.5 and 5Hz), 3.60 (1H, dd, J 11.5 and 3.5Hz), 4.12 (2H, m), 4.35 (2H, m), 5.37 (1H, s) 6.06 (1H, d, J 8Hz), 6.75 (1H, d, J 2Hz), 7.08–7.77 (17H, m), 8.07 (1H, s); Anal. ($C_{36}H_{35}N_3O_4.0.25H_2O$) C, H, N.

INTERMEDIATE EXAMPLE H (R)-Tricyclo[3.3.1$^{3,7}$]dec-2-yl [2-[[2-hydroxy-2-phenylethyl]amino]-1-(1H-indol-3-ylmethyl)-1-methyl-2-oxoethyl]carbamate A solution of 2-adamantyloxycarbonyl-α-methyl-D-tryptophan (0.060 g, 0.15 mmol) in ethyl acetate (7 mL) was treated with dicyclohexylcarbodiimide (0.034 g, 0.165 mmol) and 1-hydroxybenzotriazole (0.022 g, 0.163 mmol). After stirring for two hours at room temperature, 2-amino-1-phenyl ethanol (0.021 g, 0.153 mmol) in ethyl acetate (2 mL) was added and the reaction mixture stirred for a further two hours. The suspension was then filtered and the filtrate concentrated in vacuo to leave a colorless gum (0.175 g). The crude product was chromatographed over alumina using 80% EtOAc:20% n-hexane as eluant, to give the title compound as a slightly impure white solid (0.058 g, 74%); IR (film) 3338, 2927, 2855, 1690 and 1622 $cm^{-1}$; NMR (inter alia) ($CDCl_3$) $\delta 1.50$–2.05 (17H, m), 3.15–3.55 (4H, m), 3.75 (1H, m), 4.85 (1H, m), 5.10 and 5.20 (each 0.5H, s), 6.55 (1H, m), 7.00–7.40 (9H, m), 7.60 (1H, d, J 9Hz) 8.15 (1H, 2s).

INTERMEDIATE EXAMPLE I (4-Nitrophenyl)methyl[1R-(1α, 2α, 3β)]-2-[(chlorocarbonyl)-oxy]-1,7,7-trimethylbicyclo[2.2.1]heptane-3-acetate Method as for Intermediate Example B except using [IR-(2-endo, 3-exo]-3-hydroxy-4,7,7-trimethyl bicyclo [2.2.1]heptane-2-acetic acid, para nitro benzyl ester; IR (film) 1773 and 1741 $cm^{-1}$; NMR ($CDCl_3$) $\delta 0.88$ (3H, s), 0.89 (3H, s), 1.05 (3H, s), 1.06–1.15 (1H, m), 1.25–1.40 (1H, m), 1.50–1.80 (3H, m), 2.45 (1H, dd, J 7 and 15Hz), 2.55–2.85 (2H, m), 4.41 (1H, d, J 4Hz), 5.20 (2H, s), 7.50 (2H, d, 8Hz), 8.22 (2H, d, J 8Hz ).

EXAMPLE 1

(±)-Tricyclo[3.3.1$^{3,7}$]dec-1-yl [1-(1H-indol-3-ylmethyl)-1-methyl-2-oxo-2-[(2-phenylethyl)amino] ethyl]carbamate To a solution of N-[(tricyclo[3.3.1.1$^{3,7}$]dec-1-yloxy) carbonyl]-α-methyl-DL-tryptophan (1.0 g, 2.5 mmol) in 1,4 dioxan (40 mL) was added a solution of pentafluorophenol (0.465 g, 2.5 mmol) in 1,4 dioxan (5 mL) and stirred at room temperature for 15 minutes, cooled to 0° C. and a solution of dicyclohexylcarbodiimide (0.547 g, 2.65 mmol) in 1,4 dioxan (10 mL) was added dropwise. This was allowed to stir at room temperature for two hours before phenethylamine (0.333 g, 2.75 mmol) was added in one portion. The mixture was left stirring for 24 hours.

The reaction mixture was filtered before removing the solvent in vacuo, and the residue taken up in ethyl acetate (30 mL) and washed with 1M citric acid solution (2×10 mL), saturated NaHCO$_3$ solution (3'10 mL), 1M NaOH solution (2×10 mL), brine (2×10 mL), and water (2×20 mL). The organic phase was dried over MgSO$_4$ and the solvent evaporated in vacuo to yield a white solid (0.617 g, 49%), mp 84°–86° C. (EtOAc); IR (film) 1700, 1660 cm$^{-1}$; NMR (CDCl$_3$), δ1.50 (3H, s), 1.63 (6H, br.s), 2.00–2.05 (6H, m), 2.14 (3H, br.s), 2.66 (1H, t, J 7.2Hz), 2.67 (1H, t, J 6.9Hz), 3.19 (1H, d, J 14.5Hz), 3.4–3.50 (3H, m), 4.93 (1H, br.s), 6.30 (1H, br.s), 6.98–7.60 (10H, m), 8.24 (1H, br.s).

EXAMPLE 2

(±)-Trans-2-chlorocyclohexyl [1-(1H-indol-3-ylmethyl)-1-methyl-2-oxo-2-[(2-phenylethyl)amino] ethyl]carbamate To a stirred solution of trans(−)-2-chlorocyclohexyl chloroformate (0.16 g, 0.75 mmol) in anhydrous THF (5 mL) at room temperature was added dropwise a solution of α-methyl-DL-tryptophylphenethylamide (0.23 g, 0.7 mmol) in THF (5 mL), followed by a solution of triethylamine (0.07 g, 0.7 mmol) in THF (5 mL). The reaction was complete after 30 minutes by thin layer chromatographic analysis. The solvent was removed in vacuo and the residue taken up in ethyl acetate (30 mL) and washed successively with 1M aqueous citric acid (2×20 mL), saturated NaHCO$_3$ solution (2×20 mL), 1M NaOH solution (20 mL) and water (4×20 mL). The organic phase was dried over MgSO$_4$ and filtered. Removal of the solvent by vacuum distillation gave the title compound (0.273 g, 81%), a white solid crystallized from ether-hexane, mp 69°–78° C. (ether-hexane); IR (film) 1709 and 1656 cm$^{-1}$; NMR (CDCl$_3$) δ1.2–1.4 (3H, m), 1.54 (3H, s), 1.6–1.8 (3H, m), 2.03–2.23 (2H, m), 2.63–2.69 (2H, m), 3.2–3.5 (4H, m), 3.72–3.79 (1H, m), 4.67–4.73 (1H, m), 5.23 (1H, br.s), 6.1–6.2 (1H, m), 7.0–7.6 (10H, m), 8.08 (1H, br.s); Anal. (C$_{27}$H$_{32}$N$_3$O$_3$Cl), C, H, Cl, N.

EXAMPLE 3

(±)-Trans -2-chlorocyclohexyl [2-[[1-(hydroxymethyl)-2-phenyethyl]amino]-1-(1H-indol-3-ylmethyl)-1-methyl-2-oxoethyl]carbamate. (D-tryptophan residue; L-phenylalanine residue).

To a stirred solution of (±)-trans-2-chlorocyclohexyl chloroformate (1.94 g, 9.1 mmol) in anhydrous THF (10 mL) at room temperature was added dropwise a solution of α-methyl-D-tryptophan-L-phenylalaninol (2.9 g, 8.3 mmol) in THF (20 mL), followed by a solution of triethylamine (9.92 g, 9.1 mmol) in THF (10 mL). The reaction was complete after 30 minutes as assayed by thin layer chromatography. The reaction mixture was filtered and the solvent removed in vacuo. The residue was purified by chromatography over silica using CH$_2$Cl$_2$ then 4% MeOH:93% CH$_2$Cl$_2$ as eluants. Recrystallization from ethyl acetate gave the product (3.1 g, 73%) as white needles, mp 117°–127° C. (EtOAc); IR (film) 1699 and 1600 cm$^{-1}$; NMR (CDCl$_3$) δ1.20–1.45 (3H, m), 1.32 (3H, s), 1.40 (3H, s), 1.70–1.80 (3H, m), 2.09–2.25 (2H, m), 2.67–2.83 (2H, m); 3.28–3.52 (3H, m); 3.68–3.83 (2H, m), 4.10–4.30 (1H, m), 4.68–4.80 (1H, m), 5.97 (1H, s), 6.08 (1H, s), 6.09 1H, d, J 7.9 Hz), 6.19 (1H, d, J 7.6 Hz), 6.91–7.60 (10H, m), 8.08 (1H, m); Anal. (C$_{28}$H$_{34}$N$_3$O$_4$Cl.0.25 H$_2$O), C, H, N, Cl.

EXAMPLE 4

2-[[2-[[[2- chlorocyclohexyl)oxy]-carbonyl]amino]-3-(1H-indol-3-yl)-2-methyl-1-oxo-propyl]amino]-3-phenylpropyl butanedioate A solution of 2-chlorocyclohexyl [2-[[1-(hydroxymethyl)-2-phenylethyl]amino]1-(1H-indol-3-ylmethyl)-1-methyl-2-oxoethyl]carbamate (1.3 g, 2.54 mmol), succinic anhydride (0.254 g, 2.54 mmol) and 4-N,N-dimethylaminopyridine (0.62 g, 5.08 mmol) in dry ethyl acetate (50 mL) was refluxed for 18 hours. The reaction mixture was then washed with 1M citric acid solution, then water and dried over MgSO$_4$. Concentration in vacuo yielded an oil which was subjected to silica gel chromatography using 10% MeOH:90% CH$_2$Cl$_2$ as eluant to give the title compound (0.86 g, 55%) as an amorphous solid, mp 75° C. (EtOAc/hexane); IR (film) 3370, 1723 and 1659 cm$^{-1}$; NMR (CDCl$_3$) δ1.30 (3H, m), 1.45 (1.5H, s), 1.58 (1.5H, s), 1.66 (3H, m) 2.16 (2H, m), 2.60 (5H, m), 2.79 (1H, dd J 11 and 6 Hz), 3.28 (2H, Abq J$_{AB}$ 14.5 Hz); 3.85 (3H, m), 4.45 (1H, m), 4.70 (1H, m), 5.45 (1H, br.s), 6.5 (1H, m), 6.90–7.70 (10H, M), 8.37 (0.5H, s) and 8.49 (0.5H, s). Anal. (C$_{32}$H$_{38}$N$_3$O$_7$Cl), C, H, N, Cl.

EXAMPLE 5

[R-(R*,S*)]-N-[1-(hydroxymethyl)-2-phenylethyl]-α-methyl-α-[[tricyclo[3.3.1.1$^{3,7}$]dec-1-ylacetyl)-amino]-1H-indole-3-propanamide A solution of α-methyl-D-tryptophyl-L-phenylalaninol (1 g, 2.85 mmol) and 4-N,N-dimethylaminopyridine (0.35 g, 2.87 mmol) in dry THF (50 mL) at 0° C. was treated dropwise, with stirring, with a solution of 1-adamantylacetyl chloride (0.605 g, 2.85 mmol). A precipitate formed immediately. The reaction mixture was left until all starting materials were consumed as assayed by TLC and IR spectroscopy. The final TLC showed three spots (10% MeOH:90% CH$_2$Cl$_2$). The reaction mixture was washed with 1M citric acid solution and extracted into ethyl acetate. The organic phase was then washed with water and dried over MgSO$_4$. Concentration in vacuo gave a syrup (1.7 g) which was chromatographed over silica using 2% MeOH:98% CH$_2$Cl$_2$ as eluant to yield the title compound (1.35 g, 90%) as a white solid crystallized from ethyl acetate-hexane, mp 91°–94° C. (EtOAc-hexane); IR (KBr) 3304 and 1652 cm$^{-1}$; NMR (CDCl$_3$) δ1.48 (9H, m), 1.59 (6H, m), 1.76 (2H, q, J 13 Hz), 1.9 (3H, m), 2.74 (2H, d, J 7Hz), 3.21 (1H, half ABq J 14.5Hz), 3.30 (1H, 6, J 6Hz), 3.40 (1H, half Abq J 14.5Hz), 3.45 (1H, m), 3.70 (1H, m), 4.16 (1H, m), 5.91 (1H, s), 6.38 (1H, d, J 8Hz), 6.92 (1H, d, J 3Hz), 7.07–7.27 (7 H, m), 7.35 (1H, d, J 8Hz), 7.56 (1H, d, J 8Hz) and 8.54 (1H, s); Anal. (C$_{33}$H$_{41}$N$_3$O$_3$.0.25 H$_2$O), C, H, N.

EXAMPLE 6

(±)-Tricyclo[3.3.1.1$^{3,7}$]dec-2-yl [1-(1H-indol-3-ylmethyl)-1-methyl-2-oxo-2[(2-phenylethyl)amino]ethyl]carbamate Method was as described for Example 2 but using 2-adamantyl chloroformate. The product was obtained as a solid from CCl$_4$-hexane (0.385 g, 77%), mp (noncrystalline)

79°–85° C.; IR (film) 1701 and 1656 cm$^{-1}$; NMR (CDCl$_3$) δ1.5–1.6 (2H, m), 1.54 (3H, s), 1.7–2.0 (12H, m), 2.6 (2H, t, J 7Hz), 3.26 (1H, d, J 14.5Hz), 3.40–3.50 (3H, m), 4.79 (1H, br.s), 5.15 (1H, br.s), 6.20 (1H, t), 6.95–7.11 (10H, m), 8.08 (1H, s); Anal. (C$_{31}$H$_{37}$N$_3$O$_3$), C, H, N.

EXAMPLE 7

(±)-Endo-1,7,7-trimethylbicyclo[2.2.1]hept-2-yl-[1-(1H-indol-3-ylmethyl)-1-methyl-2-oxo-2-[(2-phenylethyl)amino]ethyl]-carbamate Method was as described for Example 2, but using 1-(S)-2-endobornyl chloroformate. The crude residue was chromatographed over silica using CHCl$_3$ as eluant to obtain the product (0.443 g, 88%) as a colorless foam, mp (noncrystalline) 65°–69° C.; IR (film) 3327, 1702 and 1658 cm$^{-1}$; NMR (CDCl$_3$) δ0.81 (3H, s), 0.85 (3H, s), 0.89 (3H, s), 0.96–1.02 (1H, m), 1.11–1.30 (3H, m), 1.54 (1.5H, s), 1.54 (1.5H, s), 1.65–1.82 (2H, m), 2.32 (1H, m), 2.65 (2H, t, J 7Hz), 3.25 (1H, half ABq, J 14.5Hz), 3.39–3.49 (3H, m), 4.84 (1H, m), 5.21 (1H, br.s), 6.14 (1H, br.s), 6.95 (1H, d, J 2Hz), 7.03–7.26 (7H, m), 7.35 (1H, d, J 8Hz), 7.58 (1H, d, J 8Hz) and 8.18 (1H, s).

EXAMPLE 8

(±)-Exo-1,7,7-trimethylbicyclo[2.2.1]hept-2-yl-[1-(1H-indol-3-ylmethyl)-1-methyl-2-oxo-2-[(2-phenylethyl)amino]ethyl]- carbamate Method was as described for Example 2, but using (±)-exo-bornyl chloroformate. The crude residue was chromatographed over silica using CHCl$_3$ as eluant to give the title product as a pale yellow foam (0.294 g, 59%), mp (noncrystalline) 61°–65° C.; IR (film) 1705 and 1658 cm$^{-1}$; NMR (CDCl$_3$) δ0.75–1.30 (13H, m), 1.45–1.82 (6H, m), 2.63 (2H, m), 3.23 (1H, half ABq J 14.5Hz), 3.35–3.52 (3H, m), 4.56 (1H, m), 5.18 (0.5H, s), 5.25 (0.5H, s), 6.16 (1H, m), 6.95 (1H, d, J 2Hz), 6.99–7.25 (7H, m), 7.34 (1H, d, J 8Hz), 7.57 (1H, d, J 8Hz), and 8.19 (1H, s).

EXAMPLE 9

(±)-Exo-bicyclo[2.2.1]hept-2-yl [1-(1H-indol-3-ylmethyl)-1-methyl-2-oxo-2-[(2-phenylethyl)amino] ethyl]carbamate Method was as described for Example 2 but using (±) exo-norbornyl chloroformate. The crude residue was chromatographed over silica using CH$_2$Cl$_2$ then 2% MeOH:98% CH$_2$Cl$_2$ as eluants to yield the title compound (0.346 g, 75%) as a colorless foam, mp (noncrystalline) 74°–78° C.; IR (film) 3341, 1703 and 1656 cm$^{-1}$; NMR (CDCl$_3$) δ1.06–1.16 (3H, m), 1.33–1.51 (3H, m), 1.53 (1.5H, s), 1.54 (1.5H, s), 1.65–1.70 (2H, m), 2.24 (2H, br.s), 2.65 (2H, m), 3.21 (1H, half ABq J 14.5Hz), 3.39–3.47 (3H, m), 4.51 (1H, d, J 6.5Hz), 5.09 (1H, s), 6.15 (1H, br.s), 6.95 (1H, d, J 2Hz), 7.03–7.25 (7H, m), 7.35 (1H, d, J 8Hz), 7.57 (1H, d, J 8Hz), 8.24 (1H, s); Anal. (C$_{28}$H$_{33}$N$_3$O$_3$.0.25 H$_2$O), C, H, N.

EXAMPLE 10

(±)-Endo-bicyclo[2.2.1]hept-2-yl [1-(1H-indol-3-ylmethyl)-1-methyl-2-oxo-2-[(2-phenylethyl)amino] ethyl ]carbamate Method was as described for Example 2, but using (±)-endo-norbornyl chloroformate. The crude residue was chromatographed over silica using 50% EtOAc:50% n-hexane as eluant to obtain the title compound (0.318 g, 69%) as a colorless foam, mp (noncrystalline) 62°–68° C.; IR (film) 3325, 1703, and 1654 cm$^{-1}$; NMR (CDCl$_3$) δ0.94 (1H, m), 1.19–1.40 (4H, m), 1.48–1.72 (5H, m), 1.95 (1H, m), 2.19 (1H, br.s), 2.43 (1H, br.s), 2.65 (2H, t, J 7Hz), 3.23 (1H, half ABq J 14.5 Hz), 3.39–3.48 (3H, m), 4.88 (1H, m), 5.17 (0.5 H, s), 5.21 (0.5H,s), 6.16 (1H, m), 6.94 (1H, d, J 2Hz), 7.04–7.25 (7H, m), 7.35 (1H, d, J 8Hz), 7.57 (1H, d, J 8Hz), 8.16 (1H, s); Anal. (C$_{28}$H$_{33}$N$_3$O$_3$.0.75 H$_2$O), C, H, N.

EXAMPLE 11

2,5-Methano-1H-inden-7-yl [2-[[1-(hydroxymethyl)-2-phenylethyl]amino]-1-(1H-indol-3-ylmethyl)-1-methyl-2-oxoethyl]carbamate Synthetic method was as described for Example 3 but using 4-protoadamantylchloroformate. The product was chromatographed over silica using 4% MeOH:96% CH$_2$Cl$_2$ as eluant to give the title compound (80%) as a white amorphous solid and as a mixture of two diastereoisomers (about the protoadamantane; D-tryptophan residue). mp 90°–92° C. (EtOAc-hexane), (IR) film) 3318, 1691 and 1662 cm$^{-1}$; NMR (CDCl$_3$) δ1.34 (1.5 H, s), 1.36 (1.5 H, s), 1.3–2.5 (14H, m), 2.74–2.78 (2H, m), 3.13 (1H, br.s), 3.43 (1H, m), 3.67 (1H, m), 4.17 (1H, br.s), 4.95 (1H, dt, J 3 and 8Hz), 5.03 (0.5 H, s), 5.06 (0.5H, s), 6.22 (1H, d, J 8Hz), 6.89 (1H, S), 7.05–7.26 (7H, m), 7.33 (1H, d, J 8Hz), 7.54 (1H, d, J 8Hz) and 8.51 (1H, br.s); Anal. (C$_{32}$H$_{39}$N$_3$O$_4$), C, H, N.

EXAMPLE 12

2-[3-1H-indol-3-yl)-2-methyl-2-[[[(octahydro-2,5-methano-1H-inden-7-yl)oxy]carbonyl]amino]-1-oxopropyl]-3-phenylpropyl butanedioate Synthetic method as described for Example 4 except using the alcohol from Example 11. Product chromatographed over silica using 2% MeOH:98% CHCl$_3$ as eluant to give a white amorphous sol id (80% ) and a mixture of two diastereoisomers (about protoadamantane), mp 56°–57° C. (EtOAc-hexane); IR (film) 1724 and 1659 cm$^{-1}$; NMR (CDCl$_3$) δ1.25–2.50 (17H, m), 2.59 (6H, m), 3.25 (2H, 2x ABq, J 14.5Hz), 3.91 (2H, m), 5.51 (1H, br), 6.62 (1H, m), 6.92–7.57 (10H, m), 8.65 (1H, br.s), and 9.04 (1H, br); Anal. (C$_{36}$H$_{43}$N$_3$O$_7$.1.25H$_2$O), C, H, N.

EXAMPLE 13

(R)-Tricyclo[3.3.1.1$^{3,7}$]dec-1-yl-[1-(1H-indol-3-ylmethyl)-1-methyl-2-oxo-2-[(2-phenylethyl)amino] ethyl]carbamate Synthetic method was as described for Example 1 but using 2-adamantyloxycarbonyl-α-methyl-D-tryptophan. The product was chromatographed over silica using 4% MeOH:96% CH$_2$Cl$_2$ as eluant to give the title compound (0.13 g, 26%) as a white solid, mp 82°–88° C. (CHCl$_3$-hexane); IR (film) 1699 and 1659 cm$^{-1}$; NMR (CDCl$_3$) δ1.5–1.6 (17H, m), 2.67 (2H, 6, J 7Hz), 3.26 (1H, d, J 14.5Hz), 3.4–3.5 (3H, m), 4.80 (1H, br.s), 5.15 (1H, br.s), 6.17 (1H, br.s), 6.95–7.60 (10H, m) and 8.05 (1H, br.s); Anal. (C$_{31}$H$_{37}$N$_3$O$_3$.0.25H$_2$O), C, H, N.

EXAMPLE 14

(±)-trans-2-Chlorocyclohexyl-[2-[[1-(hydroxymethyl)-2-phenylethyl]amino]-1-(1H-indol-3ylmethyl)-1-methyl-2-oxoethyl]carbamate Synthetic method was as described for Example 3, except α-methyl-L-tryptophan-L-phenylalaninol was used. The product was chromatographed over silica using 4% MeOH:96% CH$_2$Cl$_2$ as eluant to give the title compound (60%) as a colorless foam; mp (noncrystalline) 82°–86° C.; IR (film) 3402, 1703 and 1657 cm$^{-1}$; NMR (CDCl$_3$) δ1.32 (3H, m), 1.54 (1.5H, s), 1.57 (1.5H, s), 1.58–1.75 (4H, m), 2.04 (1H, m), 2.20 (1H, m), 2.66 (2H, m), 3.15 (1H, half ABq, J 14.5Hz), 3.26 (1H, half ABq, J 14.5Hz), 3.45 (1H, dd, J 6 and 11Hz), 3.60 (0.5H, m), 3.75 (1.5H, m), 4.05 (0.5H, m), 4.17 (0.5H, m), 4.70 (1H, m), 5.27 (0.5H, s), 5.29 (0.5H, s), 6.12 (1H, m), 6.88 (0.5H, d, J 2Hz), 6.92 (0.5H, d, J 2Hz), 7.08–7.28 (7H, m), 7.30 (1H, d, J 8Hz), 7.57 (1H, d, J 8Hz), and 8.13 (1H, br.s); Anal. (C$_{28}$H$_{34}$N$_3$O$_4$Cl), C, H, N, Cl.

EXAMPLE 15

[R-(R*,S*)]-Tricyclo[3.3,1.1$^{3,7}$]dec-2-yl-[2-[[1-(hydroxymethyl)-2-phenylethyl]amino]-1-(1H-indol-3-ylmethyl)-1-methyl-2-oxoethyl]carbamate

Step 1

Following the procedure from Example G, Fmoc-α-methyl-D-tryptophyl-L-phenylalaninol (7 g, 12.2 mmol) was dissolved in a 20% solution of piperidine in DMF (50 mL) and left stirring 12 hours at room temperature. The solvent was then evaporated and the residue chromatographed on silica using CH$_2$Cl$_2$ then 4% MeOH:96% CH$_2$Cl$_2$ as eluants to yield the product (4 g, 95%) as a colorless foam. IR (film 3305 and 1646 cm$^{-1}$; NMR (CDCl$_3$) δ1.28 (3H, s), 2.71 (2H, ABx, J 8 and 13.5Hz), 2.78 (1H, half ABq, J 14Hz), 2.91 (3H, br.s), 3.43 (1H, half ABq, J 14Hz), 3.45 (2H, ABx, J 6 and 11Hz), 4.03 (1H, m), 6.96 (1H, d, J 2Hz), 7.03–7.23 (7H, m), 7.29 (1H, d, J 8Hz), 7.67 (1H, d, J 7.5Hz) and 8.64 (1H, s).

Step 2

A solution of the α-methyl-D-tryptophyl-L-phenylalaninol (0.5 g, 1.42 mmol) and 4-N,N-dimethylaminopyridine (0.2 g, 1.64 mmol), in anhydrous THF (20 mL) was treated dropwise with a solution of 2-adamantylchloroformate (1.4 mmol) in anhydrous THF (20 mL) at room temperature. The reaction was monitored by IR spectroscopy. Once complete, the reaction mixture was diluted with ethyl acetate and washed with 1M citric acid solution, then water. The dried (MgSO$_4$) organic phase was evaporated to dryness and chromatographed over silica using 2% MeOH:98% CH$_2$Cl$_2$ as eluant. This gave the required compound (65% along with 20% carbonate impurity. NOTE: Some of the more acid labile urethanes required chromatography on neutral stationary phases. mp 96°–100° C. (EtOAc-hexane); IR (KBr) 3316, 1695 and 1658 cm$^{-1}$; NMR (CD$_3$OD) δ1.28 (3H, s), 1.55 (2H, m), 1.68–2.06 (12H, m), 2.76 (2H, ABx, J 13.5 and 17Hz), 3.31 (2H, Abq, J 14.5Hz), 3.45 (2H, m), 4.12 (1H, m), 4.78 (1H, br.s) and 6.8–7.5 (10H, m); Anal (C$_{32}$H$_{39}$N$_3$O$_4$), C, H, N.

EXAMPLE 16

[R-(R*,S*)]-2-[[3-(1H-indol-3-yl)-2-methyl-1-oxo-2-[[(tricyclo[3.3.1.1$^{3,7}$dec-2-yloxy)carbonyl]amino]propyl]amino]-3-phenylpropyl butanedioate Following the procedure as described for conversion of Example 4, this compound was prepared from the product of Example 15. The product was isolated as a single diastereoisomer, chromatographed over a reverse phase silica stationary phase using 50% MeOH:50% H$_2$O, then 75% MeOH:25% H$_2$O eluants to give a white amorphous solid (98% yield), mp 66°–69° C. (MeOH-H$_2$O); IR (film) 1718 and 1660 cmHH-1; NMR (CDCl$_3$) δ1.54 (5 H, m), 1.70–2.00 (12H, m), 2.62 (4H, s), 2.76 (2H, ABx, J 13 and 13.5Hz), 3.33 (2H, ABq, J 14.5Hz), 3.90 (2H, m), 4.35 (1H, m), 4.88 (1H, br. s), 6.8 (1H, s), 7.1–7.3 (7H, m), 7.34 (1H, d, J 8Hz), 7.59 (1H, d, J 8Hz) and 8.25 (1H, s); Anal. (C$_{36}$H$_{23}$N$_3$O$_7$), C, H, N.

EXAMPLE 17

2-[[3-(1H-indol-3-yl)-2-methyl-1-oxo-2-[[(tricyclo-[3.3.1.1$^{3,7}$]dec-2-yloxy)carbonyl]amino]propyl]amino]-1-phenylethyl butanedioate A solution of the alcohol from Example H (0.058 g, 0.113 mmol) in ethyl acetate (10 mL) was refluxed with succinic anhydride (0.013 g, 0.13 mmol) and 4-N,N-dimethylaminopyridine (0.027 g, 0.22 mmol), for 24 hours. The reaction mixture was then washed with 1M citric acid solution and the organic phase dried over MgSO$_4$. Evaporation of the solvent in vacuo yielded colorless gum (0.13 g) which was subjected to chromatography over silica using 10% MeOH:90% CH$_2$Cl$_2$ then 20% MeOH:80% CH$_2$Cl$_2$ as eluants, to yield the title compound as a noncrystalline white solid (0.021 g, 30%) and a mixture of two diastereoisomers, mp 94°–100° C. (MeOH—CH$_2$Cl$_2$); IR (film) 3352, 2911, 2855, 1722 and 1665 cm$^{-1}$; NMR (CDCl$_3$) δ1.45–2.10 (17H, m), 2.60 (4H, br.s), 3.15–3.50 (4H, m), 3.85 (1H, br.m), 4.90 (1H, 2 br.s), 5.60 (0.5 H, s), 5.00 (0.5H, s); 6.95–7.60 (10H, m); Anal. (C$_{35}$H$_{41}$N$_3$O$_7$.1.25H$_2$O), C, H, N.

EXAMPLE 18

α-[[[(7,7-dimethyl-2-oxobicyclo[2.2.1]-hept-1-yl)-methyl]sulfonyl]amino]-N-[1-(hydroxymethyl)-2-phenylethyl]-α-methyl-1H-indole-3-propanamide- (Trp center R, phenylalanyl center S)

A solution of the free base from Example 15, Step 1 (0.322 g, 0.92 mmol) and 4-N,N-dimethylaminopyridine (0.25 g, 2 mmol) in anhydrous THF (20 mL ) was treated dropwise with a solution of 10-(+)-camphorsulphonylchloride (0.23 g, 0.92 mmol) in THF (15 mL). The reaction mixture was left stirring at room temperature for four hours before being quenched with water. The reaction mixture was diluted with ethyl acetate and washed with saturated NaHCO$_3$ solution then water, then 1M citric acid solution, then water. The dried (MgSO$_4$) organic phase was evaporated in vacuo and the residue chromatographed over silica using 2% MeOH:98% CH$_2$Cl$_2$ then 4% MeOH:96% CH$_2$Cl$_2$ as eluants to give the title compound as a foam. An amorphous solid was obtained from EtOAc-hexane (0.4 g, 70%); mp 81°–85° C. (EtOAc-hexane); IR (KBr) 3259, 1742, 1672, 1359, and 1170 cm$^{-1}$; NMR (CDCl$_3$) δ0.75 (3H, s), 1.01 (3H, s), 1.28 (1H, m), 1.48 (1H, m), 1.64–1.99 (7H, m), 2.24 (1H, br.s), 2.29 (1H, br.s), 2.57 (1H, m), 2.76 and 3.33 (2H, ABq, J 14.5Hz), 3.40 (2H, m), 3.39 (1H, m), 4.10 (2H, m), 5.80 (3H, br. ), 6.78 (2H, d, J 7Hz), 7.07–7.25 (5H, m), 7.40 (1H, d, J 8Hz), 7.51 (1H, d, J 8Hz), 7.57 91H, s) and 9.60 (1H, s).

EXAMPLE 19

[R-(R*,S*)]-4-[[2-[[3-(1H-indol-3-yl)-2-methyl-1-oxo-2-[[(tricyclo[3.3.1.1$^{3,7}$]dec-2-yloxy)carbonyl] amino]propyl]amino]-3-phenylpropyl]amino]-4-oxobutanoic acid

Step 1

A cooled (ice-water bath) solution of tert-butyl-oxycarbonyl-L-phenylalaninol (2.043 g, 8.14 mmol) in anhydrous pyridine (9 mL) was treated with p-toluene sulphonyl chloride (1.6 g, 8.14 mmol) with stirring. This mixture was left overnight at 4° C. before being poured into ice water (600 mL). The solid formed was filtered, washed with ice-cold water then n-hexane, and dried in vacuo to give the required tosylate (3 g, 95%) pure enough to be used in Step 2 without further purification, mp 96°–98° C. (EtOAc-hexane); IR (KBr), 3320, 3029, 2978 and 1713 cm$^{-1}$; NMR (CDCl$_3$) δ1.38 (9H, s); 2.45 (3H, s), 2.8 (2H, m), 3.9 (3H, m), 4.71 (1H, br.), 7.05–7.79 (9H, m).

Step 2

A solution of the tosylate from Step 1 (3 g, 7.4 mmol) in anhydrous, N,N-dimethylformamide (20 mL) was treated with sodium azide (0.52 g, 8 mmol) and the resulting mixture heated to 120° C. for 1.5 hours. This was allowed to cool and then concentrated in vacuo. The syrup was diluted with ethyl acetate and washed with water (X3). The organic phase was dried over MgSO$_4$ and evaporated to give the azide (1.31 g) as a slightly impure waxy solid, and used as such in Step 3, mp 44°–45° C.; IR (film) (inter alia) 3341, 2978, 2101 and 1698 cm$^{-1}$.

Step 3

A solution of the impure urethane (1.17 g) as prepared in Step 2, was dissolved in dichloromethane (25 mL) and stirred with p-toluene sulphonic acid (1 g, 5.3 mmol) at room temperature for 18 hours. The solvent was evaporated in vacuo and the residue redissolved in ethyl acetate. This solution was washed with water, saturated NaHCO$_3$ solution then water and the organic phase dried over MgSO$_4$. The solvent was removed in vacuo to give a crude syrup (0.6 g) which was fractionated over silica using 5% MeOH:95% CH$_2$Cl$_2$ as eluant to give the pure free amine (0.4 g, 54%) as a syrup. (IR) film, 2100 cm$^{-1}$, NMR (CDCl$_3$) δ1.28 (2H, s), 2.54 (1H, half ABx, J 18 and 12Hz), 2.76 (1H, half ABx, J 18 and 12Hz), 3.10–3.34 (3H, m) 7.14–7.31 (5H, m).

Step 4

A solution of 2-adamantyloxycarbonyl-α-methyl-D-tryptophan (0.9 g, 2.27 mmol) and pentafluorophenol (0.418 g, 2.27 mmol) in anhydrous ethyl acetate (35 mL) at 0° C. was treated with a solution of dicyclohexylcarbodiimide (0.468 g, 2.27 mmol) in ethyl acetate (6 mL). This mixture was allowed to warm to room temperature and stirred a further two hours before the amine (0.4 g, 2.27 mmol) as prepared in Step 3, was added. This mixture was left 48 hours, filtered, and the filtrate washed with saturated NaHCO$_3$ solution, then water, then 1M citric acid solution and water again. The organic phase was dried over MgSO$_4$ and the solvent evaporated in vacuo to give a syrup which was chromatographed over reverse phase silica using 20% H$_2$O:80% MeOH as eluant. This gave [R-(R*,S*)]-tricyclo [3.3.1.1$^{3,7}$]dec-2-yl [2-[[1-(azidomethyl)-2-phenylethyl] amino]-1-(1H-indol-3-ylmethyl)-1-methyl-2-oxoethyl]carbamate (0.6 g, 48%), which was crystallized from EtOAc-n-hexane, mp 77°–78° C. (EtOAC-n-hexane); IR (film) 3339, 2909, 2102, 1699 and 1668 cm$^{-1}$; NMR (CDCl$_3$) δ1.45–2.1 (17H, m), 2.73 (2H, m), 3.10 (2H, m), 3.40 (2H ABq, J 14Hz), 4.25 (1H, m), 4.84 (1H, s), 5.17 (1H, s), 6.45 (1H, d, J-8Hz), 6.95 (1H, d, J 2Hz), 7.00–7.60 (9H, m), and 8.61 (1H, s); Anal. (C$_{32}$H$_{38}$N$_6$O$_3$).

Step 5

A solution of [R-(R*,S*)]-tricyclo[3.3.1.1$^{3,7}$]dec-2-yl-[2-[[1-(azidomethyl)-2-phenylethyl]amino]-1-(1H-indol-3-yl-methyl)-1-methyl-2-oxoethyl]carbamate (0.2 g, 0.36 mmol) in 5% acetic acid:95% ethanol (100 mL) was treated with 10% palladium on carbon (0.02 g, 10% w/w) and put under an atmosphere of hydrogen at a pressure of 51 psi at 30° C. with agitation. After no more hydrogen was seen to be taken up, the mixture was filtered over celite and concentrated in vacuo to a foam (0.25 g) which was used immediately in Step 6. IR (film 1676 br cm$^{-1}$.

Step 6

The crude amine acetate (0.25 g) as prepared in Step 5, was dissolved in anhydrous ethyl acetate (30 mL) and treated with succinic anhydride (0.15 g, 1.5 mmol) and DMAP (0.15 g, 1.23 mmol) and heated under reflux for 18 hours. The solution was then washed with 1M citric acid solution then water. The organic phase was dried over MgSO$_4$ and evaporated in vacuo. The resultant residue was chromatographed over reverse phase silica using 20% H$_2$O:80% MeOH as eluant to give the title compound (0.1 g, 44% from Step 5) as a white solid crystallized from ethyl acetate-hexane, mp 110°–114° C. (EtOAc-hexane); IR (film) 3306, 2906, 2854, 1695 and 1651 cm$^{-1}$; NMR (CDCl$_3$) δ1.34–1.97 (17H, m), 2.38 (2H, m), 2.55 (2H, m) 2.62 (2H, m), 2.98 (1H, m), 3.27 (2H, m), 3.45 (1H, m), 4.20 (1H, m), 4.77 (1H, s), 5.43 (1H, br.s), 6.05 (1H, br.s), 6.43 (1H, br.s), 6.85–7.55 (10H, m) and 8.91 (1H, s); Anal. (C$_{36}$H$_{44}$N$_4$O$_6$), C, H, N.

EXAMPLE 19A

[R-(R*,S*)]-4-[[2-(1H-Indol-3-yl)-2-methyl-1-oxo-2-[[tricyclo[3.3.1.1$^{3,7}$]dec-2-yloxylcarbonyl]amino] propyl]-amino]-3-phenylpropyl]amino]-4-oxo-2-butenoic acid

Step 1

A suspension of mono methyl fumarate (200 mg, 1.54 mmol) in EtOAc (20 mL) was treated with pentafluorophenol (340 mg, 1.85 mmol), and dicyclohexylcarbodiimide (349 mg, 1.69 mmol) and allowed to stir for 3 hours. After this time the suspension was filtered and the filtrate treated with the amine from Example 19 Step 5 (816 mg, 1.54 mmol) and left stirring for 18 h at room temp. The reaction mixture was then filtered, the filtrate evaporated in vacuo and the residue chromatographed over reverse phase silica gel using 75% MeOH in H$_2$O as eluant to give the product as an amorphous white solid (867 mg, 88%); mp 161°–166° C. (MeOH:H$_2$O); [α]$^{20}$$_D$+13.3° (c=1.04, MeOH); IR (film)

1728, 1700 and 1666 cm$^{-1}$; NMR (CDCl$_3$) δ1.34 (3H, s), 1.50–1.60 (2H, m), 1.70–2.10 (12H, m), 2.73 (2H, d, J 7Hz), 3.10–3.25 (1H, m), 3.28 (1H, d, J 15Hz), 3.38, (1H, d, J 15Hz), 3.70–3.80 (1H, m) 3.75 (3H, s), 4.25–4.35 (1H, m), 4.80 (1H, s), 5.00 (1H, s), 6.12 (1H, d, J 8Hz), 6.80 (1H, d, J 16Hz), 6.92 (1H, d, J 16Hz), 6.93 (1H, d, J 2Hz), 7.05–7.30 (8H, m), 7.35 (1H, d, J 8Hz), 7.57 (1H, d, J 8Hz), 8.21 (1H, s); Anal. C$_{37}$H$_{44}$N$_4$O$_3$.H$_2$O; C, H, N.

Step 2

The methyl ester from step 1 (867 mg, 1.35 mmol) as a solution in THF (35 mL) at 0° C. was treated dropwise with aqueous LiOH solution (13.5 mL of a 0.1M soln, 1.35 mmol). The resultant mixture was stirred at 0° C. for 4.5 h and allowed to warm to room temperature and acidified with 1M citric acid soln. The mixture was concentrated to one third of its original volume and the residue extracted with EtOAc (75 mL) and washed with H$_2$O (75 mL). The organic phase was dried over MgSO$_4$, filtered and evaporated in vacuo. The residue then was purified by chromatography over reverse phase silica gel using 75% MeOH in H$_2$O as eluant to give the product as an amorphous white solid (611 mg, 72%); mp 166°–170° C. (MeOH/H$_2$O); [α]$^{20}_D$+105.2° (c=1.07, MeOH); IR (film) 3341, 1706 and 1665 cm$^{-1}$; NMR (CDCl$_3$) δ1.38 (3H, s), 1.45–1.55 (2H, m), 1.70–2.10 (12H, m), 2.00 (CO$_2$H and H$_2$O), 2.60–2.80 (2H, m), 3.10–3.20 (1H, br m), 3.22 (1H, d, J 12Hz), 3.34 (1H, d, J 14Hz), 3.50–3.60 (1H, br m), 4.20–4.30 (1H, br m), 4.78 (1H, s), 5.23 (1H, s), 6.35–6.45 (1H, br m), 6.75 (1H, d, J 15.5Hz), 6.89 (1H, d, J 15.5Hz), 6.90 (1H, d, J 2Hz), 7.00–7.30 (8H, m), 7.31 (1H, d, J 8Hz), 7.54 (1H, d, J 8Hz), 8.54 (1H, s); Anal. C$_{36}$H$_{42}$N$_4$O$_6$; C, H, N.

EXAMPLE 20 (Compound 20)

[R-(R*,R*)-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid

Step 1

To a solution of tert-butyloxycarbonyl-D-2-phenylglycinol (5.85 g, 24.7 mmol) in anhydrous dichloromethane (60 mL) at 0° C. was added triethylamine (5.08 g, 50.3 mmol) followed by p-toluene sulphonylchloride (6.8 g, 35.7 mmol) as a solution in dichloromethane (10 mL). The reaction mixture was allowed to warm to room temperature and left 18 hours. The mixture was then diluted with dichloromethane (100 mL) and washed with 1M citric acid solution. The organic phase was dried over MgSO$_4$ and evaporated in vacuo to leave a solid which was recrystallized from ethyl acetate-hexane (6.8 g, 70%), mp 114°–118° C. (EtOAC-hexane); IR (film) 3388, 2978, 1713, 1365 and 1176 cm$^{-1}$; NMR (CDCl$_3$) δ1.40 (9H, s), 2.43 (3H, s), 4.20 (2H, m), 4.89 (1H, br.s), 5.10 (1H, br.s), 7.27 (2H, m), 7.31 (5H, m), 7.65 (2H, d, J 8Hz); Anal. (C$_{20}$H$_{25}$NO$_5$S), C, H, N.

Step 2

Method was as described for Example 19, Step 2, but using the rosylate prepared in Example 20, Step 1 (2.37 g, 70%), not purified, mp 76°–78° C.; IR (film), 3380, 2095, 1682 and 1515 cm$^{-1}$; NMR (CDCl$_3$) δ1.44 (9H, s), 3.763 (2H, m), 4.87 (1H, br. s), 5.03 (1H, br. s), 7.30–7.40 (5H, m).

Step 3

Method was as described for Example 19, Step 3, but using the urethane prepared in Example 20, Step 2 (3.43 g, >100%) used without further purification in Step 4; IR (film) 3030 and 2104 cm$^{-1}$; NMR (CDCl$_3$) δ3.37 (1H, dd, J 8 and 12Hz), 3.52 (1H, dd, J 5 and 12Hz), 4.13 (1H, dd, J 5 and 8 Hz), 7.20–7.40 (5H, m).

Step 4

To a solution of benzyl- hemisuccinate (3.14 g, 1B.1 mmol) in ethyl acetate (60 mL) was added N,N-dicyclohexylcarbodiimide (3.42 g, 16.6 mmol) and 1-hydroxybenzotriazole (2.24 g, 16.6 mmol). The reaction mixture was left one hour before the amine (2.23 g) as prepared in Step 3 was added as a solution in ethyl acetate (5 mL). This final mixture was left stirring for a further three hours before being filtered and the filtrate evaporated in vacuo to yield a gum (10 g) which was chromatographed over silica using 25% EtOAc:75% n-hexane then 50% EtOAc:50% n-hexane as eluants to yield the required amidoazide (3.96 g, 70%) as a white solid, mp 51°–54° C. (EtOAC-hexane); IR (film) 3295, 3065, 2103, 1736 and 1651 cm$^{-1}$; NMR (CDCl$_3$) δ2.55 (2H, t, J 7Hz), 2.72 (2H, t, J 6Hz), 3.63 (2H, d, J 7Hz), 5.12 (2H, s), 5.16 (1H, m), 6.25 (1H, br.d), 7.30–7.40 (10H, m); Anal. (C$_{19}$H$_{20}$N$_{12}$O$_2$), C, H, N.

Step 5

To a solution of the amidoazide (1.659 g, 4.7 mmol) as prepared in Step 4, in absolute ethanol (45 mL) was added Lindlar catalyst (0.664 g, 40% w/w). The reaction was then put under an atmosphere of hydrogen for three hours. The reaction mixture was then filtered over celite and washed with ethanol. The solvent was evaporated in vacuo and the residue used immediately without further purification in Step 6 (1.07 g, ca. 70%). IR (film) 3325, 1733, 1703 and 1651 cm$^{-1}$; NMR ((CD$_3$)$_2$SO) δ2.65 (2H, m), 2.70 (2H, m), 4.74 (1H, br.q), 5.08 (2H, s), 7.20–7.40 (10H, m), 8.25 (1H, d).

Step 6

2-Adamantyloxycarbonyl-α-methyl-D-tryptophan (1.36 g, 3.4 mmol), as a solution in ethyl acetate (30 mL) was treated sequentially with N,N-dicyclohexylcarbodiimide (0.778 g, 3.8 mmol) and 1-hydroxybenzotriazole (0.51 g, 3.8 mmol) and left stirring for one hour before the amine (1.07 g) as prepared in Step 5 was added as a solution in ethyl acetate (5 mL). The resulting reaction mixture was left stirring at room temperature for 18 hours before being filtered. The liltrate was concentrated in vacuo to give a gum (3.4 g) which was chromatographed over reverse phase silica using 30% H$_2$O:70% MeOH then 20% H$_2$O:80% MeOH as eluants to yield the required product (1.403 g, 41% from Step 5) as a noncrystalline solid. IR (film) 3305, 2856, 1729, 1695 and 1651 cm$^{-1}$; NMR (CDCl$_3$) δ1.47 (3H, s), 1.50–2.05 (14H, m), 2.57 (2H, m), 2.70 (2H, g, J 5Hz), 3.35 (1H, m), 3.40 (2H, dd, J 15Hz), 3.95 (1H, m), 4.86 (1H, br.s), 5.11 (3H, s), 6.40 (1H, br.s), 7.00 (1H, d), 7.05–7.35 (9H, m), 7.57 (1H, d, J 7Hz), 3.27 (1H, s).

Step 7

A solution of the benzyl ester, as prepared in Step 6 (1.403 g, 2.0 mmol), in absolute ethanol (50 mL) was treated with 10% palladium on carbon (0.14 g, 10% w/w) and placed under an atmosphere of hydrogen for four hours. The reaction mixture was then filtered over celite and washed with ethanol, then acetone. The filtrate was concentrated in vacuo to yield the title compound (0.967 g, 79%) which was recrystallized from methanol, mp 142°–146° C. (MeOH); IR (film 3306, 2908, 1713 and 1670 cm$^{-1}$; NMR ((CD$_3$)$_2$SO) δ1.20 (3H, s), 1.49 (2H, br.s), 1.65–1.85 (5 H, m), 1.95 (4H, m), 2.39 (4H, br. s), 3.40 (4H, br .m), 4.69 (1H, br. s ), 4.96 (1H, br. d J 6Hz ), 6.70 (1H, s ), 6.90 (2H, s), 7.01 (1H, 5, J 7Hz), 7.22 (1H, m), 7.31 (5H, br.s), 7.44 (1H, d, J 7Hz), 7.78 (1H, br.s), 8.30 (1H, s) and 10.85 (1H, s); Anal. (C$_{35}$H$_{42}$N$_4$O$_6$.0.5 H$_2$O), C, H, N.

EXAMPLE 20A

In an analogous manner but using 1-(S)-2-endobornyloxy-carbonyl-[D]-α-methyltryptophan, [1S -[1α,2β [S*(S*)], 4α]]-4-[[2-[[3-(1H-indol-3-yl)-2-methyl-1-oxo-2-[[[(1,7,7-trimethylbicyclo[2.2.1]hept-2-yl)oxy]carbonyl] amino]propyl]amino]-1-phenylethyl]amino]-4-oxobutanoic acid was prepared.

EXAMPLE 21

(R)-tricyclo[3.3.1.1$^{3,7}$]dec-2-yl [1-(1H-indol-3-ylmethyl)-1-methyl-2[methyl(2-phenylethyl)amino]-2-oxoethyl]carbamate The method is as described in Example 19, Step 4, except N-Methyl-phenethylamine was used. 50 mg was obtained (61% yield) as an amorphous white solid, mp 90°–95° C. (MeOH-H$_2$O); IR (film), 3295, 2855, 1698 and 1625 cm$^{-1}$; NMR (CDCl$_3$) δ1.5–2.0 (17H, m) 2.84 (2H, br.t, J 7Hz), 3.07 (3H, br.s), 3.4–3.8 (4H, m) 4.86 (1H, br.s), 5.28 (1H, br.s), 6.95–7.30 (8H, m); 7.35 (1H, d, J 8Hz), 7.56 (1H, d, J 8Hz), 8.2 (1H, br.s); Anal. (C$_{32}$H$_{39}$N$_3$O$_3$), C, H, N.

EXAMPLE 22

[R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl] amino]propyl]amino]-1-pbenylethyl]amino]-4-oxo-2-butenoic acid

Step 1

To a solution of tert butyloxycarbonyl-D-phenylglycinol (5.85 g, 24.7 mmol) in anhydrous dichloromethane (60 mL) at 0° C. was added triethylamine (5.08 g, 50.3 mmol) followed by p-toluene sulphonyl chloride (6.8 g, 35.7 mmol) as a solution in dichloro-methane (10 mL). The reaction mixture was allowed to warm to room temperature and left 18 hours. The mixture was then diluted with dichloromethane (100 mL) and washed with 1M citric acid solution (100 mL). The organic phase was dried over anhydrous MgSO$_4$ and evaporated in vacuo to leave a solid which was recrystallized from ethyl acetate/n-hexane; (6.8 g, 70%). mp 114°–118° C. (EtOAc/n-hexane); IR (film) 3388, 2978, 1713, 1365, and 1176 cm$^{-1}$; NMR (CDCl$_3$) δ1.40 (9H, s), 2.43 (3H, s), 4.20 (2H, m), 4.89 (1H, br.s), 7.27 (2H, m), 7.31 (5H, m), 7.65 (2H, d, J 8Hz); Anal. (C$_{20}$H$_{25}$NO$_5$S), C, B, N.

Step 2

A solution of the tosylate (4.67 g, 11.9 mmol) in anhydrous DMF (60 mL) was treated with sodium azide (868 mg, 13.4 mmol). The mixture was heated to 120° C. for 1.5 hours. After cooling, the solution was poured into water (250 mL), and the aqueous layer extracted with an equal volume of ether. The ethereal phase was washed with water, dried over MgSO$_4$ and the solvent removed in vacuo to yield the desired azide as a white crystalline solid, used without further purification (2.37 g, 70%), mp 76°–78° C.; IR (film) 3380, 2095, 1682, and 1515 cm$^{-1}$; NMR (CDCl$_3$) δ1.44 (9H, s), 3.76 (2H, m), 4.87 (1H, br.s), 5.03 (1H, br.s), 7.30–7.40 (5H, m).

Step 3

A solution of the azide (6.44 g, 24.6 mmol) in anhydrous ethyl acetate (100 mL) was subjected to an atmosphere of hydrogen at a pressure of 45 psi over Lindlar catalyst (2.58 g, 40% w/w) for 6 hours at room temperature. After this time the reaction mixture was filtered through filter aid and washed through with more ethyl acetate. The crude product, in solution, was used immediately in the next step of the reaction sequence. IR (film) 3350, 3000, and 1696 cm$^{-1}$; NMR (CDCl$_3$) δ1.43 (9H, s), 2.10 (2H, br.s), 3.10 (2H, br.s), 4.70 (1H, m), 5.45 (1H, br.s), 7.25–7.40 (5H, m).

Step 4

To a solution of Fmoc-α-Me-D-Trp-OH (1.800 mg, 4.091 mmol) in ethyl acetate (35 mL) was added N,N'-dicyclohexylcarbodiimide (927 mg, 4.50 mmol) and 1-hydroxybenzotriazole hydrate (689 mg, 4.50 mmol). After stirring at room temperature of 1 hour, the amine (965 mg, 4.09 mmol), in ethyl acetate (5 mL) was added to the suspension. After stirring for a further 3 hours, the reaction mixture was filtered and the liltrate evaporated in vacuo to yield a gum (2.9 g). The crude product was purified by column chromatography using 25% to 75% EtOAc in n-hexane as eluant, to yield the desired amide as a yellow, noncrystalline solid (1970 mg, 73%), mp 78°–82° C.; IR (film) 3300, 3100–2900, 1695, and 1660 cm$^{-}$; NMR (CDCl$_3$) δ1.40 (9H, br.s), 1.50 (3H, s), 3.30–3.50 (3H, m), 3.65 (1H, m), 4.15 (1H, br.s), 4.41 (2H, br.s), 4.75 (1H, m), 5.35 (1H, s), 5.45 (1H, m), 6.55 (1H, br.s), 6.83 (1H, br.s), 7.10–7.45 (12H, m), 7.50–7.65 (3H, m), 7.75 (2H, m), 8.05 (1H, br.s).

Step 5

To a cooled solution (0° C.) of the urethane (3.611 g, 5.488 mmol) in anhydrous dichloromethane (40 mL) was added B-toluene sulphonic acid (1.301 g, 6.839 mmol). The reaction mixture was allowed to warm to room temperature and left 18 hours. Dichloromethane (100 mL) was then added and the mixture washed with saturated sodium hydrogen carbonate solution (100 mL). The organic phase was dried (MgSO$_4$) and evaporated to yield the amine as a yellow noncrystalline solid purified by chromatography using 5% MeOH in CH$_2$Cl$_2$ as eluant (2.915 g, 95%), mp 84°–88° C.; IR (film) 3300–3400, 1713, and 1658 cm$^{-1}$; NMR (CDCl$_3$) δ1.50 (3H, s), 1.65 (2H, br.s), 3.15 (1H, m), 3.25 (1H, Ha of ABq, J 15Hz), 3.45–3.55 (2H, m), 3.95 (1H, m), 4.15 (1H, t, J 8Hz), 4.35–4.50 (2H, m), 5.32 (1H, s), 6.43 (1H, br.t), 6.77 (1H, d, J 12Hz), 7.05–7.45 (12H, m), 7.50–7.65 (3H, m), 7.75 (2H, m), 8.05 (1H, s); m/e 559 (M+, base peak); Anal. (C$_{35}$H$_{34}$N$_4$O$_3$.0.25C$_6$H$_{14}$), C, H, N.

Step 6

Fmoc-α- Me-D-TrpNHCH$_2$CH(NHCOCHCHCO$_2$Me)Ph; [R-[R*, R*-(E)]]-4-[[2-[[2-[[(9H-Fluoren-9-ylmethoxy)carbonyl]amino]-3-(1H-indol-3-yl)-2-methyl-1-oxopropyl]amino]-1-phenylethyl]amino]-4-oxo-2-butenoic acid methyl ester To a solution of mono-methyl fumarate (330 mg, 2.54 mmol) in ethyl acetate (50 mL) was added 1-hydroxybenzotriazole hydrate (390 mg, 2.55 mmol) followed by N,N-dicyclohexyl-carbodiimide (570 mg, 2.77 mmol). After stirring for 1 hour at room temperature, the amine from step 5 (1.40 g, 2.51 mmol) in ethyl acetate (3 mL) was added and the resulting suspension stirred on 18 hours. The reaction mixture was then filtered, the filtrate evaporated in vacuo and the residue purified by chromatography over silica gel using 50 to 75% EtOAc in n-hexane as eluant to yield the product as a white amorphous solid. (1.21 g, 72%), mp 78°–82° C.; IR (film) 3309, 3064, 2950, 1724, and 1668 cm$^{-1}$; NMR (CDCl$_3$) δ1.39 (3H, s) 3.30 (3H, m), 3.69 (3H, s), 4.05 (1H, m) 4.16 (1H, t, J 8Hz), 4.40 (1H, dd, J 8 and 11Hz), 5.16 (1H, s), 5.21 (1H, m), 6.21 (1H, m) 6.78 (1H, d, J 15Hz), 6.79 (1H, d, J 2Hz), 7.03 (1H, d, J 15Hz), 7.15 to 7.60 (16H, m), 7.77 (2H, t, J 8Hz), 8.17 (iH, s); Anal. (C$_{40}$H$_{38}$N$_4$O$_6$.5H$_2$O), C, H, N.

Step 7

H-α-Me-D-TrpNHCH$_2$CH(NHCOCHCHCO$_2$Me)Ph; [R-[R*, R*-(E)]]-4-[[2-[[2-Amino-3-(1H-indol-3-yl)-2-methyl-1-oxopropyl]amino]-1-phenylethyl]amino]-4-oxo-2-butenoic acid methyl ester Piperidine (156 mg, 1.84 mmol) was added to a solution of the urethane (1.21 g, 1.81 mmol) in anhydrous DMF (20 mL) at 0° C. The reaction mixture was allowed to warm to room temperature, and after 4 hours was concentrated to a gum. This crude product was chromatographed over silica-gel using 2.5% to 5% MeOH in CH$_2$Cl$_2$ was eluant to give the amine as a noncrystalline, pale yellow solid (801 mg, 97%). mp 75°–77° C.; IR (film) 3400–3300, 3100, 2900, 1728, 1660, and 1646 cm$^{-1}$; NMR (CDCl$_3$) δ1.41 (3H, s), 1.60 (2H, br.s), 2.81 (1H, Ha of ABq, J 15Hz), 3.45–3.60 (3H, m), 5.00 (1H, m), 6.80 (1H, d, J 16Hz), 6.90–7.20 (9H, m), 7.40 (1H, d, J 8Hz), 7.64 (2H, br.d, J 8Hz), 7.90 (1H, t, J 6Hz), 8.31 (1H, br.s); Anal. (C$_{25}$H$_{28}$N$_4$O$_4$), C, H, N.

Step 8

2-Adoc-α-Me-D-TrpNHCH$_2$CH(NHCOCHCHCO$_2$Me)Ph; [R-[R*, R*-(E)]]-4-[[2-[[3-(1H-Indol-3-yl)-2-methyl-1-oxo-2-[[(tricyclo[3.3.1.1$^{3,7}$]dec-2-yloxy)carbonyl]-amino]propyl]amino]-1-phenylethyl]amino]-4-oxo-2-butenoic acid methyl ester To an ice-cooled solution of the amine (794 mg, 1.77 mmol) in anhydrous THF (10 mL) was added 2-adamantyl chloroformate (380 mg, 1.77 mmol) in THF (3 mL) followed by the triethylamine (215 mg, 2.13 mmol) in TBF (2 mL) dropwise. The reaction mixture was stirred at room temperature for 3 hours and then concentrated in vacuo to give a brown residue (11 g). The crude product was purified by column chromatograpby using 60% ethyl acetate/n-hexane as eluant to give the desired urethane (51c) as an amorphous solid (734 mg, 66%), mp 109°–112° C.; IR (film) 3440–3300, 2900, 1720, and 1667 cm$^{-1}$; NMR (CDCl$_3$) δ1.42 (3H, s), 1.54 (2H, m), 1.70–2.05 (12H, m), 3.34 (1H, Ha of ABq, J 14Hz), 3.42 (1H, m), 3.50 (1H, Hb of ABq, J 14Hz), 3.79 (3H, s), 4.05 (1H, m), 4.84 (1H, br.s), 5.03 (1H, s), 5.20 (1H, m), 6.35 (1H, m), 6.82 (1H, d, J 15Hz), 6.95–7.35 (10H, m), 7.57 (2H, d, J 8Hz), 8.30 (1H, s); Anal. (C$_{36}$H$_{42}$N$_4$O$_6$.0.5H$_2$O), C, H, N.

Step 9

2-Adoc-α-Me-D-TrpNHCH$_2$CH(NHCOCHCHCO$_2$H)Ph; [R-[R*, R*(E)]]-4-[[2-[[3-(1H-indol-3-yl)-2-methyl-1-oxo-2-[[(tricyclo[3.3.1.1$^{3,7}$]dec-2-yloxy)carbonyl]amino] propyl]amino]-1-phenylethyl]amino]-4-oxo-2-butenoic acid Aqueous lithium hydroxide (12.16 mL of a 0.1M solution, 1.22 mmol) was added dropwise to a solution of the methyl ester (726 mg, 1.16 mmol) in THF (73 mL) at 0° C. over a 2-hour period. The reaction mixture was then allowed to warm to room temperature and left stirring for 18 hours. After this time hydrochloric acid (1.34 mL of a 1M solution) was added and the mixture concentrated. Ethyl acetate (150 mL) and water were then added and the separated organic phase dried over MgSO$_4$ and evaporated to give a crude solid. This chromatographed over reverse phase silica using 75% MeOH in H$_2$O as eluant to yield the desired product as an amorphous solid (324 mg, 46%), mp 145°–150° C.; [α]$^{20}$+13.70 (c=0.24, CHCl$_3$); IR (film) 3300, 2910, 1706, and 1667 cm$^{-1}$; NMR (DMSO-d6) δ1.18 (3H, s), 1.74 (2H, m), 1.65–2.00 (12H, m), 3.30–3.50 (4H+H$_2$O), 4.66 (1H, br.s), 5.06 (1H, m), 6.52 (1H, d, J 15Hz), 6.77 (1H, br.s), 6.90–7.10 (4H, m), 7.20–7.35 (6H, m), 7.44 (1H, d, J 8Hz), 7.82 (1H, t, J 6Hz), 8.78 (1H, br. s), 10.85 (1H, s); Anal. (C$_{35}$H$_{40}$N$_4$O$_6$.0.5H$_2$O), C, H, N.

EXAMPLE 23

[R-(R*,S*)]-[[2-[[3-(1H-indol-3-yl)-2-methyl-1-oxo-2-[[(tricyclo[3.3.1.1$^{3,7}$]dec-2-yloxy)carbonyl]amino-propyl]amino]-3-phenylpropyl]sulfinyl]acetic acid Step 1

Sodium periodate (908 mg, 4.24 mmol) in water (10 mL) was added dropwise to sulphide BOCNHCH(CH$_2$SCH$_2$CO$_2$Et)CH$_2$Ph (750 mg, 2.12 mmol) in methanol (20 mL) at room temperature. This mixture was left for 2 hours, concentrated to one-third its volume and partitioned between ethyl acetate and a sodium chloride solution. The organic phase was dried over MgSO$_4$, filtered and evaporated in vacuo to a white solid (782 mg, 100%) which was a mixture of two diastereoisomers and used as such without further purification. IR (film) 1739, 1689, and 1046 cm$^{-1}$; NMR (CDCl$_3$) δ1.27 (3H, t, J 7Hz), 1.41 (4.5H, s), 1.42 (4.5H, s), 2.92–3.20 (4H, m), 3.66–3.84 (2H, m), 4.18–4.29 (3H, m), 4.80 (0.5 H, br.), 5.30 (0.5 H, br.), 7.19–7.35 (5H, m).

Step 2

H$_2$NCH(CH$_2$SOCH$_2$CO$_2$Et)CH$_2$Ph; (S)-[(2-Amino-3-phenylpropyl)sulfinyl]acetic acid ethyl este.r The N-BOC-protected sulphoxide (462 mg, 1.25 mmol) was stirred in dichloromethane containing trifluoroacetic acid (5 mL of 1:1 mixture) for 1 hour at room temperature. All volatiles were removed in vacuo to give a syrup which was used without further purification (479 mg).

Step 3

**2- Adoc-α-Me-D-TrpNHCH($CH_2SOCH_2CO_2Et$)$CH_2$Ph; [R-(R*,S*)]-[ [2-[[3-(1H-indol-3-1)-2-methyl-1-oxo-2-[[(tricyclo [3.3.1,1$^{3,7}$]dec-2-yloxy)carbonyl]amino]propyl] amino]-3-phenylpropyl]sulfinyl]acetic acid ethyl ester**

N,N'-Dicyclohexylcarbodiimide (165 mg, 0.801 mmol) was added to a solution of 2-ADOCαMe-D-TrpOH (286 mg, 0.720 mmol) and 1-hydroxybenzotriazole hydrate (122 mg, 0.797 mmol) in ethyl acetate (10 mL). After 1 hour the crude amine salt (63)) (345 mg, 0.9 mmol) and triethylamine (243 mg, 2.40 mmol) in ethyl acetate (10 mL) was added dropwise and the mixture allowed to stir at room temperature for 22 hours. This mixture was filtered and the filtrate washed with 1M citric acid solution (2×10 mL), saturated sodium hydrogen carbonate solution (2×10 mL) and a sodium chloride solution (10 mL). The organic phase was dried over $MgSO_4$, filtered and evaporated in vacuo and the residue chromatographed over silica gel using 2% MeOH in $CH_2Cl_2$ as eluant to give the product as a white amorphous solid (263 mg, 56%) as a mixture of two diastereoisomers, mp 87°–99° C.; IR (film) 1719, 1659, and 1072 cm$^{-1}$; NMR (CDCl) δ1.22–1.28 (3H, m), 1.47–2.00 (17H, m), 2.81–3.14 (4H, m), 3.22–3.49 (2H, m), 3.56–3.79 (2H, m), 4.16–4.23 (2H, m), 4.48 (1H, m), 4.80 (1H, s), 5.21 (1H, s) 6.77–7.62 (11H, m); MS m/e (EI) 648 (72) 130 (100); Anal. ($C_{36}H_{45}N_3O_6S$), C, H, N, S.

Step 4

**2-Adoc-α-Me-D-TrpNHCH($CH_2SOCH_2CO_2H$)$CH_2$Ph; [R-(R*,S*)]-[ [2-[[3-(1H-indol-3-yl)-2-methyl-1-oxo-2-[[(tricyclo [3.3.1.1$^{3,7}$]dec-2-yloxy)carbonyl]amino]propyl] amino]-3-phenylpropyl]sulfinyl]acetic acid**

Lithium hydroxide (8.3 mL of a 0.1M solution, 0.83 mmol) was added dropwise to a cooled solution of ester (487 mg, 0.752 mmol) in THF (45 mL). The mixture was stirred for 6 hours at room temperature, then hydrochloric acid (9.1 mL of a 0.1M solution, 0.91 mmol) was added and the THF evaporated. The residue was taken up in ethyl acetate and washed with water, the organic phase was dried over $MgSO_4$, filtered, and concentrated to a residue which was chromatographed over reverse phase silica gel using 80% MeOH in $H_2O$ as eluant and yielded the product as an amorphous white solid (304 mg, 65%), mp 125°–141° C.; IR (film) 1709 and 1664 cm$^{-1}$; NMR (CDCl$_3$) δ1.50–2.04 (17H, m), 2.68–3.05 (4H, m), 3.16–3.77 (4H, m), 4.39–4.46 (1H, m), 4.80 (1H, br.s), 5.46 (2H, br.), 6.99–7.34 (10H, m), 7.54 (1H, d, J 8Hz), 8.79 (1H, br.); MS m/e (FAB) 620 (100); Anal. ($C_{34}H_{41}N_3O_6$·1.2 $H_2O$), C, H, N, S.

EXAMPLE 24

**[R-(R*,S*)]-[[2-[[2-[[3-(1H-indol-3-yl)-2-methyl-1-oxo-2-[[(tricyclo[3.3.1.1$^{3,7}$]dec-2-yloxy)carbonyl] amino]propyl]amino]-3-phenylpropyl]thio]acetic acid**

Step 1

BOCNHCH($CH_2$OMs)$CH_2$Ph; (S)-[1-[[(Methylsulfonyl)oxy]methyl]-2-phenylethyl]-carbamic acid 1,1-dimethyl ethyl ester

Methane sulphonyl chloride (2.51 g, 21.9 mmol) in anhydrous THF (10 mL) was added dropwise to a solution of N-tert.-BOC-L-phenylalaninol (5.00 g, 19.9 mmol) and triethylamine (2.77 g, 27.4 mmol) in anhydrous THF (20 mL) at 0° C. After 1 hour the reaction mixture was filtered and the filtrate concentrated in vacuo to a solid which was recrystallized from ethyl acetate-n-hexane (6.35 g, 97%), mp 106°–108° C. (EtOAc/n-hexane); IR (film) 1682, 1356, and 1167 cm$^{-1}$; NMR (CDCl$_3$) δ1.38 (9H, s), 2.81–2.91 (2H, m), 3.01 (3H, s), 4.09–4.25 (3H, m), 4.72 (1H, br.s), 7.20–7.35 (5H, m).

Step 2

BocNHCH($CH_2SCH_2CO_2Et$)$CH_2$Ph; (S)-[[2-[[(1,1-Dimethylethoxy)carbonyl]amino]-3-phenylpropyl] thio]acetic acid ethyl ester

Ethyl-2-mercaptoacetate (1.206 g, 10.4 mmol) in anhydrous THF (10 mL) was added dropwise at room temperature to a suspension of 60% sodium hydride (400 mg, 10.0 mmol) stirred in THF (30 mL). After 1.5 hours, the mesylate (2) (3.0 g, 9.11 mmol) in THF (15 mL) was added dropwise over a 5-minute period. After stirring for 24 hours at room temperature the solvent was removed in vacuo and the residue partitioned between ethyl acetate and sodium chloride solution. The organic phase was dried over $MgSO_4$, filtered and the solvent evaporated in vacuo to give an oil which was chromanographed over silica gel using $CH_2Cl_2$ as eluant to give the product as a syrup (1.58 g, 49%), IR (film) 1733 and 1713 cm$^{-1}$; NMR (CDCl$_3$) δ1.26 (3H, t, J 7Hz), 1.41 (9H, s), 2.66–2.89 (4H, m), 3.25 (2H, dd, J 4 and 14Hz), 4.03 (1H, m), 4.18 (2H, q, J 7Hz), 4.75 (1H, s), 7.18–7.32 (5H, m).

Step 3

$H_2$NCH($CH_2SCH_2CO_2Et$)$CH_2$Ph.$CF_3CO_2H$; (S)-[(2-Amino-3-phenylpropyl)thio]acetic acid ethyl ester trifluoroacetate (SALT) (1:1)

The N-protected ester (225 mg, 0.637 mmol) was stirred for 30 minutes in neat trifluoroacetic acid (3 mL) at room temperature. Excess trifluoroacetic acid was evaporated in vacuo to give the crude trifluoroacetate salt, which was used immediately without further purification, yield 321 mg.

Step 4

**2-Adoc-α-Me-D-TrpNHCH($CH_2SCH_2CO_2Et$)$CH_2$Ph; [R-(R*,S*)]-[ [2-[[3-(1H-Indol-3-yl)-2-methyl-1-oxo-2-[[(tricyclo [3.3.1.1$^{3,7}$]dec-2-yloxy)carbonyl]amino]propyl] amino]-3-phenylpropyl]thio]acetic acid ethyl ester**

N,N'-dicyclohexylcarbodiimide (145 mg, 0.704 mmol) was added to a stirred solution of 2-Adoc-α-Me-D-TrpOH (254 mg, 0.640 mmol) and 1-hydroxybenzotriazole hydrate (122 mg, 0.797 mmol), in ethyl acetate (10 mL). After 1 hour 4-dimethyl-aminopyridine (20 mg, 0.16 mmol) was added followed by a solution of the trifluoroacetate salt (59) 235 mg, 0.64 mmol) and triethylamine (152 mg, 1.50 mmol) in ethyl acetate (10 mL). After stirring at room temperature for 24 hours, the reaction mixture was filtered and the filtrate washed with 1M citric acid solution (2×20 mL), saturated sodium hydrogen carbonate solution (2×20 mL), then sodium chloride solution (20 mL). The organic phase was dried over $MgSO_4$ and filtered. The filtrate was evaporated in vacuo and the residue chromatographed over silica gel using $CH_2Cl_2$ then 2% MeOH in $CH_2Cl_2$ as eluants to give the product as a white foam (293 mg, 73%), mp 63°–68° C.;

IR (film) 1713 and 1658 cm$^{-1}$; NMR (CDCl$_3$) δ1.25 (3H, t, J 7Hz), 1.52–2.00 (17H, m), 2.64–2.86 (4H, m) 3.21 (2H, dd, J 4 and 15Hz), 3.31 (1H, Ha of AB$_q$, J 15Hz) 3.49 (1H, Hb of AB$_q$, J 15Hz) 4.16 (2H q, J 7Hz) 4.31 (1H m) 4.8 (1H, br.), 5.23 (1H, br.), 6.72 (1H, d, J 8Hz) 6.94 (1H, d, J, 2Hz), 7.07–7.26 (7H, m) 7.34 (1H, d, J 8Hz) 7.62 (1H, d, J 8Hz), 8.17 (1H, br.); MS m/e (FAB) 632 (100); Anal. (C$_{36}$H$_{45}$N$_3$O$_5$S); C, H, N, S.

Step 5

2- Adoc-α-Me-D-TrpNHCH(CH$_2$SCH$_2$CO$_2$H)CH$_2$Ph; [R-(R*,S*)]-[[2-[[3-(1H-Indol-3-yl)-2-methyl-1-oxo-2-[[3.3.1.1$^{3,7}$]dec-2-yloxy)carbonyl]amino]propyl]amino]-3-phenylpropyl]thio]acetic acid To a solution of the ethyl ester (100 mg, 0.16 mmol) in ethanol (2 mL) was added 1M NaOH (0.17 mL) solution. The resulting homogenous reaction mixture was stirred at room temperature for 2 hours. After this time the solution was concentrated in vacuo and the residue partitioned between ethyl acetate and 1M HCl solution. The organic layer was washed with saturated sodium chloride solution, dried (MgSO$_4$) and concentrated to yield an amorphous solid (80 mg). This crude product was then purified by reverse phase column chromatography using 66% MeOH in H$_2$O as eluant to yield the desired product (61) as an amorphous solid (61 mg, 63%), mp 112°–130.5° C.; IR (film) 1709 and 1657 cm$^{-1}$; NMR (CDCl$_3$) δ1.50–1.99 (16H, m), 2.45–2.85 (4H, m), 3.15–3.25 (3H, m), 3.44 (1H, Ha of AB$_q$, J 15Hz), 4.29 (1H, m), 4.82 (1H, br.s), 5.40 (1H, br.s), 6.79 (1H, br.m), 6.98–7.25 (9H, m), 7.31 (1H, d, J 8Hz), 7.56 (1H, d, J 8Hz) 8.44 (1H, br.s). MS m/e. (FAB) 135 (100) 604 (13) Anal. (C$_{34}$H$_{41}$N$_3$O$_5$S.0.1H$_2$O), C, H, N, S.

EXAMPLE 25

[R-(R*,S*)]-[[2-[[3-(1H-indol-3-yl)-2-methyl-1-oxo-2-[[tricyclo[3.3.1.1$^{3,7}$]dec -2-yloxy)carbonyl]amino]propyl]amino]-3-phenylpropyl]sulfonyl]acetic acid

Step 1

BocNHCH(CH$_2$SO$_2$CH$_2$CO$_2$Et)CH$_2$Ph; (S)-[[2-[[(1,1-Dimethylethoxy)carbonyl]amino]-3-phenylpropyl]sulfonyl]acetic acid ethyl ester A solution of potassium permanganate (411 mg, 2.60 mmol) in water (5 mL) was added dropwise over 5 minutes to a solution of the sulphide, BOCNHCH(CH$_2$SCH$_2$CO2Et)CH$_2$Ph, (459 mg, 1.3 mmol) in 50% aqueous acetic acid (10 mL). After 1 hour, a 30% solution of hydrogen peroxide was added until the mixture went colorless. This was then diluted with ethyl acetate and washed with saturated sodium hydrogen carbonate solution. The dried (MgSO$_4$) organic phase was filtered and solvent removed in vacuo to yield the sulphone as a white amorphous solid (424 mg, 85%), mp 141°–142° C.; IR (film), 1741, 1692, 1323, and 1138 cm$^{-1}$; NMR (CDCl$_3$) δ1.28 (3H, t, J 7Hz), 1.41 (9H, s), 2.99–3.03 (2H, m), 3.43–3.51 (2H, m), 4.00–4.11 (2H, m), 4.23 (2H, q, J 7Hz), 4.40 (1H, m), 4.95 (1H, br.), 7.20–7.34 (5H, m).

Step 2

H$_2$NCH(CH$_2$SO$_2$CH$_2$CO$_2$Et)CH$_2$Ph.CF$_3$CO$_2$H; (S)-[(2-Amino-3-phenylpropyl)sulfonyl]acetic acid ethyl ester trifluoroacetate (salt) (1:1)

Method as for Example 24, Step 3, except using N-protected ester above, (yield—439 mg from 424 mg).

Step 3

2-Adoc-α-Me-D-TrpNHCH(CH$_2$SO$_2$CH$_2$CO$_2$Et)CH$_2$Ph; [R-(R*,S*)]-[[2-[[3-(1H-Indol-3-yl)-2-methyl-1-oxo-2-[[(tricyclo[3.3.1.1$^{3,7}$]dec-2-yloxy)carbonyl]amino]propyl]amino]-3-phenylpropyl]sulfonyl]acetic acid ethyl ester Method as for Example 24, Step 4, except using the above amine, (yield 55%), mp 69°–80° C.; IR (film) 1739, 1704, and 1665 cm$^{-1}$; NMR (CDCl$_3$) δ1.25 (3H, t, J 7 Hz), 1.46 (3H, s), 1.52–2.04 (14H, m), 2.91 (1H, dd, J 7 and 14 Hz), 3.02 (1H, dd, J 7 and 14 Hz), 3.18–3.52 (4H, m), 3.85 (1H, Ha of ABq, J 15hZ), 4.01 (1H, Hb of ABq, J 15 Hz), 4.13–4.22 (2H, m), 4.64–4.68 (1H, m) 4.79 (1H, s) 5.07 (1H, s), 6.95–7.39 (10H, m), 7.59 (1H, d, J 8 Hz) 8.15 (1H, br.); MS m/e 664 (100); Anal. (C$_{36}$H$_{45}$N$_3$O$_7$S), C, H, N, S.

Step 4

2-Adoc-α-Me-D-TrpNHCH(CH$_2$SO$_2$CH$_2$CO$_2$H)CH$_2$Ph; [R-(R*,S*)]-[[2-[[3-(1H-Indol-3-yl)-2-methyl-1-oxo-2-[[(tricyclo[3.3.1.1$^{3,7}$]dec-2-yloxy)carbonyl]amino]propyl]amino]-3-phenylpropyl]sulfonyl]acetic acid Method as for Example 24, Step 5, except using the carbonic ester, (yield 63%) white amorphous solid, mp 121°–136° C.; IR (film) 1713, 1664, 1317, and 1116 cm$^{-1}$; NMR (CDCl$_3$) δ1.46–2.01 (17H, m), 2.94 (2H, d, J 6 Hz), 3.17–3.44 (4H, m), 3.92 (2H, br.) 4.63 (1H, m), 4.80 (1H, br.s), 5.32 (2H, br.) 6.95–7.25 (9H, m), 7.31 (1H, d, J 8 Hz), 7.54 (1H, d, J 8 Hz), 8.46 (1H, br.s); MS m/e 658 (FAB) (100); Anal. (C$_{34}$H$_{41}$N$_3$O$_7$S.0.1H$_2$O), C, H, N, S.

EXAMPLE 26

[R-(R*,S*)]-β-[[3-(1H-indol-3-yl)-2-methyl-1-oxo-2-[[tricyclo[3.3.1.1$^{3,7}$]dec-2-yloxy)carbonyl]amino]propyl]amino]-4-iodo-benzenebutanoic acid

Step 1

(S)-2-t-Butyloxycarbonylamino-3-(4-iodophenyl)propionic acid (0.79 g, 2.0 mmol) was dissolved in anhydrous THF (10 mL) under nitrogen and N-methylmorpholine (0.20 g, 2.0 mmol) was added. The mixture was chilled in ice/salt and isobutylchloroformate (0.27 g, 2.0 mmol) was added dropwise. After stirring for 20 min the mixture was filtered and the precipitate washed with THF. A solution of diazomethane (approx 7 mmol) in Et$_2$O was added in one portion to the chilled filtrate, and the solution stirred overnight. After evaporation to dryness, the residue was dissolved in EtOAc and washed with water, 10% citric acid soln, saturated NaHCO$_3$ solution and water. After drying over MgSO$_4$, the solvents were evaporated and the residue recrystallized from EtOAc to give the title compound as pale yellow crystals (0.43 g, 52%); mp 119°–122° C.; IR (film) 2114 cm$^{-1}$; NMR (CDCl$_3$) δ1.41 (9H, s), 2.85–3.05 (2H, m), 4.30–4.50 (1H, m), 5.00–5.10 (1H, m), 5.20–5.30 (1H, s), 6.93 (2H, d, J 8 Hz), 7.62 (2H, d, J 8 Hz); Anal ($C_{15}H_{18}IN_3O_3$), C, H, N.

Step 2

The diazoketone obtained in Step 1 (1.07 g, 2.58 mmol) was suspended in 2-(trimethysilyl) ethanol and a solution of silver benzoate (0.10 g) in triethylamine (1 mL) was added dropwise. After nitrogen evolution had ceased, further silver benzoate (0.01 g) in triethylamine (0.10 mL) was added. After stirring for 15 min the mixture was diluted with EtOAc, treated with charcoal and filtered. The solution was washed with 1M $NaHCO_3$ soln, water, 1M hydrochloric acid, water, 1M $NaHCO_3$ solution and water. The organic phase was dried over $MgSO_4$, filtered and evaporated. The residue was purified by flash chromatography eluting with 20% EtOAc/n-hexane, giving a pale yellow oil (0.80 g, 61%); NMR ($CDCl_3$) δ0.05 (9H, s), 0.95–1.00 (2H, m), 1.40 (9H, s), 2.40 (1H, dd, J 6, 16 Hz), 2.47 (1H, dd, J 6, 16 Hz), 2.76 (1H, dd, J 7, 14 Hz), 2.80–2.95 (1H, m), 4.05–4.20 (3H, m), 5.00–5.10 (1H, bd), 6.94 (2H, d, J 8 Hz), 7.61 (2H, d, J 8 Hz); Anal ($C_{20}H_{32}INO_4Si$), C, H, N.

Step 3

To a solution of (S)-trimethylsilylethyl-3-t-butyl oxycarbonylamino-4-(4-iodophenyl)butyrate (0.75 g, 1.5 mmol) from Step 2 in $CH_2Cl_2$ (10 mL) was added trifluoroacetic acid (0.6 mL, 7.8 mmol). After stirring at room temperature overnight the solution was washed with saturated $NaHCO_3$ solution and water. After drying over $MgSO_4$ the solution was filtered and evaporated to dryness to give the desired amine as an oil (0.60 g, 99%); NMR ($CDCl_3$) δ0.04 (9H, s), 0.95–1.00 (2H, m), 2.29 (1H, dd, J 6, 16 Hz), 2.45 (1H, dd, J 4, 16 Hz), 2.55 (1H, dd, J 8, 13 Hz), 2.71 (1H, dd, J 6, 13 Hz), 3.45–3.50 (1H, m), 4.15–4.20 (2H, m), 6.96 (2H, d, J 8 Hz), 7.63 (2H, d, J 8 Hz); Anal ($C_{15}H_{24}INO_2Si$), C, H, N.

Step 4

α-Methyl-N-[(tricyclo[3.3.1.1$^{3,7}$]dec-2-yloxy) carbonyl]-R-tryptophan (0.55 g, 1.4 mmol) was stirred in EtOAc (20 mL) under nitrogen. 1-Hydroxy benzotriazole hydrate (0.21 g, 1.4 mmol) was added followed by N,N'-dicyclohexylcarbodiimide. After stirring for 2 h at room temperature the mixture was filtered and to the filtrate was added a solution of (S)-trimethylsilylethyl 3-amino-4(4-iodophenyl) butyrate (0.60 g, 1.5 mmol) from Step 3 in EtOAc (10 mL). After stirring for 16 h the mixture was concentrated in vacuo and the residue purified by flash chromatography eluting with 30% EtOAc/n-hexane. The product was recrystallized twice from EtOAc/n-hexane to give the desired amide as colorless crystals (0.4 g, 36%); mp 98°–103° C.; NMR ($CDCl_3$) δ0.02 (9H, s), 0.90–1.00 (2H, m), 1.45–2.05 (17H, m), 2.32 (2H, d, J 5 Hz), 2.62 (1H, dd, J 8, 14 Hz), 2.75 (1H, dd, J 7, 14 Hz), 3.30 (1H, d, J 15 Hz), 3.45 (1H, d, J 15 Hz), 4.03–4.16 (2H, m), 4.30–4.45 (1H, m), 4.78 (1H, s), 5.11 (1H, s), 6.87 (2H, d, J 9 Hz), 6.90 (1H, d, J 3 Hz), 7.07 (1H, d, J 7 Hz), 7.09 (1H, t, J 7 Hz), 7.15 (1H, t, J 8 Hz), 7.32 (1H, d, J 8 Hz), 7.54 (2H, d, J 8 Hz), 7.58 (1H, d, J 8 Hz), 8.06 (1H, s).

Step 5

To an ice-cooled solution of the ester obtained in Step 4 (0.30 g, 0.38 mmol) in THF (25 mL) under nitrogen was added dropwise a solution of tetrabutylammonium fluoride (1.0 M in THF, 1.0 mL, 1.0 mmol). After stirring at room temperature for 1 h the reaction mixture was concentrated in vacuo. The residue was taken up in EtOAc and washed with a 10% citric acid solution followed by brine. The organic solution was dried over $MgSO_4$ and concentrated in vacuo. The residue was taken up in MeOH and water added giving the title compound as a colorless solid (0.12 g, 59%); mp 104°–109° C.; NMR ($d_6$-DMSO) δ1.21 (3H, s), 1.45–1.60 (2H, m), 1.70–2.05 (12H, m), 2.30–2.50 (2H, m), 2.65–2.85 (2H, m), 3.14 (1H, d, J 15 Hz), 3.37 (1H, d, J 15 Hz), 4.20–4.35 (1H, m), 4.69 (1H, s), 6.73 (1H, bs), 6.90–7.20 (5H, m), 7.33 (1H, d, J 8 Hz), 7.48 (1H, d, J 8 Hz), 7.61 (2H, d, J 8 Hz), 7.65 (1H, d, J 9 Hz), 10.90 (1H, s), 12.25 (1H, bs); Anal ($C_{33}H_{38}IN_3O_5$), C, H, N.

EXAMPLE 27

[R-(R*,R*)]-[2-[[3-(1H-Indol-3-yl-2-methyl-1-oxo-2-[[(1(tricyclo[[(3.3.1.1$^{3,7}$]dec-2-yloxy)carbonyl] amino]propyl]amino]-1-phenylethoxy]acetic acid Step 1

To stirred solution of (R)-2-chloro-1-phenylethanol (3.56 g, 22.89 mmol) in anhydrous DMF (40 mL) was added sodium azide (1.64 g, 25.18 mmol) in one portion. After 8 h at 100° C. the mixture was poured onto ice and extracted with $Et_2O$ (3×100 mL). The combined $Et_2O$ extracts were washed with water (3×50 mL), dried over $MgSO_4$, filtered and the solvent removed in vacuo. The residue was purified by chromatography over silica gel using $CH_2Cl_2$ as eluant which gave the desired azide (3.10 g, 85%) as a colorless oil; IR (film) 3413 and 2107 cm$^{-1}$; NMR ($CDCl_3$) δ2.86 (1H, d, J 3.0 Hz), 3.32–3.44 (2H, m), 4.75–4.80 (1H, m), 7.26–7.37 (5 H, m); Anal ($C_8H_9N_3O$), C, H, N.

Step 2

To a suspension of 60% NaH (149 mg, 3.71 mmol) in anhydrous THF (3 mL) at 0° C. and under an $N_2$ atmosphere was added tetramethylethylene diamine (0.90 mL, 5.94 mmol) followed by a solution of (R)-2-azido-1-phenylethanol from Step 1 (485 mg, 2.97 mmol) in anhydrous THF (3 mL) added over 3 min. The cold solution was stirred for 1.S h and then a solution of methyliodoacetate (742 mg, 3.71 mmol) in anhydrous THF (3 mL) was added dropwise. After 24 h at room temperature the solution was diluted with $Et_2O$ (25 mL) and washed with 5% citric acid solution (2×25 mL) and brine (25 mL). The $Et_2O$ layer was dried ($MgSO_4$), filtered and the solvents removed in vacuo. The residue was purified by chromatography over silica gel using $CH_2Cl_2$ as eluant which gave the desired ether (257 mg, 37%) as a white waxy solid; mp 37°–41° C.; IR (film) 2105 and 1757 cm$^{-1}$; NMR ($CDCl_3$) δ3.29 (1H, dd, J 3.9, 12.9 Hz), 3.60 (1H, dd, J 8.1, 12.9 Hz), 3.74 (3H, s,), 3.95 (1H, d, J 16.1 Hz), 4.12 (1H, d, J 16.4 Hz), 4.67 (1H, dd, J 4.0, 8.1 Hz), 7.32–7.42 (5H, m); Anal ($C_{11}H_{13}N_3O_3$), C, H, N.

Step 3

A solution of the azido ester from Step 2 (247 mg, 1.05 mmol) and 10M HCl solution (0.53 mL, 5.3 mmol) in absolute EtOH (50 mL) was reduced over 10% Pd/C (25 mg) at 40° C. under an atmosphere of $H_2$ at 45 psi for 5 h. The catalyst was filtered off and the solvent removed in vacuo to give the amine hydrochloride (287 mg) which was without further purification in the next step; IR (film) 1738 cm$^{-1}$.

Step 4

To a stirred solution of α-methyl-N-[(tricyclo[3.3.1.1$^{3,7}$] dec-2-yloxy)carbonyl]-R-tryptophan (333 mg, 0.84 mmol) and 1-hydroxy benzotriazole hydrate (161 mg, 1.05 mmol) in EtOAc (30 mL) was added N,N'-dicyclohexylcarbodiimide (191 mg, 0.92 mmol). After 1 h at room temperature triethylamine (0.174 mL, 1.25 mmol) was added followed by dropwise addition of a solution of the amine hydrochloride from Step 3 (272 mg, 1.05 mmol) in EtOAc (10 mL). After 24 h the reaction mixture was filtered and the EtOAc solution washed with 5% citric acid solution (2×25 mL), saturated NaHCO$_3$ solution (2×25 mL), 5% citric acid solution (25 mL) and brine (25 mL). The EtOAc extract was dried over MgSO$_4$, filtered and the solvent removed in vacuo. the residue was purified by chromatography over silica using 30% EtOAc/n-hexane then 70% EtOAc/n-hexane as eluant to give the desired amide as a white solid (200 mg, 40%); mp 74°–81° C.; IR (film) 1743, 1705 and 1659 cm$^{-1}$; NMR (CDCl$_3$) δ1.26 (3H, t, J 7.2 Hz), 1.48–2.04 (17H, m), 3.17–3.26 (1H, m), 3.48–3.60 (2H, m), 3.61–3.68 (1H, m), 3.81 (1H, d, J 16.8 Hz), 4.07 (1H, d, J 17.0 Hz), 4.15–4.32 (3H, m), 4.84 (1H, s), 5.60 (1H, br s), 7.03–7.42 (10H, m), 7.68 (1H, d, J 7.8 Hz), 8.14 (1H, s); Anal (C$_{35}$H$_{43}$N$_3$O$_6$), C, H, N.

Step 5

To a stirred solution of the ester from Step 4 (178 mg, 0.30 mmol) in EtOH (10 mL) at 0° C. was added dropwise 1.0M NaOH solution (0.33 mL, 0.33 mmol). The cooled solution was stirred for 2.5 h and then at room temperature for 21 h. A 1.0M HCl solution (0.36 mL, 0.36 mmol) was added and the solvents removed in vacuo. The residue was dissolved in EtOAc (25 mL) and then washed with brine (25 mL). The EtOAc extract was dried over MgSO$_4$, filtered and the solvent removed in vacuo. The residue was purified by chromatography over reverse phase silica using 67% MeOH:33% H$_2$O then 75% MeOH:25% H$_2$O as eluant giving the acid as a white solid (67 mg, 39%); mp 198°–212° C.; IR (film) 1700 and 1649 cm$^{-1}$; NMR (CDCl$_3$) δ1.54–2.01 (17H, m), 3.13–3.17 (1H, m), 3.21–3.55 (3H, m), 3.70–3.75 (1H, m), 3.95 (1H, d, J 16.6 Hz), 4.12 (1H, m), 4.18 (1H, br s), 7.01–7.63 (10H, m); Anal (C$_{33}$H$_{39}$N$_3$O$_6$·0.5 H$_2$O), C, H, N.

EXAMPLE 28

[[3-[[3-(1H-Indol-3-yl)-2-methyl-1-oxo-2-[[tricyclo(3.3.1.1$^{3,7}$]dec-2-yloxy)carbonyl]amino]propyl]amino]-1-oxo-2-phenylpropyl]amino]acetic acid
(TRP center is R, other center is RS).

Step 1

A solution of RS-ethylphenylcyanoacetate (5.0 g, 26.43 mmol) and 10M HCl (13.2 mL, 132 mmol) in EtOH (200 mL) was reduced over 10% Pd/C at 30° C. under an atmosphere of H$_2$ at 45 psi for 18 h. The catalyst was filtered off and the solvent removed in vacuo giving a solid residue. Recrystallization from EtOH:Et$_2$O (1:3, 100 mL) gave the amine (4.90 g, 81%) as white prisms; mp 158°–160° C. (EtOH:Et$_2$O); NMR (d$^4$-MeOH) δ1.22 (3H, t, J 7.1 Hz), 3.22 (1H, dd, J 6.0, 12.9 Hz), 3.55 (1H, dd, J 8.9, 12.9 Hz), 4.09–4.28 (3H, m), 7.28–7.43 (5H, m); Anal (C$_{11}$H$_{16}$Cl N O$_2$·0.1 H$_2$O), C, H, N.

Step 2

To a stirred solution of α-methyl-N-[(tricyclo[3.3.1.1$^{3,7}$] dec-2-yloxy)carbonyl]-R-tryptophan (397 mg, 1.0 mmol) and 1-hydroxybenzotriazole hydrate (191 mg, 1.25 mmol) in EtOAc (40 mL) was added N,N'-dicyclohexylcarbodiimide (227 mg, 1.10 mmol). After 1 h the amino ester hydrochloride from Step 1 (253 mg, 1.10 mmol) was added followed by dropwise addition of a solution of triethylamine (0.153 mL, 1.10 mmol) in EtOAc (5 mL). After stirring at room temperature for 20 h the mixture was filtered and the EtOAc solution washed with 5% citric acid solution (2×25 mL), saturated NaHCO$_3$ solution (2×25 mL), 5% citric acid solution (25 mL) and brine (25 mL). The EtOAc extract was then dried over MgSO$_4$, filtered and the solvent removed in vacuo. The residue was purified by chromatography over silica using 1% MeOH:99% CH$_2$Cl$_2$ as eluant which gave the desired amide (361 mg, 63%) as a white solid; mp 68°–77° C.; IR (film) 1719 and 1661 cm$^{-1}$; NMR (CDCl$_3$) δ1.17 (3H, t, J 7.1 Hz), 1.47–1.99 (17H, m), 3.24–3.44 (2H, m), 3.61–3.90 (3H, m), 4.05–4.14 (2H, m), 4.80 (1H, br s), 5.05–5.20 (1H, m), 6.50–6.70 (1H, m), 6.92–7.59 (10H, m), 8.16–8.18 (1H, m); Anal (C$_{34}$H$_{41}$N$_3$O$_5$·0.25 H$_2$O), C, H, N.

Step 3

To a stirred solution of the ester from Step 2 (1.28 g, 2.23 mmol) in THF (130 mL) at 0° C. was added dropwise over 75 min 0.1M LiOH solution (24.6 mL, 2.46 mmol). The cooled solution was stirred for 27 h with gradual warming to room temp. A 1.0M HCL solution (2.7 mL, 2.7 mmol) was added and the THF removed in vacuo. The residue was extracted with EtOAc (2×50 mL) and the combined organic extracts washed with brine (1×50 mL). The EtOAc layer was dried over MgSO$_4$, filtered and the solvent removed in vacuo. The residue was purified by chromatography over reverse phase silica using 67% MeOH:33% H$_2$O as eluant which gave the desired acid as a mixture of 2 diastereoisomers and as a white solid; mp 179°–188° C.; IR (film) 1700, 1657 cm$^{-1}$; NMR (d$^4$-MeOH) δ1.31 and 1.33 (3H, 2s), 1.54–2.03 (14H, m), 3.18–3.81 (5H, m), 4.75 (1H, br s), 6.94–7.50 (10H, m); Anal (C$_{32}$H$_{37}$N$_3$O$_5$·1.0 H$_2$O), C, H, N.

Step 4

To a stirred solution of the acid from Step 3 (272 mg, 0.50 mmol) and 1-hydroxybenzotriazole hydrate (96 mg, 0.63 mmol) in EtOAc (30 mL) was added N,N'-dicyclohexylcarbodiimide (124 mg, 0.60 mmol). After 1 h at room temperature glycine benzylester hydrochloride (151 mg, 0.75 mmol) was added followed by triethylamine (0.112 mL, 0.80 mmol). The mixture was stirred at room temperature for 24 h and then filtered. The EtOAc solution was washed with 5% citric acid solution (2×25 mL), saturated NaHCO$_3$ solution (2×25 mL), 5% citric acid solution (25 mL) and brine (25 mL). The EtOAc solution was dried over MgSO$_4$, filtered and the solvent removed in vacuo. The residue was purified by chromatography over silica using 50% EtOAc:50% n-hexane to give the desired amide as a white solid and as a mixture of 2 diastereoisomers (222 mg, 64%); mp 86°–95° C.; IR (film) 1742, 1710 and 1661 cm$^{-1}$; NMR (CDCl$_3$) δ1.49–2.03 (17H, m), 3.22–3.53 (4H, m), 3.68–3.80 (2H, m), 3.94–4.13 (1H, m), 4.80 (1H, m), 5.06–5.40 (3H, m), 5.74–5.78 (1H, m), 6.78–7.39 (10H, m), 7.57 and 7.65 (1H, 2d, J 8 Hz), 8.06 and 8.22 (1H, 2s); Anal (C$_{41}$H$_{46}$N$_4$O$_6$·0.25 H$_2$O), C, H, N.

Step 5

A solution of the benzylester from Step 4 (145 mg, 0.21 mmol) in absolute EtOH (50 mL) was reduced over Pd(OH)$_2$/C (15 mg) at 40° C. under an atmosphere of H$_2$ at 45 psi for 6 h. Filtration of the catalyst and removal of the solvent in vacuo gave a foam. Purification by chromatography over reverse phase silica using 67% MeOH:33% H$_2$O then 75% MeOH:25% H$_2$O gave the product as a white solid and as 2 diastereoisomers (62 mg, 49%); mp 122°–131° C.; IR (film) 1700 and 1661 cm$^{-1}$; NMR (d$_6$-DMSO) δ1.22–1.97 (17H, m), 3.17–3.67 (6H, m), 3.90 (1H, dd, J 7.5, 15.1 Hz), 4.71 (1H, br s), 6.61–6.65 (1H, m), 6.92–7.08 (3H, m), 7.24–7.48 (7H,m), 7.62 and 7.81 (1H, 2br s), 8.29–8.36 (1H, m), 10.88 (1H, s); Anal (C$_{34}$H$_{40}$N$_4$O$_6$.0.75 H$_2$O), C, H, N.

EXAMPLE 29

(R)-[[[2-[[3-(1H-indol-3-yl)-1-oxo-2-methyl-2-[[(tricyclo[3.3.1.1$^{3,7}$]dec-2-yloxy)carbonyl]amino]propyl] amino]-1-phenylethylidene]amino]oxy]acetic acid

Step 1

To a stirred suspension of α-aminoacetophenone hydrochloride (6.60 g, 38.5 mmol) in anhydrous THF (100 mL) at 0° C. was added 2-(trimethylsilyl) ethyl chloroformate (7.0 g, 38.5 mmol ) followed by a solution of triethylamine (7.78 g, 76.9 mmol) in THF (30 mL). The reaction was complete after 10 h as assayed by thin layer chromatography. The reaction mixture was filtered and the solvent removed in vacuo. The residue was purified by chromatography over silica using 25% EtOAc/n-hexane to give the desired urethane (5.62 g, 53%) as a yellow crystalline solid; IR (film) 1692 cm$^{-1}$; NMR (CDCl$_3$) δ0.05 (9H, s), 1.19 (2H, t, J 7 Hz), 4.16 (2H, t, J 4 Hz), 4.64 (2H, d, J 4 Hz), 5.72 (1H, bs), 7.42 (2H, t, J 7 Hz), 7.52–7.57 (1H, m), 7.90 (2H, d, J 7 Hz).

Step 2

To a stirred solution of the ketone from Step 1 (5.62 g, 20.1 mmol) in absolute EtOH (50 mL) was added a solution of hydroxylamine hydrochloride (2.31 g, 33.2 mmol) and sodium acetate (3.30 g, 40.2 mmol) in water (25 mL). The reaction mixture was refluxed and reaction was complete after 18 h as assayed by thin layer chromatography. The reaction was cooled to room temperature and the solvent removed in vacuo. The organic material was extracted with EtOAc (2×100 mL) washed with water (2×50 mL) and dried over MgSO$_4$. The solvent was removed in vacuo. The residue was purified by chromatography over silica using 25% EtOAc/n-hexane then 50% EtOAc/n-hexane to give the oxime (3.01 g, 51%) as a pale yellow crystalline solid; mp 61°–65° C.; IR (film) 1692 cm$^{-1}$; NMR (CDCl$_3$) δ0.02 (9H, s), 1.23–1.28 (2H, t, J 7 Hz), 4.16 (2H, t, J 8 Hz), 4.45 (2H, d, J 6 Hz), 5.37 (1H, bs), 7.38 (3H, t, J 3 Hz), 7.74 (2H, bs), 8.30 (1H, bs).

Step 3

To a stirred solution of the oxime from Step 2 (1.85 g, 6.3 mmol) in toluene (30 mL) was added tetrabutylammonium bromide (0.37 g, 1.1 mmol) and methyl 2 bromo acetate (1.93 g, 12.6 mmol ). To this reaction mixture a NaOH solution (5 mL, 10% w/w) was added dropwise. The reaction was complete after 4 h as assayed by thin layer chromatography. The reaction mixture was diluted with Et$_2$O (50 mL), the organic layer washed with water, dried with MgSO$_4$ and the solvent removed in vacuo. The residue was purified by chromatography over silica using 25% EtOAc/n-hexane then 50% EtOAc/n-hexane to give the desired oxime ether (1.02 g, 49%) as a pale yellow oil. This was stored under nitrogen in the fridge until required; IR (film) 1751, 1717 cm$^{-1}$; NMR (CDCl$_3$) δ0.03 (9H, s), 0.99–01.02 (2H, m), 3.79 (3H, s), 4.16–4.22 (2H, m), 4.45 (2H, d, J 6 Hz), 4.81 (2H, s), 6.05 (1H, bs), 7.36–7.39 (3H, m), 7.75–7.77 (2H, m).

Step 4

To a stirred solution of the ester from Step 3 (1.00 g, 2.7 mmol) in acetonitrile (50 mL) under a nitrogen atmosphere was added a 1B tetrabutylammonium fluoride solution in THF (2 mL, 6.9 mmol). The reaction was complete after 70 h as assayed by thin layer chromatography. The solvent was removed in vacuo, the residue extracted with EtOAc (2×50 washed with saturated NaHCO$_3$ soln, water and dried over MgSO$_4$. The solvent was removed in vacuo and the residue purified by chromatography over silica using 5% MeOH/CH$_2$Cl$_2$ to give the amine (0.265 g, 44 %) as a yellow oil; IR (film) 1757 cm$^{-1}$; NMR (CDCl$_3$) δ1.67 (2H, bs), 3.77 (3H, s), 3.92 (2H, bs), 4.78 (2H, s), 7.37–7.40 (3H, m), 7.61–7.64 (2H,m).

Step 5

To a stirred solution of α-methyl-N-[(tricyclo[3.3.1.1$^{3,7}$] dec-2-yloxy)carbonyl]-R-tryptophan (446 mg, '1.13 mmol) in EtOAc (20 mL) was added 1-hydroxybenzotriazole hydrate (189 mg, 1.23 mmol) followed by a solution of N,N'-dicyclohexylcarbo-diimide (278 mg, 1.35 mmol) in EtOAc (5 mL). The mixture was stirred for 1 h after which time the amine from Step 4 (250 mg, 1.13 mmol) in EtOAc (10 mL) was added. This mixture was stirred for 24 hours, filtered and the solvent removed in vacuo. The residue was purified by chromatography using 25% EtOAc/n-hexane, then 50% EtOAc/n-hexane as eluants. This gave the desired amide (379 mg, 56%), as a white foam; NMR (CDCl$_3$) δ1.47–1.96 (17H, m), 3.46 (2H, bs), 3.72 (3H, bs), 4.53 (2H, d, J 5 Hz), 4.75 (2H, s), 4.81 (1H, bs), 6.58 (1H, bs), 6.87–7.72 (12H, m), 7.90 (1H, bs).

Step 6

To a solution of the methyl ester from Step 5 (100 mg, 0.17 mmol) in THF (8 mL) at −15° C. was added 0.1M LiOH (1.75 mL, 0,175 mmol) dropwise over a 1 h period. The resulting solution was allowed to slowly warm to room temperature over 10 hours. The reaction mixture was acidified with 1M HCl to pH 4 and the solvent removed in vacuo. The organic residue was extracted with EtOAc (2×20 mL), washed with water, dried over MgSO$_4$ and filtered. The solvent was then removed in vacuo. The crude product was purified by reverse phase chromatography using 2.5:1 MeOH:H$_2$O. This gave the desired acid (55 mg, 56%) as a white foam; mp 138°–142° C.; IR (film) 1726, 1703 cm$^{-1}$; NMR (d$_6$-DMSO) δ1.08 (3H, bs), 1.47–1.90 (14H, m), 3.16 (2H, s), 4.43 (2H, d, J 4 Hz), 4.64 (1H, bs), 4.70 (2H, bs), 6.56 (1H, bs), 6.87–7.54 (10H, m), 8.04 (1H, bs), 10.8 (1H, bs); Anal (C$_{33}$H$_{38}$N$_4$O$_6$), C, H, N.

EXAMPLE 30

[R-(R*,S*)]-β-[[3-(1H-Indol-3-yl)-2-methyl-1-oxo-2-[[(tricyclo[3.3.1.1$^{3,7}$]dec-2-yloxy)carbonyl]amino] propyl]amino]benzenebutanoic acid

Step 1

To a stirred solution of N-t-butyloxycarbonyl-S-phenylalanine (7.12 g, 26.8 mmol) and N-methylmorpholine (3.0 mL, 26.8 mmol) in anhydrous THF (50 mL) at −10° C. was added dropwise isobutylchloroformate (3.4 mL, 26.8 mmol). After 20 min the N-methyl-morpholine hydrochloride was filtered off and a solution of diazomethane (33.4 mmol) in Et$_2$O (50 mL) was added in one portion to the filtrate at −10° C. The cooled solution was stirred for 30 min and then for 16 h at room temp. The solvents were removed in vacuo and the residue dissolved in EtOAc (50 mL) and washed with water (2×25 mL), 5% citric acid solution (2×25 mL), 1M NaHCO$_3$ (25 mL) and brine (25 mL). The EtOAc solution was dried over MgSO$_4$, filtered and the solvent removed in vacuo to give the diazoketone as a pale yellow solid (7.04 g, 90%); IR (film) 2109, 1709 and 1641 cm$^{-1}$; NMR (CDCl$_3$) δ1.41 (9H, s), 3.02 (2H, d, J 6.8 Hz), 4.40 (1H, br s), 5.08–5.21 (2H, m), 7.17–7.33 (5H, m).

Step 2

To a stirred solution of 2-oxo-3-(t-butyloxycarbonylamino)-3-phenylpropanol (7.04 g, 24.0 mmol) from Step 1 in MeOH (70 mL) was added 7 mL of a solution of silver (I) benzoate (1.37 g, 6.0 mmol) in triethylamine (14 mL) causing evolution of nitrogen. When nitrogen evolution has ceased a further portion of the silver (I) benzoate solution (0.28 mL) was added and the resulting brown colored solution was stirred for 15 min. After this time the solution was treated with charcoal, filtered and the solvents removed in vacuo giving a residue which was dissolved in EtOAc (50 mL). The yellow EtOAc solution was washed with water (2×25 mL), 1M NaHCO$_3$ (2×25 mL), 1M HCl (2×25 mL), 1M NaHCO$_3$ (25 mL) and brine (25 mL). The EtOAc solution was then dried (MgSO$_4$), filtered and the solvent removed in vacuo giving the methyl ester as an oil (5.27, 75%); IR (film) 1741 and 1713 cm$^{-1}$; NMR (CDCl$_3$) δ1.40 (9H, s), 2.40–2.55 (2H, m), 2.77–2.95 (2H, m), 3.67 (3H, s), 4.08–4.17 (1H, m), 4.97 (1H, br s), 7.11–7.31 (5H, m).

Step 3

To a stirred solution of methyl-3-(t-butyloxycarbonylamino)-4-phenylbutyrate (4.16 g, 14.19 mmol) from Step 2 in CH$_2$Cl$_2$ (10 mL) was added trifluoroacetic acid (10 mL). After stirring for 1 h at room temperature the solvents were removed in vacuo giving the desired amine as an oil which was used without further purification in the next step.

Step 4

To a stirred solution of α-methyl-N-[(tricyclo[3.3.1.1$^{3,7}$]dec-2-yloxy)carbonyl]-R-tryptophan (4.5 g, 11.35 mmol) and 1-hydroxybenzotriazole hydrate (1.92 g, 12.54 mmol) in EtOAc (100 mL) at room temperature was added N,N'-dicyclohexylcarbodiimide (2.93 g, 14.19 mmol). After 1 h 4-dimethylaminopyridine (0.14 g, 1.14 mmol) was added followed by dropwise addition of a solution of methyl-3-amino-4-phenylbutyrate trifluoroacetic acid salt (4.36 g, 14.19 mmol) from Step 3 and triethylamine (4.5 mL, 32.00 mmol) in EtOAc (25 mL) and the mixture stirred at room temperature for 72 h. The reaction mixture was then filtered and the EtOAc solution washed with 5% citric acid solution (2×25 mL), saturated NaHCO$_3$ solution (2×25 mL), 5% citric acid solution (50 mL) and brine (50 mL). The EtOAc layer was dried (MgSO$_4$), filtered and the solvent removed in vacuo. The residue was purified by chromatography over silica using 1% MeOH:99% CH$_2$Cl$_2$ as eluant which gave the desired amide (3.27 g, 50%) as a white solid; mp 78°–84° C.; IR (film) 1722 and 1658 cm$^{-1}$; NMR (CDCl$_3$) δ1.45 (3H,s), 1.50–2.16 (14H, m), 2.40 (2H, d, J 5.1 Hz), 2.71 (1H, dd, J 7.9, 13.7 Hz), 2.84 (1H, dd, J 6.6, 13.7 Hz), 3.30 (1H, d, J 14.7 Hz), 3.47 (1H, d, J 14.7 Hz), 3.60 (3H, s), 4.42–4.45 (1H, m), 4.81 (1H, s), 5.14 (1H, s), 6.89–7.28 (9H, m), 7.33 (1H, d, J 8.0 Hz), 7.59 (1H, d, J 7.5 Hz), 8.20 (1H, s); Anal (C$_{34}$H$_{41}$N$_3$O$_5$.0.25 H$_2$O), C, H, N.

Step 5

To a solution of the methyl ester from Step 4 (2.5 g, 4.37 mmol) in THF (250 mL) at 0° C. was added dropwise over 50 min an aqueous solution of 0.1M LiOH (48 mL, 4.80 mmol). The cooled solution was then allowed to warm to room temperature over 2 h and stirred at this temperature for a further 20 h. After this time 1M HCl (5.3 mL, 5.3 mmol) was added and the solution washed with Et$_2$O (2×100 mL), the Et$_2$O extract dried (MgSO$_4$), filtered and the solvents removed in vacuo which gave the acid as a white solid (2.24 g, 92%; mp 123°–137° C.; IR (film) 1708 and 1658 cm$^{-1}$; NMR (CDCl$_3$) δ1.51–2.00 (17H, m), 2.27–2.34 (2H, m), 2.70 (1H, dd, J 8.1, 13.5 Hz), 2.82 (1H, dd, J 6.3, 13.6 Hz), 3.23 (1H, d, J 14.7 Hz), 3.43 (1H, d, J 14.7 Hz), 4.42 (1H, m), 4.81 (1H, s), 5.41 (1H, br s), 6.87–7.31 (10H, m), 7.55 (1H, d, J 7.8 Hz), 8.50 (1H, s); Anal (C$_{33}$H$_{39}$N$_3$O$_5$.0.1 H$_2$O), C, H, N.

EXAMPLE 31

[R-(R*,S*)]-N-[3-[[3-(1H-Indol-3-yl)-2-methyl-1-oxo-2-[[(tricyclo-[3.3.1.1$^{3,7}$]dec-2-yloxy)carbonyl]propyl]amino]-4-phenylbutyl]glycine Step 1

To a stirred solution of the acid from Step 5 (291 mg, 0.52 mmol) and 1-hydroxybenzotriazole hydrate (88 mg, 0.65 mmol) in EtOAc (30 mL) was added N,N'-dicyclohexylcarbo-diimide (129 mg, 0.62 mmol). After 1 h at room temperature 4-dimethylaminopyridine (6 mg, 0.05 mmol) was added followed by triethylamine (0.109 mL, 0.78 mmol) and glycine ethyl ester hydrochloride (109 mg, 0.78 mmol). The mixture was stirred at room temperature for 2 h and then filtered. The EtOAc solution was washed with 5% citric acid solution (2×25 mL), saturated NaHCO$_3$ solution (2×25 mL), 5% citric acid solution (25 mL) and brine (25 mL). The EtOAc solution was dried over MgSO$_4$, filtered and the solvent removed in vacuo. The residue was purified by chromatography over silica using 2% MeOH:98% CH$_2$Cl$_2$ as eluant giving the desired amide as a white solid (212 mg, 64%); mp 82°–94° C.; IR (film) 1741, 1705 and 1651 cm$^{-1}$; NMR (CDCl$_3$) δ1.27 (3H, t, J 7 Hz), 1.37 (3H, s), 1.50–2.01 (14H, m), 2.30 (1H, dd, J 4.4, 14.0 Hz), 2.51 (1H, dd, J 3.9, 13.7 Hz), 2.70–2.85 (2H, m), 3.31 (2H, s), 3.75 (1H, dd, J 5.2, 17.8 Hz), 4.09–4.23 (3H, m), 4.39–4.48 (1H, m), 4.74 (1H, br s), 5.17 (1H, s), 6.73 (1H, m), 6.81 (1H, d, J 2.1 Hz), 7.06–7.28 (8H, m), 7.32 (1H, d, J 7.9 Hz), 7.57 (1H, d, J 7.8 Hz), 8.16 (1H, br s); Anal (C$_{37}$H$_{46}$N$_4$O$_6$), C, H, N.

Step 2

To a stirred solution of the ethyl ester from Step 1 (788 mg, 1.23 mmol) in EtOH (75 mL) at 0° C. was added NaOH solution (13.5 mL of a 0.1M soln, 1.35 mmol) over 10 min. The cold solution was stirred with gradual re-warming to room temperature for 5.5 h. The EtOH was removed in vacuo and 5% citric acid solution (25 mL) added to the residue. The aqueous solution was extracted with Et$_2$O (2×25 mL) the Et$_2$O extract dried over MgSO$_4$, filtered and the solvent removed in vacuo to give the desired acid as a white foam (553 mg, 73%); mp 98°–103° C.; IR (film) 1700 and 1657 cm$^{-1}$; NMR (CDCl$_3$) δ1.37–1.98 (17H, m), 2.25–2.32 (2H, m), 2.69–2.79 (2H, m), 3.20 (1H, d, J 14.6 Hz), 3.29 (1H, d, J 14.5 Hz), 3.76 (1H, dd, J 4.7, 18.1 Hz), 4.04 (1H, dd J 5.8, 17.7 Hz), 4.36–4.40 (1H, m), 4.75 (1H, s), 5.37 (1H, br s), 6.83–7.19 (10H, m), 7.29 (1H, d, J 8.0 Hz), 7.53 (1H, d, J 7.8 Hz), 8.40–8.65 (1H, m); Anal (C$_{35}$H$_{42}$N$_4$O$_6$.1 H$_2$O), C, H, N.

EXAMPLE 32

2-[[[2-[[3-(1H-indol-3-yl)-2-methyl-1-oxo-2-[[(tricyclo-[3.3.1.1$^{3,7}$]dec-2-yloxy)carbonyl]amino]propyl]amino]-1-phenylethyl]amino]carbonyl]cyclopropanecarboxylic acid (cyclopropane ring is trans-(±) other centers are R)

Step 1

A solution (R)-β-[1-(phenylmethyl)amino]benzeneethanol (6.44 g, 23.8 mmol) in anhydrous CH$_2$Cl$_2$ (50 mL) was treated with triethylamine (2.88 g, 28.5 mmol), followed by a solution of p-toluene sulphonyl chloride (5.43 g, 28.5 mmol) in CH$_2$Cl$_2$ (20 mL). After stirring for 18 h at room temperature, the reaction mixture was washed with 1M citric acid solution (2×50 mL) and the organic phase dried over MgSO$_4$, filtered and the solvent evaporated in vacuo to give a crude, pale yellow solid (8.49 g) mp 103–105, 5° C. (EtOAc/n-hexane); IR (film) 3410, 1703, 1361 and 1190 cm$^{-1}$; NMR (CDCl$_3$) δ2.42 (3H, s), 4.25 (2H, m), 4.98 (1H, br s), 5.07 (2H, s), 5.35 (1H, br s), 7.20–7.40 (12H, m), 7.65 (2H, d, J 8 Hz); Anal (C$_{16}$H$_{17}$NO$_3$) C,H,N. This crude solid (7.57 g) was dissolved in anhydrous DMF (100 mL) and treated with sodium azide (1.21 g, 18.6 mmol) then warmed to 80° C. for 3 hours, cooled and poured into ice water (200 mL). This mixture was extracted with Et$_2$O (2×200 mL) and the combined organic phases washed with H$_2$O (200 mL), dried over MgSO$_4$ and evaporated in vacuo to yield a yellow oil (4.95 g) ; IR (film) 3300, 2130 and 1697 cm$^{-1}$; NMR (CDCl$_3$) δ3.66 (2H, m), 4.95 (1H, m), 5.09 (1H, d, J 11 Hz), 5.12 (1H, d, J 11 Hz), 5.31 (1H, m), 7.25–7.45 (10H, m). This crude oil (5 g) in EtOAc (100 mL) was treated with Lindlar catalyst (2 g, 40% w/w) and placed under an atmosphere of hydrogen at 45 psi at 30° C. for 6 hours then filtered through filter aid to give a solution of the desired amine (R)-β-[1-(phenylmethyl)amino]benzeneethanol which was used immediately assuming a quantitative yield; IR (film) 3300, 1703 cm$^{-1}$.

Step 2

A solution of the acid, α-methyl-N-[(tricyclo[3.3.1.1$^{3,7}$]dec-2-yloxy)carbonyl]-R-tryptophan (4.60 g, 11.6 mmol) in EtOAc (30 mL) was treated with 1-hydroxybenzotriazole hydrate (1.96 g, 12.8 mmol) and N,N'-dicyclohexylcarbodiimide (2.87 g, 13.9 mmol) and stirred at room temperature for 2 h before the amine from Step 1 (4.46 g, 16.9 mmol) in EtOAc (10 mL) was added. After stirring a further 18 h the mixture was filtered, concentrated in vacuo and purified by silica gel chromatography to give the desired urethane as a white solid (6.17 g, 56%); mp 69°–73° C.; [α]$^{20}_D$+8.9° (c=1, MeOH); IR (film) 3350, 1700 and 1662 cm$^{-1}$; NMR (CDCl$_3$) δ1.54 (5H, br), 1.60–1.95 (14H, m), 3.23 (1H, d, J 14 Hz), 3.35 (1H, m), 3.43 (1H, d, J 14 Hz), 3.72 (1H, m) 4.79 (2H, br s), 5.07 (2H, s), 5.13 (1H, s), 5.90 (1H, br s), 6.43 (1H, br s), 6.93 (1H, s), 7.10–7.40 (13H, m), 7.55 (1H, d, J 8 Hz), 7.95 (1H, s); Anal (C$_{39}$H$_{44}$N$_4$O$_5$.0.5 H$_2$O) C, H, N.

Step 3

A solution of the benzyl urethane from Step 2 (6.17 g, 8.94 mmol) in absolute EtOH (50 mL) was treated with Pearlman's catalyst (620 mg, 10% w/w/). The mixture was put under an atmosphere of hydrogen at 45 psi for 18 h at 25° C., filtered and concentrated in vacuo to yield the amine tricyclo[3.3.1.1$^{3,7}$]dec-2-yl[R-(R*,R*)]-[2-[(2-amino-2-phenylethyl)amino]-1-(1H-indol-3-ylmethyl)-1-methyl-2-oxoethyl]carbamate as a white foam, pure enough to be used directly in the next step (4.44 g, 89%); mp 91°–94° C.; [α]$^{20}_D$+10.3° (c=1, MeOH); IR (film) 3340, 1701 and 165 cm$^{-1}$; NMR (CDCl$_3$) δ1.54 (5H, br s), 1.70–2.05 (14H, m), 3.15 (1H, ddd, J 6, 8 and 14 Hz), 3.31 (1H, d, J 15 Hz), 3.54 (1H, d, J 15 Hz), 3.55 (1H, m), 3.97 (1H, m) 4.82 (1H, s), 5.15 (1H, s), 6.49 (1H, br s), 6.96 (1H, d, J 2 Hz), 7.10–7.40 (8H, m), 7.59 (1H, d, J 8 Hz), 8.19 (1H, s); Anal (C$_{31}$H$_{38}$N$_4$O$_3$.0.75 H$_2$O), C, H, N.

Step 4

A solution of RS-mono methyl cyclopropanedicarboxylate (126 mg, 0.88 mmol) in anhydrous EtOAc (10 mL) was treated with 1-hydroxybenzotriazole hydrate (132 mg, 0.86 mmol) and N,N'-dicyclohexylcarbodiimide (186 mg, 0.90 mmol ) and stirred at room temperature for 2 h before the amine from Step 3 (300 mg, 0.58 mmol) was added. After stirring for a further 3 h the reaction mixture was filtered, concentrated in vacuo and purified by silica gel chromatography to give the desired amide as a mixture of 2 diastereoisomers (258 mg, 69%); mp 118°–122° C.; IR (film) 3320, 2909, 2855, 1720, 1700, 1659 and 1531 cm$^{-1}$; NMR (CDCl$_3$) δ1.25–2.05 (20H, m), 2.15 (2H, m), 3.32 (2H, m), 3.48 (1H, d, J 14 Hz), 3.67 and 3.69 (3H, 2s), 3.95 (1H, m), 4.84 (1H, br s), 5.04 (1H, s), 5.11 (1H, br s), 6.40 (1H, br s), 6.95 and 6.97 (1H, 2d, J 3 Hz), 7.10–7.35 (9H, m) 7.55 and 7.58 (1H, 2d, J 4 Hz), 8.24 (1H, s); Anal (C$_{37}$H$_{42}$N$_4$O$_6$.0.5 H$_2$O), C, H, N.

Step 5

The methyl ester from Step 4 (238 mg, 0.37 mmol) as a solution in THF (20 mL) at 0° C. was treated dropwise with aqueous LiOH solution (3.72 mL of 0.1M soln, 0.37 mmol). The resulting mixture was stirred at 0° C. for 4 h and then allowed to warm to room temperature over 16 h. After this time the reaction was acidified with 1M HCl (0.5 mL), concentrated in vacuo and extracted with EtOAc. The organic phase was dried over MgSO$_4$, filtered and evaporated in vacuo. The residue was purified by reverse phase column chromatography, eluant 2.5:1 MeOH: H$_2$O, to give the desired acid as an amorphous white solid and a mixture of two diastereoisomers (45 mg, 20%); mp 138°–142° C.; NMR (d$_6$-DMSO) δ1.14 (2H, m), 1.28 (3H s), 1.52 (2H, br s), 1.70–2.15 (14H, m), 3.10–3.50 (4H, m, +H$_2$O), 4.71 (1H, s), 5.05 (1H, m), 6.46 (1H, br s), 6.94 (2H, br s), 7.03 (1H, t, J 7 Hz), 7.24 (1H, m), 7.31 (5 H, br s), 7.46 (1H, d, J 7 Hz), 7.68 (1H, m), 8.43 (1H, br s), 10.75 (1H, br s); Anal (C$_{36}$H$_{42}$N$_4$O$_6$.0.5 H$_2$O), C, H, N.

EXAMPLE 33

Tricyclo[3.3.1.1$^{3,7}$]dec-2-yl [R,(R*,S*]-[1-(1H-indol-3-ylmethyl)-1-methyl-2-oxo-2-[[2-[[1-oxo-3-(1H-tetrazol-5-yl)propyl]amino]-2-phenylethyl]-amino]ethyl]carbamic acid ester

Step 1

To a solution of methyl 3-cyanopropionate (1 g, 8.8 mmol) in anhydrous DMF (15 mL) was added NaN$_3$ (0.77 g, 11.9 mmol) and NH₄Cl (0.65 g, 11.9 mmol). The reaction was then heated to 110° C. for 48 h. After this time the reaction mixture was concentrated in vacuo and the residue partitioned between saturated NaHCO₃ solution and Et₂O. The aqueous phase was separated, acidified to pH3 with 1M HCl and extracted with EtOAc. The organic extract was then dried over MgSO₄ and concentrated in vacuo to give the desired tetrazote as a colourless liquid (0.75 g, 69%); IR (film) 2400–3400 br, 1738 cm$^{-1}$; NMR (CDCl₃) δ2.89 (2H, t, J 7 Hz), 3.30 (2H, t, J 7 Hz), 3.70 (3H, s).

Step 2

To a solution of the tetrazole from Step 1 (0.36 g, 2.9 mmol) in anhydrous DMF (7 mL) was added cesium carbonate (1.05 g, 3.2 mmol) and benzyl bromide (0.53 g, 3.1 mmol). The reaction mixture was stirred at room temperature for 72 h. After this time the reaction mixture was filtered and concentrated in vacuo. The residue was partitioned between water and Et₂O and the organic layer was dried, MgSO₄, and evaporated to yield a gummy residue (0.4 g). The residue was purified by column chromatography, eluant 50% EtOAc/n-hexane, to give the desired benzyl tetrazole in its two tautomeric forms (0.25 g, 34%); tautomer-I (144 mg, fastest running fraction); IR (film) 3025, 1739 cm$^{-1}$; NMR (CDCl₃) δ2.83 (2H, t, J 7 Hz), 3.20 (2H, t, J 7 Hz), 3.65 (3H, s), 5.70 (2H, s), 7.35 (5H, s); tautomer II (104 mg, slowest running fraction) IR (as above); NMR (CDCl₃) δ2.90 (2H, t, J 7 Hz), 3.00 (2H, t, J 7 Hz), 3.70 (3H, s), 5.60 (2H, s), 7.25 (2H, m), 7.35 (3H, m).

Step 3

To an ice-cooled solution of the combined tautomeric forms of the benzyl tetrazole from Step 2 (248 mg, 1.0 mmol) in THF (15 mL) was added 0.1M LiOH solution (10.6 mL, 1.0 mmol) dropwise over 2 h. The reaction mixture was then slowly allowed to warm to room temperature over 16 h. After this time the reaction was acidified to pH3 with 1M HCl and concentrated in vacuo. The residue was partitioned between water and EtOAc and the organic layer was dried (MgSO₄) and concentrated in vacuo to yield the desired acid as a colourless liquid (151 mg, 65%) and as a mixture of two tautomers of the benzyl tetrazole; IR (film) 2600–3600, 1729 cm$^{-1}$; NMR (CDCl₃) δ2.90 (α3H, m) and 3.20 (α1H, t, J 7 Hz), 5.55 and 5.65 (2H, s), 7.35 (5H, s).

Step 4

To a solution of the acid from Step 3 (135 mg, 0.58 mmol) in anhydrous EtOAc (10 mL) was added pentafluorophenol (108 mg, 0.58 mmol) and N,N'-dicyclohexylcarbodiimide (120 mg, 0.58 mmol). After stirring at room temperature for 1 h the amine, tricyclo[3.3.1.1$^{3,7}$]dec-2-yl [R-(R*,R*)]-[2-[(2-amino-2-phenylethyl)amino]-1-(1H-indol-3-ylmethyl)-1-methyl-2 oxoethyl]carbamate from Step 3, (300 mg, 0.58 mmol) in EtOAc (2 mL) was added. The reaction mixture was stirred for 16 h, filtered and concentrated in vacuo. The residue was purified by column chromatography, eluant 3:1 EtOAc/n-hexane, to give the desired amide as two tautomeric forms around the benzyl tetrazole moiety (115 mg, 27%); mp 100°–105° C.; IR (film) 3300, 2912, 1690 and 1661 cm$^{-1}$; tautomer I (105 mg, fastest running fraction); NMR (CDCl₃) δ1.47 (3H, s), 1.50–2.00 (14H, m), 2.73 (2H, t, J 7 Hz), 3.20 (2H, t, J 7 Hz), 3.33 (2H, d, J 15 Hz and m), 3.45 (1H, d, J 15 Hz), 3.92 (1H, m), 4.81 (1H, br s), 5.10 (1H, m), 5.13 (1H, s), 5.65 (2H, s), 6.39 (1H, m), 6.93 (1H, d, J 7 Hz), 6.99 (1H, d, J 2 Hz), 7.05–7.20 (7H, m), 7.32 (6H, s), 7.57 (1H, d, J 8 Hz), 8.50 (1H, s); tautomer II (110 mg, slowest running fraction); NMR (CDCl₃) δ1.45 (3H, s), 1.50 (2H, m), 1.65–1.95 (12H, m), 2.75–2.95 (3H, m), 3.10 (1H, m), 3.25 (2H, m), 3.45 (1H, d, J 15 Hz), 4.00 (1H, m), 4.75 (1H, br s), 5.05 (1H, m), 5.10 (1H, s), 5.45 (2H, s), 6.47 (1H, m), 6.95–7.35 (14H, m), 7.45 (1H, d, J 7 Hz), 7.60 (1H, d, J 7 Hz), 8.80 (1H, s); Anal (C₄₂H₄₈N₈O₄.0.85 H₂O), C, H, N.

Step 5

A solution of the benzyltetrazole tautomer mixture from Step 4 (100 mg, 0.14 mmol) in absolute EtOH (50 mL) was treated with Pearlman's catalyst (20 mg, 20% w/w). The mixture was put under an atmosphere of hydrogen at 45 psi for 18 h at 50° C., filtered and concentrated in vacuo to yield a gum (100 mg). The residue was purified by reverse phase column chromatography—eluant 3:1 MeOH:H₂O—to yield the desired tetrazole as a white solid (30 mg, 34%); mp 169°–173° C.; IR (film) 3300, 2907, 1704, 1659 and 1535 cm$^{-1}$; NMR (d$^6$-DMSO) δ1.28 (3H, s), 1.46 (2H, m), 1.65–1.95 (12H, m), 2.45 (2H, m), 2.89 (2H, t, J 7 Hz), 3.20–3.50 (4H, m, and H₂O ), 4.67 (1H, br s), 4.98 (1H, m), 6.80–7.05 (4H,m), 7.25 (6H, m), 7.46 (1H, d, J 8 Hz), 8.35 (2H, m), 10.90 (1H, s); Anal (C₃₅H₄₂N₈O₄.1 H₂O), C, H, N.

EXAMPLE 34

Carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl]-, tricyclo[3.3.1.1$^{3,7}$]dec-2-yl ester, [R, (R*,S*]

Step 1

To a solutionn of methyl 3-cyanopropionate (1 g, 8.8 mmol) in anhydrous DMF (15 mL) was added NaN₃ (0.77 g, 11.9 mmol) and NH₄Cl (0.65 g, 11.9 mmol). The reaction was then heated to 110° C. for 48 h. After this time the reaction mixture was concentrated in vacuo and the residue partitioned between saturated NaHCO₃ solution and Et₂O. The aqueous phase was separated, acidified to pH3 with 1M HCl and extracted with EtOAc. The organic extract was then dried over MgSO₄ and concentrated in vacuo to give the desired tetrazole as a colourless liquid (0.75 g, 69%); IR (film) 2400–3400 br, 1738 cm$^{-1}$; NMR (CDCl₃) δ2.89 (2H, t, J 7 Hz), 3.30 (2H, t, J 7 Hz), 3.70 (3H, s).

Step 2

To a solution of the tetrazole from Step 1 (0.36 g, 2.9 mmol) in anhydrous DMF (7 mL ) was added caesium carbonate (1.05 g, 3.2 mmol ) and benzyl bromide (0.53 g, 3.1 mmol ). The reaction mixture was stirred at room temperature for 72 h. After this time the reaction mixture was filtered and concentrated in vacuo. The residue was partitioned between water and Et₂O and the organic layer was dried, MgSO₄, and evaporated to yield a gummy residue (0.4 g). The residue was purified by column chromatography, eluant 50% EtOAc/n-hexane, to give the desired benzyl tetrazole in its two tautomeric forms (0.25 g, 34%); tautomer- I (144 mg, fastest running fraction); IR (film) 3025, 1739 cm$^{-1}$; NMR (CDCl₃) δ2.83 (2H, t, J 7 Hz), 3.20 (2H, t, J 7 Hz), 3.65 (3H, s), 5.70 (2H, s), 7.35 (5H, s); tautomer II (104 mg, slowest running fraction) IR (as above); NMR (CDCl₃) δ2.90 (2H, t, J 7 Hz), 3.00 (2H, t, J 7 Hz), 3.70 (3H, s), 5.60 (2H, s), 7.25 (2H, m), 7.35 (3H, m).

Step 3

To an ice-cooled solution of the combined tautomeric forms of the benzyl tetrazole from Step 2 (248 mg, 1.0 mmol) in THF (15 mL) was added 0.1M LiOH solution (10.6 mL, 1.0 mmol) dropwise over 2 h. The reaction mixture was then slowly allowed to warm to room temperature over 16 h. After this time the reaction was acidified to pH3 with 1M HCl and concentrated in vacuo. The residue was partitioned between water and EtOAc and the organic layer was dried (MgSO$_4$) and concentrated in vacuo to yield the desired acid as a colourless liquid (151 mg, 65%) and as a mixture of two tautomers of the benzyl tetrazole; IR (film) 2600–3600, 1729 cm$^{-1}$; NMR (CDCl$_3$) δ2.90 (≈3 H, m) and 3.20 (≈1 H, t, J 7 Hz), 5.55 and 5.65 (2H, s), 7.35 (5H, s).

Step 4

To a solution of the acid from Step 3 (135 mg, 0.58 mmol) in anhydrous EtOAc (10 mL) was added pentafluorophenol (108 mg, 0.58 mmol) and N,N'-dicyclohexylcarbodiimide (120 mg, 0.58 mmol). After stirring at room temperature for 1 h the amine, tricyclo[3.3.1.1$^{3,7}$]dec-2-yl[R-(R*,R*)]-[2-[(2-amino-2-phenylethyl)amino]-1-(1H-indol-3-ylmethyl)-1-methyl-2-oxoethyl]carbamate from Step 3 (300 mg, 0.58 mmol) EtOAc (2 mL) was added. The reaction mixture was stirred for 16 h, filtered and concentrated in vacuo. The residue was purified by column chromatography, eluant 3:1 EtOAc/a-hexane, to give the desired amide as two tautomeric forms around the beazyl tetrazole moiety (115 mg, 27%); mp 100°–105° C.; IR (film) 3300, 2912, 1690 and 1661 cm$^{-1}$; tautomer I (105 mg, fastest running fraction); NMR (CDCl$_3$) δ1.47 (3H, s), 1.50–2.00 (14H, m), 2.73 (2H, t, J 7 Hz), 3.20 (2H, t, J 7 Hz), 3.33 (2H, d, J 15 Hz and m), 3.45 (1H, d, J 15 Hz), 3.92 (1H, m), 4.81 (1 H, br s), 5.10 (1H, m), 5.13 (1H, s), 5.65 (2H, s), 6.39 (1H, m), 6.93 (1H, d, J 7 Hz), 6.99 (1 H, d, J 2 Hz), 7.05–7.20 (7H, m), 7.32 (6 H, s), 7.57 (1H, d, J 8 Hz), 8.50 (1 H, s); II (110 mg, slowest running fraction); NMR (CDCl$_3$) δ1.45 (3H, s), 1.50 (2H, m), 1.65–1.95 (12H, m), 2.75–2.95 (3 H, m), 3.10 (1H, m), 3.25 (2H, m), 3.45 (1H, d, J 15 Hz), 4.00 (1H, m), 4.75 (1H, br s), 5.05 (1H, m), 5.10 (1H, s), 5.45 (2H, s), 6.47 (1H, m), 6.95–7.35 (14H, m), 7.45 (1H, d, J 7 Hz), 7.60 (1H, d, J 7 Hz), 8.80 (1H, s); Anal (C$_{42}$H$_{48}$N$_8$O$_4$·0.85 H$_2$O), C, H, N.

Step 5

A solution of the benzyltetrazole tautomer mixture from Step 4 (100 mg, 0.14 mmol) in absolute EtOH (50 mL) was treated with Pearlman's catalyst (20 mg, 20% w/w). The mixture was put under an atmosphere of hydrogen at 45 psi for 18 h at 50° C., filtered and concentrated in vacuo to yield a gum (100 mg). The residue was purified by reverse phase column chromatography—eluant 3:1 MeOH:H$_2$O—to yield the desired tetrazole as a white solid (30 mg, 34%); mp 169°–173° C.; IR (film) 3300, 2907, 1704, 1659 and 1535 cm$^{-1}$; NMR (d$^6$-DMSO) δ1.28 (3H, s), 1.46 (2H, m), 1.65–1.95 (12H, m), 2.45 (2H, m), 2.89 (2H, t, J 7 Hz), 3.20–3.50 (4H, m, and H$_2$O), 4.67 (1H, br s), 4.98 (1H, m), 6.80–7.05 (4H,m), 7.25 (6H, m), 7.46 (1H, d, J 8 Hz), 8.35 (2H, m), 10.90 (1H, s); Anal. (C$_{35}$H$_{42}$N$_8$O$_4$·1 H$_2$O), C, H, N.

EXAMPLE 35

Benzeneheptanoic acid, α-[[3-(1H-indol-3-yl)-2-methyl-1-oxo-2-[[(tricyclo[3.3.1.1$^{3,7}$]dec-2-yloxy)carbonyl]amino]propyl]amino]-, [R-(R*, S*)]

Step 1

To a stirred solution of N-(t-butyloxycarbonyl)phenylalanine (13 g, 49.0 mmol) and N-methylmorpholine (11 mL, 100 mmol) in CH$_2$Cl$_2$ (125 mL) at −10° C. was added isobutyl chloroformate (6.5 mL, 50.0 mmol). After 15 min at −10° C. N,O-dimethylhydroxylamine hydrochloride (5.02 g, 51.5 mmol) was added and the cold solution stirred for 1 h then at room temperature for 3 h. The mixture was poured into water (100 mL) and the organic layer separated. The aqueous layer was extracted with CH$_2$Cl$_2$ (2×100 mL), the combined organic layers dried (MgSO$_4$), filtered and the solvents removed in vacuo. The residue was purified by filtering through silica using 2% MeOH:98% CH$_2$Cl$_2$ as eluant which gave the product (14.39 g, 95%) as an oil; NMR (CDCl$_3$) δ1.38 (9H, s), 2.84–3.16..(5H, m), 3.65 (3H, s), 4.94–4.96 (1H, m), 5.22–5.25 (1H, m), 7.16–7.30 (5H, m).

Step 2

To a stirred solution of the hydroxamate from Step 1 (1.38 g, 4.48 mmol) in anhydrous THF (20 mL ) at 0° C. was added dropwise a solution of 1.0M LiAH$_4$ in THF (11.7 mL, 11.70 mmol). After 30 min wet Et$_2$O (100 mL) was added followed by an ice-cooled 20% citric acid solution (100 mL). After a further 30 min the Et$_2$O layer was separated and the aqueous solution was extracted once with Et$_2$O (100 mL). The combined Et$_2$O extracts were washed with saturated NaHCO$_3$ solution (50 mL), water (50 mL), 5% citric acid solution (50 mL) and water (50 mL). The Et$_2$O solution was then dried over MgSO$_4$, filtered and the solvent removed in vacuo to give a white solid (1.09 g, 97%); IR (film) 3367, 1733 and 1689 cm$^{-1}$; NMR (CDCl$_3$) δ1.43 (9H, s), 3.11 (2H, d, J 6 Hz), 4.38–4.45 (1H, m), 5.10 (1H, m), 7.15–7.35 (5H, m), 9.62 (1H, s).

Step 3

Methyl-4-bromocrotonate (4.48 g, 25 mmol) and triphenylphosphine (6.55 g, 25 mmol) were heated together at 150° C. for 25 min. Recrystallization of the brown residue from EtOH/Et$_2$O gave the phosphonium salt (5.76 g, 52%) as an off white solid; mp 180°–181° C.

Step 4

To a stirred solution of the phosphonium salt from Step 3 (1.91 g, 4.33 mmol) in water (100 mL) was added dropwise 1M NaOH (4.5 mL, 4.5 mmol). After 10 min the product was extracted into CH$_2$Cl$_2$ (50 mL) which was dried over MgSO$_4$, filtered and the solvent removed in vacuo. The residue was dissolved in hot EtOAc and insoluble material filtered off. The volume of the filtrate was reduced and 40:60 petrol added causing the ylid to precipitate out (0.86, 55%); mp 132°–143° C.

Step 5

To a stirred solution of the ylid from Step 4 (800 mg, 2.22 mmol) in anhydrous THF (20 mL) at room temperature was added a solution of 2-(t-butyloxycarbonylamino)-3-phenylpropanol (553 mg, 2.22 mmol) in THF (10 mL). After 3 h the solvents were removed in vacuo and the residue purified by chromatography on silica using CH$_2$Cl$_2$ then 1% MeOH:99% CH$_2$Cl$_2$ as eluant. Removal of the solvent in vacuo gave the desired product (271 mg, 37%) as a white crystalline solid; IR (film) 3357, 1713 and 1646 cm$^{-1}$; NMR (CDCl$_3$) δ1.40 (9H, s), 2.78–2.92 (2H, m), 3.73 (3H, s), 4.53–4.81 (2H, m), 5.82 (1H, d, J 15.4 Hz), 6.03 (1H, dd, J 5.4, 15.3 Hz), 6.20 (1H, dd, J 10.8, 15.3 Hz), 7.14–7.31 (6H, m).

Step 6

To a stirred solution of the ester from Step 5 (335 mg, 1 mmol) in CH$_2$Cl$_2$ (5 mL) was added trifluoroacetic acid (5 mL). After 1 h at room temperature the solvents were removed in vacuo to give the desired amine as a residue which was used without further purification in the next step.

Step 7

To a stirred solution of α-methyl-N-[(tricyclo[3.3.1.1$^{3,7}$]dec-2-yloxy)carbonyl]-R-tryptophan (441 mg, 1.11 mmol) and 1-hydroxybenzotriazole hydrate (213 mg, 1.39 mmol) in EtOAc (20 mL) was added N,N'-dicyclohexylcarbodiimide (252 mg, 1.22 mmol). After 1 h at room temperature the amine salt from Step 6 (349 mg, 1.01 mmol) and triethylamine (0.292 mL, 2.10 mmol) were added dropwise in EtOAc (10 mL) over 5 min. After 24 h the solution was filtered and the filtrate washed with 5% citric acid solution (2×25 mL), saturated NaHCO$_3$ solution (2×25 mL), 5% citric acid solution (25 mL) and brine (25 mL). The EtOAc extract was then dried (MgSO$_4$), filtered and the solvent removed in vacuo. The residue was purified by chromatography over silica using 1% MeOH:99% CH$_2$Cl$_2$ as eluant which gave the amide pr. oduct (286 mg, 46%) as a white solid; mp 111°–125° C.; IR (film) 1703 and 2646 cm$^{-1}$; NMR (CDCl$_3$) δ1.43 (3H, s), 1.50–1.98 (14H, m), 2.75–2.80 (2H, m), 3.26 (1H, d, J 14.7 Hz), 3.52 (1H, d, J 14.7 Hz), 3.73 (3H, s), 4.81–4.85 (2H, m), 5.07 (1H, s), 5.78 (1H, d, J 15.4 Hz), 5.94 (1 H, dd, J 5.4, 5.4 Hz), 6.14 (1H, dd, J 10.6, 15.5 Hz), 6.37 (1H, d, J 8.1 Hz), 6.91 (1H, d, J 2.2 Hz), 7.10–7.27 (8H, m), 7.34 (1H, d, J 8.0 Hz), 7.58 (1H, d, J 7.9 Hz), 8.15 (1H, s) ; Anal (C$_{37}$H$_{43}$N$_3$O$_5$), C, H, N.

Step 8

A solution of the unsaturated ester from Step 7 (227 mg, 0.37 mmol)in absolute EtOH (30 mL) was hydrogenated over 10% Pd/C (25 mg) at 30° C. under an atmosphere of hydrogen at 50 psi for 6.5 h. The catalyst was filtered off and washed with solvent. the combined filtrates were concentrated in vacuo to give the product as a foam (145 mg, 64%); IR (film) 1718 and 1657 cm$^{-1}$; NMR (CDCl$_3$) δ1.22–1.98 (23H, m), 2.24 (2H, t, J 7.4 Hz), 2.63 (1H, dd, J 6.9, 13.7 Hz), 2.73 (1H, dd, J 6.1, 13.7 Hz), 3.26 (1H, d, J 14.7 Hz), 3.51 (1H, d, J 14.7 Hz), 3.65 (3H, s), 4.12–4.14 (1 H, m), 4.80 (1H, s), 5.14 (1H, s), 6.13 (1H, d, J 8.5 Hz), 6.91 (1H, d, J 2.3 Hz), 7.08–7.29 (7H, m), 7.34 (1H, d, J 7.9 Hz), 7.60 (1H, d, J 7.7 Hz), 8.34 (1H, s).

Step 9

To a stirred solution of the methyl ester from Step 8 (145 mg, 0.24 mmol) in THF (15 mL) at 0° C. was added dropwise an aqueous solution of LiOH (2.6 mL of 0.1M soln, 0.26 mmol). The solution was stirred and slowly allowed to warm to room temperature over 24 h. A 0.1M HCl (2.9 mL, 0.29 mmol) solution was then added and the reaction mixture extracted with Et$_2$O (2×25 mL). The Et$_2$O extracts were dried over MgSO$_4$, filtered and the solvent removed in vacuo. The residue was purified by chromatography over reverse phase silica using 75% MeOH:25% H$_2$O as eluant. This gave the desired acid (55 mg, 38%) as a white solid; mp 79°–90° C.; IR (film) 1709 and 1655 cm$^{-1}$; NMR (CDCl$_3$) δ1.20–1.97 (23H, m), 2.22 (2H, t, J 7.2 Hz), 2.60 (1H, dd, J 6.8, 13.6 Hz), 2.71 (1H, dd, J 6.0, 13.5 Hz), 3.24 (1H, d, J 14.7 Hz), 3.47 (1H, d, J 14.7 Hz), 4.10 (1H, m), 4.80 (1H, s), 5.34 (1H, s), 6.20 (1H, d, J 8.5 Hz), 6.93 (1H, d, J 2.0 Hz), 7.05–7.24 (7H, m), 7.33 (1H, d, J 7.9 Hz), 7.57 (1H, d, J 7.7 Hz), 8.67 (1H, s); Anal (C$_{36}$H$_{45}$N$_3$O$_5$.0.25 H$_2$O), C, H, N.

EXAMPLE 36

Methyl-(±)-β-[[(2-phenylethyl)amino]carbonyl]-1β-[[(tricylo-[3.3.1.1$^{3,7}$]dec-2-yloxy)carbonyl]amino]-1H-indole-3-butanoate

Step 1

(±)-N-formyltryptophan (10.00 g, 43 mmol) was suspended in H$_2$O (100 mL). Caesium carbonate (7.70 g, 23.5 mmol) was added portion-wise to the soln. The solution was stirred until all (±)-N-formyltryptophan had dissolved completely. The solvent was then evaporated in vacuo, the residue dissolved in anhydrous DMF (50 mL) and benzylbromide (7.50 g, 44 mmol) was added. The solution was left stirring for 4 h, Et$_2$O (200 mL) added, and the solution washed with H$_2$O (100 mL). The etheral layer was dried (MgSO$_4$) and concentrated in vacuo to yield the desired benzyl ester (14.32 g, ∝100%); mp 85°–86° C.; IR (film) 3294, 1739, 1673 cm$^{-1}$; NMR (CDCl$_3$) δ3.28 (2H, d, J 7 Hz), 5.02 (3H, m), 6.66 (1H, d, J 8 Hz), 6.77 (1H, s), 7.03–7.33 (8H, m), 7.50 (1H, d, J 7 Hz), 7.98 (1H, s), 8.94 (1H, s); Anal (C$_{19}$H$_{18}$N$_2$O$_3$.0.1 H$_2$O), C, H, N.

Step 2

(±)-Benzyl-N-formyltryptophan ester from Step 1 (8.16 g, 24.8 mmol) was suspended in anhydrous DMF (100 mL) under an atmosphere of nitrogen. 4-Dimethylaminopyrridine (Ca. 0.1 g) dissolved in DMF (5 mL) was injected via a syringe. Di-t-butyldicarbonate (5.43, 24.8 mmol) in DMF (10 mL) was added dropwise. The mixture was left stirring at room temperature for 24 h. The solution was concentrated in vacuo and the residue dissolved in Et$_2$O (100 mL). The etheral solution was washed with 10% citric acid soln, dried (MgSO$_4$), filtered and concentrated to dryness. The desired indole protected product was isolated by column chromatography (75% EtOAc/n-hexane) to give a yellow oil (3.58 g, 34%); IR (film) 3257, 1734, 1687 cm$^{-1}$; NMR (CDCl$_3$) δ1.64 (9H, s), 3.22 (1H, d), 3.24 (1H, d) 5.04 (3H, m), 6.99 (1H, d, J 8 Hz), 7.15–7.32 (7H, m), 7.41 (1H, s), 7.49 (1H, d, J 8 Hz), 8.09 (1H, d, J 8 Hz), 8.14 (1H, s); Anal (C$_{24}$H$_{26}$N$_2$O$_5$.0.33 H$_2$O), C, H, N.

Step 3

1-[(1,1-dimethylethoxy)carbonyl]-N-formyl-DL-tryptophan benzyl ester from Step 2 (3.04 g, 7.20 mmol) was dissolved in CH$_2$Cl$_2$ (10 mL) under an atmosphere of nitrogen. The solution was cooled to 0° C. in an ice-salt bath. Triethylamine (2.21 g, 21.6 mmol) was added followed by triphosgene (0.80 g, 2.4 mmol ) in CH$_2$Cl$_2$ (15 mL). The solution was allowed to warm to room temperature and was left to stir for 10 h. The solvent was then concentrated in vacuo, and the residue was taken up in Et$_2$O. Triethylamine hydrochloride was filtered off, the filtrate concentrated to dryness and the product was isolated by flash chromatography (75% EtOAc/n-hexane) to give the desired isonitrile as a yellow oil (2.54 g, 87%); IR (film) 2149, 1735 cm$^{-1}$; NMR (CDCl$_3$) δ1.67 (9H, s), 3.29 (1H, dd, J 7, 15 Hz), 3.41 (1H, dd, J 7, 15 Hz), 4.60 (1H, dd, J 7, 7 Hz), 5.18 (2H, s), 7.23–7.36 (7H, m), 7.49 (1H, d, J 8 Hz), 7.57 (1H, s), 8.15 (1H, d, J 8 Hz); Anal (C$_{24}$H$_{24}$N$_2$O$_4$.0.5 H$_2$O), C, H, N.

Step 4

The isonitrile from Step 3 (2.05 g, 5.1 mmol) was dissolved in anhydrous THF (15 mL) and the solution cooled to −78° C. under an atmosphere of argon. HMPA (0.88 mL, 5.1 mmol) was added followed by a solution of lithium bis (trimethytsilyl) amide (6.0 mL of 1.0M soln). After stirring for 30 min at −78° C. methyl iodide (0.31 mL, 5.2 mmol) was added slowly. After a further 3 h the mixture was allowed to warm to room temperature and was stirred for a further 1 h. The solvent was then concentrated in vacuo, the residue dissolved in water and extracted with $Et_2O$ (2×25 mL). The combined organic extracts were dried ($MgSO_4$), filtered and concentrated in vacuo. The crude product was purified by flash chromatography (50% $Et_2O$/n-hexane) to yield the desired alkylated product as a white solid (1.94 g, 79%); mp 29°–30° C.; IR (film) 2138, 1741 $cm^{-1}$; NMR ($CDCl_3$) δ1.58 (9H, s), 2.72 (1H, d, J 17 Hz), 3.13 (1H, d, J 17 Hz), 3.20 (1H, d, J 15 Hz), 3.29 (1H, d, J 15 Hz), 3.54 (3H, s), 4.99 (1H, d, J 12 Hz), 5.03 (1H, d, J 12 Hz), 7.07–7.28 (7H, m), 7.42 (1H, d, J 8 Hz), 7.54 (1H, s), 8.05 (1H, d, J 8 Hz); Anal ($C_{27}H_{28}H_2O_6$), C, H, N.

Step 5

1-Methyl-(±)-β- cyano-1-[(1,1-dimethylethoxy)carbonyl]-β-[(phenylmethoxy)carbonyl]-1H-indole-3-butanoate (0.241 g, 0.50 mmol) was dissolved in EtOH (5 mL). The solution cooled to −5° C. in an acetone-ice bath and ethanolic HCL was added dropwise. Water (0.1 mL) was added and the reaction was warmed to room temp. The solution was left to stir for 24 h and the solvent concentrated in vacuo. The oil was dissolved in EtOAc (50 mL) and washed with a 10% $Na_2CO_3$ solution (50 mL). The organic layer was dried ($MgSO_4$), filtered and concentrated in vacuo. The product was isolated by flash chromatography (50% EtOAc/n-hexane) to yield the desired amine (0.120 g, 67%) as a yellow oil; IR (film) 3350, 3245, 1741 $cm^{-1}$; NMR ($CDCl_3$) δ2.12 (2H, br s), 3.17 (1H, d, J 18 Hz), 3.28 (1H, d, J 18 Hz), 3.37 (1H, d, J 15 Hz), 3.43 (3H, s), 3.53 (1H, d, J 15 Hz), 4.82 (1H, d, J 12 Hz), 4.92 (1H, d, J 12 Hz), 6.73 (1H, d, J 2 Hz), 6.95–7.21 (8H, m), 7.47 (1H, s), 8.42 (1H, s).

Step 6

Methyl-(±)-β-amino-β-[(phenylmethoxy)carbonyl]-1H-indole-3-butanoate (120 mg, 0.33 mmol) from Step 5 was dissolved in anhydrous THF (10 mL) under argon. Triethylamine (53 μl, 0.40 mmol) was injected. The solution was cooled to 0° C. in an ice-salt bath and 2-adamantyl chloroformate (77 mg, 0.36 mmol) dissolved in THF (5 mL) was injected. The solution was stirred for 12 h at room temperature before triethylamine hydrochloride was filtered off. Dichloromethane (50 mL) was added and the solution was washed with water (2×25 mL). The organic layer was dried ($MgSO_4$), filtered and concentrated in vacuo. The product was isolated by flash chromatography (50% $Et_2O$/n-hexane) to furnish the desired urethane (105 mg, 58%); mp 61°–62° C.; IR (film) 3412, 1738 $cm^{-1}$; NMR ($CDCl_3$) δ1.49–2.09 (14H, m), 3.12 (1H, d, J 15 Hz), 3.30 (1H, d, J 15 Hz), 3.38 (3H, s), 3.72 (1H, d, J 15 Hz), 3.80 (1H, d, J 15 Hz), 4.83 (1H, br s), 4.98 (1H, d, J 12 Hz), 5.11 (1H, d, J 12 Hz), 6.88 (1H, s), 6.79 (1H, s), 7.03 (1H, t, J 7 Hz), 7.14 (1H, t, J 7 Hz), 7.17–7.34 (6H, m), 7.48 (1H, d, J 8 Hz), 8.30 (1H, s); Anal ($C_{32}H_{36}N_2O_6$), C, H, N.

Step 7

To methyl-(±)-β-[(phenylmethoxy)carbonyl]-β-[[(tricyclo[3.3.1.1³,⁷]dec-2-yloxy)carbonyl]amino]-1H-indole-3-butanoate (105 mg, 0.19 mmol) from Step 6 in a 250 mL vessel was added palladium on charcoal (10%, Ca 20 mg) and EtOH (75 mL). The vessel was sealed in a Parr Hydrogenation Apparatus and charged with $H_2$ gas (45 psi). Shaking was initiated after pressurization and continued for 12 h. Upon completion the palladium on charcoal was filtered off and the filtrate concentrated in vacuo. The product was purified by flash chromatography 2:1 MeOH/$H_2O$ to yield the desired acid as a white powder (77 mg, 88%); mp 108°–109° C.; IR (film) 3413, 1733 $cm^{-1}$; NMR ($CDCl_3$) δ1.47–2.07 (14H, m), 3.14 (1H, d, J 16 Hz), 3.26 (1H, d, J 16 Hz), 3.64 (3H, s), 3.76 (1H, d, J 15 Hz), 3.84 (1H, d, J 15 Hz), 4.83 (1H, br s), 5.75 (1H, br s), 5.96 (1H, s), 6.98–7.04 (2H, m), 7.10 (1H, t, J 7 Hz), 7.28 (1H, d, J 8 Hz), 7.61 (1H, d, J 8 Hz), 8.34 (1H, s); Anal ($C_{25}H_{30}N_2O_6$), C, H, N.

Step 8

Methyl-(±)-β-[[(tricyclo-[3.3.1.1³,⁷]dec-2-yloxy)carbonyl]amino]-1H-indole-3-butanoate (200 mg, 0.44 mmol) from Step 7 was dissolved in anhydrous THF (10 mL). Pentafluorophenol (88 mg, 0.48 mmol) was added followed by N,N'-dicyclohexylcarbodiimide (100 mg, 0.48 mmol). The solution was left stirring for 2 h before phenylethylamine (60 mg, 0.50 mmol) was injected into the soln. The mixture was left stirring for 16 h. The solution was concentrated in vacuo, EtOAc added and dicyclohexylurea filtered off. The filtrate was concentrated in vacuo and the product was isolated by flash chromatography (25% EtOAc/n-hexane) to give a white solid (180 mg, 73%; mp 78°–79° C.; IR (film) 3333, 1730, 1659 $cm^{-1}$; NMR ($CDCl_3$) δ1.51–2.04 (14H, m), 2.61 (2H,m), 2.94 (1H, d, J 16 Hz), 3.21 (1H, d, J 16 Hz), 3.37 (1H, d, J 7 Hz), 3.41 (1H, d, J 7 Hz), 3.46 (1H, d, J 15 Hz), 3.57 (1H, d, J 15 Hz), 3.62 (3H, s), 4.78 (1H, br s), 5.88 (1H, br s), 6.58 (1H, br s), 6.92 (1H, d, J 2 Hz), 7.03–7.26 (7H, m), 7.33 (1H, d, J 8 Hz), 7.56 (1H, d, J 8 Hz); Anal ($C_{33}H_{39}N_3O_5·0.75 H_2O$), C, H, N.

EXAMPLE 37

Carbamic acid, [1-(1H-indol-3-ylmethyl)-1-[[(2-phenylethyl)-amino]carbonyl]-3-butynyl]-, (tricyclo-[3.3.1.1³,⁷]dec-2-yl ester, (±)

Example 37 is prepared by using propargyl bromide in step 4 of Example 36.

EXAMPLE 38

Bicyclo[2.2.1]heptane-2-acetic acid, 3-[[[[2-[[1-(hydroxymethyl)-2-phenylethyl]amino]-1-(1H-indol-3-ylmethyl)-1-methyl-2-oxoethyl]amino]carbonyl]oxy]-4,7,7-trimethyl-, [1R-[1α, 2β, 3α[R* (S*)], 4α]]

Step 1

Method exactly as for Example 5 except using (4-nitrophenyl)methyl[1R-(1α, 2α, 3β)]-2-[(chlorocarbonyl)oxy]-1,7,7-trimethylbicyclo[2.2.1]-heptane-3-acetate; mp 78°–81° C.; $[α]_D^{20}$ +6.2° (c=0.62; Me©H. ); IR (film) 1729, 1696 and 1660 $cm^{-1}$; NMR ($CDCl_3$) δ0.79 (3H, s), 0.85 (3H, s), 0.96 (3H, s), 1.05–1.20 (1H, m), 1.20–2.00 (7H, m), 2.43 (1H, dd, J 8 and 15 Hz), 2.60–2.70 (1H, m), 2.75–2.90 (3H, m), 3.00–3.10 (1H, m), 3.29 (1H, d, J 15 Hz), 3.35–3.50 (2H, m), 3.40 (1H, d, J, 14 Hz), 4.10–4.30 (2H, m), 5.07 (1H, br s), 5.13 (2H, s), 6.23 (1H, br d, J 7 Hz), 6.98 (1H, d, J 2 Hz), 7.00–7.25 (7H, m), 7.32 (1H, d, J 8 Hz), 7.43 (2H, d, J, 8 Hz), 8.15 (2H, d, J 8 Hz), 8.39 (1H, s) ; Anal. $C_{41}H_{48}O_8N_4$; C, H, N.

Step 2

The ester from Step 1 (430 mg, 0.59 mmol) as a solution in absolute EtOH (100 mL) was treated with 10% Pd/C (43 mg, 10% w/w), and the resulting mixture put under an atmosphere of hydrogen at a pressure of 50 psi with agitation for 1 h. After this time the mixture was filtered over filter aid and the solvent removed in vacuo and the residue chromatographed over reverse phase silica gel using 50% MeOH in $H_2O$ as eluant to give the acid as a white solid (130 mg, 37%); mp 93.7°–97.5° C. (MeOH/$H_2O$); $[\alpha]_D^{20}$ +7.7° (c=0.96, MeOH); IR (film) 1708 and 1660 $cm^{-1}$; NMR (CDCl$_3$) δ 0.75 (3H, s), 0.82 (3H, s), 0.93 (3H, s), 1.05–1.40 (2H, m), 1.46 (3H, s), 1.50–1.65 (3H, m), 2.27 (1H, dd, J 8 and 13 Hz), 2.35–2.49 (1H, m), 2.50–2.60 (1H, m), 2.67 (1H, dd, J 7 and 14 Hz), 2.90 (1H, dd, J 7 and 14 Hz), 3.12 (1H, d, J 15 Hz), 3.28 (1H, d, J 15 Hz), 4.05–4.20 (1H, m), 4.31 (1H, d, J 4 Hz), 4.40–4.70 (1H, br), 5.21 (1H, br s), 6.57 (1H, d, J 9 Hz), 6.94 (1H, br s), 7.05–7.30 (7H, m), 7.33 (1H, d, J 8 Hz), 7.55 (1H, d, J 8 Hz), 8.54 (1H, s); Anal. $C_{34}H_{43}N_3O_6 \cdot 0.5 H_2O$; C, H, N.

EXAMPLE 39

[1R-[1α, 2α[R*(S*)]]] and [1S-[1α, 2α[S*(R*)]]][[2-[[[2-[[1-(hydroxymethyl)-2-phenylethyl]amino]-1-(1H-indol-3-ylmethyl)-1-methyl-2-oxoethyl]amino]carbonyl]oxy]-1-methylcyclohexyl]carbonyl] glycine Step 1

Method as for Example 5 except using phenylmethyl cis-(±)-[[[2-[(chlorocarbonyl) oxy]1-methyl-1-cyclohexyl] carbonyl]amino]acetate, mp 78°–81° C.; IR (film) 3600–3200, 3000–2800, 1760, 1705 and 1651 $cm^{-1}$; NMR (CDCl$_3$) δ 1.16 (1.5H, s), 1.19 (1.5H, s), 1.20–2.20 (11H, m), 2.78 (2H, d, J 8 Hz), 3.20–3.75 (4H, m), 3.80–4.00 (1H, m), 4.10–4.30 (2H, m), 4.78 (0.5H, t J 6 Hz), 4.90–5.10 (2.5H, m), 5.26 (0.5H, br s), 5.52 (0.5H, br s), 6.38 (0.5H, d, J 8 Hz), 6.48 (0.5H, d, J 8 Hz), 6.52–6.65 (1H, m), 6.90–7.00 (1H, m), 7.00–7.50 (13H, m), 7.57 (1H, d, J 8 Hz), 8.05 (1H. br); Anal. $C_{39}H_{46}N_4O_7 \cdot 0.5 H_2O$; C, H, N.

Step 2

The ester from step 1 (60 mg, 0.09 mmol) and 10% Pd/C (50 mg), in absolute EtOH (50 mL) was put under an atmosphere of hydrogen at 50 psi and 25° C. with agitation for 4 h. After this time the mixture was filtered over filter aid and concentrated in vacuo and the residue chromatographed over reverse phase silica gel using 60% MeOH in $H_2O$ as eluant to give the product as a non-crystalline solid (40 mg, 80%); mp 94°–99° C.; IR (film) 1709 and 1694 $cm^{-1}$; NMR (CDCl$_3$) δ 1.10–2.00 (13H, m), 2.10–2.30 (1H, m), 2.72 (1H, dd, J 6 and 14 Hz), 2.84 (1H, dd, J 7 and 14 Hz), 3.15–3.60 (4H, m), 3.75–4.05, (2H, m), 4.15–4.30 (1H, br s), 4.55–4.75 (0.5H, m), 4.80–5.00 (0.5H, m), 6.90–7.10 (3H, m).

EXAMPLE 40

Butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-[1R-[1α[R*(R*)]2β]]-((−)-isomer)

The amine 60K in Scheme IX (100 mg, 0.21 mmol) as a solution in EtOAc (30 mL) was treated with succinic anhydride (30 mg, 0.3 mmol) and left stirring at room temperature for 18 h before the solvent was removed in vacuo and the residue chromatographed over reverse phase silica gel using 60% MeOH in $H_2O$ as eluant to give the product (93 mg, 77%); mp 106°–111° C. (MeOH/$H_2O$); $[\alpha]_D^{20}$ –33.5° (c=0.81 MeOH) IR (film) 3320, 2933, 2860, 1714 and 1661 $cm^{-1}$; NMR (CDCl$_3$) δ 0.88 (3H, d, J 6.5 Hz), 1.0–1.35 (4H, m), 1.47 (3H, s), 1.40–1.80 (4H, m), 1.95–2.05 (1H, br m), 2.40–2.65 (4H, m), 3.20–3.35 (3H, m), 3.75–3.85 (1H, m), 4.20–4.30 (1H, m), 4.90–5.00 (1H, br s), 5.30–5.40 (1H, br s), 6.40–6.50 (1H, br s), 6.97 (1H, s), 7.05–7.30 (8H, m), 7.33 (1H, d, J 8 Hz), 7.54 (1H, d, J 8 Hz), 8.60 (1H, s); MS(FAB) m/e 577.2 (M+1) and 217.0 (100); Anal. $C_{32}H_{40}N_4O_6 \cdot 0.5 H_2O$; C, H, N.

EXAMPLE 41

2-Butenoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-, [1R -[1α[R*(R*)], 2β]]-((−)-isomer)

A stirred solution of mono (2-trimethyl silyl) ethyl fumarate (350 mg, 0.7 mmol) in EtOAc (20 mL) and pentafluorophenol (184 mg, 1.00 mmol) was treated with dicyclohexylcarbodiimide (218 mg, 1.05 mmol) and the amine 6K (Scheme IX) (1 mmol) and left for 18 h at room temp. The reaction mixture was then filtered and the filtrate washed with $H_2O$ (2×20 mL) and dried over $MgSO_4$. The solvent was then removed in vacuo and the residue chromatographed over reverse phase silica gel using 75% MeOH in $H_2O$ as eluant to give the slightly impure ester (400 mg) which was dissolved in THF (20 mL) and treated with tetrabutyl ammonium fluoride in THF (3 mL of a 1M soln, 3 mmol) and left stirring at room temperature for 1.5 h. After this time the reaction mixture was concentrated in vacuo and the residue taken up in EtOAc (30 mL) and washed with 1M citric acid solution (30 mL) then $H_2O$ (30 mL). The organic phase was dried over $MgSO_4$ and concentrated in vacuo and the residue chromatographed over reverse phase silica gel using 75% MeOH in $H_2O$ as eluant to give the product as a white solid, (200 mg, 47%); mp 131°–135° C. (MeOH/$H_2O$); $[\alpha]_D^{20}$ –36.1° (c=1 MeOH); IR (film) 3307 2933 2858 1707 and 1666 $cm^{-1}$; NMR (CDCl$_3$) δ 0.85 (3H, d, J 6.5 Hz), 1.00–1.75 (11H, m), 1.95–2.05 (1H, br m), 3.22 (1H, d, J 14.5 Hz), 3.33 (1H, d, J 14.5 Hz), 3.50–3.80 (2H, m), 3.50–4.20 (1 Hz br), 4.20–4.30 (1H, m), 5.10–5.20 (1H, br s), 5.30 (1H, br s), 6.64 (1H, br s), 6.79 (1H, d, J 15 Hz), 6.90–7.35 (10H, m), 7.50 (1H, d, J 8 Hz), 7.79 (1H, br s), 8.59 (1H, s); MS (FAB) m/e 575.1 (M+1) and 288.9 (100); Anal. $C_{33}H_{38}N_4O_6 \cdot 0.25 H_2O$; C, H, N.

EXAMPLE 42

Butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R -[1α[R*(S*)],2β]]-((−)-isomer)

Methods were employed exactly as for Example 19 except using trans (−)-2-methylcyclohexyloxycarbonyl-α- methyl-R-tryptophan (2K in Scheme I) (216 mg, 61%); mp 97°–102° C. (MeOH/H$_2$O); [α]$_D^{20}$+37° (c=0.22, MeOH); IR (film) 3315, 2930, 2859, 1700 and 1660 cm$^{-1}$; NMR (CDCl$_3$) δ0.82 (3H, d, J 6.5 Hz), 1.00–1.75 (11H, m), 1.90–2.00 (1H, br s), 2.40–2.70 (6H, m), 2.85–3.00 (1H, br m), 3.23 (1H, d, J 14.5 Hz), 3.30 (1H, d, J 14.5 Hz), 3.45–3.65 (1H, br s), 4.20–4.30 (2H, br m), 5.26 (1H, s), 5.10–5.80 (1H, br), 6.15–6.25 (1H, br s), 6.90–7.20 (9H, m), 7.33 (1H, d, J 8 Hz), 7.53 (1H, d, J 8 Hz), 8.72 (1H, s); MS (FAB) m/e 591.2 (M+1, 100); Anal. C$_{33}$H$_{42}$N$_4$O$_6$; C, H, N.

EXAMPLE 43

2-Butenoic acid, 4-[[2-[[3-)1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R[1α[R*(S*)], 2β]]-((−)-isomer)

Methods were employed exactly as for Example 19A except using trans (−)-2-methylcyclohexyloxycarbonyl-α-methyl-R-tryptophan (170 mg, 7.3%); mp 118°–128° C. (MeOH/H$_2$O); [α]$_D^{20}$+74° (c=0.42, MeOH); IR (film) 3500–3200, 2933, 2858, 1695 and 1662 cm$^{-1}$; NMR (CD$_3$OD) δ0.89 (3H, d, J 6.5 Hz), 1.00–1.80 (11H, m), 2.00–2.10 (1H, br m), 2.65–2.75 (2H, m), 2.95–3.05 (1H, m), 3.16 (1H, d, J 14.5 Hz), 3.36 (1H, d, J 14.5 Hz), 3.60–3.70 (1H, m), 4.30–4.40 (2H, m), 6.72 (1H, d, J 15 Hz), 6.90–7.30 (9H, m), 7.30 (1H, d, J 8 Hz), 7.50 (1H, d, J 8 Hz); MS (FAB) m/e 589.2 (M+1) 220.2 (100) ;. Anal. C$_{33}$H$_{40}$N$_4$O$_6$.H$_2$O; C, H, N.

EXAMPLE 44

Carbamic acid, [2-[[1-(hydroxymethyl)-2-hydroxy-2-phenylethyl]amino]-1-(1H-indol-3-ylmethyl)-1-methylethyl]-, tricyclo[3.3.1.1$^{3,7}$]dec-2-yl ester Method were employed exactly as for Example 19, step 4 except the amine used was L(+)-threo-2-amino-1-phenyl-1,3-propanediol. Yield 2 g, 73%; mp 69°–73° C.; [α]$_D^{20}$+ 47.3° (c=0.97, MeOH); IR (film) 3396, 1695 and 1663 cm$^{-1}$; NMR (CDCl$_3$) δ1.48 (3H, s), 1.52–1.97 (14H, m), 3.10 (1H, br s), 3.17 (1H, d, J 15 Hz), 3.27 (1H, d, J 15 Hz), 3.72–4.10 (4H, m), 4.77 (1H, br s), 5.01 (1H, d, J 3.5 Hz), 5.26 (1H, s), 6.69 (1H, d, J 7.5 Hz), 6.81 (1H, d, J 2 Hz), 7.09–7.40 (8H, m), 7.55 (1H, d, J 8 Hz), 8.13 (1H, s) ; Anal. C$_{32}$H$_{39}$N$_3$O5.0.25 H$_2$, C, H, N.

EXAMPLE 45

Carbamic acid, [1-(1H-indol-2-ylmethyl)-1-methyl-2-oxo-2-[(2-phenylethyl)amino]ethyl]-, tricyclo[3.3.1.1$^{3,7}$]-dec-2-yl ester, (±)

Step 1

1-(4-Methylphenyl)sulfonyl-1H-indole-2-carboxylic acid ethyl ester

To a stirred suspension of sodium hydride (3.7 g, 120 mmol, 80% in paraffin oil) in dry THF (75 mL), a solution of indol-2-carboxylic acid ethyl ester (18.9 g, 100 mmol) in dry THF (75 mL) was added in 1 hour with stirring while the inner temperature was maintained under 30° C. The reaction mixture was stirred for 30 min. and then a solution of p-toluenesulphonyl chloride (22.9 g, 120 mmol) in dry THF (75 mL) was added dropwise to the stirring reactant. After two hours stirring at room temperature and one hour at 45° C. the solvent was evaporated in vacuo and the residue partitioned between water and ethyl ether. The organic phase was dried over MgSO$_4$ and the solvent evaporated to leave a solid which was recrystallized from diisopropyl ether (26.89, 78%), m.p. 92°–95° C.

Step 2

2-Hydroxyethyl-1-(4-methylphenyl)sulfonyl-1H-indole

To stirred solution of Red-Al (sodium dihydro-bis(2-methoxyethoxy)aluminate≈70% in toluene) (30 mL) in dry THF (100 mL) cooled at 5° C. and under nitrogen was added dropwise and at this temperature a solution of compound of step 1 (26,8 g, 78 mmol) in dry THF (75 mL). After stirring one hour at 5° C. and then one hour at room temperature the mixture was cooled at 10° C. and treated dropwise with 2N NaOH, to effect hydrolysis of the intermediate complex. The organic phase was separated and the solvent in vacuo evaporated. The residue was solved in ethyl ether, the solution washed with water, dried over MgSO$_4$ and evaporated to give the required alcohol (23.3 g, 98%) as a yellow oil; IR (film) 3500, 1597 cm$^{-1}$.

Step 3

2-Bromomethyl-1-(4-methylphenyl)sulfonyl-1H-indole

To a solution of triphenylphosphine (20.2 g, 77 mmol) in dry CH$_2$Cl$_2$ (80 mL) was added dropwise a solution of bromine (11.9 g, 77 mmol) in dry CH$_2$Cl$_2$ (40 mL). The stirring was continued for one hour and then a solution of compound of step 2 (23.2 g, 77 mmol) in dry CH$_2$Cl$_2$ (40 mL) was added dropwise. The resulting mixture left stirring for 12 hours. After removing the solvent the residue was taken up in ethyl acetate and washed with water. The organic extract was dried over MgSO$_4$ and the solvent evaporated in vacuo. The residue was chromatographed over silica gel using toluene as eluant to give a yellow oil (21.0 g, 75 %); IR (film) 1600 cm$^{-1}$, MS ((70eV): m/z 363 (M+,12.6), 129 (100).

Step 4

Racemic 2-Methyl-3-[[1-(4-methylphenyl)sulfonyl]-1H-indol-2-yl]-N-(phenylmethylene)alanine methyl ester To a stirred solution of KOt.Bu (5.1 g, 45 mmol) in dry THF (25 mL) cooled at −40° C. was added dropwise at this temperature a solution of N-(phenylmethylene)-DL-alanine methyl ester (8.7 g, 45 mmol) in dry THF (40 mL) under nitrogen. The mixture was stirred one hour at −40° C. and then was added dropwise maintaining the temperature a solution of compound of step 3 (16.5g, 45 mmol) in dry THF (50 mL). After the addition was completed the mixture was stirred 2 hours at −20° C., then allowed to warm to room temperature and left overnight. The solvent was evaporated in vacuo given a resin, which on trituration with ethyl ether and water gave the required compound (16.5 g, 75%) as a white solid, m.p. 151°–154° C.

Step 5

Racemic 2-Methyl-3-[[1-(4-methylphenyl)sulfonyl]-1H-indol-2-yl]alanine methyl ester A suspension of compound of step 4 (16.1 g, 34 mmol) in ethanol (100 mL) and 2N hydrochloric acid (20 mL) was stirred overnight. After removing the solvent in vacuo the residue was suspended in water (400 mL), made basic with $Na_2CO_3$, extracted with ethyl ether and dried over $MgSO_4$. The solvent was evaporated providing an oil. This was subjected to silica gel chromatography using ethyl acetate/toluene 8:92 (v/v) then methanol/toluene 1:99 (v/v) as eluants to give the required compound (9.9 g, 75%) as an oil; IR (film) 1735 $cm^{-1}$.

Step 6

Racemic N-[(2-Adamantyloxy)carbonyl]-2-methyl-3-[[1-(4-methylphenyl)sulfonyl]-1H-indol-2-yl]alanine methyl ester To a stirred solution of compound of step 5 (9.9 g, 25 mmol) in dry THF (100 mL) was added a solution of 2-adamantylchloroformate (6.4 g, 30 mmol) in dry THF (15 mL) dropwise followed by a solution of triethylamine (6.1 g, 56 mmol) in dry THF (15 mL). After one hour stirring, the reaction mixture was filtered and the solvent removed in vacuo. The residue was stirred with a mixture of light petroleum (100 mL) and ethyl ether (20 mL) to give the required compound as a colourless solid, which was removed by filtration (13.9 g, 96%), m.p. 119°–122° C.

Step 7

Racemic N-[(2-Adamantyloxy)carbonyl]-2-methyl-3-(1H-indol-2-yl]alanine

A mixture of compound of Step 6 (6.8 g, 12 mmol) and KOH (2.7 g, 48 mmol) in ethanol (100 mL) was stirred for 60 hours at 70° C. After removing the solvent in vacuo the residue was partitioned between water (150 mL) and ethyl ether. The clear water phase was separated, acidified to pH 4.5 when an oil precipitated out which slowly solidified. The solid was collected by filtration, washed successively with water and dried to give the desired carboxylic acid (3.9 g, 81%) as a white solid, m.p. 210°–216° C.

Step 8

A mixture of compound of Step 7 (0.53 g, 1.3 mmol) and 1,1'-carbonyldiimidazole (0.22 g, 1.3 mmol) in dry THF (8 mL) was stirred for one hour. To this mixture was then added dropwise a solution of 2-phenethylamine (0.17 g, 1.4 mmol) in dry THF (4 mL). After stirring ovrnight the solvent was evaporated in vacuo. The residue was solved in ethyl ether, washed with water, dried over $MgSO_4$ and the solvent evaporated to leave a colourless foam which was crystallized from diisopropylether to yield the title compound (0.42 g, 64%), m.p. 168°–169° C.

EXAMPLE 46A+B

Carbamic acid, [2-[1-(hydroxyethyl)-2-phenylethyl]-amino-1-(1H-indol-2-ylmethyl)-1-methyl-2-oxo]ethyl-, tricyclo[3.3.1.1$^{3,7}$]dec-2-yl ester Method was as described for Example 45 above but instead using (S)-(−)-2-amino-3-phenyl-1-propanol in Step 8. The crude residue was chromatographed over silica gel using 1% MeOH:99% $CH_2Cl_2$ as eluant.

Diastereomer 1

Diastereomer 1 (0.26 g, 24%) was obtained as a foam softens at 87° C., Rf 0.70 ((MeOH:$CH_2Cl_2$1:99).

Diastereomer 2

Diastereomer 2 (0.20 g, 18%) was obtained as a foam softens at 90° C., Rf 0.65 (MeOH:$CH_2Cl_2$1:99).

EXAMPLE 47A+B

4-[[2-[[3-(1H-indol-2-yl)-2-methyl-1-oxo-2-[[(tricyclo-[3,3.1.1$^{3,7}$]dec-2-yloxy)carbonyl]amino]propyl]amino]-1-phenylethyl]amino]-4-oxobutanoic acid benzyl ester Method was as described for Example 45 above but instead using the amine of Step 5 of Example 20. The crude residue was chromatographed over silica gel using 1% MeOH:99% $CH_2Cl_2$ as eluant.

Diastereomer 1

Diastereomer 1 (0.17 g, 13%) was obtained as amorphous pale beige solid, mp 86°–90° C.; Rf 0.40 (MeOH:$CH_2Cl_2$ 1:99) (107°–115° C. after stirring with ethyl ether).

Diastereomer 2

Diastereomer 2 (0.21 g, 17%) was obtained as amorphous pale beige solid, mp 88°–92° C.; Rf 0.35 (MeOH:$CH_2Cl_2$ 1:99) (148°–153° C. after stirring with ethyl ether).

EXAMPLE 48

4-[[2-[[3-(1H-indol-2-yl)-2-methyl-1-oxo-2-[[(tricyclo-[3.3,1.1$^{3,7}$]dec-2-yloxy)carbonyl]amino]propyl]amino]-1-phenylethyl]amino]-4-oxobutanoic acid

Diastereomer 1

Method was as described for Step 7 of Example 20 above but instead using the compound of Example 47A.

EXAMPLE 49

4-[[2-[[3-(1H-indol-2-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid

Diastereomer 2

Method was as described for Step 7 of Example 20 above but instead using the compound of Example 47B.

EXAMPLE 50

(R)-[2-[[2-(1-Cyclohexen-1-yl)ethyl]amino]-1-(1H-indol-3-ylmethyl)-1-methyl-2-oxoethyl carbamic acid, tricyclo[3 3,1.1$^{3,7}$]dec-2-yl ester To a solution of 2-Adoc-αMe-Trp-OH (0.15 g, 0.38 mmol) in ethyl acetate was added 1-hydroxybenzotriazole hydrate (0.058 g, 0.38 mmol) and N,N'-dicyclohexylcarbodiimide (0.078 g, 0.38 mmol). After stirring at room temperature for 2 hours the mixture was filtered and a solution of 2-(1-cyclohexenyl)ethylamine (0.047 g, 0.38 mmol) in ethyl acetate was added. After stirring overnight the mixture was evaporated to dryness and the residue purified by chromatography eluting with ethyl acetate/hexane 1:1 to give the title compound as an amorphous solid (0.16 g, 82%); mp 77°–79° C.; $[\alpha]_D^{20}$+19.8° (c=0.47, CHCl$_3$); NMR (CDCl$_3$) δ1.40–2.00 (27H, m), 3.15–3.30 (3H, m), 3.47 (1H, d, J 14.7 Hz), 4.83 91H, s), 5.25 (2H, s), 6.08 (1H, bs), 7.01 (1H, d, J 2.3 Hz), 7.11 (1H, t, J 7.7 Hz), 7.18 (1H, t, J 8.1 Hz), 7.35 (1H, d, J 7.9 Hz), 7.59 (1H, d, J 8.0 Hz), 8.15 (1H, s); Anal. C$_{31}$H$_{41}$N$_3$O$_3$; C, H, N.

EXAMPLE 51

(R)-[1-(1H-indol-3-ylmethyl)-1-methyl-2-oxo-2-[[2-(2-pyridinyl)ethyl]amino]ethyl]carbamic acid, tricyclo[3.3.1.1$^{3,7}$]dec-2-yl ester Following the procedure in Example 50, 2(2-pyridyl) ethylamine gave the title compound (0.15 g, 81%); mp 89°–91° C.; $[\alpha]_D^{20}$+21.8° (c=0.93 CHCl$_3$); NMR (CDCl$_3$) δ1.45–2.00 (17H, m), 2.86 (2H, t, J 6.2 Hz), 3.36 (1H, d, J 15.0 Hz), 3.42 (1H, d, J 14.8 Hz), 3.50–3.65 (2H, m), 4.75 (1H, s), 5.34 (1H, bs), 6.94 (1H, s), 7.00–7.20 (4H, m), 7.25–7.35 (2H, m), 7.50–7.60 (2H, m), 8.20 (1H, bs), 8.43 (1H, d, J 4.2 Hz); Analysis C$_{30}$H$_{36}$N$_4$O$_3$.0.25 (C$_4$H$_8$O$_2$), C, H, N.

EXAMPLE 52

[R-(R*,S*)]-4-Amino-β-[[3-(1H-indol-3-yl)-2-methyl-1-oxo-2-[[(tricyclo[3.3 1.1$^{3,7}$]dec-2-yloxy)carbonyl]amino]propyl]amino]benzenebutanoic acid 2-Adoc-αMe-TrpNHCH(CH$_2$C$_6$H$_4$NH$_2$)CH$_2$CO$_2$H.

Step 1

Following the procedure of Example 26, Step 1, using (S)- -2-t-butyloxycarbonylamino-3-(4-nitrophenyl)propionic acid (1.85 g, 6 mmol) gave the diazoketone as yellow crystals (1.21 g, 60%); mp 122–°4° C.; $[\alpha]_D^{20}$–41.0° (c=1, MeOH); NMR (CDCl$_3$) δ1.40 (9H, s), 3.04 (iH, dd, J 13.6, 6.8 Hz), 3.23 (1H, dd, J 13.7, 6.6 Hz), 4.46 (1H, bs), 5.08 (1H, bs), 5.34 (1H, s), 7.37 (2H, d, J 8.5 Hz), 8.17 (2H, d, J 8.5 Hz); Analysis C$_{15}$H$_{18}$N$_4$O$_5$, C, H, N.

Step 2

Following the procedure of Example 26, Step 2, the diazoketone from Step 1 (1.13 g, 3.4 mmol) gave the trimethylsilylethyl ester as a low melting solid (1.22 g, 83%); mp 31°–34° C.; $[\alpha]_D$–20.0° (c=1, MeOH), NMR (CDCl$_3$), δ0.04 (9H, s), 0.95–1.05 (2H, m), 1.36 (9H, s), 2.43 (1H, dd, J 16.1, 6.0 Hz), 2.53 (1H, dd, J 16.1, 5.4 Hz), 2.92 (1H, dd, J 13.5, 7.0 Hz), 2.96–3.06 (1H, m), 4.10–4.25 (3H, m), 5.12 (1H, bd), 7.36 (2H, d, J 8.6 Hz), 3.15 (2H, d, J 8.6 Hz). Anal. C$_{20}$H$_{32}$N$_2$O$_6$Si, C, H, N.

Step 3

Following the procedure of Example 26, Step 3, the (S)-trimethylsilylethyl-3-t-butyloxycarbonylamino-4-(4-nitrophenyl)butyrate (1.1 g, 2.6 mmol) gave the required amine as an oil (0.31 g, 37%). $[\alpha]_D^{20}$+1.1 (c=0.5, MeOH), NMR (CDCl$_3$) δ0.04 (9H, s), 0.95–1.05 (1H, m), 2.34 (1H, dd, J 15.9, 8.2 Hz), 2.47 (1H, dd, J 15.9, 4.4 Hz), 2.74 (1H, dd, J 13.4, 8.2 Hz), 2.90 (1H, dd, J 13.4, 5.5 Hz), 3.47–3.56 (1H, m), 4.15–4.25 (2H, m), 7.39 (2H, d, J 8.5 Hz), 8.18 (2H, d, J 8.5 Hz). Anal. C$_{15}$H$_{24}$N$_2$O$_4$Si, C, H, N.

Step 4

Following the procedure of Example 26, Step 4, the amine obtained in Step 3 (0.28 g, 0.9 mmol) gave the required amide (0.6 g, 95%), mp 73°–8° C. $[\alpha]_D$+4.3° (c=1, MeOH). NMR (CDCl$_3$), δ0.04 (9H, s), 0.95–1.05 (2H, m), 1.40–2.05 (17H, m), 2.36 (2H, d, J 4.7 Hz), 2.81 91H, dd, J 13.7, 7.1 Hz), 2.93 (1H, dd, J 13.7, 7.2 Hz), 3.27 (1H, d, J 14.7 Hz), 3.49 (1H, d, J 14.7 Hz), 4.05–4.25 (2H, m), 4.40–4.55 (1H, m), 4.80 (1H, s), 5.07 (1H, s), 6.96 (1H, d, J 2.3 Hz), 7.05–7.35 (6H, m), 7.59 (1H, d, J 7.8 Hz), 8.10 (3H, d, J 8.5). Anal. for C$_{38}$H$_{50}$N$_4$O$_7$Si, C, H, N.

Step 5

Following the procedure of Example 26, Step 5, the ester obtained in Step 4 (1.05 g, 1.5 mmol) gave the required acid (0.90 g, 95%), mp 103°–7° C.; $[\alpha]_D$+0.5° (c=1, MeOH); NMR (d$_6$-DMSO), δ1.16 (3H, s), 1.40–2.00 (14H, m), 2.35–2.50 (2H, m), 2.85–3.00 (2H, m), 3.09 (1H, d, J 14.5 Hz), 3.25 (1H, d, obscured by water), 4.30–4.40 (1H, m), 4.65 (1H, s), 6.70 (1H, bs), 6.80–6.90 (2H, m), 7.02 (1H, 6, J 7.1 Hz), 7.29 (1H, d, J 8.0 Hz), 7.44 (3H, d, J 8.7 Hz), 7.72 (1H, d, J 8.7 Hz), 8.10 (2H, d, J 8.6 Hz), 10.83 (1H, s); Analyses C$_{33}$H$_{38}$N$_4$O$_7$ 0.5H$_2$O; C, H, N.

Step 6

The acid obtained in Step 5 (0.90 g, 1.5 mmol) was dissolved in ethanol (150 mL) and palladium hydroxide (0.09 g) added under nitrogen. The mixture was shaken under 50 psi hydrogen overnight. The catalyst was removed by filtration and the solution evaporated to dryness. Purification by reverse phase chromatography gave the title compound (0.75 g, 87%), mp 115°–120° C.; $[\alpha]_D$+11.2° (c=1, MeOH); NMR (d$_6$-DMSO), δ1.25 (3H, s), 1.40–1.55 (2H, m), 1.60–1.85 (8H, m), 1.85–2.00 (4H, m), 2.21 (1H, dd, J 15.9, 6.3 Hz), 2.32 (1H, dd, J 15.7, 6.1 Hz), 2.5 (1H, dd, obscured by DMSO), 2.61 (1H, dd, J 13.7, 6.7), 3.16 (1H, d, J 14.4), 3.3 (1H, d, obscured by water), 4.10–4.20 (1H, m), 4.67 (1H, s), 6.46 (2H, d, J 8.3 Hz), 6.66 (1H, s), 6.80 (2H, d, J 8.3 Hz), 6.85–6.90 (2H, m), 7.01 (1H, t, J 7.3), 7.29 (1H, d, J 8.0 Hz), 7.45 (1H, d, J 7.8 Hz), 7.55 (1H, d, J 8.1 Hz), 10.8 (1H, s); Analysis for C$_{33}$H$_{40}$N$_4$O$_5$.H$_2$O, C, H, N.

EXAMPLE 53

(R)-[2-[[2-(1-cyclohexyl)ethyl]amino]-1-(1H-indol-3-ylmethyl)-1-methyl-2-oxoethyl]carbamic acid Method as for Example 50 except using 1-cyclohexylethylamine. Yield 80 mg, 40%; mp 79°–81° C.; NMR (CDCl$_3$) δ0.85 (5H, m), 1.20 (7H, m), 1.55–2.05 (18H, m), 3.21 (2H, m), 3.28 (1H, d, J 15 Hz), 3.48 (1H, d, J 15 Hz), 4.84 (1H, s), 5.23 (1H, brs), 6.13 (1H, brs), 7.00 (1H, d, J 2 Hz), 7.10 (1H, t, J 7 Hz), 7.17 (1H, t, J 7 Hz), 7.34 (1H, d, J 8 Hz), 7.59 (1H, d, J 8 Hz), 8.26 (1H, s).

EXAMPLE 54

[[3-[[3-(1H-indol-3-yl)-2-methyl-1-oxo-2-[[(tricyclo [3.3.1.1$^{3,7}$]dec-2-yloxy)carbonyl]amino]propyl] amino]-2-phenylpropyl]thio]acetic acid

Step 1

To a stirred suspension of 60% NaOH (0.10 g, 2.5 mmol) in anhydrous THF (3 mL) at 0° C. was added ethyl-2-mercaptoacetate (0.274 mL, 2.5 mmol). After 15 minutes at 0° C. the mixture was heated at 50° C. for 1 hour. The mixture was recooled to 0° C. and the rosylate 1,1-dimethylethyl (±)-[2-[[[(4-methylphenyl)sulfonyl]oxy]methyl ]-3-phenylbutyl]carbamate (0.406 g, 1.0 mmol) in anhydrous THF (3 mL) was added dropwise over 2 minutes. The cold mixture was stirred for 2 hours and then at room temperature for 24 hours. Et$_2$O (20 mL) was added and the mixture washed once with water (20 mL ). The aqueous layer was extracted once more with Et$_2$O (20 mL), the combined Et$_2$O extract dried over MgSO$_4$, filtered, and the solvent removed in vacuo. The residue was purified by chromatography on silica using CH$_2$Cl$_2$ then 2% MeOH:98% CH$_2$Cl$_2$ as eluants, giving the product (0.214 g, 61%) as a syrup. IR (film) 1713 cm$^{-1}$; NMR (CDCl$_3$) 1.27 (3H, t, J 7.3 Hz), 1.40 (9H, s), 2.91–2.95 (2H, m), 2.99–3.07 (1H, m), 3.11 (2H, s), 3.24–3.33 (1H, m), 3.61–3.65 (1H, m), 4.16 (2H, q, J 7.0 Hz), 4.50 (1H, b), 7.19–7.35 (5H, m); Anal. (C$_{18}$H$_{27}$NO$_4$S), C, H, N, S.

Step 2

To a stirred solution of the protected ester from Step 1 (0.212 g, 0.60 mmol) in CH$_2$Cl$_2$ (2 mL) was added TFA (2 mL). After 1 hour at room temperature the solvent was removed in vacuo. This gave the product as a syrup which was used without further purification.

Step 3

Tricyclo[3.3.1.1$^{3,7}$]decyl 3-(1H-indol-3-ylmethyl)-3-methyl-4,11-dioxo-7-phenyl-17-oxa-9-thia-2,5-diazatetradecanoate To a stirred solution of the acid 2-Adoc-α-MeTrp (0.238 g, 0.60 mmol) and 1-hydroxybenzotriazolemonohydrate (0.110 g, 0.72 mmol) in EtOAc (25 mL) at room temperature was added N,N'-dicyclohexyl carbodiimide (0.155 g, 0.75 mmol). After 1 hour Et$_3$N (0.125 mL, 0.90 mmol) was added followed by a solution of the amine salt (0.22 g, 0.60 mmol) from Step 2 in EtOAc (10 mL) added dropwise over 45 minutes. The mixture was stirred for 72 hours at room temperature and the N,N'-dicyclohexylurea filtered off. The EtOAc solution was washed with aqueous 5% citric acid solution (2×20 mL), saturated NaHCO$_3$ solution (2×20 mL), 5% citric acid (20 mL), and brine (20 mL). The EtOAc solution was dried over MgSO$_4$, filtered, and the solvent removed in vacuo. The residue was purified by chromatography on silica using 67% n-hexane:33% EtOAc, then 50% n-hexane:50% EtOAc as eluants to give a mixture of diastereomers (0.237 g, 67%) as a white solid, mp 57°–62° C.; IR (film) 3352, 1713 and 1658 cm$^{-1}$; NMR (CDCl$_3$) 1.26 (3H, t, J 7.2 Hz), 1.49 and 1.50 (3H, 2s), 1.53 (2H, s), 1.71–1.93 (12H, m), 2.84–2.90 (3H, m), 2.85 (2H, d, J 5.4 Hz), 3.08 (2H, s), 3.20–3.43 (3H, m), 3.61–3.75 (1H, m), 4.15 (2H, q, J 7.1 Hz), 4.75 and 4.76 (1H, 2s), 5.16 (1H, s), 6.19–6.27 (1H, m), 6.91–7.26 (8H, m), 7.36 (1H, d, J 8.0 Hz), 7.54–7.58 (1H, m). 8.37 (1H, s); Anal. (C$_{36}$H$_{45}$N$_3$O$_5$S.0.25 H$_2$O) C, H, N, S.

Step 4

To a stirred solution of the ethylester from Step 3 (0.169 g, 0.27 mmol) in EtOH (6 mL) at 0° C. was added 0.1N NaOH (2.9 mL of an aqueous solution, 0.29 mmol) dropwise over 15 minutes. The cold solution was stirred for 2 hours and then at room temperature for 18 hours. 0.1N HCl (3.5 mL of an aqueous solution, 0.35 mmol) was added to the mixture and the solvent removed in vacuo. The residue was extracted into EtOAc (25 mL) and washed with brine (25 mL). The EtOAc was dried over MgSO$_4$, filtered, and the solvent removed in vacuo. Purification of the residue by reverse phase silica chromatography using 75% MeOH:25% H$_2$O as eluant gave the product (0.091 g, 56%) as a white solid, mp 78°–93° C.; IR (film) 3391, 1708 and 1652 cm$^{-1}$; NMR (CDCl$_3$) 1.44–1.53 (5H, m), 1.75–1.99 (12H, m), 2.78–2.84 (3H, m), 3.10–3.43 (5H, m), 3.61–3.70 (1H, m), 4.77 (1H, s), 5.23–5.40 (2H, m), 6.29–6.35 (1H, m), 6.93–7.24 (8H, m), 7.37 (1H, d, J 7.9 Hz), 7.55 91H, d, J 7.8 Hz), 8.60 (1H, s); Anal. (C$_{34}$H$_{41}$N$_3$O$_5$S), C, H, N, S.

EXAMPLE 55

γ-[[[3-(1H-indol-3-yl)-2-methyl-1-oxo-2-[[(tricyclo [3.3.1.1$^{3,7}$]dec-2-yloxy)carbonyl]amino]propyl] amino]methyl]benzenebutanoic acid Step 1

To a stirred solution of 3-t-butoxycarbonylamino-2-phenylpropionaldehyde (0.376 g, 1.51 mmol) in anhydrous THF (25 mL) was added methyl(triphenylphosphoranylidene)acetate (0.555 g, 1.66 mmol) and the mixture was stirred for 2 hours at room temperature. The solvent was removed in vacuo and the residue purified by chromatography over silica using 67% n-hexane:33% EtOAc as eluant giving the product (0.209 g, 45%) as a white solid, mp 59°–65° C.; IR (film) 3366 and 1714 cm$^{-1}$; NMR (CDCl$_3$) 1.42 (9H, s), 3.37–3.67 (2H, m), 3.71–3.81 (4H, m), 4.54 (1H, bs), 5.85 (1H, dd, J 15.8, 1.2 Hz), 7.08 (1H, dd, J 15.7, 7.7 Hz), 7.18–7.36 (5H, m); Anal. (C$_{17}$H$_{23}$NO$_4$), C, H, N.

Step 2

To a stirred solution of the ester from Step 1 (0.25 g, 0.82 mmol) in CH$_2$Cl$_2$ (2 mL) was added TFA (2 mL) and the mixture stirred for 1 hour at room temperature. Removal of the solvents in vacuo gave the product as a syrup which was used without further purification in Step 3.

Step 3

Methyl 5-[[3-(1H-indol-3-yl)-2-methyl-1-oxo-2-[ [(tricyclo[3.3.1.1$^{3,7}$]dec-2-yloxy]carbonyl]amino] propyl]amino]-4-phenyl-2-pentenoate To a stirred solution of the acid 2AdocαMeTrp (R) (0.325 g, 0.82 mmol) and 1-hydroxybenzotriazole monohydrate (0.157 g, 1.03 mmol) in EtOAc (30 mL) at room temperature was added N,N'-dicyclohexylcarbodiimide (0.186 g, 0.90 mmol). After 1 hour Et$_3$N (0.171 mL) was added followed by dropwise addition of a solution of the amine salt from Step 2 (0.262 g, 0.82 mmol) in EtOAc (5 mL) over 5 minutes and the mixture stirred for 24 hours. Then N,N'-dicyclohexylurea was filtered off and the EtOAc solution was washed with aqueous 5% citric acid solution (2×25 mL) saturated NaHCO$_3$ solution (2×25 mL) 5% citric acid (25 mL) and brine (25 mL). The RtOAc was dried over MgSO$_4$, filtered, and the solvent removed in vacuo. Purification of the residue by chromatography on silica using 67% n-hexane:33% EtOAc then 50% n-hexane:50% EtOAc gave the product (0.342 g, 71%) as a white solid, mp 80°–93° C.; IR (film) 3352, 1708, and 1657 cm$^{-1}$; NMR (CDCl$_3$) 1.49–1.93 (17H, m), 3.20 (1H, d, J 14.7 Hz), 3.42–3.69 (4H, m), 3.71 (3H, s), 4.75 (1H, s), 5.09 (1H, s), 5.75 (1H, d, J 15.7 Hz), 6.17–6.22 (1H, m), 6.93–7.28 (9H, m), 7.36 (1H, d, J 8.0

Hz), 7.55–7.59 (1H, m), 8.31 (1H, s); Anal. ($C_{35}H_{41}N_3O_5$), C, H, N.

Step 4

Methyl γ-[[[3-(1H-indol-3-yl)-2-methyl-1-oxo-2-[[(tricyclo[3.3.1.1$^{3,7}$]dec-2-yloxy)carbonyl]amino]propyl]amino]methyl]benzenebutanoate The ester from Step 3 (0.228 g, 0.39 mmol) was hydrogenated over 10% palladium on charcoal in absolute ethanol (50 mL) under an atmosphere of hydrogen at 45 psi and 30° C. for 7 hours. The catalyst was filtered and the solvent removed in vacuo, giving the product (0.217 g, 95%) as a white solid, mp 69°–76° C.; IR (film) 1714 and 1660 cm$^{-1}$; NMR (CDCl$_3$) 1.48–1.93 (19H, m), 2.11–2.17 (2H, m), 2.50–2.68 (1H, m), 3.14–3.65 (7H, m), 4.74 (1H, s), 5.11 (1H, bs), 6.00–6.13 (1H, m), 6.90–6.99 (3H, m), 7.08–7.22 (5H, m), 7.35 (1H, d, J 8.0 Hz), 7.54–7.58 (1H, m), 8.28 (1H, bs); Anal. ($C_{35}H_{43}N_3O_5 \cdot 0.5\ H_2O$), C, H, N.

Step 5

γ-[[[3-(1H-indol-3-yl)-2-methyl-1-oxo-2-[[(tricyclo-[3.3.1.1$^{3,7}$]dec-2-yloxy)carbonyl]amino]propyl]amino]methyl]benzenebutanoic To a stirred solution of the methyl ester (0.151 g, 0.26 mmol) in THF (15 mL) at 0° C. was added 0.1N LiOH (2.8 mL of an aqueous solution, 0.28 mmol) dropwise over 50 minutes. The cold mixture was stirred for 6 hours and then at room temperature overnight. 0.1N HCl (3.1 mL of an aqueous solution, 0.31 mmol) was added and the solvent removed in vacuo. The residue was diluted with water (10 mL) and extracted with Et$_2$O (2×25 mL). The Et$_2$O was dried over MgSO$_4$, filtered, and the solvent removed in vacuo. Purification of the residue by reverse phase chromatography using 75% MeOH:25% H$_2$O as eluant gave the product (0.070 g, 47%) as a white solid, mp 117°–122° C.; IR (film) 3328, 1711, and 1660 cm$^{-1}$; NMR (CDCl$_3$)(1.48–1.51 (5H, m), 1.69–2.0 (14H, m), 2.05–2.20 (2H, m), 2.42–2.75 (1H, m), 3.10–3.65 (4H, m), 4.74 (1H, s), 5.39 (1H, bs), 6.14–6.17 (1H, m), 6.87–7.25 (8H, m), 7.34 (1H, d, J 7.9 Hz), 7.54 (1H, d, J 5.4 Hz), 8.70 (1H, bs); Anal. ($C_{34}H_{41}N_3O_5 \cdot 1\ H_2O$), C, H, N.

EXAMPLE 56

Phenylmethyl δ-[[(2-phenylethyl)amino]carbonyl]-δ-[[(tricyclo[3.3.1.1$^{3,7}$]dec-2-yloxy)carbonyl]amino]-1H-indole-3-hexanoate

Step 1

Ethyl-3-mercaptopropionate (1.30 mL, 10.0 mmol) was stirred and dissolved in a mixture of AcOH (50 mL) and water (25 mL, crushed ice) and Cl$_2$ gas bubbled through the mixture for 1 hour while maintaining the temperature at 0°–15° C. Et$_2$O (100 mL) was added and the mixture washed with brine (2×50 mL). The Et$_2$O extracts were washed with aqueous 5% NaHSO$_3$ solution (2×50 mL), dried over MgSO$_4$, filtered, and the solvent removed in vacuo to give the product (1.35 g, 67%) as a syrup; IR (film) 1729, 1376, and 1170 cm$^{-1}$; NMR (CDCl$_3$) 1.30 (3H, t, J 7.2 Hz), 3.04 (2H, t, J 7.4 Hz), 4.02 (2H, t, J 7.3 Hz), 4.23 (2H, q, J 7.1 Hz).

Step 2

To a stirred solution of the amine 2AdocαMeTrpCH$_2$CH(NH$_2$)Ph (0.257 g, 0.50 mmol) in anhydrous THF (25 mL) was added 4-dimethylamino pyridine (0.067 g, 0.55 mmol) and a solution of the sulphonic chloride from Step 1 (0.22 g, 1.10 mmol) in anhydrous THF (2 mL). The mixture was stirred for 5 days at room temperature and then diluted with Et$_2$O (25 mL) and washed with brine (25 mL). The Et$_2$O extracts were dried over MgSO$_4$, Filtered, and the solvent removed in vacuo. Purification of the residue by chromatography on silica using 50% n-hexane:50% EtOAc gave the product (0.086 g, 25%) as a white solid, mp 70°–86° C.; [α]$_D^{20}$ –7.8° (c=0.12 CH$_2$Cl$_2$); IR (film) 1738, 1695, 1665, 1376, and 1152 cm$^{-1}$; NMR (CDCl$_3$) 1.26 (3H, t, J 7.0 Hz), 1.54–1.99 (17H, m), 2.60–2.67 (2H, m), 2.88–3.01 (1H, m), 3.03–3.11 (1H, m), 3.28–3.49 (3H, m), 3.64 (1H, bin), 4.12 (2H, q, J 7.1 Hz), 4.53–4.55 (1H, m), 4.71 (1H, s), 5.30 (1H, s), 6.14 (1H, d, J 7.5 Hz), 6.60 (1H, b), 7.03–7.38 (9H, m), 7.59 (1H, d, J 7.7 Hz), 8.46 (1H, s); Anal. ($C_{36}H_{46}N_4O_7S$), C, H, N.

Step 3

To a stirred solution of the ethyl ester from Step 2 (0.08 g, 0.12 mmol) in EtOH (10 mL) at 0° C. was added 0.1N NaOH (1.3 mL of an aqueous solution, 0.13 mmol) dropwise over 1.5 hours. The cold solution was stirred for 2 hours and then at room temperature for 20 hours. 0.1N HCl (1.4 mL of an aqueous solution, 0.14 mmol) was added and the solvent removed in vacuo. The residue was extracted into EtOAc (25 mL) and washed with brine (2×10 mL). The EtOAc was dried over MgSO$_4$, filtered, and the solvent removed in vacuo. The residue was purified by reverse phase silica chromatography using 75% MeOH:25% H$_2$O as eluant, giving the product (0.025 g, 32%) as a white solid, mp 115°–136° C.; IR (film) 3378, 1715, 1700, 1659, 1378, and 1152 cm$^{-1}$; NMR (CDCl$_3$) 1.50–1.97 (17H, m), 2.50–2.77 (2H, m), 2.94 (1H, bm), 3.08 (1H, bm), 3.22–3.44 (3H, m), 3.64 (1H, bm), 4.51 (1H, bin), 4.85 (1H, s), 5.43 (1H, b), 6.24 (1H, b), 7.04–7.33 (9H, m), 7.55 (1H, d, J 7.6 Hz), 8.53 (1H, s); Anal. ($C_{34}H_{42}N_4O_7S \cdot 1CH_3OH$), C, H, N.

EXAMPLE 57

(R)-4-[2-[2-[[3-(1H-indol-3-yl)-2-methyl-1-oxo-2-[[(tricyclo[3.3.1.1$^{3,7}$]dec-2-yloxy)carbonyl]amino]propyl]amino]ethyl]phenyl]amino]-4-oxo-, butanoic acid

Step 1

To a stirred solution of o-nitrophenethylalcohol (1.67 g, 10.0 mmol) in CH$_2$Cl$_2$ (25 mL) at 0° C. was added Et$_3$N (1.53 mL, 11.0 mmol) followed by dropwise addition of a solution of tosylchloride (1.91 g, 10.0 mmol) in CH$_2$Cl$_2$ (25 mL) over 1.5 hours. The mixture was stirred for 60 hours at room temperature and then washed with aqueous 5% citric acid solution (2×25 mL) and water (25 mL). The CH$_2$Cl$_2$ was dried over MgSO$_4$, filtered, and the solvent removed in vacuo. Chromatography of the residue on silica using 67% n-hexane:33% EtOAc as eluant gave the product (2.33 g, 73%) as a white crystalline solid, mp 49°–49.5° C.; IR (film) 1526, 1359, and 1177 cm$^{-1}$; NMR (CDCl$_3$) 2.43 (3H, s), 3.26 (2H, t, J 6.3 Hz), 4.35 (2H, t, J 6.3 Hz), 7.26 (2H, d, J 8.1 Hz), 7.36–7.43 (2H, m), 7.51–7.57 (1H, m), 7.67 (2H, d, J 8.3 Hz), 7.93 (1H, d, J 8.2 Hz); Anal. ($C_{15}H_{15}NO_5S$), C, H, N.

Step 2

To a stirred solution of the rosylate from Step 1 (2.0 g, 6.22 mmol) in anhydrous DMF (40 mL) was added sodium azide (0.445 g, 6.85 mmol) and the mixture heated at 100° C. for 2 hours. The mixture was poured onto ice (100 g) and extracted with Et$_2$O (2×100 mL). The combined Et$_2$O extracts were washed with brine (100 mL), dried over MgSO$_4$, filtered, and the solvent removed in vacuo to give the product (1.11 g, 93%) as an oil; IR (film) 2095, 1526, and 1347 cm$^{-1}$; NMR (CDCl$_3$) 3.18 (2H, t, J 6.8 Hz), 3.63 (2H, t, J 6.9 Hz), 7.40–7.46 (2H, m), 7.56–7.64 (1H, m), 7.91–8.01 (mH, m).

Step 3

The azide from Step 2 (0.90 9, 4.68 mmol) dissolved in absolute EtOH (50 mL) was hydrogenated at 30° C. and 45 psi H$_2$ over Lindlar catalyst (0.09 g) for 16 hours. The catalyst was filtered and the solvent removed in vacuo, giving the product (0.635 g, 99%) as an oil; IR (film) 3349 cm$^{-1}$; NMR (CDCl$_3$) 2.61–2.65 (2H, m), 2.81 (4H, b), 2.90–2.97 (2H, m), 6.63–6.73 (2H, m), 6.99–7.10 (2H, m).

Step 4

To a stirred solution of the acid 2AdocαMeTrp (1.31 g, 3.30 mmol) in EtOAc (100 mL) was added 1-hydroxybenzotriazole monohydrate (0.632 g, 4.13 mmol) and N,N'-dicyclohexylcarbodiimide (0.748 g, 3.63 mmol). The mixture was stirred for 1 hour at room temperature and then the amine from Step 3 (0.45 g, 3.30 mmol) in EtOAc (10 mL) was added in one portion. The mixture was stirred at room temperature for 24 hours and the N,N'-dicyclohexylurea was filtered off. The EtOAc solution was washed with aqueous 5% citric acid solution (2×50 mL), saturated NaHCO$_3$ solution (2×50 mL), 5% citric acid solution (50 mL), and brine (50 mL). The EtOAc was dried over MgSO$_4$, filtered, and the solvent removed in vacuo. The residue was purified by chromatography on silica using 33% n-hexane:67% EtOAc as eluant, giving the product (1.43 g, 84%) as an off-white solid, mp 102°–106° C.; [α]20D+22.9° (c=0.12; CH$_2$Cl$_3$); IR (film) 3339, 1699, and 1646 cm$^{-1}$; NMR (CDCl$_3$) 1.50–1.94 (1H, m), 2.57 (2H, t, J 7.2 Hz), 3.31–3.48 (4H, m), 4.81 (1H, s), 5.29 (1H, br s), 6.62–6.69 (3H, m), 6.91–7.20 (5H, m), 7.34 (1H, d, J 7.9 Hz), 7.58 (1H, d, J 7.7 Hz), 8.19 (1H, s).

Step 5

To a stirred solution of the amine from Step 4 (0.20 g, 0.39 mmol) in EtOAc (10 mL) was added succinic anhydride (0,117 g, 1.17 mmol) and 4-dimethylaminopyridine (01.42 g, 1.17 mmol) and the resulting mixture heated at reflux for 17 hours. The cooled solution was diluted with EtOAc (25 mL) and washed with 1.0M HCl (2×25 mL) and water (25 mL). The EtOAc was dried over MgSO$_4$, filtered, and the solvent removed in vacuo. The residue was purified by reverse phase chromatography on silica using 75% MeOH:25% H$_2$O as eluant which gave the product (0.106 g, 44%) as a white solid, mp 118°–122° C.; [α]$_D^{20}$+16.0° (c=0.11, acetone); IR (film) 1705 and 1650 cm$^{-1}$; NMR (DMSO) 1.31 (3H, s), 1.49 (2H, s), 1.69–1.93 (16H, m), 2.53–2.64 (4H, m), 3.21 (2H, m), 4.69 (1H, s), 6.69 (1H, s), 6.93–7.09 (4H, m), 7.16 (2H, d, J 6.4 Hz), 7.30 (1H, d, J 8.1 Hz), 7.46 (2H, d, J 7.9 Hz), 7.93 (1H, s), 9.48 (1H, s), 10.86 (1H, s); Anal. (C$_{35}$H$_{42}$N$_4$O$_6$.0.5 H$_2$O), C, H, N.

EXAMPLE 58

4-[[3-[2-[[3-(1H-indol-3-yl)-2-methyl-1-oxo-2-[[(tricyclo[3.3.1.1$^{3,7}$]dec-2-yloxy]carbonyl]amino]propyl]amino]ethyl]phenyl]amino]-4-oxobutanoic acid Method as for Example 57 except using m-nitrophenethyl alcohol; mp 78°–82° C.; NMR (d$^6$-DMSO) δ1.33 (3H, s), 1.50 (2H, brs), 1.70–2.00 (12H, m), 2.65 (2H, m), 3.10–3.40 (4H, obscured by H$_2$O), 4.69 (1H, brs), 6.60 (1H, brs), 6.82 (1H, d, J 7 Hz), 6.93 (2H, brs), 7.01 91H, t, J 7 Hz), 7.17 (1H, t, J 7 Hz), 7.29 (1H, d, J 8hz), 7.44 (3H, brs), 7.82 (1H, brs), 9.90 (1H, s), 10.85 (1H, s).

EXAMPLE 59

[R-(R*,R*)]-tricyclo[3.3.1.1$^{3,7}$]dec-2-yl ester, [1-(1H-indol-3-ylmethyl)-1-methyl-2-oxo-2-[[2-[[(1H-1,2,4-triazol-5-ylthio)acetyl]amino]-2-phenylethyl]amino]ethyl]carbamate

Step 1

A solution of PFP (0.072 g, 0.389 mmol) and bromoacetic acid (0.054 mg, 0.389 mmol) in ethyl acetate 910 mL) was stirred at room temperature and dicyclohexylcarbodiimide (0.987 g, 0.389 mmol) was added all at once. After stirring for 3 hours at room temperature the mixture was filtered, the precipitate washed with a little ethyl acetate, and to the filtrate was added the amine from Step 3, Example 32 (0.32 g, 0.389 mmol). This mixture was stirred at room temperature for 17 hours, filtered, and concentrated to a frothy solid. Chromatography on silica using 75% EtOAc:25% hexane as eluant yielded the bromide as a noncrystalline white solid (0.175 g, 71%), pure enough to be used directly; mp 184°–187.5° C.; IR (KBr) 3299, 2911, 1657, and 1530 cm$^{-1}$; NMR (CDCl$_3$) δ1.45–2.04 (17H, m), 3.32 and 3.46 (2H, ABq, J 14.6 Hz), 3.4 (m, 1H), 3.81 and 3.89 (2H, ABq, J 12.3 Hz), 3.95 (1H, br.m), 4.89 (1H, s), 5.03 (1H, s), 5.12 (1H, brs), 6.39 (1H, brs), 6.97 (1H, d, J 2.3 Hz), 7.10 (1H, t, J 7 Hz), 7.16–7.37 (7H, m), 7.57 (1H, d, J 8hz), 7.65 (1H, d, J 8 Hz), 8.14 (1H, s).

Step 2

The bromo compound from Step 1 (0.1 g, 0,157 mmol) and 3-mercapto-1H-1,2,4-triazole (0.016 g, 0.157 mmol) were stirred in dry THF (10 mL) under an atmosphere of N$_2$ with external cooling via an ice-salt bath and triethylamine (0.016 mL, 0.022 mL, 0.157 mmol) was added via a syringe. The mixture was allowed to warm to room temperature overnight, then filtered and concentrated in vacuo. The residue was chromatographed on silica using 75% EtOAc:25% hexane as eluant to yield the title compound (Example 59) as a noncrystalline white solid (0.093 g, 93%), mp 102°–107.5° C.; IR (KBr) 3306, 2909, 1657, and 1517 cm$^{-1}$; NMR (CDCl$_3$) 1.49–2.01 (17H, m), 3.21 (1H, brm), 3.28 and 3.45 (2H, ABq, J 14.6 Hz), 3.66 and 3.73 (2H, ABq, J 15.5 Hz), 4.05 (1H, brm), 4.85 (1H, s), 5.14 (1H, brs), 5.19 (1H, s), 6.50 (1H, brs), 6.97 (1H, s), 7.08 (1H, t, J 7.3 Hz), 7.15–7.36 (8H, m), 7.55 (1H, d, J 7.8 Hz), 7.91 (1H, brs), 8.07 (1H, s), 8.35 (1H, s); Anal. (C$_{35}$H$_{41}$N$_7$O$_4$.0.2 EtOAc), C, H, N.

EXAMPLE 60

[R-(R*,R*)]-tricyclo[3.3.1.1³,⁷]dec-2-yl [2-[[2-[[(1H-imidazol-2-ylthio)acetyl]amino]-2-phenylethyl]amino]-1-(1H-indol-3-ylmethyl)-1-methyl-2-oxoethyl]carbamate The bromo compound from Step 1, Example 59 (0.1 g, 0.157 mmol), 2-mercaptoimidazole (0.016 g, 0.157 mmol) and triethylamine (0.073 g, 0.1 mL, 0.714 mmol, 4.5 eq.) were stirred in dry THF (10 mL) at room temperature under an atmosphere of nitrogen for 3 hours. After this time the reaction was concentrated and partitioned between EtOAc and water. The organic layer was dried (MgSO$_4$), filtered, and concentrated to yield a white foam. Chromatography on silica using 10% MeOH:90% EtOAc as eluant gave the title compound (Example 60) as a noncrystalline white solid (0.094 g, 90%), mp 112°–122° C.; IR (KBr) 3244, 2908, 1657, and 1521 cm$^{-1}$; NMR (CDCl$_3$) 1.43–2.04 (17H, m), 3.27 (1H, m), 3.32 and 3.48 (2H, ABq, J 14.6 Hz), 3.58 (2H, s), 4.11 (1H, brm), 4.86 (1H; s), 5.06 (1H, s), 5.12 (1H, m), 6.47 (1H, brs), 6.98 (1H, d, J 2.2 Hz), 7.07–7.38 (11H, m), 7.56 (1H, d, J 8.2 Hz), 7.93 (1H, d, J 8.2 Hz), 8.29 (1H, s); Anal. (C$_{36}$H$_{42}$N$_6$O$_4$S.0.5 H$_2$O), C, H, N.

EXAMPLE 61

Methyl (±)-N-[3-(1H-indol-3-yl)-2-methyl-1-oxo-2-[[(tricyclo[3.3.1.1³,⁷]dec-2-yloxy)carbonyl]amino]propyl]-N-(2-phenylethyl)glycine Methyl (2-phenylethyl)glycinate To a stirred solution of 2-phenylethylamine (9.68 g, 40 mmol) in toluene (50 mL) was added methyl bromoacetate (6.12 g, 20 mmol) dropwise at room temperature and was left stirring for 18 hours. The reaction mixture was filtered before removing the solvent in vacuo and the residue was purified by chromatography over silica gel to yield 4.8 g (61%) of the title compound as an oil. NMR (250 MHz, CDCl$_3$) δ(1H, s), 2.92 (4H, m), 3.43 (2H, s), 3.71 (3H, s), 7.27 (5 H, m).

Methyl-α-methyl-N-[(tricyclo[3.3.1.1³,⁷]dec-2-yloxy)carbonyl]-DL-tryptophyl]-N-2-phenylethyl)glycinate N-[(Tricyclo[3.3.1.1³,⁷]dec-2-yloxy(carbonyl)]-α-methyl tryptophan (0.7 g, 2 mmol) was stirred at 0° C. in methylene chloride with bis(2-oxo-3-oxazolidinyl)phosphonic chloride (BOPCl, 0.51 g, 2 mmol) and triethylamine (0.2 g, 2 mmol). To this mixture was added methyl N(2-phenylethyl) glycinate (1.04 g, 5.4 mmol). The mixture was allowed to warm to room temperature and stirred overnight. An additional equivalent of BOPCl was added after 18 hours and the reaction mixture was stirred for 48 hours at room temperature. The solvent was evaporated in vacuo and the residue was dissolved in ethyl acetate and washed with water, 1N hydrochloric acid solution, saturated sodium bicarbonate solution, water, and then the organic layer was dried over magnesium sulfate. After filtration and concentration of the filtrate in vacuo, the residue was purified by chromatography over silica gel using 50% ethyl acetate in hexane as a solvent system to give 0.4 g (35%) of the title compound as a foam. IR (KBr) 3395, 2855, 1709, and 1635 cm$^{-1}$; NMR (250 MHz, DMSO, 70° C.) δ1.32 (3H, s), 1.35–1.62 (2H, m), 1.62–2.20 (12H, m), 2.81 (2H, m), 3.15 (1H, Ha of ABq J 14.5 Hz), 3.55 (1H, Hb of ABQ J 14.5 Hz), 3.66 (3H, s), 3.75–4.50 (5H, m), 4.79 (1H, br s), 6.90–7.36 (9H, m), 7.47 (1H, d, J 8 Hz), 10.73 (1H, br s); Anal. (C$_{34}$H$_{41}$N$_3$O$_5$), C, H, N.

EXAMPLE 62

(±)-N-[3-(1H-indol-3-yl)-2-methyl-1-oxo-2-[[(tricyclo[3.3.1.1³,⁷]dec-2-yloxy)carbonyl]amino]propyl]-N-(2-phenylethyl)glycine N-[α-methyl-N-[(tricyclo[3.3.1.1³,⁷]dec-2-yloxy)carbonyl]-DL-tryptophyl]-N-(2-phenylethyl)glycine To a stirred solution of methyl N-[α-methyl-N[(tricyclo [3.3.1.1³,⁷]dec-2-yloxycarbonyl)-DL-tryptophyl]-N-(2-phenylethyl) glycinate (285 mg, 0.5 mmol) in dioxane (10 mL) and water (5 mL) was added lithium hydroxide-1-hydrate (42 mg, 1.0 mmol) and the resulting mixture was stirred overnight at room temperature. The reaction mixture was concentrated, acidified with dilute HCl, and extracted with ethyl acetate (2×50 mL). After drying over magnesium sulfate and concentration, flash column chromatography yielded the title compound which was crystallized from ethyl acetate and hexane to give 80 mg (29%) of white solid, mp 100°–105° C. IR (KBr) 3388, 2908, 2855, 1710 cm$^{-1}$; NMR (250 MHz, DMSO, 70° C.) 1.30 (3H, s), 1.1–1.58 (2H, m), 1.58–2.18 (12H, m), 2.56–2.92 (2H, m), 2.92–3.6 (4H, m), 3.6–4.26 (4H, m), 4.76 (1H, br s), 6.82–7.38 (9H, m), 7.45 (1H, d, J 7.7 Hz), 10.70 (1H, br s).

EXAMPLE 63

Methyl 7-[(2-phenylethyl)amino]heptanoate

To a mixture of 2-phenylethylamine (1.09 g, 9 mmol) and triethylamine (1.37 g, 13.5 mmol) in toluene (50 mL) was added methyl 7-bromoheptanoate (2.0 g, 9 mmol) and refluxed overnight. The reaction mixture was filtered and concentrated. Flash column chromatography over silica gel using 100% ethyl acetate yielded a yellow oil (0.62 g, 20%) NMR (250 MHz, CDCl$_3$), 1.12–1.40 (4H, m), 1.40–1.72 (4H, m), 2.29 (2H, t), 2.63 (2H, t), 2.75–2.96 (4H, m), 2.96–3.1 (1H, br s), 3.66 (3H, s), 7.00–7.38 (5H, m).

Methyl (±)-7-[[3-(1H-indol-3yl)-2-methyl-1-oxo-2-[[(tricyclo[3.3.1.1³,⁷]dec-2-yloxy)carbonyl]amino]propyl](2-phenylethyl)amino]heptanoate Method was as described for Example 61 but using methyl 7-[(2-phenylethyl)amino]heptanoate. The title compound was obtained as a white foam (0.135 g, 25%), mp 75°–80° C. NMR (250 MHz, DMSO, 100° C.) 1.05–1.35 (4H, m), 1.31 (3H, s), 1.35–1.60 (6H, m), 1.60–1.82 (8H, m), 1.82–2.25 (4H, m), 2.26 (2H, t), 2.78 (2H, m), 3.0–3.82 (7H, m), 3.58 (3H, s), 4.75 (1H, br s), 6.80–7.10 (4H, m), 7.10–7.38 (5H, m), 7.45 (1H, d, J 8 Hz), 10.69 (1H, br s); Anal. (C$_{39}$H$_{51}$N$_3$O$_5$), C, H, N.

EXAMPLE 64

(±)-7-[[3-(1H-indol-3-yl-)-2-methyl-1-oxo-2-[[tricyclo[3.3.1.1³,⁷]dec-2-yloxycarbonyl]amino]propyl](2-phenylethyl)amino]heptanoic acid Method was as described for Example 62 but using methyl (±)-7-[[3-(1H-indol-3-yl)-2-methyl-1-oxo-2-[[tricyclo[3.3.1.1³,⁷]dec-2-yloxy)carbonyl]amino]propyl]-N-(2-phenylethyl)amino]heptanoate. The titled compound was obtained as white foam (60 mg, 80%), mp 105°–112° C. NMR (250 MHz, DMSO, 100° C.) 1.05–1.38 (4H, m), 1.31

(3H, s), 1.38–1.62 (6H, m), 1.62–2.10 (12H, m), 2.17 (2H, t), 2.78 (2H, m), 2.95–3.95 (7H, m), 4.75 (1H, br s), 6.85–7.12 (4H, m), 7.12–7.38 (5H, m), 7.45 (1H, d, J 8 Hz), 10.69 (1H, br s), 11.65 (1H, br s); Anal. ($C_{38}H_{49}N_3O_5$), C, H, N.

EXAMPLE 65

(Intermediate )

2-Adamantyloxycarbonyl-α-methyl-D,L-tryptophan succinimide ester

To a solution of 2-adamantyloxycarbonyl-α-methyl-DL-tryptophan (1 g, 2.5 mmoles) and 1,3-dicyclohexylcarbodiimide (0.86 g, 4.2 mmoles) in ethylene glycol dimethyl ether (50 mL) was added N-hydroxysuccinimide (0.45 g, 3.8 mmoles). The solution was stirred at 25° C. for 16 hours and filtered. After washing with ethylene glycol dimethyl ether, the filtrate was concentrated to a white solid. Recrystallization from 1,4- dioxane, ethyl acetate, and hexane gave 0.94 g (75%) of product; $^1$H NMR (DMSO-$d_6$ δ1.40–2.50 (17H, m), 2.80 (4H, s), 3.13 (1H, d, J 14 Hz), 3.70 (1H, d, J 14 Hz), 4.73 (1H, br s), 6.93 (1H, t, J 7.5 Hz), 7.05 (1H, t, J 7.5 Hz), 7.18 (1H, s), 7.33 (1H, d, J 8 Hz), 7.47 (1H, d, J 8 Hz), 7.56 (1H, s), 11.0 (.1H, br s).

EXAMPLE 66

Tricyclo[3.3.1.1$^{3,7}$]dec-2-yl (±)-[1-(1H-indol-3-ylmethyl)-1-methyl-2-[[2-(4-morpholinyl)ethyl]amino]-2-oxoethyl]carbamate 2-Adamantyloxycarbonyl-α-methyl-DL-tryptophan succinimide ester (0.1 g, 0.2 mmoles ) dissolved in ethylene glycol dimethyl ether (5 mL) was treated with 4-(2-aminoethyl)morpholine (0.03 g, 0.21 mmoles) and triethylamine (0.023 g, 0.22 moles). The solution was stirred for 3 hours at 25° C., then filtered. The filtrate was concentrated, suspended in water, and extracted with ethyl acetate (2X). The organic extracts were combined, washed with water (2X), dried over magnesium sulfate, and filtered. Concentration of the filtrate left a foam. Purification by flash chromatography (silica gel, ethyl acetate/hexane/isopropyl alcohol eluant) gave 0.55 g (53%) of product; $^1$H NMR (CDCl$_3$) δ1.51–1.98 (17H, m), 2.17–2.25 (6H, m), 3.19–3.29 (4H, m), 3.46–3.50 (4H, m), 4.83 (1H, br s), 5.34 (1H, br s), 6.55 (1H, br s), 7.05–7.20 (3H, m), 7.34 (1H, d, J 8 Hz), 7.59 (1H, d, J 8 Hz), 8.12 (1H, br s ).

EXAMPLE 67

Tricyclo[3.3.1.1$^{3,7}$]dec -2-yl (1)-[1-(1H-indol-3-ylmethyl)-1-methyl-2-oxo-2-[[2-(1-piperidinyl)ethyl]amino]ethyl]carbamate In a manner analogous to Example 66, 2-adamantyloxycarbonyl-α- methyl-DL-tryptophan succinimide ester (0.1 g, 0.2 moles ) was reacted with 1-(2-aminoethyl)piperidine (0.027 g, 0.21 moles) to give 0.065 g (54%) of product; $^1$H NMR (CDCl$_3$) δ1.40–2.0 (23H, m), 2.20 (6H, m), 3.21 (2H, m), 3.33 (1H, d, J 15 Hz), 3.47 (1H, d, J 15 Hz), 4.84 (1H, br s), 5.40 (1H, br s), 6.67 (1H, br s), 7.03–7.20 (3H, m), 7.35 (1H, d, J 8 Hz), 7.60 (1H, d, J 8 Hz ), 8.11 (1H, br s).

EXAMPLE 68

Tricyclo[3.3.1.1$^{3,7}$]dec-2-yl (1)-[1-(1H-indol-3-ylmethyl)-1-methyl-2-oxo-2-[[2-(1-pyrrolidinyl)ethyl]amino]ethyl]carbamate In a manner analogous to Example 66, 2-adamantyloxycarbonyl-α-methyl-DL-tryptophan succinimide ester (0.1 g, 0.2 moles) was reacted with 1-(2aminoethyl)pyrrolidine (0.024 g, 0.21 moles) to give 0.074 g (74%) of product; $^1$H NMR (CDCl$_3$) δ1.50–1.99 (21H, m), 2.48 (6H, br s), 3.33 (2H, m), 3.35 (1H, d, J 14 Hz), 3.47 (1H, d, J 14 Hz), 4.83 (1H, br s), 5.36 (1H, br s), 6.86 (1H, br s), 7.02–7.17 (3H, m), 7.35 (1H, d, J 8 Hz), 7.61 (1H, d, J 8 Hz), 8.13 (1H, br s).

EXAMPLE 69

Tricyclo[3.3.1.1$^{3,7}$]dec-2-yl (±)-[2-[[2-(1H-indol-3-yl)ethyl]amino]-1-(1H-indol-3-ylmethyl)-1-methyl-2-oxoethyl]carbamate A solution of 0.50 g (1.26 mmol) of 2-adamantyloxycarbonyl-α-methyl-DL-tryptophan and 0.19 g (1.41 mmol) of 1-hydroxybenzotriazole hydrate in 20 mL of anhydrous EtOAc (under a N$_2$ atmosphere) was treated in one portion with 0.34 g (1.65 mmol) of 1,3-dicyclohexylcarbodiimide. The mixture was stirred at room temperature for 2 hours, treated with 0.26 g (1.62 mmol) of tryptamine, and stirred for an additional 18 hours. The precipitated solid was filtered, washed with a small amount of fresh EtOAc, and discarded. The filtrate was diluted to 150 mL with EtOAc and washed with 5% aqueous citric acid (3×150 mL), brine (1×150 mL), 5% aqueous NaHCO$_3$ (3×150 mL), and brine again. The organic layer was dried (Na$_2$SO$_4$) and evaporated (vacuum) to a tan solid. The residue was chromatographed (E. Merck prepacked Lobar column, 37×440 mm, eluted with 2% MeOH in CH$_2$Cl$_2$) to yield the purified product as a white foam, 0.32 g (47%); $^1$H NMR (CDCl$_3$) δ1.46–1.92 (17H, m), 2.83 (2H, t, J 7 Hz), 3.23 (1H, d, J 15 Hz), 3.40 (1H, d, J 15 Hz), 3.52 (2H, m), 4.78 (1H, br s), 5.23 (1H, br s), 6.12 (1H, m), 6.77 (1H, m), 6.82 (1H, m), 7.06–7.58 (8H, m), 7.96 (2H, br s).

EXAMPLE 70

Tricyclo[3.3.1.1$^{3,7}$]dec-2-yl (±)-[2-[[2-(benzo[b]thien-3-yl)ethyl]amino]-1-(1H-indol-3-ylmethyl)-1-methyl-2-oxoethyl]carbamate A solution of 0.50 g (1.26 mmol) of 2-adamantyloxycarbonyl-α-methyl-DL-tryptophan and 0.18 g (1.33 mmol) of 1-hydroxybenzotriazole hydrate in 8 mL of anhydrous DMF (under a N$_2$ atmosphere) was treated in one portion with 0.27 9 (1.41 mmol) of 1-(3-dimethylaminopropyl)-3-ethylcarbodiimide hydrochloride. The mixture was stirred at room temperature for 2 hours, treated with 0.30 g (1.40 mmole) of 3-[2-aminoethyl]benzo[b]thiophene hydrochloride plus 0.25 mL (0.18 g, 1.79 mmol) of Et$_3$N, and stirred for an additional 18 hours. The reaction mixture was partitioned between 100 mL of EtOAc and 150 mL of H$_2$O. The layers were separated and the aqueous layer extracted with fresh EtOAc (3×75 mL). The combined organic layers were washed with 5% aqueous citric acid (3×150 mL), brine (1×150 mL), 5% aqueous NaHCO$_3$ (3×150 mL), and brine again. The organic layer was dried (Na$_2$SO$_4$) and evaporated (vacuum) to an off-white foam. The residue was chromatographed (230–400 mesh SiO$_2$ in a 21×300 mm column, eluted with 2% MeOH in CH$_2$Cl$_2$) to yield the purified product as a white foam, 0.40 g (57%); $^1$H NMR (CDCl$_3$) δ1.47–1.92 (17H, m), 2.92 (2H, t, J 7 Hz), 3.25 (1H, d, J 15 Hz), 3.46–3.57 (3H, m), 4.79 (1H, br s), 5.14 (1H, br s), 6.27 (1H, m), 7.02 (2H, m), 7.11–7.86 (8H, m), 8.10 (1H, br s).

EXAMPLE 71

Tricyclo[3.3.1.1$^{3,7}$]dec-2-yl (±)-[2-[[2-(1H-benzimidazol-2-yl)ethyl]amino]-1-(1H-indol-3-ylmethyl)-1-methyl-2-oxoethyl]carbamate Following the procedure of Example 70, the title compound was prepared from 0.50 g (1.26 mmol) of 2-adamantyloxycarbonyl-α-methyl-DL-tryptophan and 0.33 g (1.41 mmol) of 1H-benzimidazole-2-ethanamine dihydrochloride with 0.5 mL of added triethylamine. The purified product after chromatography was obtained as a white foam, 0.38 g (56%); $^1$H NMR (CDCl$_3$) δ1.46–1.91 (17H, m), 3.01–3.16 (2H, m), 3.27 (1H, d, J 15 Hz), 3.43 (1H, d, J 15 Hz), 3.58 (2H, m), 4.80 (1H, br s), 5.23 (1H, s), 6.67 (1H, m), 6.89–7.72 (10H, m), 8.28 (1H, br s).

EXAMPLE 72

Tricyclo[3.3.1.1$^{3,7}$]dec-2-yl (±)-[2-[[2-(3,4-dihydro-1-naphthalenyl) ethyl]amino]-1-(1H-indol-3-ylmethyl)-1-methyl-2-oxoethyl ]carbamate Following the procedure of Example 70, the title compound was prepared from 0.50 g (1.26 mmol) of 2-adamantyloxycarbonyl-α- methyl-DL-tryptophan and 0.29 g (1.38 mmol) of 3,4-dihydro-1-naphthalene ethanamine hydrochloride. The purified product after chromatography was obtained as a white foam, 0.41 g (59%); $^1$H NMR (CDCl$_3$) δ1.48–1.99 (17H, m), 2.39–2.50 (2H, m), 2.67–2.82 (3H, m), 3.23–3.57 (3H, m), 3.99 (2H, t, J 5.0 Hz), 4.84 (1H, br s), 5.24 (1H, br s), 5.73 (1H, m), 6.16 (1H, m), 7.00–7.63 (9H, m), 8.12 (1H, br s).

EXAMPLE 73

Tricyclo[3.3.1.1$^{3,7}$]dec-2-yl (±)-[1-(1H-indol-3-ylmethyl)-1-methyl-2-oxo-2-[[2-(2-thienyl) ethyl] amino]ethyl]carbamate To a solution of 2-adamantyloxycarbonyl-α-methyl-DL-tryptophan (0.401 g, 1.01 mmol) in dry ethyl acetate (6 mL) and N,N-dimethylformamide (4 mL) under nitrogen atmosphere was added 1-hydroxybenzotriazole (0.138 g, 1.02 mmol) followed by 1-(3-dimethylaminopropyl)-3-ethylcarbodiimide (0.199 g, 1.04 mmol). this mixture was stirred 2 hours, then triethylamine (0.18 mL, 1.3 mmol) and 2-thiopheneethaneamine hydrochloride (0.214 g, 1.30 mmol) were added. After stirring the resulting mixture an additional 18 hours, the mixture was diluted with ethyl acetate (20 mL), and washed with aqueous 1N citric acid, saturated aqueous sodium bicarbonate, and brine solutions. The organic phase was dried over MgSO$_4$, concentrated, purified by flash chromatography (SiO$_2$, 4×20 cm, 230–400 mesh, 67% ethyl acetate/hexane eluant), and dried for 48 hours under vacuum at 60° C. to provide 0.310 g (61%) of product; $^1$H NMR (CDCl$_3$) δ1.49–1.60 (2H, m), 1.55 (3H, s), 1.65–2.00 (12H, m), 2.88 (2H, t, J 6 Hz), 3.26 (1H, d, J 14 Hz), 3.40–3.60 (3H, m), 4.82 (1H, br s), 5.17 (1H, br s), 6.36 (1H, br s), 6.69 (1H, d, J 2 Hz), 6.85–6.90 (1H, m), 6.95 (1H, d, J 2 Hz), 7.00–7.22 (3H, m), 7.36 (1H, d, J 8 Hz), 7.58 (1H, d, J 8 Hz), 8.29 (1H, br s).

EXAMPLE 74

Tricyclo[3.3.1.1$^{3,7}$]dec-2-yl (±)-[1-(1H-indol-3-ylmethyl)-1-methyl-2-[[2-(1-methyl-1H-pyrrol-2-yl) ethyl]amino]-2-oxoethyl]carbamate To a solution of 2-adamantyloxycarbonyl-α-methyl-DL-tryptophan (0.401 g, 1.01 mmol) in dry ethyl acetate (4 mL) and N,N-dimethylformamide (4 mL) under nitrogen atmosphere was added 1-hydroxybenzotriazole (0.139 g, 1.03 mmol) followed by 1-(3-dimethylaminopropyl)-3-ethylcarbodiimide (0.199 g, 1.04 mmol). This mixture was stirred 2 hours and 0.16 g (1.3 mmole) of 2-(2-aminoethyl)-1-methylpyrrole was added. After stirring an additional 18 hours, the resulting mixture was diluted with ethyl acetate (20 mL), and washed with aqueous 1N citric acid, saturated aqueous sodium bicarbonate, and brine solutions. The organic phase was dried over MgSO$_4$ and purified by flash chromatography (SiO$_2$, 4×20 cm, 230–400 mesh, 67% ethyl acetate/ hexane eluant). Concentration followed by drying under vacuum for 48 hours at 60° C. provided 0.301 g (59%) at product; $^1$H NMR (CDCl$_3$) δ1.49–1.60 (2H, m), 1.56 (3H, s), 1.70–2.00 (12H, m), 2.61 (2H, t, J 7 Hz), 3.23–3.55 (4H, m), 3.50 (3H, s), 4.82 (1H, br s), 5.20 (1H, br s), 5.76 (1H, br s), 6.00 (1H, t, J 3 Hz), 6.34 (1H, br s), 6.53 (1H, br s), 6.97 (1H, br s), 7.09–7.19 (2H, m), 7.36 (1H, d, J 8 Hz), 7.59 (1H, d, J 8 Hz), 8.16 (1H, br s).

EXAMPLE 75

Tricyclo[3.3.1.1$^{3,7}$]dec-2-yl (±)-[1-(1H-indol-3-ylmethyl)-1-methyl-2-oxo-2-[[2-(2-pyridinyl)ethyl] amino]ethyl]carbamate To a solution of 2-adamantyloxycarbonyl-α-methyl-DL-tryptophan (0.400 g, 1.01 mmol) in ethyl acetate (6 mL) and N,N-dimethylformamide (4 mL) under nitrogen atmosphere was added 1-hydroxybenzotriazole (0.138 g, 1.02 mmol) followed by 1-(3-dimethylaminopropyl)-3-ethylcarbodiimide hydrochloride (0.198 g, 1.03 mmol). This mixture was stirred 2 hours and 2 (2-aminoethyl)pyridine (0.16 mL, 1.3 mmol) was added. After stirring an additional 18 hours, the resulting mixture was diluted with ethyl acetate (20 mL), and washed with aqueous 1N citric acid, aqueous saturated sodium bicarbonate, and brine solutions. The organic phase was dried over MgSO$_4$, concentrated, and purified by flash chromatography (SiO$_2$, 230–400 mesh, ethyl acetate eluant). After concentration, the residue was dried under vacuum at 60° C. for 48 hours to provide 0,365 g (72%) of product; $^1$H NMR (CDCl$_3$) δ1.40–1.60 (2H, m), 1.56 (3H, s), 1.65–1.95 (12H, m), 2.88 (2H, t, J 6 Hz), 3.39 (2H, d, J 5 Hz), 3.50–3.70 (2H, m), 4.75 (1H, br s), 5.35 (1H, br s), 6.40 (1H, d, J 2 Hz), 7.00–7.20 (4H, m), 7.22–7.35 (2H, m), 7.52–7.60 (2H, m), 8.20 (1H, br s), 8.40–8.45 (1H, m).

EXAMPLE 76

Tricyclo[3.3.1.1$^{3,7}$]dec-2-yl (±)-[2-[[2-(1H-imidazol-4-yl)ethyl]amino]-1-(1H -indol-3-ylmethyl)-1-methyl-2-oxoethyl]carbamate To a solution of 2-adamantyloxycarbonyl-α-methyl-DL-tryptophan (0.401 g, 1.01 mmol) in dry ethyl acetate (6 mL) and N,N-dimethylformamide (4 mL) under nitrogen atmosphere was added pentafluorophenol (0.189 g, 1.03 mmol) followed by 1-(3-dimethylaminopropyl)-3-ethylcarbodiimide (0.200 g, 1.04 mmol). This mixture was stirred 2 hours, then triethylamine (0.36 mL, 2.6 mmol) and histamine dihydrochloride (0.240 g, 1.30 mmol) were added. After stirring an additional 40 hours, the resulting mixture was diluted with ethyl acetate (20 mL), and washed with water. The organic phase was dried over MgSO$_4$, concentrated, purified by flash chromatography (SiO$_2$, 4×20 cm, 230–400 mesh, 10% methanol/dichloromethane eluant), and dried for 48 hours under vacuum at 70° C. to provide 0.234 g (47%) of product; $^1$H NMR (CDCl$_3$) δ1.40–1.60 (2H, m), 1.57 (3H, s), 1.65–2.00 (13H, m), 2.65–2.75 (2H, m), 3.25–3.45 (4H, m), 4.82 (1H, br s), 5.42 ([H, br s), 6.67 (1H, s), 6.81 (1H, br s), 6.91 (1H, br s),7.00–7.20 (2H, m), 7.34 (1H, d, J 7 Hz), 7.46 (1H, s), 7.55 (1H, d, J 7 Hz), 8.67 (1H, br s).

EXAMPLE 77

Tricyclo[3.3.1.1$^{3,7}$]dec-2-yl (±)-[1-(1H-indol-3-ylm-ethyl)-1-methyl-2-oxo-2-[[2-(2-pyrazinyl)ethyl]amino]ethyl]carbamate A room temperature solution of 0.40 g (1.01 mmol) of 2-adamantyloxycarbonyl-α-methyl-DL-tryptophan and 0.15 g (1.11 mmol) of 1-hydroxybenzotriazole hydrate in 15 mL of anhydrous ethyl acetate under N$_2$ atmosphere was treated with 0.23 g (1.11 mmol) of 1,3-dicyclohexylcarbodiimide in one portion. The reaction was stirred for 1.75 hours and treated with 0.12 g (1.22 mmol) of triethylamine and 0.17 g (1.07 mmol) of 2-pyrazineethaneamine hydrochloride. The reaction as stirred for 1.75 hours and filtered. The filtrate was washed with aqueous 1M citric acid (2×15 mL), saturated aqueous NaHCO$_3$ (2×15 mL), and saturated aqueous NaCl (15 mL), dried over Na$_2$SO$_4$, and concentrated in vacuo. The residue was treated with 1,2-dimethoxyethane (5 mL), allowed to stand at 0°–5° C. for 16 hours, filtered, and concentrated in vacuo. Chromatography (flash, SiO$_2$, 230–400 mesh, 0.5% triethylamine/10% isopropanol/ethyl acetate eluant, 15×2.5 cm) gave a clear oil upon solvent removal. The residue was dissolved in methanol (10 mL) and water (1 mL) and concentrated in vacuo until a solid formed. The solid was suspended in water, filtered, and dried to give 0.32 g (63%) of the desired product as a white solid; mp 97°–101° C.; $^1$H NMR (CDCl$_3$) δ1.4–2.0 (17H, m), 2.87 (2H, m), 3.29 (1H, d, J 15 Hz), 3.46 (1H, d, J 15 Hz), 3.62 (2H, m), 4.74 (1H, br s), 5.23 (1H, br s), 6.95 (2H, br s), 7.0–7.2 (2H, m), 7.33 (1H, d, J 8 Hz), 7.58 (1H, d, J 8 Hz), 8.20 (1H, br s), 8.37 (2H, s), 8.38 (1H, s).

EXAMPLE 78

Tricyclo[3.3.1.1$^{3,7}$]dec-2-yl (±)-[2-[[2-(2-furanyl)ethyl]amino]-1-(1H-indol-3-ylmethyl)-1-methyl-2-oxoethyl]carbamate A room temperature solution of 0.30 g (0.76 mmol) of 2-adamantyloxycarbonyl-α-methyl-DL-tryptophan and 0.11 g (0.81 mmol) of 1-hydroxybenzotriazole hydrate in 10 mL of anhydrous N,N-dimethylformamide under N$_2$ atmosphere was treated with 0.16 g (0.83 mmol 1-(3-dimethylaminopropyl)-3-ethylcarbodiimide hydrochloride in one portion. The reaction was stirred for 1.75 hours at room temperature and treated with 0.09 g (0.93 mmol) of triethylamine and 0.13 g (0.88 mmol) of 2-furanethaneamine hydrochloride. The reaction was stirred for 21 hours at room temperature, then partitioned between saturated aqueous NaHCO$_3$ (50 mL) and ethyl acetate (50 mL). The aqueous layer was extracted with ethyl acetate (20 mL). The combined organic extracts were washed with aqueous 1M citric acid (3×15 mL), water (2×15 mL), saturated aqueous NaHCO$_3$ (15 mL), water (15 mL), and saturated aqueous NaCl (15 mL), dried over Na$_2$SO$_4$, and concentrated in vacuo. The residue was passed through a plug of SiO$_2$ (70×230 mesh, 50% ethyl acetate-hexane eluant, 15 mL medium sintered glass funnel) to give a clear glass. The residue was dissolved in diethyl ether (3 mL), methanol (5 mL), and water (2 mL), and concentrated in vacuo until a solid formed. The mixture was treated with water, filtered, and dried to give 0.26 g (70%) of the desired product as a white solid, mp 87°–97° C.; $^1$H NMR (CDCl$_3$) δ1.5–2.0 (17H, m), 2.67–2.74 (2H, m), 3.29 (1H, d, J 15 Hz), 3.46–3.49 (3H, m), 4.82 (1H, br s), 5.16 (1H, br s), 5.95 (1H, d, J 3 Hz), 6.25 (1H, dd, J 3 Hz and J 2 Hz), 6.37 (1H, br s), 6.97 (1H, d, J 2 Hz), 7.1–7.3 (3H, m), 7.36 (1H, d, J 8 Hz), 7.59 (1H, d, J 8 Hz), 8.18 (1H, br s).

EXAMPLE 79

Tricyclo[3.3.1.1$^{3,7}$]dec-2-yl (±)-[1-(1H-indol-3-ylm-ethyl)-1-methyl-2-oxo-2-[[2-(1H-1,2,4-triazol-3-yl)ethyl]]amino]ethyl ]carbamate Following the method for Example 78, except using 2.4 equivalents of triethylamine and 1.2 equivalents of 1H-1,2,4-triazole-3-ethaneamine dihydrochloride, work-up after 2.5 hours, and using t-butyl methyl ether and hexane to precipitate the product after work-up, gave the desired product as a white solid in 44% yield, mp 124°–128° C.; $^1$H NMR (CDCl$_3$) δ1.5–2.0 (17H, m), 2.97 (2H, br s), 3.26 (1H, d, J 15 Hz), 3.41 (1H, d, J 15 Hz), 3.35–3.65 (2H, m), 4.85 (1H, br s), 5.30 (1H, s), 6.71 (1H, br s), 6.93 (1H, s), 7.07 and 7.09 (1H, dd, J$^1$=7 Hz and J$^2$=7 Hz), 7.16 and 7.19 (1H, dd, J$^1$=7 Hz and J$^2$=7 Hz), 7.34 (1H, d, J 7 Hz), 7.56 (1H, d, J 7 Hz), 7.87 (1H, s), 8.45 (1H, br s).

EXAMPLE 83

Tricyclo[3.3.1.1$^{3,7}$]dec-2-yl(±)-[2-[[2-(5,6-dimethyl-1H-benzimidazol-2-yl)ethyl]amino]-(1H-indol-3-ylmethyl)-1-methyl-2-oxoethyl]carbamate In a manner analogous to Example 66, 2-adamantyloxy-carbonyl-α-methyl-DL-tryptophan succinimide ester (0.3 g, 0.6 mmoles) was reacted with 5,6-dimethyl-1H-benzimidazole-2-ethanamine dihydrochloride (0.17 g, 0.64 mmoles) to give 0.21 g (61%) of product. $^1$H NMR (CDCl$_3$) δ1.50–1.95 (17H, m), 2.32 (6H, s), 3.04 (2H, m), 3.38 (2H, m), 3.60 (2H, m), 4.71 (1H, br s), 5.86 (1H, br s), 6.96–7.12 (3H, m), 7.25 (2H, s), 7.33 (1H, d, J 8 Hz), 7.52–7.55 (3H, m), 10.05 (1H, br s).

EXAMPLE 84

Tricyclo[3.3.1.1$^{3,7}$]dec-2-yl (1)-[2-[[2-(5-acetyl-1H-benzimidazol-2-yl)ethyl]amino]-1-(1H-indol-3-ylm-ethyl)-1-methyl-2-oxoethyl ]carbamate In a manner analogous to Example 66, 2-adamantyloxy-carbonyl-α-methyl-DL-tryptophan succinimide ester (0.3 g, 0.6 mmoles) was reacted with 1-[2-(2-aminoethyl)-1H-benzimidazol -5-yl]ethanone dihydrochloride (0.18 g, 0.61 mmoles) to give 0.1 g (30%) of product; $^1$H NMR (CDCl$_3$) δ1.46–1.91 (17H, m), 2.63 (3H, s), 3.13 (2H, m), 3.26 (1H, d, J 14 Hz), 3.43 (1H, d, J 14 Hz), 3.59 (2H, m), 4.77 (1H, br s), 5.25 (1H, s), 6.69 (1H, br s), 6.95 (1H, s), 7.06–7.20 (2H, m), 7.33 (1H, d, J 8 Hz), 7.52 (1H, br s), 7.57 (1H, d, J 8 Hz), 7.85 (1H, d, J 8 Hz), 8.16 (1H, br s), 8.40 (1H, br s), 11.00 (1H, br s).

EXAMPLE 85

Tricyclo[3.3–1.1³,⁷]dec-2-yl (±)-[1-(1H-indol-3-ylmethyl)-1-methyl-2-oxo-[[2-(2-quinolinyl)ethyl]amino]ethyl]carbamate To a stirred solution of 2-adamantyloxycarbonyl-α-methyl-DL-tryptophan (1.59 g, 4.0 mmole) in dry THF (50 mL) at −22° C. was added N-methylmorpholine (0.644 g, 6.3 mmole) and isobutyl chloroformate (0.632 g, 4.6 mmole). The mixture was stirred at −22° C. for 1 hour and then a solution of 2-(2-aminoethyl)quinoline (0.690 g, 4.0 mmole) in dry THF (15 mL) was added. After stirring at this temperature 4 hours the reaction mixture was allowed to stir at room temperature 15 hours. The solvent was removed in vacuo and the residue was taken up in EtOAc and washed with 5% citric acid (2×50 mL), water (2×50 mL), 5% NaHCO₃ (3×50 mL), water (2×50 mL), and brine (2×50 mL). The organic phase was dried over MgSO₄ and the solvent evaporated. The residue was flash chromatographed on silica gel, eluting with EtOAc-n-hexane. The oil obtained was triturated with cold Et₂O, yielding the product as an amorphous white solid, (0.38 g, 17%); ¹H NMR (CDCl₃) δ1.41–1.88 (17H, m), 3.00–3.04 (2H, m), 3.40 (2H, q, J 9.59 Hz), 3.68–3.70 (2H, m), 4.70 (1H, s), 5.43 (1H, br s), 6.90 (1H, d, J 2.23), 6.96–7.22 (4H, m), 7.45–7.55 (2H, m), 7.63–7.70 (2H, m), 7.78 (1H, d, J 8.06), 7.89 (2H, d, J 8.10), 8.03 (1H, d, J 8.46).

EXAMPLE 86

Tricyclo[3.3.1.1³,⁷]dec-2-yl (±)-[1-(1H-indol-3-ylmethyl)-1-methyl-2-oxo-2-[[2-(2-pyridinyl)ethyl]amino]ethyl]carbamate hydrochloride To a solution of the parent base of the title compound (0.180 g, 0.360 mmol) in ethyl ester (15 mL) and methanol (1 mL) was added a saturated solution of gaseous HCl in ethyl ether (15 mL). This mixture was stirred 1 hour, concentrated, and dried under vacuum for 18 hours at 70° C. to provide 0.178 g (89%) of product; ¹H NMR (CDCl₃) δ1.50–2.10 (18H, m), 3.37 (4H, br s), 3.70 (2H, br s), 4.75 (1H, br s), 5.53 (1H, br s), 6.90–7.10 (3H, m), 7.15–7.55 (5H, m), 8.07 (1H, br s), 8.35 (1H, br s), 8.78 (1H, br s).

EXAMPLE 87

Tricyclo[3.3.1.1³,⁷]dec-2-yl (1)-[1-(1H-indol-3-ylmethyl)-1-methyl-2-oxo-2-[[2-(1-piperazinyl)ethyl]amino]ethyl]carbamate In a manner analogous to Example 66, 2-adamantyloxycarbonyl-α- methyl-DL-tryptophan succinimide ester (0.3 g, 0.6 mmoles) was reacted with 1-(2-aminoethyl)piperazine (0.08 g, 0.64 mmoles) to give 0.12 g (39%) of product. ¹H NMR (CDCl₃) δ1.38–2.15 (25H, m), 2.63 (3H, m), 3.10–3.30 (4H, m), 4.82 (1H, br s), 5.56 (1H, br s), 6.72 (1H, br s), 7.01–7.20 (3H, m), 7.30 (1H, d, J 8 Hz), 7.55 (1H, d, J 8 Hz ), 9.73 (1H, br s).

EXAMPLE 88

Carbamic acid, [1-(1H-indol-3-ylmethyl)-2-oxo-2-[(2-phenylethyl)amino]-1-[[2-(trimethylsilyl)ethoxy]methyl]ethyl-, tricyclo[3.3.1.1³,⁷]dec-2-yl ester, (±)

α-Trimethylsilylethoxymethyl-DL-tryptophan methyl ester

A solution of DL-tryptophan methyl esterbenzaldimine (4.0 g, 13 mmol) in 30 mL THF was added over 15 minutes to a mixture of 20.2 mL lithiumdiisopropylamide (10% suspension in hexan) and 70 mL dry THF, cooled to −10° C. under nitrogen atmosphere. The stirring was continued for an additional 45 minutes, keeping the temperature at −10° C. A solution of trimethylsilylethoxymethylchloride (2.2 g, 13.2 mmol) in 5 mL THF was added and the mixture stirred overnight at room temperature. The reaction mixture was decomposed with 100 mL distilled water, extracted with ethyl acetate (3×100 mL), and the organic solvent was removed in vacuo. The resulting oily residue was treated with 30 mL 1N hydrochloric acid for 1 hour at room temperature after which the reaction mixture was made basic with sodium bicarbonate and extracted with ethyl acetate (3×100 mL). The organic layer was dried over Na₂SO₄, evaporated to give the crude product which was separated by flash chromatography on silica gel using a mixture of toluene/ethanol 500:30 (v/v) as elution solvent. The fractions, containing the main product (TLC on silica gel, toluene/ethanol 10:2 (v/v), Rf 0.38) were combined and evaporated to dryness in vacuo. Trituration of the oily residue with diethyl ether gave 2.0 g (44%) of α-trimethylsilylethoxymethyl-DL-tryptophan methyl ester, mp 113°–115° C.

N-[(2-Adamantyloxy)carbonyl]-α-trimethylsilylethoxymethyl-DL-tryptophan methyl ester A mixture of α-trimethylsilylethoxymethyl-DL-tryptophan methyl ester (1.0 g, 2.8 mmol), diisopropylethylamine (0.4 g, 3 mmol) and 2-adamantylchloroformate (0.65 g, 3 mmol) in 20 mL dry THF was stirred at room temperature for 4 hours. The reaction mixture was diluted with distilled water and extracted with ethyl acetate (4×50 mL). The organic extract was washed with brine and dried over Na₂SO₄. Evaporation of the organic solvent gave the title compound as a colorless foam (1.0 g, 67.8%).

N-[(2-Adamantyloxy)carbonyl]-α-trimethylsilylethoxymethyl-DL-tryptophan

A mixture of N-[(2-adamantyloxy)carbonyl]-α-trimethylsilylethoxymethyl-DL-tryptophan methyl ester (4.5 g, 8.5 mmol), LiOH (0.22 g, 9.1 mmol), dioxane (90 mL), and water (30 mL) was stirred at 60° C. for 16 hours. After cooling, the reaction mixture was acidified to pH 4 with 1N hydrochloric acid and extracted with ethyl acetate. The organic extract was dried over Na₂SO₄ and then concentrated in vacuo. Trituration of the oily residue with diethyl ether gave the title compound as a white solid (4.0 g, 91.7%), mp 203° C. (dec.).

A solution of N-[(2-adamantyloxy)carbonyl]-α-trimethylsilylethoxymethyl-DL-tryptophan (0.6 g, 1.17 mmol) and N,N'-carbonyldiimidazol (0.21 g, 1.3 mmol) in 20 mL dry THF was stirred at room temperature for 48 hours. Then 2-phenethylamine (0.15 g, 1.3 mmol) was added to the reaction mixture and the stirring continued for an additional 24 hours. After dilution with distilled water, the product was extracted with ethyl acetate and separated by flash chromatography on silica gel using a mixture of n-hexane/ethyl acetate (2:1, v/v) as elution solvent. The desired compound was eluated from the column at first. The product was obtained as a colorless solid (0.3 g, 41.65), mp 75°–80° C.

EXAMPLE 89

α-Hydroxymethyl-DL-tryptophan methyl ester

α-Trimethylsilylethoxymethyl-DL-tryptophan methyl ester (1.0 g, 2.8 mmol) was stirred for 48 hours at room temperature in trifluoroacetic acid (10 mL). After evaporation of the acid in vacuo, the oily residue was treated with aqueous sodium bicarbonate and extracted with ethyl acetate. The organic layer was dried over $Na_2SO_4$ and evaporated to give an oil. Trituration with ethyl acetate gave 0.45 g (655) of α-hydroxymethyl-DL-tryptophan methyl ester, mp 148°–149° C.

EXAMPLE 90

Carbamic acid, [1-methyl-1-[[1-[(4-methylphenyl)sulfonyl]-1H-indol-2-yl[methyl]-2-oxo-2-[(2-phenylethyl)amino]ethyl]-, tricyclo[3.3.1.1$^{3,7}$]dec-2-yl ester. (±)

1-(4-Methylphenyl)sulfonyl-1H-indol-2-carboxylic acid ethyl ester

To a stirred suspension of sodium hydride (3.7 g, 120 mmol, 80% in paraffin oil) in dry THF (75 mL), a solution of indol-2-carboxylic acid ethyl ester (18.9 g, 100 mmol) in dry THF (75 mL) was added in 1 hour with stirring while the inner temperature was maintained under 30° C. The reaction mixture was stirred for 30 minutes and then a solution of p-toluenesulphonyl chloride (22.9 g, 120 mmol) in dry THF (75 mL) was added dropwise to the stirring reactant. After 2 hours stirring at room temperature and 1 hour at 45° C. the solvent was evaporated in vacuo and the residue partitioned between water and ethyl ether. The organic phase was dried over $MgSO_4$ and the solvent evaporated to leave a solid which was recrystallized from diisopropyl ether (26.8 g, 78%), mp 92°–95° C.

2-Hydroxyethyl-1-(4-methylphenyl)sulfonyl-1H-indole

To a stirred solution of Red-Al (sodium dihydro-bis(2-methoxyethoxy)aluminate ~70% in toluene) (30 mL) in dry THF (100 mL) cooled at 5° C. and under nitrogen was added dropwise and at this temperature a solution of compound prepared above (26.8 g, 78 mmol) in dry THF (75 mL). After stirring 1 hour at 5° C. and then 1 hour at room temperature, the mixture was cooled at 10° C. and treated dropwise with 2N NaOH, to effect hydrolysis of the intermediate complex. The organic phase was separated and the solvent in vacuo evaporated. The residue was solved in ethyl ether, the solution washed with water, dried over $MgSO_4$, and evaporated to give the required alcohol (23.3 g, 98%) as a yellow oil; IR (film) 3500, 1597 cm$^{-1}$.

2-Bromomethyl-1-(4-methylphenyl)sulfonyl-1H-indole

To a solution of triphenylphosphine (20.2 g, 77 mmol) in dry $CH_2Cl_2$ (80 mL) was added dropwise a solution of bromine (11.9 g, 77 mmol) in dry $CH_2Cl_2$ (40 mL). The stirring was continued for 1 hour and then a solution of compound prepared above (23.2 g, 77 mmol) in dry $CH_2Cl_2$ (40 mL) was added dropwise. The resulting mixture was left stirring for 12 hours. After removing the solvent the residue was taken up in ethyl acetate and washed with water. The organic extract was dried over $MgSO_4$ and the solvent evaporated in vacuo. The residue was chromatographed over silica gel using toluene as eluant to give a yellow oil (21.0 g, 75%); IR (film) 1600 cm$^{-1}$, MS ((70eV): m/z 363 (M+, 12.6), 129 (100).

Racemic

2-Methyl-3-[[1-(4-methylphenyl)sulfonyl]-1H-indol-2-yl]-N-(phenylmethylene)alanine methyl ester To a stirred solution of KOt.Bu (5.1 g, 4.5 mmol) in dry THF (25 mL) cooled at –40° C. was added dropwise at this temperature a solution of N-(phenylmethylene)-DL-alanine methyl ester (8.7 g, 45 mmol) in dry THF (40 mL under nitrogen. The mixture was stirred 1 hour at –40° C. and then was added dropwise maintaining the temperature of a solution of compound prepared above (16.5 g, 45 mmol) in dry THF (50 mL). After the addition was completed, the mixture was stirred 2 hours at –20° C., then allowed to warm to room temperature and left overnight. THe solvent was evaporated in vacuo, given a resin, which on trituration with ethyl ether and water gave the required compound (16.5 g, 75%) as a white solid, mp 151°–154° C.

Racemic 2-Methyl-3-[[1-(4-methylphenyl)sulfonyl]-1H-indol-2-yl]alanine methyl ester A suspension of compound prepared above (16.1 g, 34 mmol) in ethanol (100 mL) and 2N hydrochloric acid (20 mL) was stirred overnight. After removing the solvent in vacuo the residue was suspended in water (400 mL), made basic with $Na_2CO_3$, extracted with ethyl ether, and dried over $MgSO_4$. The solvent was evaporated, providing an oil. This was subjected to silica gel chromatography using ethyl acetate:toluene 8:92 (v/v) then methanol:toluene 1:99 (v/v) as eluants to give the required compound (9.9 g, 75%) as an oil; IR (film) 1735 cm$^{-1}$.

Racemic N-[(2-Adamantyloxy)carbonyl]-2-methyl-3-[[1-(4-methylphenyl)sulfonyl]-1H-indol-2-yl]alanine methyl ester To a stirred solution of compound prepared above (9.9 g, 25 mmol) in dry THF (100 mL) was added a solution of 2-adamantylchloroformate (6.4 g, 30 mmol) in dry THF (15 mL) followed by a solution of triethylamine (6.1 g, 56 mmol) in dry THF (15 mL dropwise. After 1 hour stirring, the reaction mixture was filtered and the solvent removed in vacuo. The residue was stirred with a mixture of light petroleum (100 mL) and ethyl ether (20 mL) to give the required compound as a colorless solid, which was removed by filtration (13.9 g, 96%), mp 119°–122° C.

Racemic N-[2-Adamantyloxy)carbonyl]-2-methyl-3-[[1-(4-methylphenyl)sulfonyl]-1H-indol-2-yl]alanine To a stirred solution of compound prepared above (0.54 g, 0.95 mmol) in a mixture of 1,4-dioxan (10 mL) and water (2 mL) was added LiOH (11.5 mg, 4.8 mmol) and stirred 5 days. After removing the solvent in vacuo, the residue was suspended in water, acidified with 1M citric acid solution to pH 4.5, and extracted with ethyl acetate. The organic phase was dried over $MgSO_4$ and evaporated in vacuo to yield the acid (0.5 g, 96%) as nearly colorless foam, mp (noncrystalline) 106° C. (sintering).

Carbamic acid, [1-methyl-1-[[1-[4-methylphenyl)sulfonyl]-1H-indol-2-yl]methyl-2-oxo-2-[(2-phenylethyl)amino]ethyl]-, tricyclo[3.3.1.1$^{3,7}$]dec-2-yl ester, (±)

A mixture of compound prepared above (0.48 g, 0.88 mmol) and 1,1'-carbonyldiimidazole (0.14 g, 0.88 mmol) in dry THF (10 mL) was stirred for 1 hour. To this mixture was then added dropwise a solution of 2-phenylethylamine (0.11 g, 0.90 mmol) in dry THF (5 mL). After stirring for 4 hours the solvent was removed in vacuo and the residue partitioned between water (25 mL) and $CH_2Cl_2$ (50 mL). The organic phase was dried over $MgSO_4$ and the solvent evaporated. The residue was chromatographed over silica gel using methanol:toluene 1:99 (v/v) as eluant to yield the title compound as a white solid, crystallized from 2-propanol (0.25 g, 43%), mp 166–°168° C.

EXAMPLE 91

Carbamic acid, [1-(1H-indol-2-ylmethyl)-1-methyl-2-oxo-2-[(2-phenylethyl)amino]ethyl]-, tricyclo[3.3.1.1$^{3,7}$]dec-2-ylester, (±)

Racemic N-[(2-Adamantyloxy)carbonyl]-2-methyl-3-(1H-indol-2-yl]alanine (Step 7 of Example 45)

A mixture of racemic N-[(2-adamantyloxy)carbonyl]-2-methyl-3-[[1-(4-methylphenyl)sulfonyl]-1H-indol-2-yl]alanine methyl ester (Step 6 of Example 45) (6.8 g, 12 mmol) and KOH (2.7 g, 48 mmol) in ethanol (100 mL) was stirred for 60 hours at 70° C. After removing the solvent in vacuo, the residue was partitioned between water (150 mL) and ethyl ether. The clear water phase was separated and acidified to pH 4.5 when an oil precipitated out, which slowly solidified. The solid was collected by filtration, washed successively with water, and dried to give the desired carboxylic acid (3.9 g, 81%) as a white solid, mp 210°–216° C.

Carbamic acid, [1-(1H-indol-2-ylmethyl)-1-methyl-2-oxo-2-[(2-phenylethyl)amino]ethyl]-, tricyclo [3.3.1.1$^{3,7}$]dec-2-yl ester, (±);

A mixture of the compound prepared above (0.53 g, 1.3 mmol) and 1,1'-carbonyldiimidazole (0.22 g, 1.3 mmol) in dry THF (8 mL) was stirred for 1 hour. To this mixture was then added dropwise a solution of 2-phenethylamine (0.17 g, 1.4 mmol) in dry THF (4 mL). After stirring overnight, the solvent was evaporated in vacuo. The residue was solved in ethyl ether, washed with water, dried over $MgSO_4$, and the solevnt evaporated to leave a colorless foam which was crystallized from diisopropylether to yield the title compound (0.42 g, 64%), mp 168°–169° C.

EXAMPLE 92a and b

Carbamic acid, [2-[1-(hydroxymethyl)-2-phenylethyl]amino-1-(1H-indol-2-ylmethyl)-1-methyl-2-oxo]ethyl-, tricyclo[3.3.1.1$^{3,7}$]dec-2-yl ester Method was described for Example 91 but using (S)-(–)-2-amino-3-phenyl-1-propanol. The crude residue was chromatographed over silica gel using 1% MeOH:99% $CH_2Cl_2$ as eluant.

Diasteromer 1 (92a)

Diastereomer 1 (0.26 g, 24%) was obtained as a foam softering at 87° C., Rf 0.70 (MeOH/$CH_2Cl_2$ 1:9).

Diastereomer 2 (92b)

Diastereomer 2 (0.20 g, 18%) was obtained as a foam softering at 90° C., Rf 0.65 (MeOH/$CH_2Cl_2$ 1:9).

EXAMPLE 93a and b

4-[[2-[[3-(1H-indol-2-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid benzyl ester Method was as described for Example 91, except the amine 12 (Scheme XI) was used. The crude residue was chromatographed over silica gel using methanol: dichloromethane 1:99 (v/v) as eluant.

Diastereomer 1 (93a)

Diastereomer 1 (0.17 g, 13%) was obtained as an amorphous pale beige solid, mp 107°–115° C. (after stirring with ethyl ether); Rf 0.4 (MeOH:$CH_2Cl_2$ 1:99).

Diastereomer 2 (93b)

Diastereomer 2 (0.21 g, 17%) was obtained as an amorphous pale beige solid, mp 148°–153° C. (after stirring with ethyl ether); Rf 0.35 (MeOH:$CH_2Cl_2$ 1:99).

EXAMPLE 94a and b

4-[[2-[[3-(1H-indol-2-yl)-2-methyl-1-oxo-2-[[(tricyclo[3.3.1.1$^{3,7}$]dec-2-yloxy)carbonyl]amino]propyl]amino]-1-phenylethyl]amino-4-oxobutanoic acid

Diastereomer 1

A solution of benzyl ester of Example 93a (0.15 g, 0.2 mmol) in absolute ethanol (10 mL) was treated with 20% Pd(OH)$_2$ on carbon (0.06 g) and placed under an atmosphere of hydrogen (50 bar) at 25° C. for 15 hours. The reaction mixture was then filtered and the filtrate concentrated in vacuo. The residue was chromatographed over silica gel using 2%–10% methanol:98%–90% dichloromethane as eluant to yield the title compound (0.065 g, 50%) as an amorphous solid, mp 180°–187° C.

4-[[2-[[3-(1H-indol-2-yl)-2-methyl-1-oxo-2-[[(tricyclo[3.3.1.1$^{3,7}$]dec-2-yloxy)carbonyl]amino]propyl]amino]-1-phenylethyl]amino-4-oxobutanoic acid

Diastereomer 2

Method was as described above except that the compound of Example 93 was used. The title compound (0.070 g, 45%) was obtained as an amorphous solid, mp 185°–190° C.

EXAMPLE 95

Tricyclo[3.3.1.1$^{3,7}$]dec-2-yl (±)[2-[(2-amino-2-phenylethyl)amino]-1-(1H-indol-2-ylmethyl)-1-methyl-2-oxoethyl]carbamate

Step 1

A solution of N-[(2-adamantyloxy)carbonyl]-2-methyl-3-(1H-indol-2-yl)-alanine (3.1 g, 8.4 mmol) and 1,1'-carbonyldiimidazole (1.4 g, 8.6 mmol) in dry THF (25 mL) was stirred for 2 hours. To this mixture was added the amine 15 (Scheme XII) in portionS. After the addition was completed the resultant mixture was stirred 6 hours at 50° C., then allowed to cool to room temperature and left overnight. After removing the solvent in vacuo the residue was partitioned between water (50 mL) and ether (100 mL). The organic phase was separated, washed, dried over $MgSO_4$, and the solvent evaporated. The residue was chromatographed over silica gel using MeOH:Ch$_2$Cl$_2$ 0.5–0.75:99.6–99.25 (v/v) as eluant. The required compound (3.3 g, 61%) was obtained as a colorless resin (mixture of isomers).

Step 2

A solution of the compound prepared above (3.3 g, 5.1 mmol) in absolute ethanol (30 mL) was treated with 20% Pd(OH)$_2$ on carbon (0.75 g) and put under an atmosphere of hydrogen (50bar) at 30° C. with agitation for 15 hours. The reaction mixture was then filtered and the filtrate concentrated in vacuo. The residue was partitioned between water (40 mL) and ethyl acetate (70 mL). The organic phase was separated, washed, dried over MgSO$_4$, and the solvent evaporated in vacuo to give the desired compound (2.6 g, 99%) as a colorless amorphous solid and a mixture of two diastereoisomers, mp 96°–102° C.

4-[[2-[[3-(1H-indol-2-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid benzyl ester A solution of benzyl-hemisuccinate (1.1 g, 5.0 mmol) and 1,1'-carbonyldiimidazole (0.8 g, 5.0 mmol) in dry THF (10 mL) was stirred for 1 hour. To this mixture was added dropwise a solution of the amine of Example 95 (2.5 g, 4.9 mmol) in dry THF (10 mL) and the resultant mixture was stirred 4 hours at 50°–55° C., then cooled to room temperature and left overnight. After removing the solvent in vacuo, the residue was partitioned between water (50 mL) and CH$_2$Cl$_2$ (100 mL). The organic phase was separated, washed, dried over MgSO$_4$, and the solvent evaporated in vacuo. The residue was chromatographed over silica gel using MeOH:CH$_2$Cl$_2$ 0.5–1.99:5–99 (v/v).

Diastereoisomer 1

The separated diastereoisomer 1 was stirred with ether (5 mL). After filtration was obtained the desired compound (0.80 g, 23%) as a colorless amorphous solid, mp 109°–113° C., Rf=0.40 (MeOH/CH$_2$Cl$_2$ 1:99).

Diastereoisomer 2

The separated diastereoisomer 2 was stirred with ether (5 mL). After filtration was obtained the desired compound (0.68 g, 20%) as a colorless amorphous solid, mp 150°–152° C., Rf=0.35 (MeOH/CH$_2$Cl$_2$ 1:99).

EXAMPLE 96

Tricyclo[3.3.1.1$^{3,7}$]dec-2-yl (±)[2-[[2-(formylamino)-2-phenylethyl]amino]-1-(1H-indol-3-ylmethyl)-1-methyl-2-oxoethyl]carbamate This compound was isolated by chromatographic separation of the crude residue of the above example, Step 3, as a colorless amorphous solid (0.40 g, 15%), mp 102°–118° C., Rf=0.30 (MeOH:CH$_2$Cl$_2$ 5:95).

TABLE I $$R^1-A-N-\overset{R^2}{\underset{H}{C}}-\overset{O}{\overset{\|}{C}}-N-\overset{R^9}{\underset{R^3}{C}}-\overset{R^{12}}{\underset{\substack{|\\CH_2-\text{(indole)}}}{C}}-\overset{R^{13}}{\underset{R^4}{C}}-Ar$$

| No. | R$^1$ | A | R$^2$ | R$^9$ | R$^3$ | R$^{12}$ | R$^4$ | R$^{13}$ | Ar |
|---|---|---|---|---|---|---|---|---|---|
| 1 | (trimethylnorbornyl) | —O—CO— | Me | H | H | H | —NHCOCH=CHCOOH | H | Ph |
| 2 | (trimethylnorbornyl) | —O—CO— | Me | Me | H | H | —NH—CO—(CH$_2$)$_2$COOH | H | Ph |
| 3 | (adamantyl) | —NHCO— | Me | H | H | H | —NHCO(CH$_2$)$_2$COOH | H | Ph |
| 4 | " | —SO$_2$— | Me | H | H | H | —NHCO(CH$_2$)$_2$COOH | H | Ph |
| 5 | " | —SO$_2$— | Me | H | —CH$_2$NHCO(CH$_2$)$_2$COOH | H | H | H | Ph |
| 6 | (fluorocyclohexyl) | —O—CO— | Me | H | —CH$_2$NHCO(CH$_2$)$_2$COOH | H | H | H | Ph |
| 7 | " | —O—CO— | Me | Me | —CH$_2$NHCO(CH$_2$)$_2$COOH | H | H | H | Ph |

TABLE I-continued $$R^1-A-N(R^2)-\overset{O}{C}-\overset{R^9}{\underset{H}{C}}-\overset{R^{12}}{\underset{R^3}{C}}-N(H^+)-\overset{R^{13}}{\underset{R^4}{C}}-Ar$$

with CH$_2$-(indol-3-yl) substituent

| No. | R¹ | A | R² | R⁹ | R³ | R¹² | R⁴ | R¹³ | Ar |
|---|---|---|---|---|---|---|---|---|---|
| 8 | CF₃-cyclohexyl | —O—CO— | Me | H | —CH₂NHCO(CH₂)₂COOH | H | H | H | Ph |
| 9 | adamantyl | —O—CO— | Me | Me | —CH₂NHCO(CH₂)₂COOH | H | H | H | Ph |
| 10 | " | —O—CO— | Me | Me | —CH₂NHCO(CH₂)₂COOH | H | H | H | Ph |
| 11 | Me,Me-norbornyl | —O—CO— | Me | H | —CH₂NHCO(CH₂)₂ | H | H | H | Ph |
| 12 | adamantyl | —O—CO— | Me | H | H | H | —NHCO(CH₂)₂ | H | Ph |
| 13 | " | —O—CO— | Me | H | —CONHOH₂CO₂H | H | H | H | Ph |
| 14 | " | —O—CO— | Me | H | —CONHCH₂CH₂COOH | H | H | H | Ph |
| 15 | " | —O—CO— | Me | Me | H | H | H | H | Ph |

TABLE I-continued $$R^1-A-\underset{H}{\overset{R^2}{\underset{|}{N}}}-\underset{H}{\overset{O}{\underset{\|}{C}}}-\underset{R^3}{\overset{R^9}{\underset{|}{C}}}-\underset{H}{\overset{R^{12}}{\underset{|}{N}}}-\underset{R^4}{\overset{R^{13}}{\underset{|}{C}}}-Ar$$

with indole-CH₂ substituent

| No. | R¹ | A | R² | R⁹ | R³ | R¹² | R⁴ | R¹³ | Ar |
|-----|----|----|----|----|----|-----|----|-----|-----|
| 16 | Cl-cyclohexyl (trans) | —O—CO— | Me | H | H | H | H | H | Ph |
| 17 | Cl-cyclohexyl | —O—CO— | Me | H | —CH₂OH | H | H | H | Ph |
| 18 | " | —O—CO— | Me | H | —CH₂OCOCH₂CH₂COOH | H | H | H | Ph |
| 19 | Me-cyclohexyl | —O—CO— | Me | H | —CH₂OCOCH₂CH₂COOH | H | H | H | Ph |
| 20 | adamantyl | —O—CO— | Me | H | H | H | H | H | Ph |
| 21 | adamantyl | —O—CO— | —CH₂O | H | H | H | H | H | Ph |
| 22 | " | —O—CO— | Me | H | —CH₂OCO(CH₂)₂COOH | H | H | H | Ph |
| 23 | " | —O—CO— | Me | H | H | H | —CH₂OCO(CH₂)₂COOH | H | Ph |

TABLE I-continued $$R^1-A-\underset{H}{\overset{R^2}{\underset{|}{C}}}-\underset{|}{\overset{O}{\underset{\|}{C}}}-\underset{|}{\overset{R^9}{N}}-\underset{|}{\overset{R^{12}}{\underset{R^3}{C}}}-\underset{|}{\overset{R^{13}}{\underset{R^4}{C}}}-Ar$$

with indole-CH₂ substituent

| No. | R¹ | A | R² | R⁹ | R³ | R¹² | R⁴ | R¹³ | Ar |
|---|---|---|---|---|---|---|---|---|---|
| 24 | bornyl (Me,Me,Me) | —O—CO— | Me | H | H | H | —NHCO(CH₂)₂COOH | H | Ph |
| 25 | " | —O—CO— | Me | H | H | H | —NHCO(CH₂)₂COOH | H | Ph |
| 26 | adamantyl | —O—CO— | Me | H | —CH₂NHCOCH=CHCOOH | H | H | H | Ph |
| 27 | " | —O—CO— | Me | H | —CH₂NHCO(CH₂)₂COOH | H | H | H | Ph |
| 28 | " | —O—CO— | Me | Me | H | H | H | H | Ph |
| 29 | " | —O—CO— | Me | H | —CH₂—S(=O)—CH₂COOH | H | H | H | Ph |
| 30 | " | —O—CO— | Me | H | —CH₂—SO₂—CH₂COOEt | H | H | H | Ph |
| 31 | " | —O—CO— | Me | H | —CH₂—S(=O)—CH₂COOEt | H | H | H | Ph |
| 32 | " | —O—CO— | Me | H | H | H | —NHCOCH=CHCOOH | H | Ph |
| 33 | " | —O—CO— | Me | H | —CH₂SCH₂COOH | H | H | H | Ph |
| 34 | bornyl (Me,Me,Me) | —O—CO— | Me | H | H | H | —NHCOCH=CH—COOMe | H | Ph |
| 35 | " | —O—CO— | Me | H | H | H | —NHCOCH=CHCOOH | H | Ph |
| 36 | adamantyl | —O—CO— | Me | H | H | H | —NHCOCH₂COOH | H | Ph |

TABLE I-continued $$R^1-A-N-C-C-N-C-C-C-Ar$$
$$\phantom{R^1-A-}H^+\phantom{-}O\phantom{-}R^9\phantom{-}R^{12}\phantom{-}R^3\phantom{-}R^4$$
(with indole-CH$_2$- substituent)

| No. | R$^1$ | A | R$^2$ | R$^9$ | R$^3$ | R$^{12}$ | R$^4$ | R$^{13}$ | Ar |
|---|---|---|---|---|---|---|---|---|---|
| 37 | " | —O—CO— | Me | H | —CH$_2$SOCH$_2$COOEt | H | H | H | Ph |
| 38 | " | —O—CO— | Me | H | —CH$_2$COOH | H | H | H | Ph |
| 39 | " | —O—CO— | Me | H | —CH$_2$CH$_2$CH(NH$_2$)COOH | H | H | H | Ph |
| 40 | (adamantyl) | —O—CO— | Me | H | —CH$_2$NHCOCH=CHCOOH | H | H | H | Ph |
| 41 | (adamantyl) | —O—CO— | Me | H | H | H | —O—CO—(CH$_2$)COOH | H | Ph |
| 42 | " | —O—CO— | Me | H | H | H | —CONH—(CH$_2$)$_2$COOH | H | Ph |
| 43 | (CH$_3$-cyclohexyl) | —O—CO— | Me | H | —CH$_2$NH—CO—CH=CHCOOH | H | H | H | Ph |
| 44 | " | —O—CO— | Me | H | —CH$_2$NH—CO—(CH$_2$)$_2$COOH | H | H | H | Ph |
| 45 | " | —O—CO— | Me | H | H | H | —NHCO—CH=CHCOOH | H | Ph |
| 46 | " | —O—CO— | Me | H | H | H | —NHCO—(CH$_2$)$_2$COOH | H | Ph |
| 47 | " | —O—CO— | Me | H | CH$_2$OH | H | H | H | Ph |
| 48 | (adamantyl) | —O—CO— | Me | H | —(CH=CH$_2$)$_2$COOH | H | H | H | Ph |

TABLE I-continued
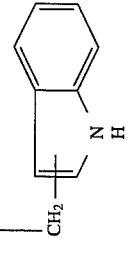
| No. | R¹ | A | R² | R⁹ | R³ | R¹² | R⁴ | R¹³ | Ar |
|---|---|---|---|---|---|---|---|---|---|
| 49 | " | —O—CO— | Me | H | H | H | —NH—CO—(CH₂)₂CO—NH— | H | Ph |
| 50 | " | —O—CO— | Me | H | —CH₂NHCOCH=CHCOOMe | H | H | H | Ph |
| 51 | " | —O—CO— | Me | H | —CH₂NHCOCH₂COOH | H | H | H | Ph |

TABLE II
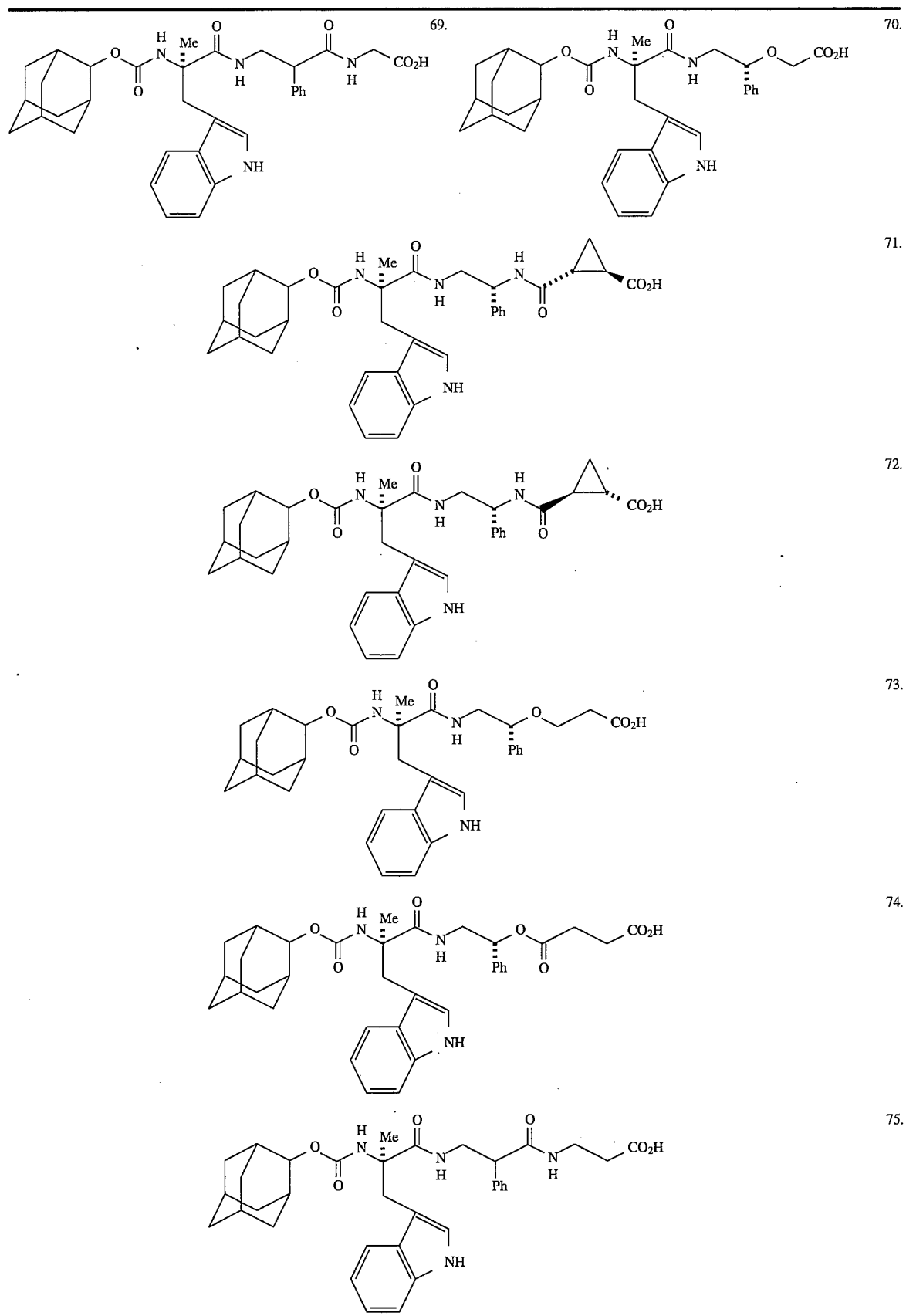

TABLE II-continued
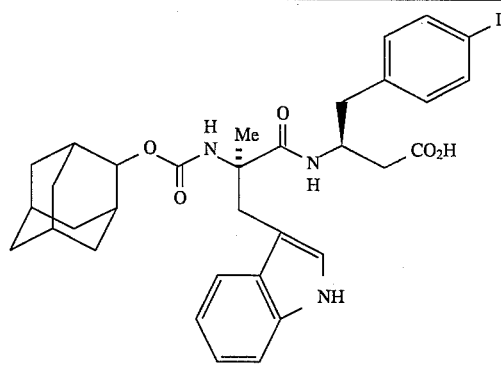 76.
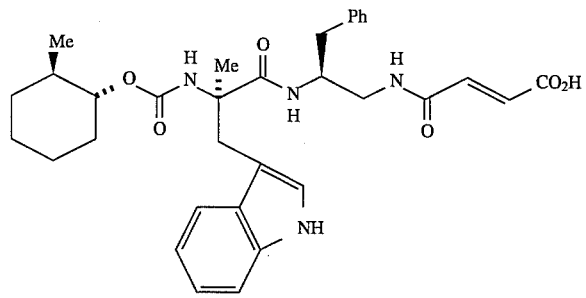 77.
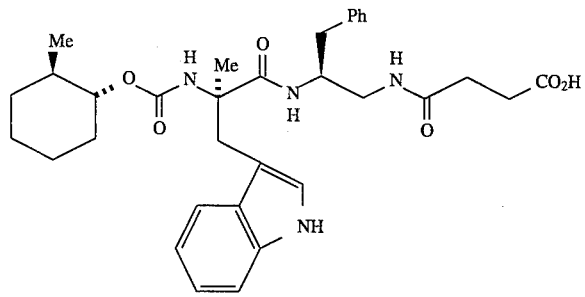 78.
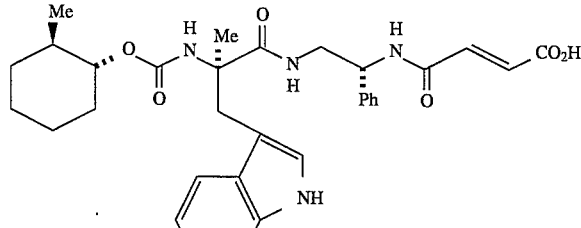 79.
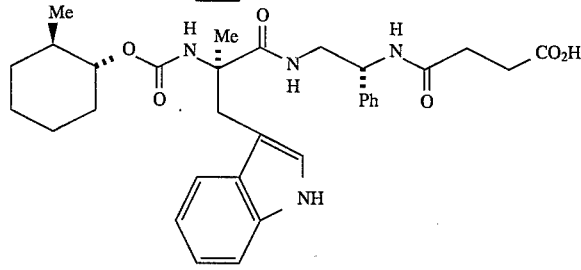 80.

TABLE II-continued
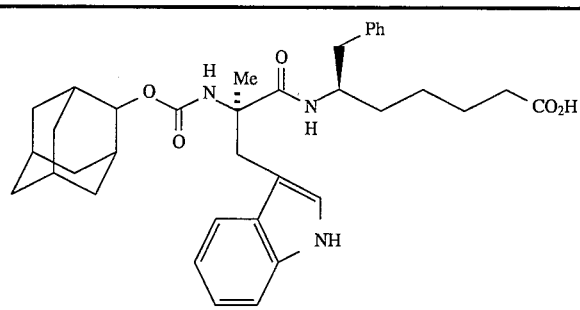 81.
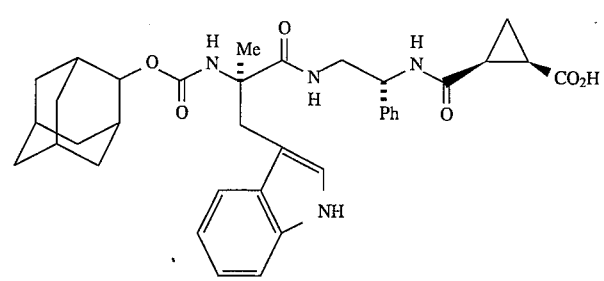 82.
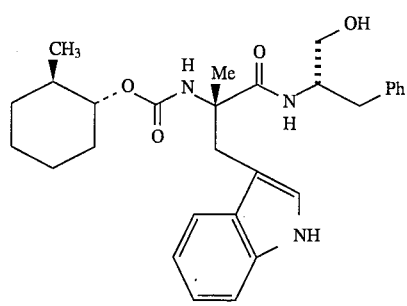 83.
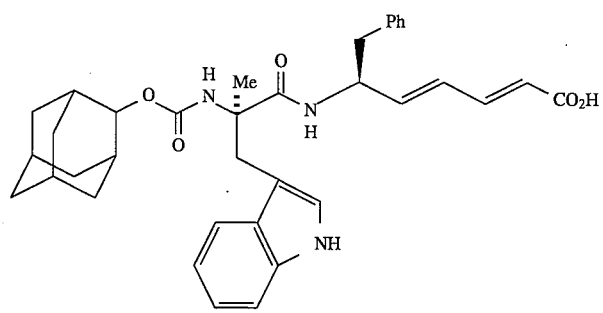 84.
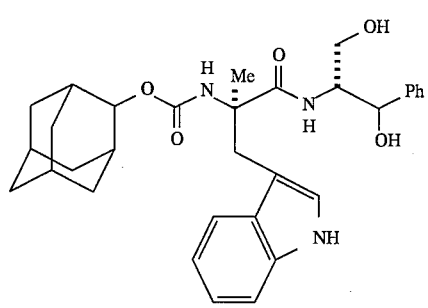 85.

TABLE II-continued
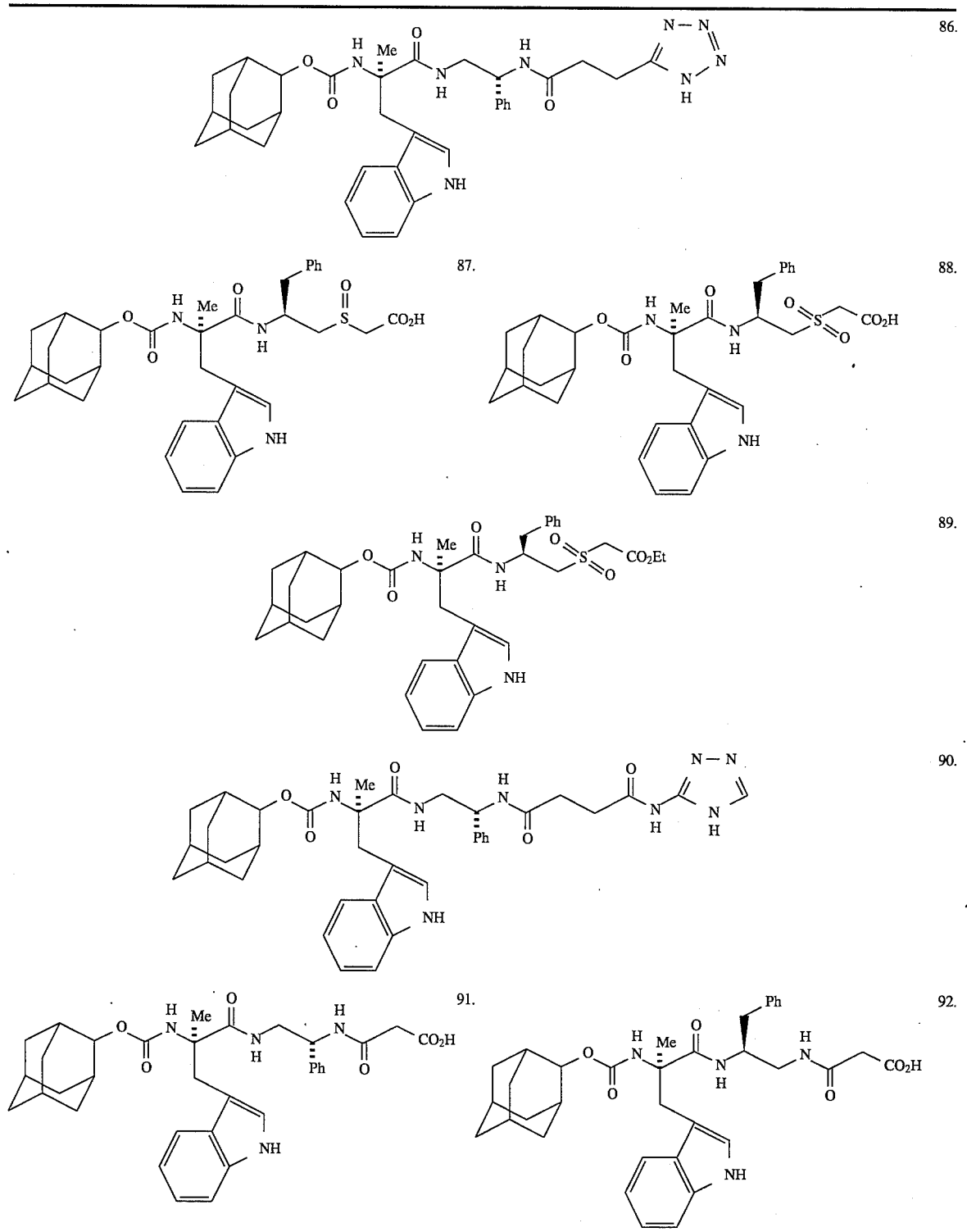

TABLE II-continued
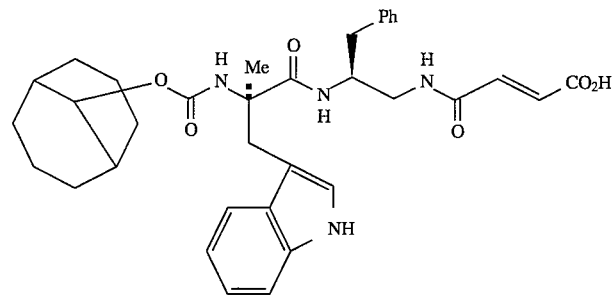
93.
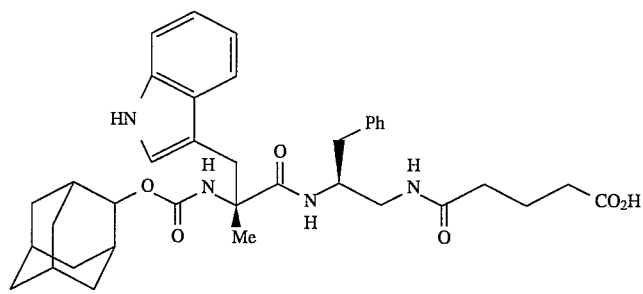
94.
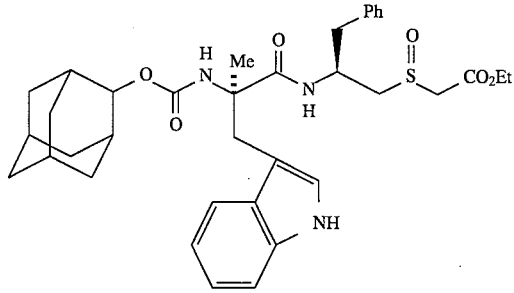
95.
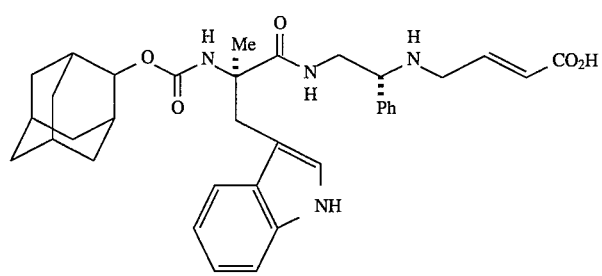
96.
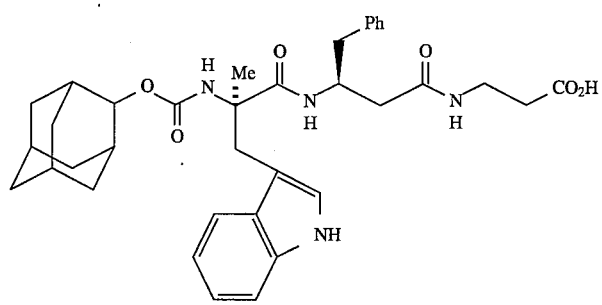
97.

TABLE II-continued
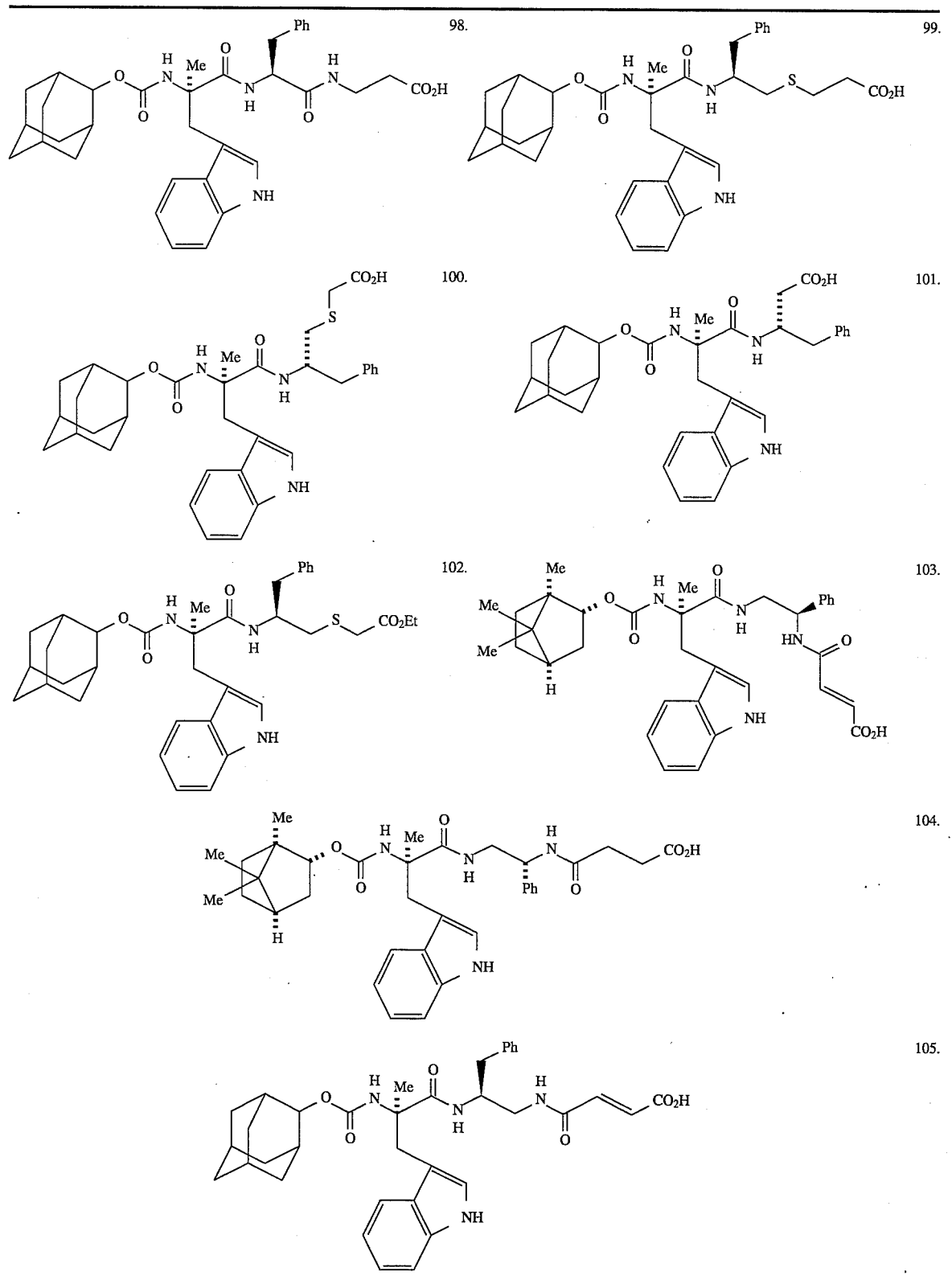

TABLE II-continued
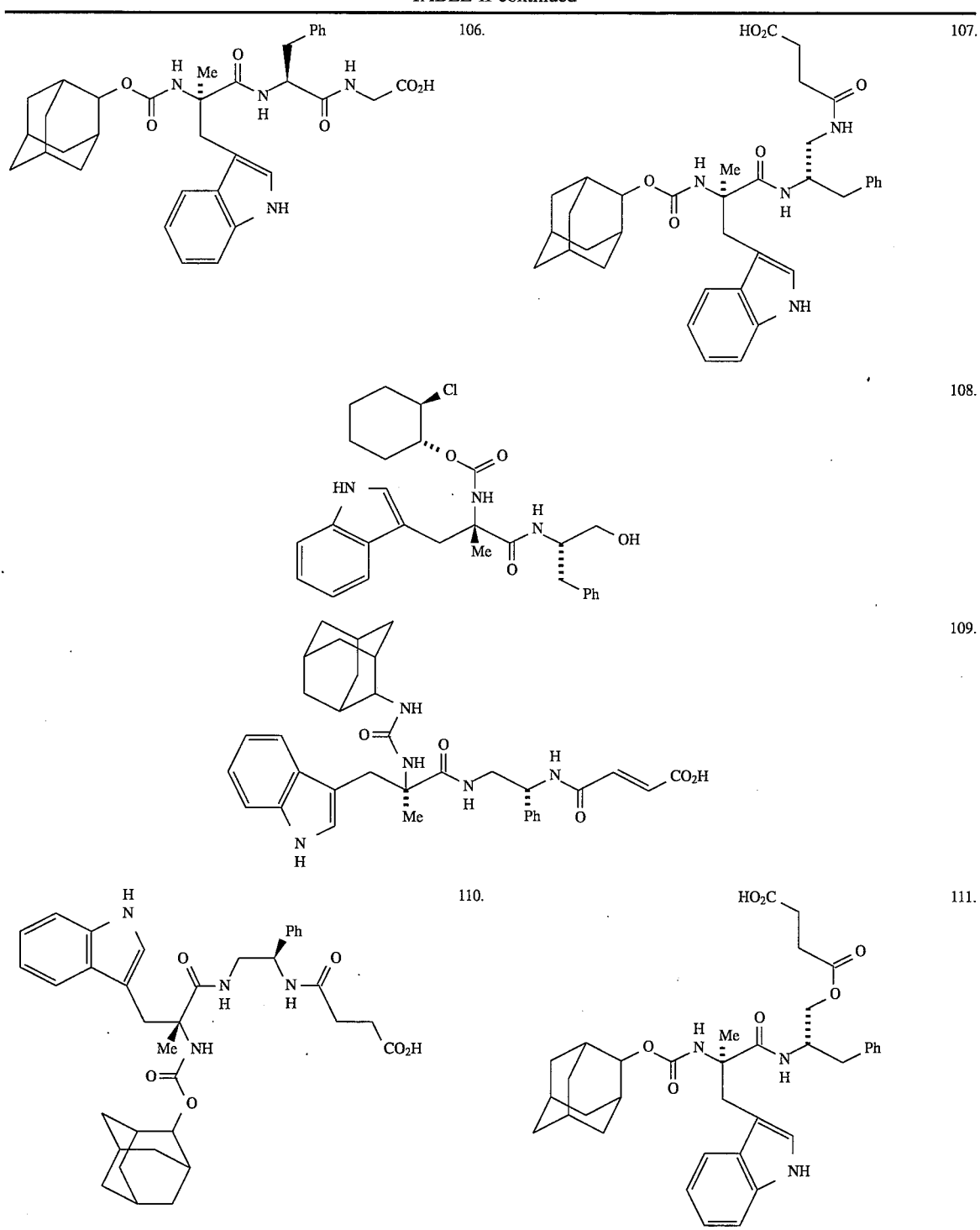

TABLE II-continued
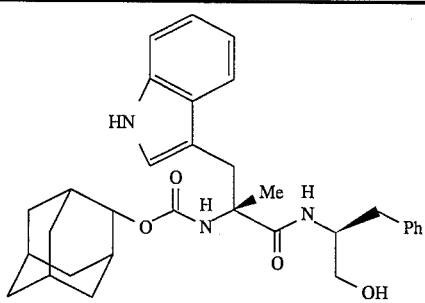
112.
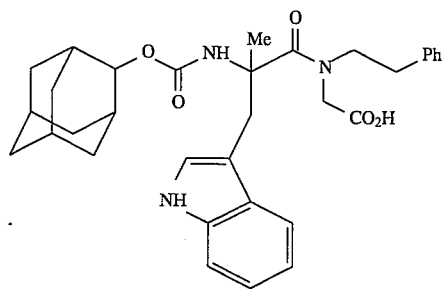
113.
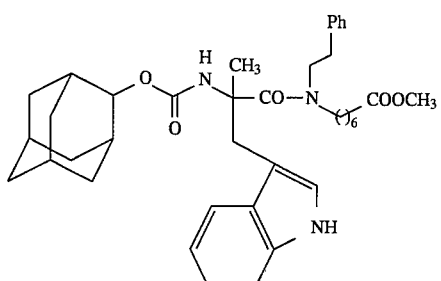
114.
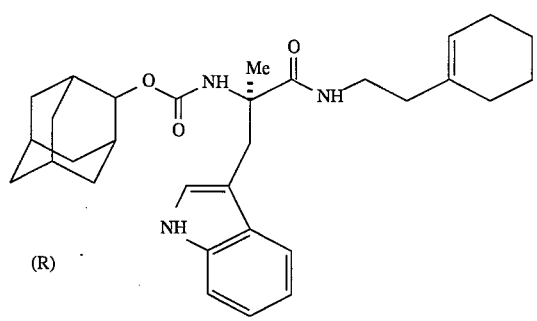
115.
(R)
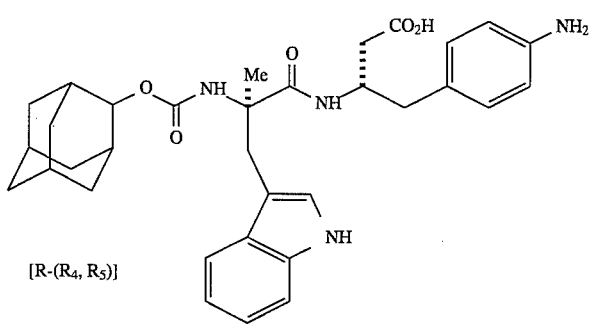
116.
[R-(R_4, R_5)]
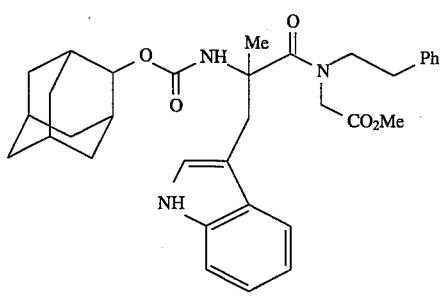
117.
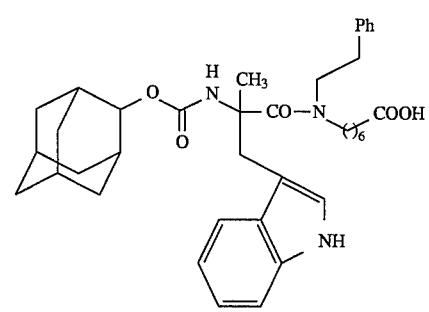
118.

TABLE II-continued
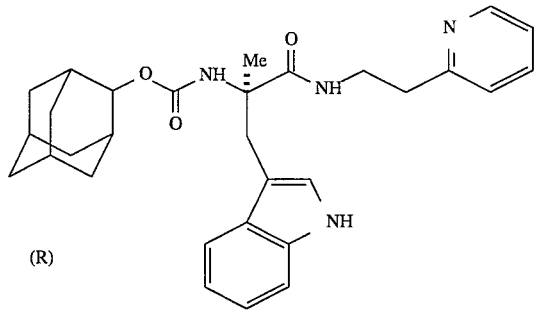
119.
(R)
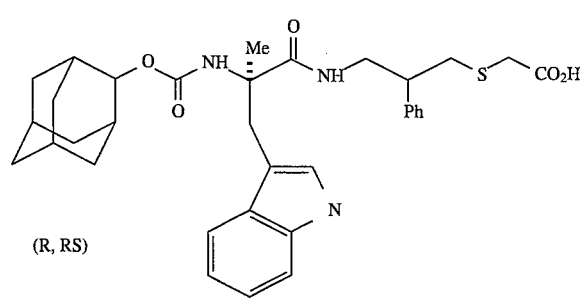
120.
(R, RS)
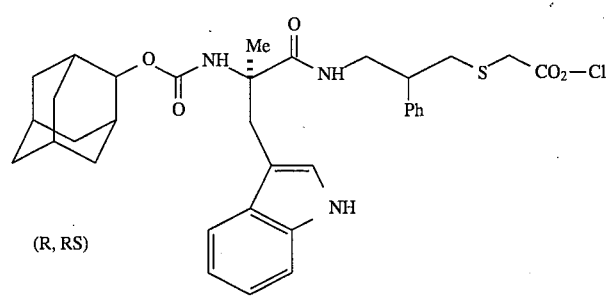
121.
(R, RS)
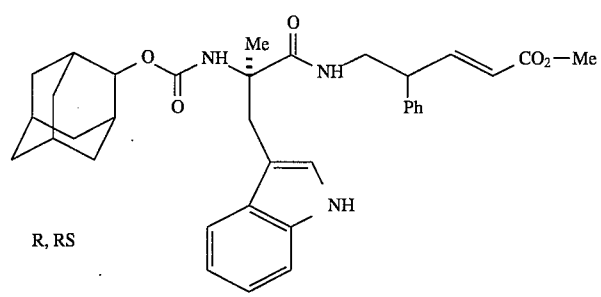
122.
R, RS
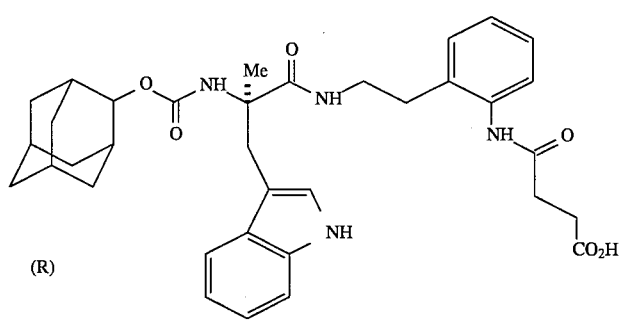
123.
(R)

TABLE II-continued
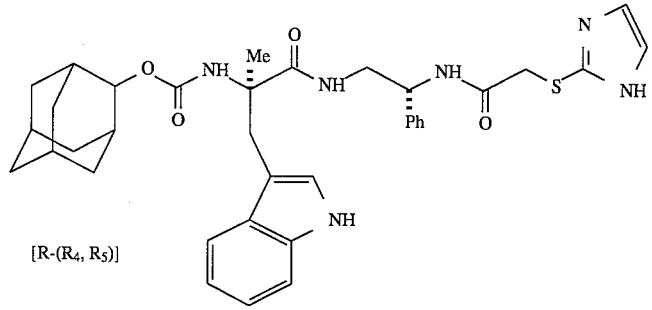
124.
[R-(R₄, R₅)]
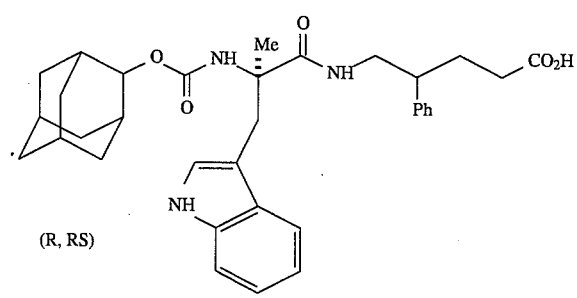
125.
(R, RS)
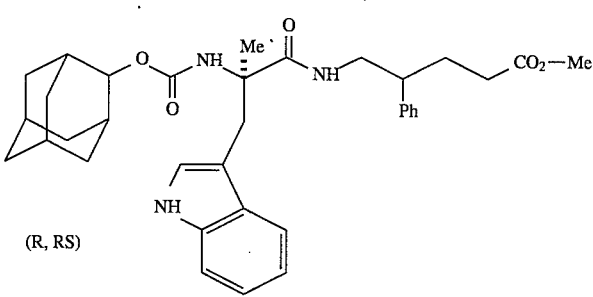
126.
(R, RS)
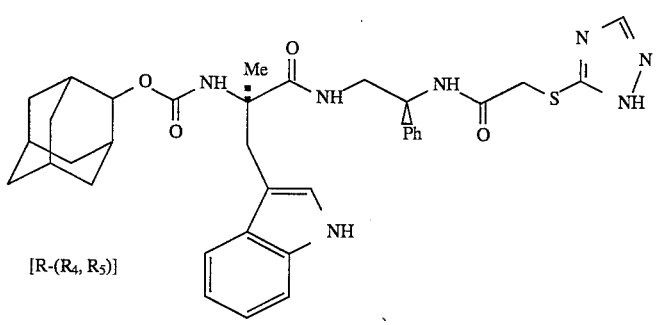
127.
[R-(R₄, R₅)]
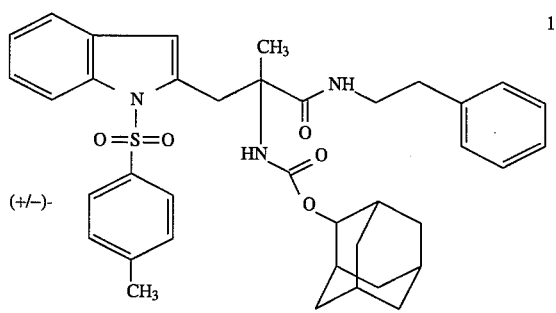
128.
(+/−)-
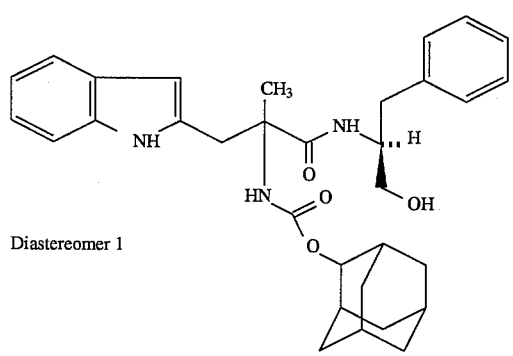
129.
Diastereomer 1

TABLE II-continued
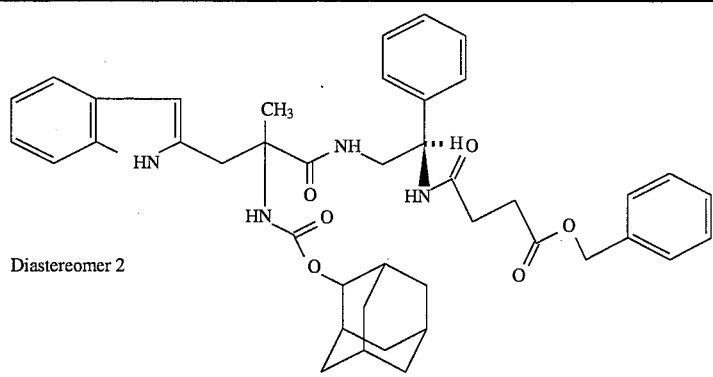
Diastereomer 2
130.
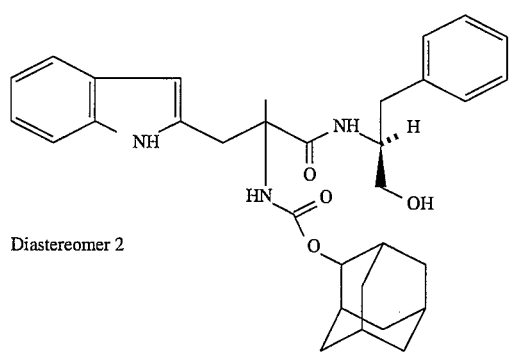
Diastereomer 2
131.
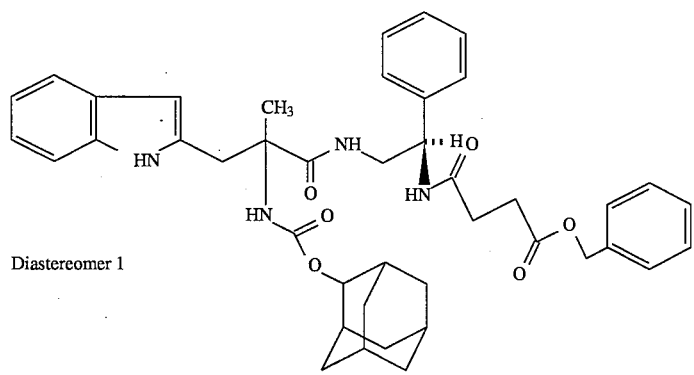
Diastereomer 1
132.
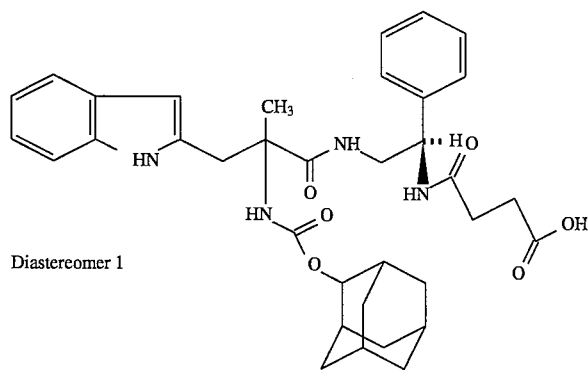
Diastereomer 1
133.

TABLE II-continued
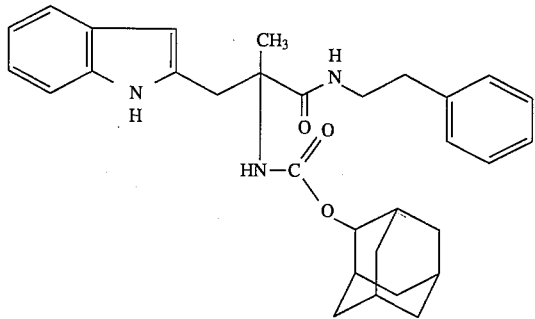
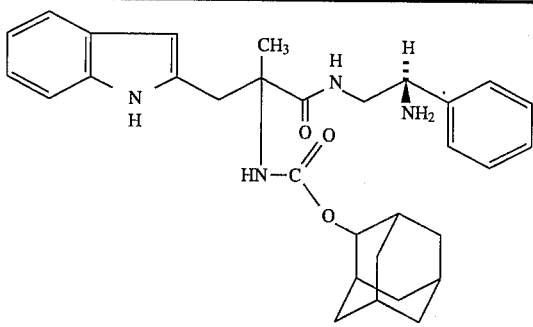
134.
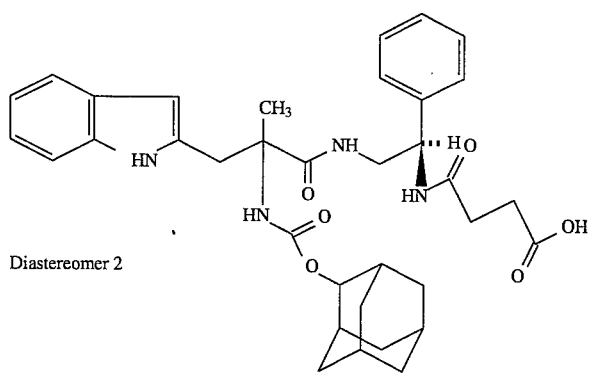
Diastereomer 2
135.
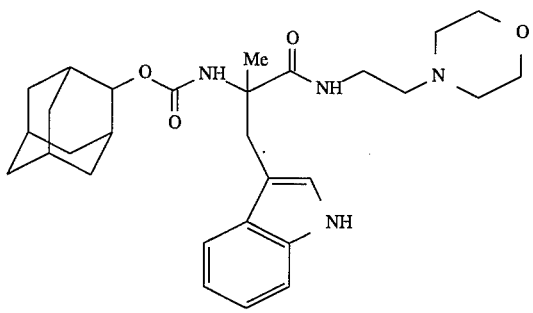
136.
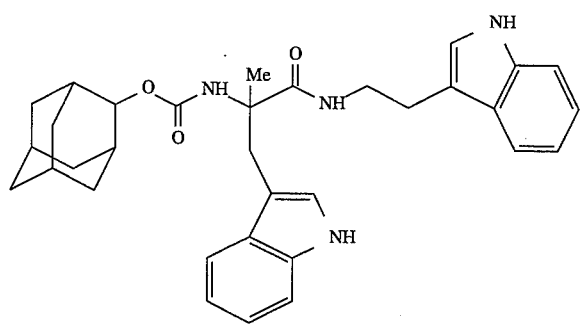
137.
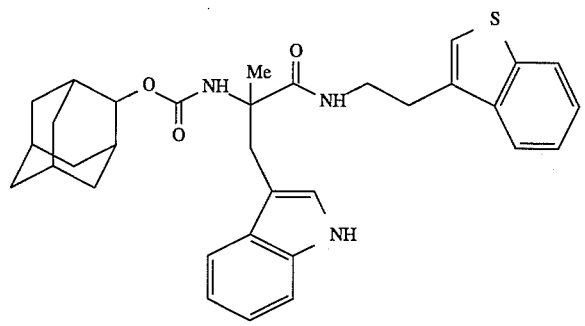

TABLE II-continued
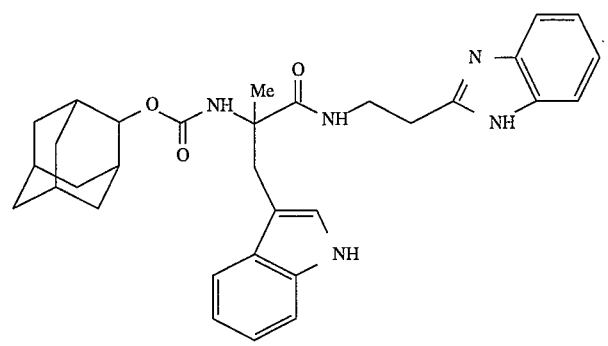
138.
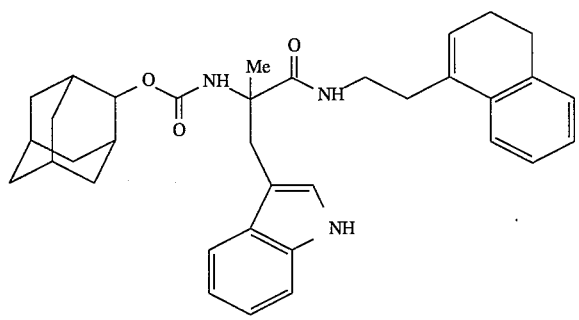
139.
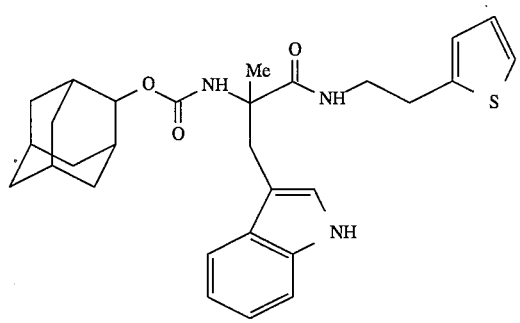
140.
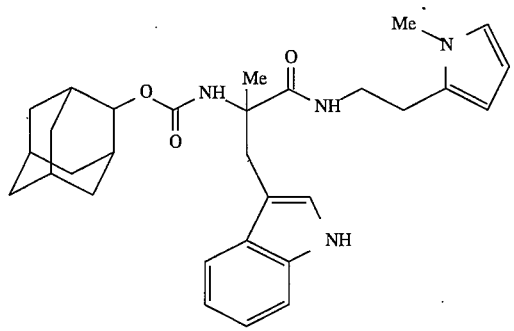
141.
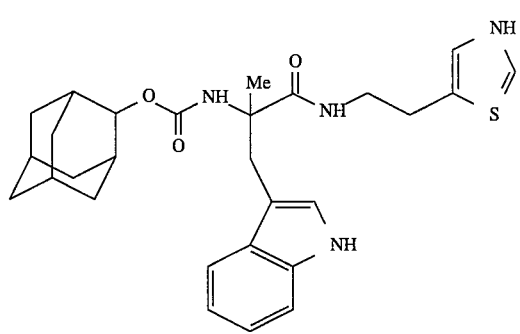
142.
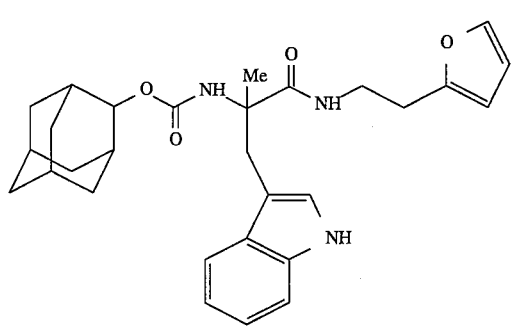
143.
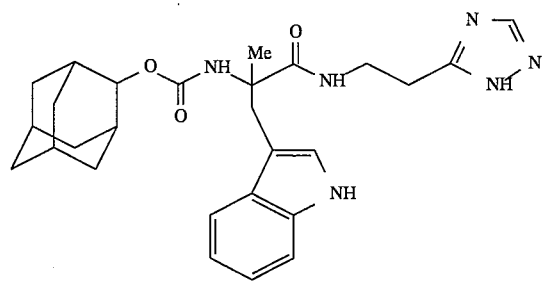
144.

TABLE II-continued

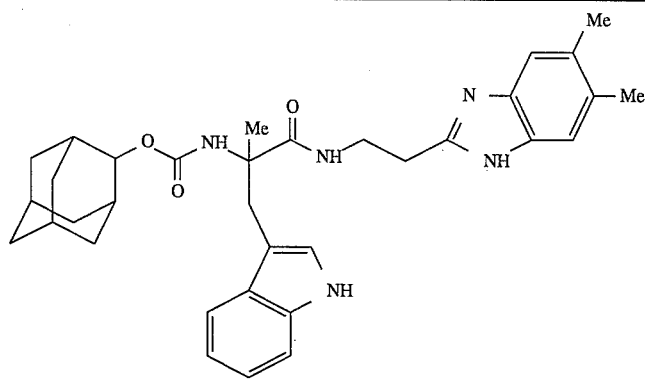

145.

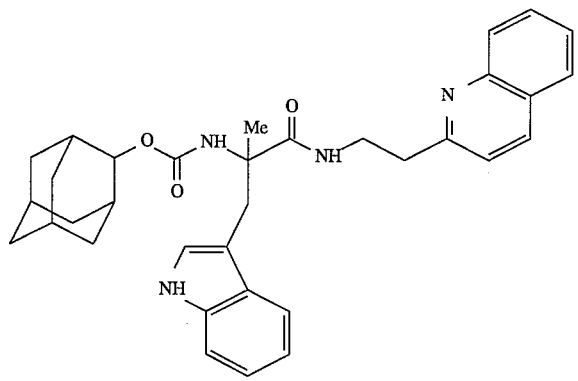

146.

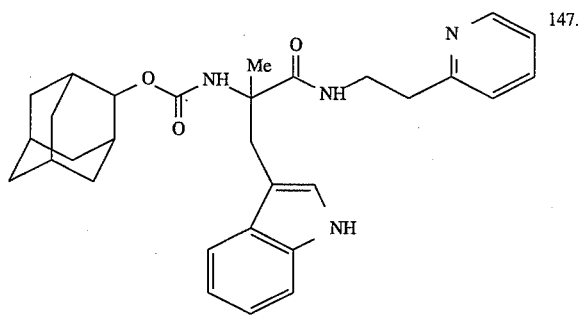

147.

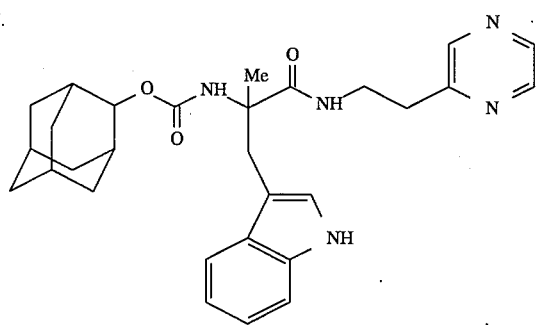

148.

We claim:
1. A compound of the formula

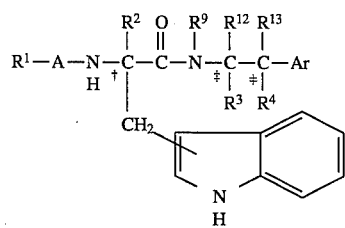

I or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR* SR*, $CO_2R^*$, $CF_3$, $NR^5R^6$, and —$(CH_2)_nOR^5$ wherein R* is a straight or branched alkyl of from one to six carbon atoms, $R^5$ and $R^6$ are each independently hydrogen or alkyl of from one to about six carbon atoms and n is an integer from zero to six;

A is —$(CH_2)_nCO$—, —$SO_2$—, —$S(=O)$—, —NHCO—,

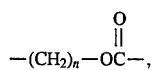

—SCO—, —O—$(CH_2)_nCO$— or —HC=CHCO— wherein n is an integer from zero to six;

$R^2$ is a straight or branched alkyl of from one to about six carbon atoms, —HC=$CH_2$, —C≡CH, —$CH_2$—CH=$CH_2$, —$CH_2$C≡CH, —$(CH_2)_nAr$, —$(CH_2)_nOR^*$, —$(CH_2)_nOAr$, —$(CH_2)_nCO_2R^*$, or —$(CH_2)_nNR^5R^6$ wherein n, R*, $R^5$ and $R^6$ are as defined above and Ar is as defined below;

$R^3$ and $R^4$ are each independently selected from hydrogen, $R^2$ and —$(CH_2)_{n'}$—B—D wherein:

n' is an integer of from zero to three;

B is a bond,

—OCO$(CH_2)_n$—,

—O(CH$_2$)$_n$—,
—SO$_2$NH(CH$_2$)$_n$—,
—NHSO$_2$(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—S—(CH$_2$)$_n$—,
—S(=O)—(CH$_2$)$_n$—,
—SO$_2$—(CH$_2$)$_n$—,

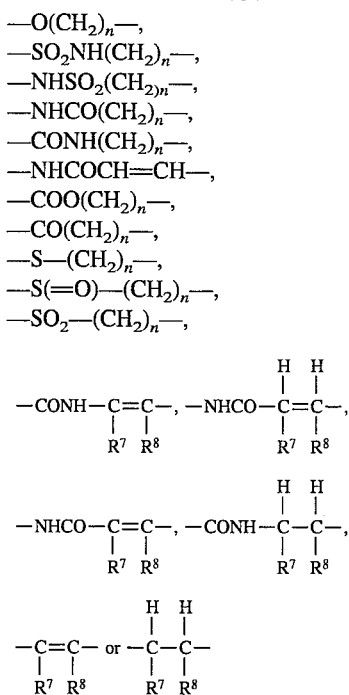

wherein R$^7$ and R$^8$ are independently selected from hydrogen and R$^2$ or together form a ring (CH$_2$)$_m$ wherein m is an integer of from 1 to 5 and n is as defined above;

D is
- —COOR*,
- —CH$_2$OR*,
- —CHR$^2$OR*,
- —CHR$_2$OR*,
- —CHR$^2$SR*,
- —CONR$^5$R$^6$,
- —CN,
- —NR$^5$R$^6$,
- —OH,
- PhSO$_2$NHCO—,
- CF$_3$CONHCO—,
- CF$_3$SO$_2$NHCO—,
- H$_2$NSO$_2$—,
- —H and acid replacements tetrazole, and

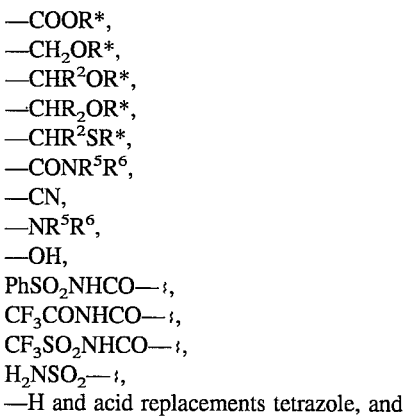

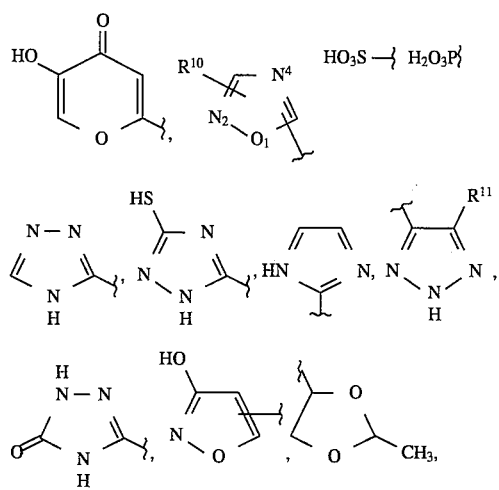

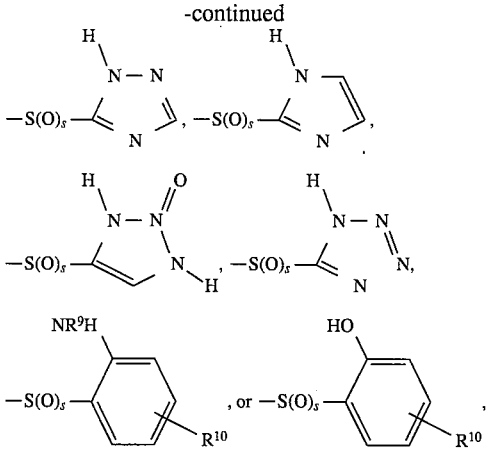

R$^{10}$ is OH, NH$_2$, CH$_3$, Cl;
R$^{11}$ is CN, CO$_2$H, or CF$_3$;
s is in integer of from 0 to 2;
wherein R*, R$^2$, R$^5$, and R$^6$ are as defined above;
R$^9$ is hydrogen or a straight or branched alkyl of from one to about six carbon atoms, —(CH$_2$)$_n$CO$_2$R*, —(CH$_2$)$_n$OAr', —(CH$_2$)$_n$Ar' or (CH$_2$)$_n$NR$^5$R$^6$, wherein n, R*, R$^5$, and R$^6$ are as defined above or taken from R$^3$ and Ar' is taken from Ar as defined below;
R$^{12}$ and R$^{13}$ are each independently hydrogen or are each independently taken with R$^3$ and R$^4$ respectively to form a moiety doubly bonded to the carbon atom: and
Ar is an unsubstituted or substituted five-membered aromatic heterocyclic ring optionally fused with a benzene ring.

2. A compound according to claim 1 wherein the cycloalkyl or polycycloalkyl has from about six to about ten carbon atoms.

3. A compound according to claim 1 wherein each substituent on the cycloalkyl or polycycloalkyl is independently methyl, F, Cl or Br.

4. A compound according to claim 1 wherein the polycycloalkyl is selected from the group consisting of

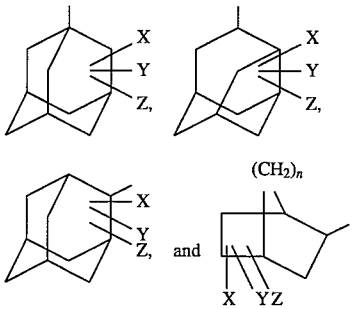

wherein W, X, Y, and Z are each independently hydrogen, a straight or branched alkyl of from one to six carbon atoms, CF$_3$, NR$^5$R$^6$, —(CH$_2$)$_n$CO$_2$R*, CN, F, Cl, Br, OR*, SR*, wherein R*, R$^5$ and R$^6$ are as defined in claim 1 and n is an integer of from 1 to 3.

5. A compound according to claim 1 wherein A is —NHCO—, OC(=O)—, —SO$_2$—, —S(=O)—, —SCO— or —CH$_2$CO—.

6. A compound according to claim 1 wherein:
R$^1$ is 2-adamantyl or 1-(S)-2-endobornyl;
A is —NHCO—, —OCO—, —SO$_2$—, —S(=O)— or —CH$_2$CO—;

$R^2$ is —$CH_3$, —$CH_2CO_2H$ or —$CH_2C\equiv CH$;
$R^3$ is —$(CH_2)_n$—B—D or H;
$R^4$ is —$(CH_2)_n$—B—D or H;
$R^9$ is hydrogen or methyl.

7. A compound according to claim 1 wherein:
$R^1$ is 2-adamantyl, 1-(S)-2-endobornyl, or 2-methyl cyclohexyl,
A is —OC(=O)—;
$R^2$ is —$CH_3$;
$R^3$ is H, $CH_2OH$, $CH_2OCOCH_2CH_2CO_2H$, $CH_2OCOCH=CHCO_2H$, $CH_2NHCOCH_2CH_2CO_2H$, $CH_2NHCOCH=CHCO_2H$, or $CH_2CO_2H$;
$R^4$ is H, —$CH_2SCH_2CO_2H$, —$CH_2SCH_2CH_2CO_2H$, —NHCOCH=CHCO_2H, —NHCOCH_2CH_2CO_2H (configuration) or NHCOCH=CHCO_2H (configuration).

* * * * *